United States Patent
Gauthier et al.

(10) Patent No.: US 11,891,444 B2
(45) Date of Patent: Feb. 6, 2024

(54) VARIABLE REGIONS FOR NKP46 BINDING PROTEINS

(71) Applicant: INNATE PHARMA, Marseilles (FR)

(72) Inventors: Laurent Gauthier, Marseilles (FR); Nadia Anceriz, Aubagne (FR); Ariane Morel, Marseilles (FR); Benjamin Rossi, Marseilles (FR)

(73) Assignee: INNATE PHARMA, Marseilles (FR)

( * ) Notice: Subject to any disclaimer, the term of this patent is extended or adjusted under 35 U.S.C. 154(b) by 333 days.

(21) Appl. No.: 17/315,547

(22) Filed: May 10, 2021

(65) Prior Publication Data

US 2021/0269523 A1    Sep. 2, 2021

Related U.S. Application Data

(62) Division of application No. 16/066,688, filed as application No. PCT/EP2016/081953 on Dec. 20, 2016, now Pat. No. 11,001,629.

(60) Provisional application No. 62/271,474, filed on Dec. 28, 2015.

(51) Int. Cl.
| | | |
|---|---|---|
| *C07K 16/28* | (2006.01) | |
| *C07K 16/46* | (2006.01) | |
| *C12N 15/66* | (2006.01) | |
| *C12N 15/64* | (2006.01) | |
| *C12N 5/10* | (2006.01) | |
| *C12N 15/00* | (2006.01) | |

(52) U.S. Cl.
CPC ...... *C07K 16/2803* (2013.01); *C07K 16/2809* (2013.01); *C07K 16/2887* (2013.01); *C07K 16/468* (2013.01); *C12N 5/10* (2013.01); *C12N 15/00* (2013.01); *C12N 15/64* (2013.01); *C12N 15/66* (2013.01); *C07K 2317/24* (2013.01); *C07K 2317/31* (2013.01); *C07K 2317/33* (2013.01); *C07K 2317/34* (2013.01); *C07K 2317/526* (2013.01); *C07K 2317/622* (2013.01); *C07K 2317/732* (2013.01); *C07K 2317/92* (2013.01); *C12N 2511/00* (2013.01); *C12N 2523/00* (2013.01)

(58) Field of Classification Search
None
See application file for complete search history.

(56) References Cited

U.S. PATENT DOCUMENTS

| | | | |
|---|---|---|---|
| 11,001,629 | B2 | 5/2021 | Gauthier et al. |
| 2019/0367609 | A1 | 12/2019 | Gauthier et al. |

FOREIGN PATENT DOCUMENTS

| | | |
|---|---|---|
| WO | WO 2005/000086 | 1/2005 |
| WO | WO 2005/105848 | 11/2005 |
| WO | WO 2015/197593 | 12/2015 |
| WO | WO 2016/207278 | 12/2016 |

OTHER PUBLICATIONS

Bolzhauser, M. "Immuntherapie der kindlichen ALL: Einfluss eines bispezifischen CD19*NKp46-Antikörpers auf die zytotoxische Aktivität von NK-Zellen gegenüber CD19+ ALL-Blasten pädiatrischer Patienten" Innaugural-Dissertation zur Erlangung des Doktorgrades der Medizin, Jan. 1, 2010, retrieved from the Internet: URL:http://d-nb.info/1003819621/34, retrieved on Aug. 27, 2015, pp. 1-116.

Kipriyanov, S. M. et al. "Recent advances in the generation of bispecific antibodies for tumor immunotherapy" Current Opinion in Drug Discovery and Development, Mar. 1, 2004, pp. 233-242, vol. 7, No. 2.

Written Opinion in International Application No. PCT/EP2016/081953, dated May 19, 2017, pp. 1-12.

*Primary Examiner* — Nora M Rooney
(74) *Attorney, Agent, or Firm* — SALIWANCHIK, LLOYD & EISENSCHENK

(57) ABSTRACT

NKp46-binding immunoglobulin variable regions, and proteins such as antibodies and multispecific proteins that comprise the variable regions are provided. The proteins can bind and specifically redirect NK cells to lyse a target cell of interest. The proteins have utility in the treatment of disease, notably cancer or infectious disease.

15 Claims, 14 Drawing Sheets

Specification includes a Sequence Listing.

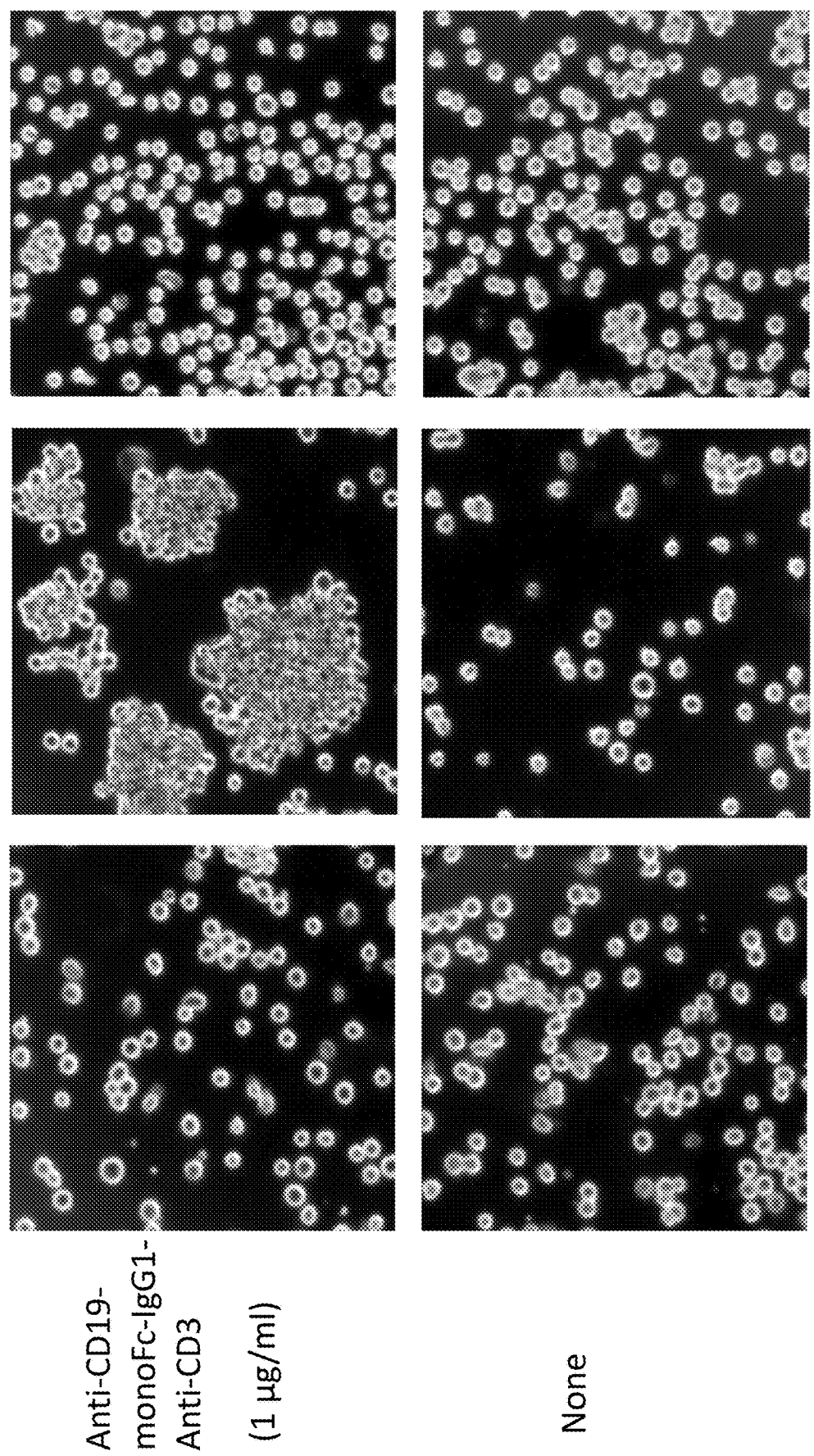

Figure 2C
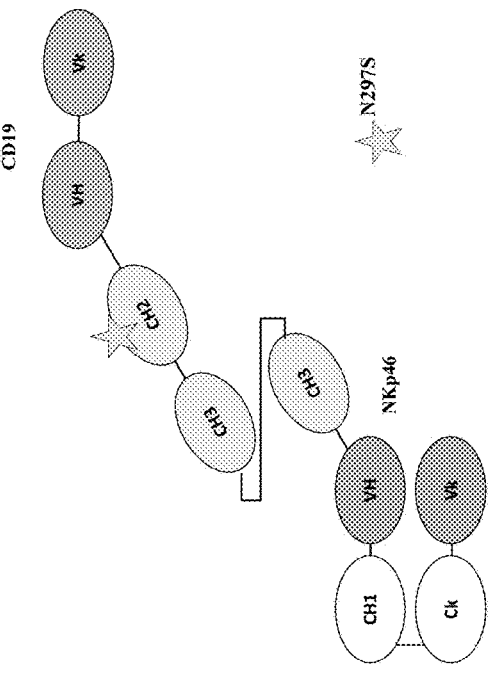
Format 12
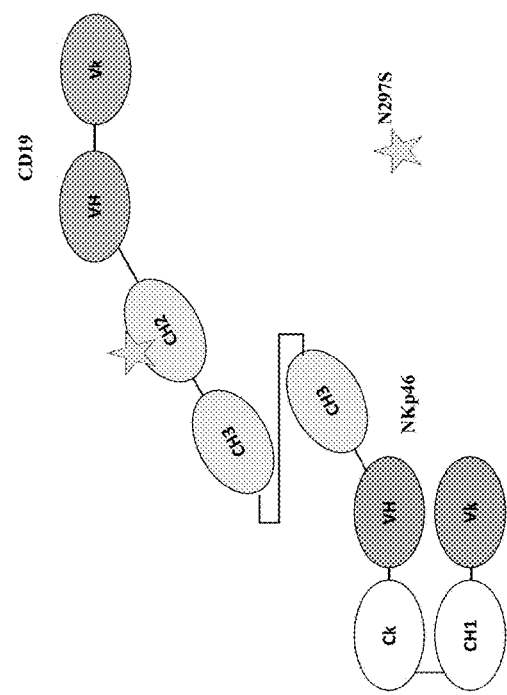
Format 11
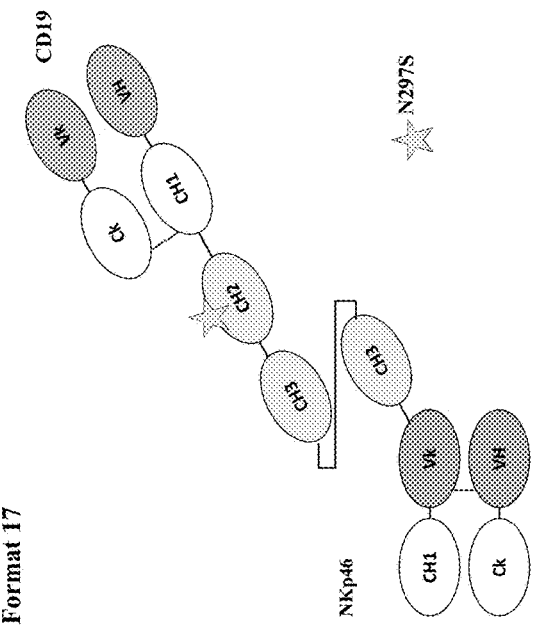
Format 17

Figure 2D
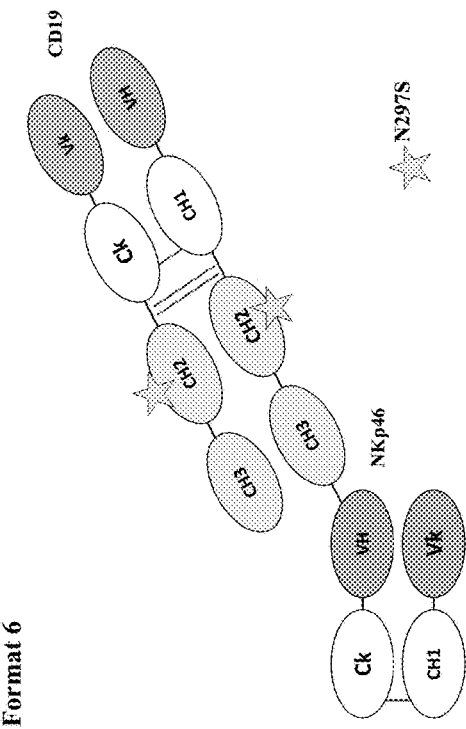
Format 6
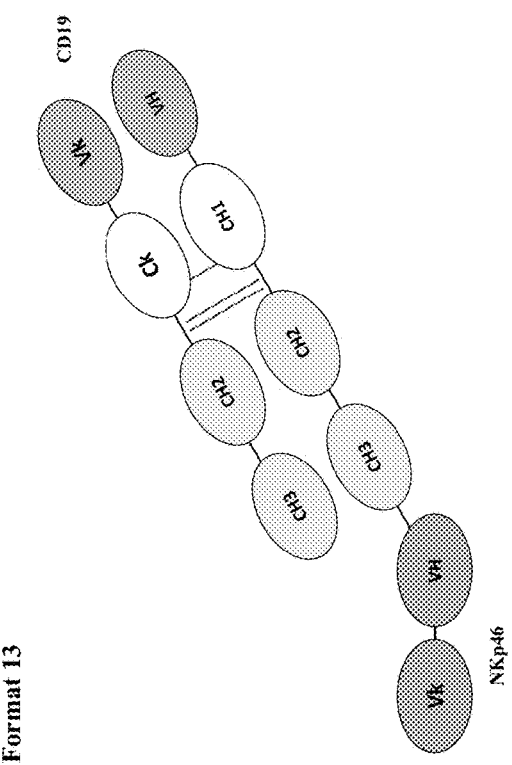
Format 13
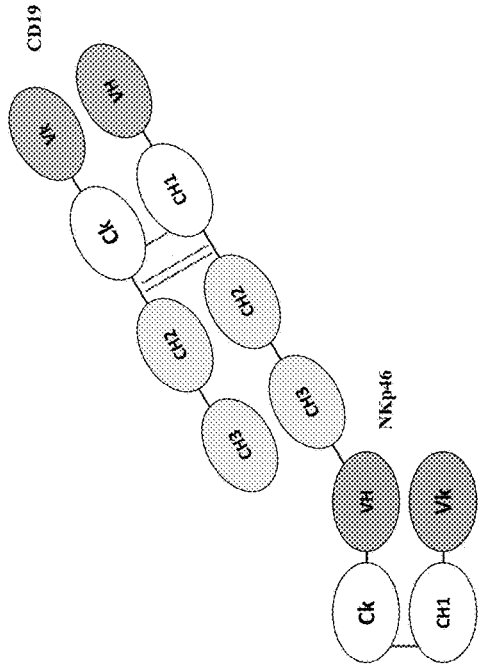
Format 5
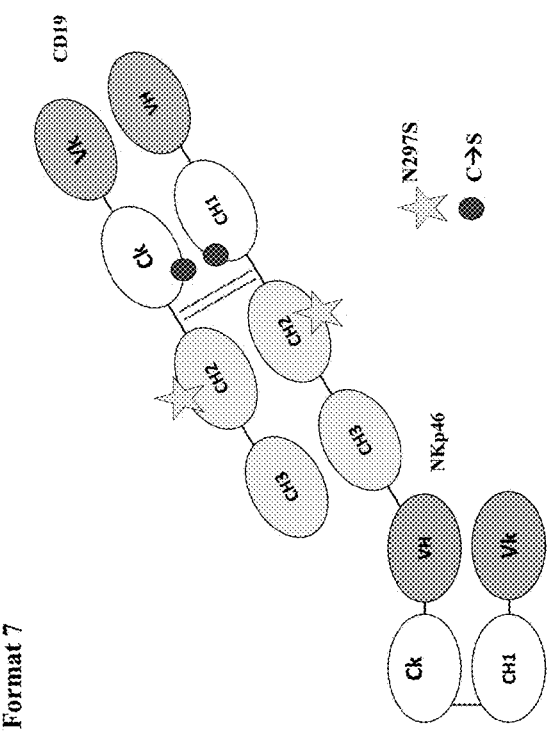
Format 7

Figure 2E
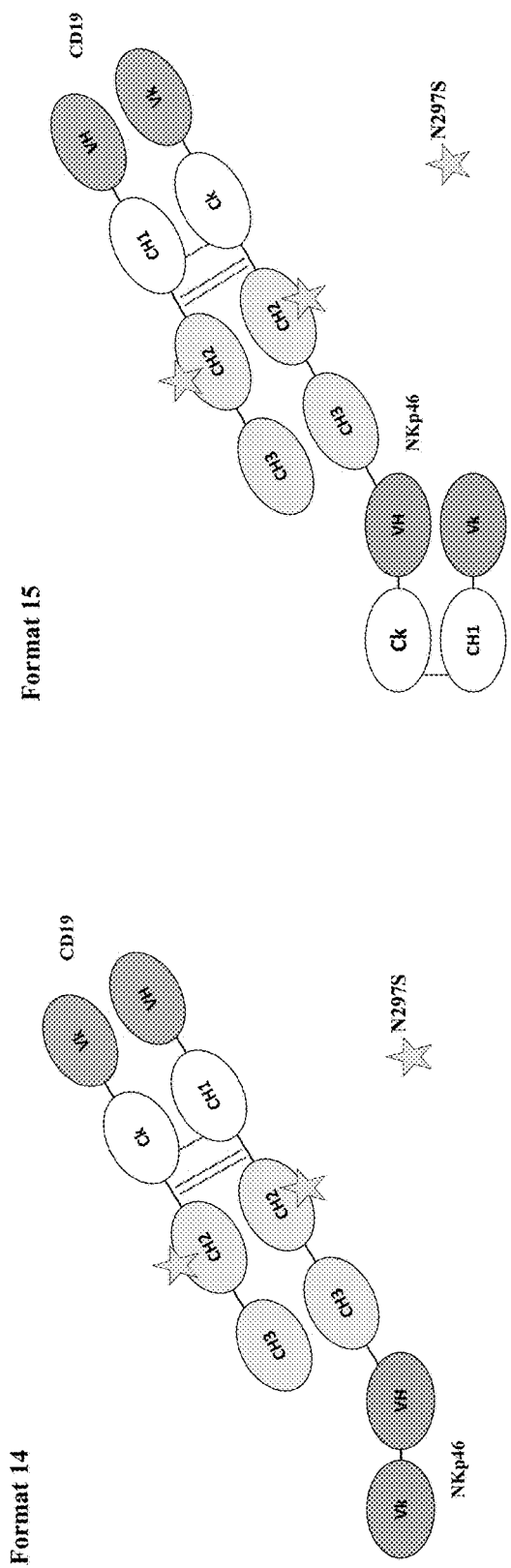
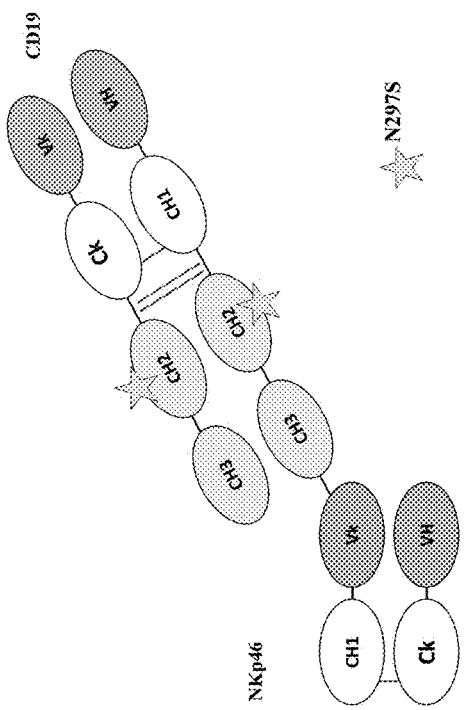

Figure 4A
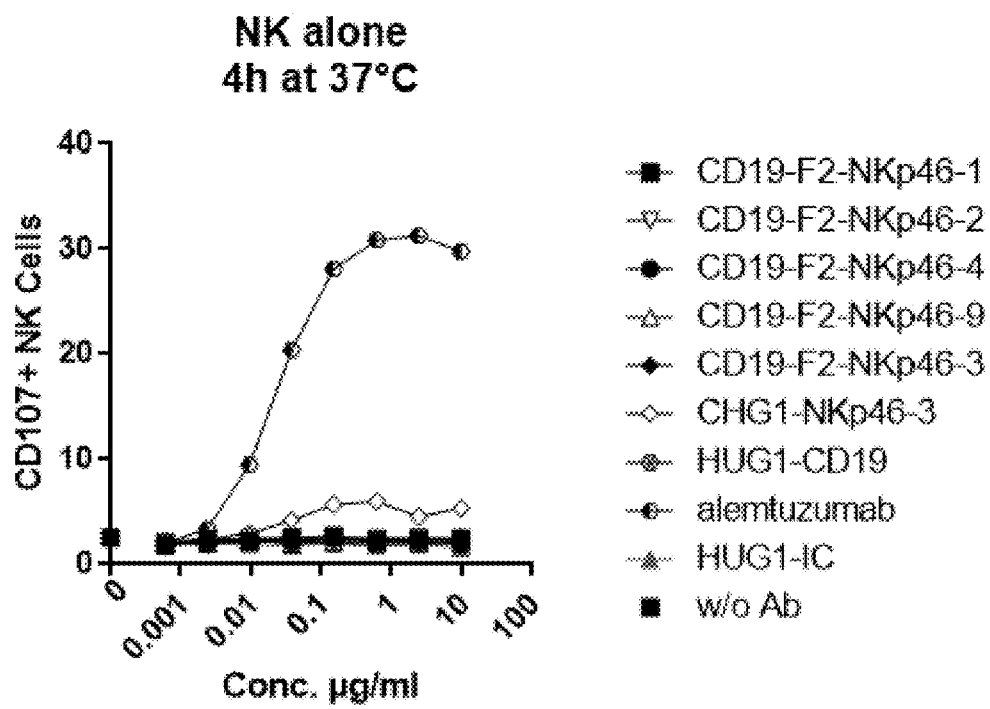
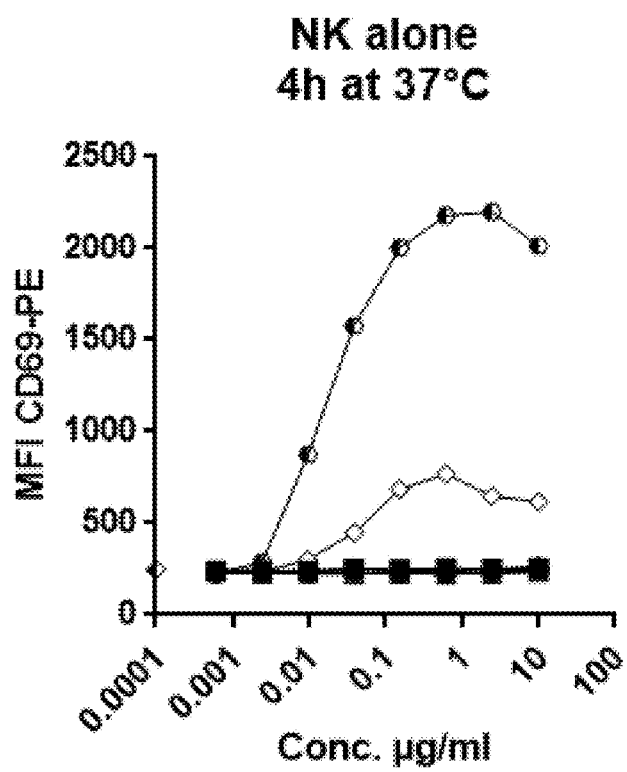

Figure 4B
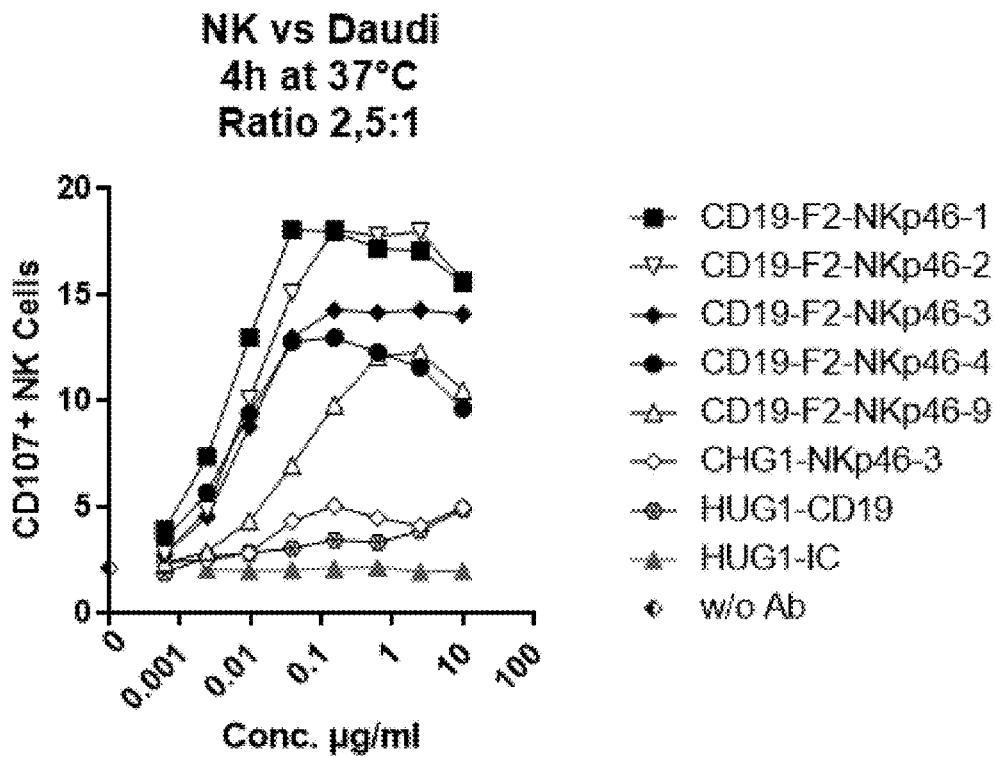
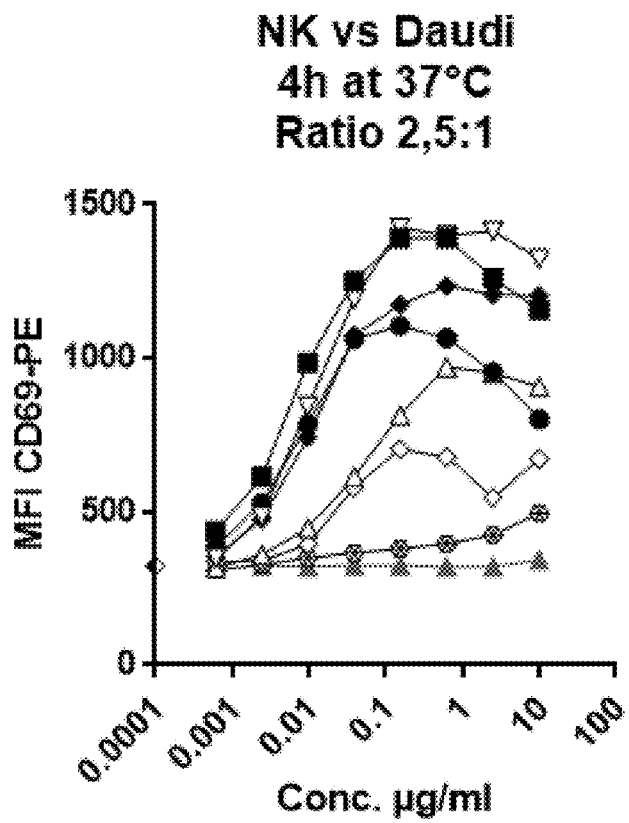

VARIABLE REGIONS FOR NKP46 BINDING PROTEINS

CROSS-REFERENCE TO RELATED APPLICATIONS

This application is a divisional of U.S. application Ser. No. 16/066,688, filed Jun. 28, 2018, now U.S. Pat. No. 11,001,629, which is the U.S. national stage application of International Patent Application No. PCT/EP2016/081953, filed Dec. 20, 2016, which claims the benefit of U.S. Provisional Application No. 62/271,474, filed Dec. 28, 2015, which are incorporated herein by reference in their entirety; including any drawings and sequence listings.

REFERENCE TO THE SEQUENCE LISTING

The present application is being filed along with a Sequence Listing in electronic format. The Sequence Listing is provided as a file entitled "NKp46-7-PCT_ST25.bd", created Dec. 19, 2016, which is 376 KB in size. The information in the electronic format of the Sequence Listing is incorporated herein by reference in its entirety.

FIELD OF THE INVENTION

Immunoglobulin variable regions, and proteins such as antibodies and multispecific proteins that comprise the variable regions are provided. The proteins can bind and specifically redirect NK cells to lyse a target cell of interest. The proteins have utility in the treatment of disease, notably cancer or infectious disease.

BACKGROUND

Bispecific antibodies binding two different epitopes offer opportunities for increasing specificity, broadening potency, and utilizing novel mechanisms of action that cannot be achieved with a traditional monoclonal antibody. A variety of formats for bispecific antibodies that bind to two targets simultaneously have been reported. Cross-linking two different receptors using a bispecific antibody to inhibit a signaling pathway has shown utility in a number of applications (see, e.g., Jackman, et al., (2010) J. Biol. Chem. 285:20850-20859). Bispecific antibodies have also been used to neutralize two different receptors. In other approaches, bispecific antibodies have been used to recruit immune effector cells, where T-cell activation is achieved in proximity to tumor cells by the bispecific antibody which binds receptors simultaneously on the two different cell types (see Baeuerle, P. A., et al, (2009) Cancer Res 69(12): 4941-4). Approaches developed to date have primarily involved bispecific antibodies that link the CD3 complex on T cells to a tumor-associated antigen. However in other examples, bispecific antibodies having one arm which binds CD16 (FcγRIIIa) and another which bound to an antigen of interest such as CD19 have been developed (see Kellner et al. (2011) Cancer Lett. 303(2): 128-139).

Natural killer (NK) cells are a subpopulation of lymphocytes that are involved in non-conventional immunity. NK cells provide an efficient immunosurveillance mechanism by which undesired cells such as tumor or virally-infected cells can be eliminated. Characteristics and biological properties of NK cells include the expression of surface antigens including CD16, CD56 and/or CD57, the absence of the alpha/beta or gamma/delta TCR complex on the cell surface; the ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

NK cell activity is regulated by a complex mechanism that involves both activating and inhibitory signals. Several distinct NK cell receptors have been identified that play an important role in the NK cell mediated recognition and killing of HLA Class I deficient target cells. One receptor, although not specific to NK cells, is FcγR3a (CD16) which is responsible for NK cell mediated ADCC. Another NK cell receptor is NKp46, a member of the Ig superfamily. It is specific to NK cells and its cross-linking, induced by specific mAbs, leads to a strong NK cell activation resulting in increased intracellular $Ca^{++}$ levels, triggering of cytotoxicity, and lymphokine release. International patent publication number WO2005/105858 (Innate Pharma) discloses use of monospecific full-length IgG anti-NKp46 antibodies that bind Fcγ receptors for treating hematological malignancies that are Fcγ-positive. Fc gamma receptors on tumor cells (e.g. B cell malignancies) were proposed to interact with the Fc domain of the anti-NKp46 antibodies which bound NK cells, such that the activated NK cells are brought into close proximity with their target cells via the two reactive portions of the antibody (e.g. the antigen-recognizing domain and the Fc domain), thereby enhancing the efficiency of the treatment.

To date, no NK cell specific bispecific antibodies have been developed. The depleting agents that recruit NK cytotoxicity such as anti-tumor antibodies are typically full-length IgG1 that mediate ADCC via CD16. Despite the existence of a variety of formats for bispecific antibodies, there remains a need in the art for proteins with new and well-defined mechanisms of action that can provide benefits over and can be used in addition to full-length antibodies.

SUMMARY OF THE INVENTION

In one aspect, the present invention arises from the discovery of antibody hypervariable regions that cross-react with both a human NKp46 polypeptide and a non-human primate (e.g. e.g. a *Macaca fascicularis*) NKp46 polypeptide. In another aspect, the present invention arises from the discovery of antibody hypervariable regions that remain functional in in single chain proteins and multi-specific proteins (e.g. a polypeptide, a single chain protein, a multi-chain protein, including but not limited to antibody-based protein formats) that bind to NKp46 on NK cells.

Provided also are the epitopes bound by the antigen binding domains. The antigen domains bind to epitopes on NKp46 that provide for highly potent antigen binding proteins. The epitopes are furthermore shared by human and non-human primates, including on NKp46 as expressed at the surface of an NK cell.

The variable regions, when incorporated into a polypeptide (e.g. antibody, Fc protein, scFv, etc.) that binds NKp46 in monovalent manner, permit the binding to NKp46 on isolated NK cells without triggering NKp46 activation (in the absence of target cells). The variable regions are capable of binding NKp46 with high affinity as single chain polypeptides, e.g., as tandem variable regions separated by a peptide linker, as well as in F(ab) form, and are capable, as monovalent binders, to bind to NKp46 epitopes that enable NK cells to be directed to lyse target cells. Such properties make them advantageous in a variety of applications, including in particular, in multispecific (e.g. bispecific) proteins that bind to NKp46 and an antigen of interest via the heavy and light chain anti-NKp46 variable regions, and to an antigen of interest on a target cell via a hypervariable region (e.g. a heavy and light chain variable region) that specifically binds the antigen of interest. Such a multispecific protein is capable of redirecting NK cells to lyse a target cell that expresses the antigen of interest, e.g. a cell that contributes to disease. It will be appreciated that while the hypervariable regions and humanized variable regions disclosed herein retain monovalent binding in single chain form and can be used advantageously in configurations where they are placed on a single polypeptide chain, they can also be used in other applications, such as other proteins where variable regions are on separate chains, e.g. bispecific antibodies and Fc proteins, or more generally monospecific and/or conventional anti-NKp46 antibodies, for example to bind, modulate and/or detect human and/or non-human primate NKp46 polypeptides, in vivo or in vitro (e.g. in a biological sample).

In one aspect, provided is an antigen binding domain (ABD) that binds both a human and a non-human primate NKp46 polypeptide (e.g. with similar affinity, as assessed for example by surface plasmon resonance and/or by flow cytometry to NKp46-expression cells, by the methods herein). In one embodiment, the ABD is capable of binding to a NKp46 polypeptide as a single chain antigen binding domain (e.g. an scFv). In one embodiment, the ABD comprises (or is comprised in) an immunoglobulin heavy and light variable region, e.g. wherein the heavy and light chain variable domains are placed on a single polypeptide chain. In another embodiment heavy and light chain variable domains are placed on different polypeptide chains within a multimeric protein. The heavy chain variable region comprises a heavy chain framework region of human origin and the light chain variable region comprises a light chain framework regions of human origin, optionally wherein the heavy and/or light chain framework regions comprise one or more amino acid modifications (e.g. substitution(s), back-mutation(s) in which a residue is substituted by the residue present in the parental (e.g., murine) framework at the position), optionally wherein the amino acid modifications provides or increases binding to a non-human primate NKp46. In one embodiment, provided is a protein, an Fc protein, an antibody or an antibody fragment that comprises such an ABD and/or variable regions. In one aspect, provided is an isolated and/or recombinant nucleic acid that encodes such an antigen binding domain (ABD).

Examples of such proteins or polypeptides include, e.g. a single polypeptide chain NKp46-binding domain (an ABD that binds human NKp46 placed on a single polypeptide chain, e.g., a polypeptide comprising a VH and VL of the separated by a (poly)peptide linker). In one embodiment, the single chain NKp46 binding domain comprises a VH and a VL domain disclosed herein, separated by a peptide linker. The single polypeptide chain may be comprised in a multi-chain polypeptide that comprises one or more further polypeptide chains, or may be isolated as a single polypeptide chain. Another example of a protein or polypeptide that comprises an anti-NKp46 ABD is a multimeric protein comprising a first and a second polypeptide chain, wherein one chain comprises a VH domain of an anti-NKp46 ABD disclosed herein and the other chain comprises the VL of an anti-NKp46 ABD disclosed herein, wherein the chains are configured so that the VH and VL form an antigen binding domain that binds NKp46.

In one aspect, provided is a protein or polypeptide (e.g. a monospecific, bispecific, or multispecific antibody or protein, a scFv, a F(ab) or F(ab)$_2$, a multispecific Fc protein) that binds a human NKp46 polypeptide, optionally that further bind a non-human primate NKp46 polypeptide, wherein the protein nor polypeptide comprises: (a) a heavy chain variable region comprising a human heavy chain framework region (FR1, FR2, and FR3) derived from a human IGHV1-69 gene, and heavy chain CDR1, 2 and 3 of a NKp46-1 antibody; and (b) a light chain variable region comprising a human light chain framework region (FR1, FR2, and FR3) derived from a human IGKV1-33 gene, and light chain CDR1, 2 and 3 of a NKp46-1 antibody. Optionally, CDRs as defined by Kabat, Chotia or IMGT numbering. In one embodiment, the protein or polypeptide binds a wild-type NKp46 polypeptide but has decreased binding to a mutant NKp46 polypeptide having a mutation (e.g., an alanine substitution) any one or more of the residues K41, E42, E119, Y121 and/or Y194 (with reference to SEQ ID NO:1) compared to binding to the wild-type NKp46). In one embodiment, the heavy chain variable region comprises an amino acid sequence sharing at least 70%, 80%, 90%, 95% or 98% identity with the amino acid sequence of SEQ ID NO: 3, and/or the light chain variable region comprises an amino acid sequence sharing at least 70%, 80%, 90%, 95% or 98% identity with the amino acid sequence of SEQ ID NO: 4. In one embodiment, the heavy chain variable region comprises an amino acid sequence of the NKp46-1 H1 or H3 variable domain (or an amino acid sequence sharing at least 80, 90%, 95% or 98% identity therewith) and the light chain variable region comprises an amino acid sequence of the NKp46-1 L1 variable domain (or an amino acid sequence sharing at least 80, 90%, 95% or 98% identity therewith).

In one aspect, provided is a protein or polypeptide (e.g. a monospecific, bispecific, or multispecific antibody or protein, a scFv, a F(ab) or F(ab)$_2$, a multispecific Fc protein) that binds a human NKp46 polypeptide, optionally that further bind a non-human primate NKp46 polypeptide, wherein the protein nor polypeptide comprises: (a) a heavy chain variable region comprising a human heavy chain framework region (FR1, FR2, and FR3) derived from a IGHV4-30-4 gene, and heavy chain CDR1, 2 and 3 of a NKp46-2 antibody; and (b) a light chain variable region comprising a human light chain framework region (FR1, FR2, and FR3) derived from a IGKV1-39 gene, and light chain CDR1, 2 and 3 of a NKp46-2 antibody. Optionally, CDRs as defined by Kabat, Chotia or IMGT numbering. In one embodiment, the heavy chain variable region comprises an amino acid sequence sharing at least 70%, 80%, 90%, 95% or 98% identity with the amino acid sequence of SEQ ID NO: 5, and/or the light chain variable region comprises an amino acid sequence sharing at 70%, 80%, 90%, 95% or 98% identity with the amino acid sequence of SEQ ID NO: 6. In one embodiment, the heavy chain variable region comprises an amino acid sequence of the NKp46-2 H1, H2 or H3 variable domain (or an amino acid sequence sharing at least 80, 90%, 95% or 98% identity therewith) and the light chain variable region comprises an amino acid sequence of the NKp46-2 L1 variable domain (or an amino acid sequence sharing at least 80, 90%, 95% or 98% identity therewith).

In one aspect, provided is a protein or polypeptide (e.g. a monospecific, bispecific, or multispecific antibody or protein, a scFv, a F(ab) or F(ab)$_2$, a multispecific Fc protein) that binds a human NKp46 polypeptide, optionally that further bind a non-human primate NKp46 polypeptide, wherein the protein nor polypeptide comprises: (a) a heavy chain variable region comprising a human heavy chain framework region (FR1, FR2, and FR3) derived from a IGHV1-69 gene, and heavy chain CDR1, 2 and 3 of a NKp46-3 antibody; and (b) a light chain variable region comprising a human light chain framework region (FR1, FR2, and FR3) derived from a IGKV3-11 and/or a IGKV3-15 gene (e.g. a mosaic variable region comprising both IGKV3-11 and IGKV3-15 sequences or segments), and light chain CDR1, 2 and 3 of a NKp46-3 antibody. Optionally, CDRs as defined by Kabat, Chotia or IMGT numbering. In one embodiment, the protein or polypeptide binds a wild-type NKp46 polypeptide but has decreased binding to a mutant NKp46 polypeptide having a mutation (e.g., an alanine substitution) any one or more of the residues P132, E133, 1135, and/or S136 (with reference to SEQ ID NO:1) compared to binding to the wild-type NKp46). In one embodiment, the heavy chain variable region comprises an amino acid sequence sharing at least 70%, 80%, 90%, 95% or 98% identity with the amino acid sequence of SEQ ID NO: 7, and/or the light chain variable region comprises an amino acid sequence sharing at least 70%, 80%, 90%, 95% or 98% identity with the amino acid sequence of SEQ ID NO: 8. In one embodiment, the heavy chain variable region comprises an amino acid sequence of the NKp46-3 H1, H3 or H4 variable domain (or an amino acid sequence sharing at least 80, 90%, 95% or 98% identity therewith) and the light chain variable region comprises an amino acid sequence of the NKp46-3 L1 variable domain (or an amino acid sequence sharing at least 80, 90%, 95% or 98% identity therewith).

In one aspect, provided is a protein or polypeptide (e.g. a monospecific, bispecific, or multispecific antibody or protein, a scFv, a F(ab) or F(ab)$_2$, a multispecific Fc protein) that binds a human NKp46 polypeptide, optionally that further bind a non-human primate NKp46 polypeptide, wherein the protein nor polypeptide comprises: (a) a heavy chain variable region comprising a human heavy chain framework region (FR1, FR2, and FR3) derived from a IGHV1-46 and/or a IGHV1-69 gene (e.g. a mosaic variable region comprising both IGHV1-46 and IGHV1-69 sequences or segments), and heavy chain CDR1, 2 and 3 of a NKp46-4 antibody; and (b) a light chain variable region comprising a human light chain framework region (FR1, FR2, and FR3) derived from a IGKV1-NL1 gene, and light chain CDR1, 2 and 3 of a NKp46-4 antibody. Optionally, CDRs as defined by Kabat, Chotia or IMGT numbering. In one embodiment, the protein or polypeptide binds a wild-type NKp46 polypeptide but has decreased binding to a mutant NKp46 polypeptide having a mutation (e.g., an alanine substitution) any one or more of the residues R101, V102, E104 and/or L105 (with reference to SEQ ID NO:1) compared to binding to the wild-type NKp46). In one embodiment, the heavy chain variable region comprises an amino acid sequence sharing at least 70%, 80%, 90%, 95% or 98% identity with the amino acid sequence of SEQ ID NO: 9, and/or the light chain variable region comprises an amino acid sequence sharing at least 70%, 80%, 90%, 95% or 98% identity with the amino acid sequence of SEQ ID NO: 10. In one embodiment, the heavy chain variable region comprises an amino acid sequence of the NKp46-4 H1 variable domain (or an amino acid sequence sharing at least 80, 90%, 95% or 98% identity therewith) and the light chain variable region comprises an amino acid sequence of the NKp46-4 L2 variable domain (or an amino acid sequence sharing at least 80, 90%, 95% or 98% identity therewith).

In one aspect, provided is a protein or polypeptide (e.g. a monospecific, bispecific, or multispecific antibody or protein, a scFv, a F(ab) or F(ab)$_2$, a multispecific Fc protein) that binds a human NKp46 polypeptide, optionally that further bind a non-human primate NKp46 polypeptide, wherein the protein nor polypeptide comprises: (a) a heavy chain variable region comprising a human heavy chain framework region (FR1, FR2, FR3) derived from a IGHV4-30-4 gene, and heavy chain CDR1, 2 and 3 of a NKp46-9 antibody; and (b) a light chain variable region comprising a human light chain framework region (FR1, FR2, FR3) derived from a IGKV1-39 gene, and light chain CDR1, 2 and 3 of a NKp46-9 antibody. Optionally, CDRs as defined by Kabat, Chotia or IMGT numbering. In one embodiment, the heavy chain variable region comprises an amino acid sequence sharing at least 70%, 80%, 90%, 95% or 98% identity with the amino acid sequence of SEQ ID NO: 13, and/or the light chain variable region comprises an amino acid sequence sharing at least 70%, 80%, 90%, 95% or 98% identity with the amino acid sequence of SEQ ID NO: 14. In one embodiment, the heavy chain variable region comprises an amino acid sequence of the NKp46-9 H2 variable domain (or an amino acid sequence sharing at least 80, 90%, 95% or 98% identity therewith) and the light chain variable region comprises an amino acid sequence of the NKp46-9 L1 or L2 variable domain (or an amino acid sequence sharing at least 80, 90%, 95% or 98% identity therewith). In one embodiment, the heavy chain variable region comprises an amino acid sequence of the NKp46-9 H3 variable domain (or an amino acid sequence sharing at least 80, 90%, 95% or 98% identity therewith) and the light chain variable region comprises an amino acid sequence of the NKp46-9 L1 or L2 variable domain (or an amino acid sequence sharing at least 80, 90%, 95% or 98% identity therewith).

In one aspect, provided is an antigen binding domain comprising a heavy chain variable region (VH) and a light chain variable region (VL) each containing human FR1, 2 and 3 framework regions, or a protein or polypeptide comprising such ABD (e.g. a monoclonal antibody, an scFv, a multispecific polypeptide, a bispecific antibody, a DART® or BiTe® or protein comprising such, etc.) that binds a human and a non-human primate NKp46 polypeptide, e.g. a cell surface NKp46 polypeptide, wherein the protein or polypeptide comprises a VH and VL combination selected from the group consisting of:

(a) a VH comprising an amino acid sequence at least 70%, 80%, 90%, 95% or 98% (or 100%) identical to the amino acid sequence of the NKp46-1 H1 or H3 variable domain shown in SEQ ID NOS: 199 or 200, respectively, and a VL comprising an amino acid sequence at least 70%, 80%, 90%, 95% or 98% identical to the amino acid sequence of the NKp46-1 L1 variable domain shown in SEQ ID NO: 201;

(b) a VH comprising an amino acid sequence at least 70%, 80%, 90%, 95% or 98% (or 100%) identical to the amino acid sequence of the NKp46-2 H1, H2 or H3 variable domain shown in SEQ ID NOS: 202, 203 or 203, respectively, and a VL comprising an amino acid sequence at least 70%, 80%, 90%, 95% or 98% identical to the amino acid sequence of the NKp46-2 L1 variable domain shown in SEQ ID NO: 205;

(c) a VH comprising an amino acid sequence at least 70%, 80%, 90%, 95% or 98% (or 100%) identical to the amino acid sequence of the NKp46-3 H1, H3 or H4 variable domain shown in SEQ ID NOS: 206, 207 or 208, respectively, and a VL comprising an amino acid sequence at least 70%, 80%, 90%, 95% or 98% identical to the amino acid sequence of the NKp46-3 L1 variable domain shown in SEQ ID NO: 209;

(d) a VH comprising an amino acid sequence at least 70%, 80%, 90%, 95% or 98% (or 100%) identical to the amino acid sequence of the NKp46-4 H1, H2 or H3 variable domain shown in SEQ ID NOS: 210, 211 or 212, and a VL comprising an amino acid sequence at least 70%, 80%, 90%, 95% or 98% identical to the amino acid sequence of the NKp46-4 L2 variable domain shown in SEQ ID NO: 213;

(e) a VH comprising an amino acid sequence at least 70%, 80%, 90%, 95% or 98% (or 100%) identical to the amino acid sequence of the NKp46-9 H2 variable domain shown in SEQ ID NO: 215, and a VL comprising an amino acid sequence at least 70%, 80%, 90%, 95% or 98% identical to the amino acid sequence of the NKp46-9 L1 or L2 variable domain shown in SEQ ID NOS: 217 or 218, respectively; or (f) a VH comprising an amino acid sequence at least 70%, 80%, 90%, 95% or 98% (or 100%) identical to the amino acid sequence of the NKp46-9 H3 variable domain shown in SEQ ID NO: 215, and a VL comprising an amino acid sequence at least 70%, 80%, 90%, 95% or 98% identical to the amino acid sequence of the NKp46-9 L1 or L2 variable domain shown in SEQ ID NOS: 217 or 218, respectively.

In one aspect, provided is an antigen binding domain comprising a heavy chain variable region (VH) and a light chain variable region (VL) each containing human FR1, 2 and 3 framework regions, or a protein or polypeptide comprising such ABD that binds a human and a non-human primate NKp46 polypeptide, wherein the protein or polypeptide comprises a VH and VL combination selected from the group consisting of:

(a) a VH comprising a CDR1, 2 and 3 of the VH domain having the amino acid sequence shown in SEQ ID NO: 3 and a FR1, 2 and 3 of a human IGHV1-69 gene segment, and a VL comprising a CDR1, 2 and 3 of the VL domain having the amino acid sequence shown in SEQ ID NO: 4 and a FR1, 2 and 3 of a human IGKV1-33 gene segment;

(b) a VH comprising a CDR1, 2 and 3 of the VH domain having the amino acid sequence shown in SEQ ID NO: 5 and a FR1, 2 and 3 of a human IGHV4-30-4 gene segment, and a VL comprising a CDR1, 2 and 3 of the VL domain having the amino acid sequence shown in SEQ ID NO: 6 and a FR1, 2 and 3 of a human IGKV1-39 gene segment;

(c) a VH comprising a CDR1, 2 and 3 of the VH domain having the amino acid sequence shown in SEQ ID NO: 7 and a FR1, 2 and 3 of a human IGHV1-69 gene segment, and a VL comprising a CDR1, 2 and 3 of the VL domain having the amino acid sequence shown in SEQ ID NO: 8 and a FR1, 2 and 3 of a human IGKV3-11 and/or IGKV3-15 gene segment;

(d) a VH comprising a CDR1, 2 and 3 of the VH domain having the amino acid sequence shown in SEQ ID NO: 9 and a FR1, 2 and 3 of a human IGHV1-46 and/or a IGHV1-69 gene segment, and a VL comprising a CDR1, 2 and 3 of the VL domain having the amino acid sequence shown in SEQ ID NO: 10 and a FR1, 2 and 3 of a human IGKV1-NL1 gene segment;

(e) a VH comprising a CDR1, 2 and 3 of the VH domain having the amino acid sequence shown in SEQ ID NO: 13 and a FR1, 2 and 3 of a human IGHV4-30-4 gene segment, and a VL comprising a CDR1, 2 and 3 of the VL domain having the amino acid sequence shown in SEQ ID NO: 14 and a FR1, 2 and 3 of a human IGKV1-39 gene segment.

In any aspect, an antigen binding domain may comprise a VH and a VL comprising an amino acid sequence at least 80%, 90%, 95% or 98% (or 100%) identical to the respective VH and VL of any one of antibodies: NKp46-1 H1L1, NKp46-1 H3L1, NKp46-2 H1L1, NKp46-2 H2L1, NKp46-2 H3L1, NKp46-3 H1L1, NKp46-3 H3L1, NKp46-3 H4L1, NKp46-4 H1L2, NKp46-4 H2L2, NKp46-4 H3L2, NKp46-9 H2L1, NKp46-9 H2L2, NKp46-9 H3L1 or NKp46-9 H3L2.

In one aspect, provided is an antigen binding domain comprising a heavy chain variable region (VH) and a light chain variable region (VL) each containing human FR1, 2 and 3 framework regions, or a protein or polypeptide (e.g., an antibody, multispecific protein) comprising such ABD that binds a NKp46 polypeptide, wherein the protein or polypeptide comprising an amino acid sequence at least 80%, 90%, 95% or 98% (or 100%) identical to the respective VH and VL of any one of antibodies: NKp46-1 H1L1, NKp46-1 H3L1, NKp46-2 H1L1, NKp46-2 H2L1, NKp46-2 H3L1, NKp46-3 H1L1, NKp46-3 H3L1, NKp46-3 H4L1, NKp46-4 H1L2, NKp46-4 H2L2, NKp46-4 H3L2, NKp46-9 H2L1, NKp46-9 H2L2, NKp46-9 H3L1 or NKp46-9 H3L2. VH and VL sequences of these antibodies are listed in Table C and Example 1 part B.

In one embodiment, a NKp46-1 VL can comprising an amino acid substitution at Kabat position 87, optionally wherein the residue at position 87 is a phenylalanine. A NKp46-1 VH can comprise an amino acid substitution at Kabat residues 27, 66 and/or 67, optionally further a substitution at Kabat residues 37, 48 and/or 91. Optionally the residue present at the particular position is the residue substituted at the position herein, e.g., as shown in Example 1.

In one embodiment, a NKp46-2 VL can comprise an amino acid substitution at Kabat position 48, optionally wherein the residue at position 48 is a valine. A NKp46-2 VH can comprise an amino acid substitution at Kabat residues 27 and/or 71, optionally further a substitution at Kabat residues 48 and/or 67, optionally further a substitution at Kabat residue 31. Optionally the residue present at the particular position is the residue substituted at the position herein, e.g., as shown in Example 1.

In one embodiment, a NKp46-3 VL can comprise an amino acid substitution at Kabat position 49, optionally wherein the residue at position 49 is a lysine. A NKp46-3 VH can comprise an amino acid substitution at Kabat residue 27, optionally further a substitution at Kabat residues 48 and/or 67, optionally further a substitution at Kabat residue 69. Optionally the residue present at the particular position is the residue substituted at the position herein, e.g., as shown in Example 1.

In one embodiment, a NKp46-4 VL can comprise an amino acid substitution at Kabat position 36 and/or 48, optionally wherein the residue at position 36 is a phenylalanine, optionally wherein the residue at position 48 is a valine. A NKp46-4 VH can comprise an amino acid substitution at Kabat residues 30, 48 and/or 93, optionally further a substitution at Kabat residue 67, optionally further a substitution at Kabat residue 69. Optionally the residue present at the particular position is the residue substituted at the position herein, e.g., as shown in Example 1.

In one embodiment, a NKp46-9 VL can comprise an amino acid substitution at Kabat position 36, optionally wherein the residue at position 36 is a cysteine, optionally further a substitution at Kabat residue 48, optionally wherein the residue at position 48 is a valine. A NKp46-9 VH can comprise an amino acid substitution at Kabat residue 71, optionally further a substitution at Kabat residue 27, optionally further a substitution at Kabat residue 48 and/or 67.

Optionally the residue present at the particular position is the residue substituted at the position herein, e.g., as shown in Example 1.

In one aspect of any embodiment, the protein or polypeptide binds NKp46 in monovalent manner. In aspect of any embodiment, the protein or polypeptide comprises or contains no more than one antigen binding domain that binds NKp46.

In one embodiment, the protein or polypeptide comprises a human Fc domain or a portion thereof, wherein the Fc domain or portion thereof is capable of binding to human neonatal Fc receptor (FcRn) and to human CD16 polypeptide. Because FcγRIIIa (CD16) is not present on all NK cells, conventional therapeutic antibodies (e.g. of human isotypes IgG1) designed to exert antibody-dependent cellular toxicity (ADCC) via FcγRIIIa may not mobilize all NK cells; the present proteins on the other hand enable all NK cells to be solicited via NKp46, and the proteins will thus be useful to activate or increase the cytolytic activity of $NKp46^+CD16^-$ NK cells as well as $NKp46^+CD16^+$ NK cells.

In one embodiment, the protein or polypeptide comprises a human Fc domain or a portion thereof, wherein the Fc domain or a portion thereof is capable of binding to human neonatal Fc receptor (FcRn) and lacks binding to human CD16 polypeptide.

In one embodiment, the protein or polypeptide is a single chain polypeptide. In one embodiment, the protein or polypeptide is a multimeric polypeptide, optionally a dimeric, trimeric or tetrameric protein.

Advantageously, in one embodiment, the presence of NK cells and target cells, a multi-specific protein can bind (i) to antigen of interest on target cells and (ii) to NKp46 on NK cells, and, when bound to both antigen of interest on target cells and NKp46, can induce signaling in and/or activation of the NK cells through NKp46 (the protein acts as an NKp46 agonist), thereby promoting activation of NK cells and/or lysis of target cells, notably via the activating signal transmitted by NKp46. In specific advantageous embodiments, the multi-specific comprises a single antigen binding domain that binds NKp46 (the protein binds to NKp46 in monovalent fashion). In one embodiment the protein is capable of, when bound to both antigen of interest on target cells and NKp46 on NK cells, inducing signaling in the NK cells through NKp46. In one embodiment, the protein comprises a first antigen binding domain and a second antigen binding domain, wherein one of the first or second antigen binding domains binds to a human NKp46 polypeptide and the other of the first or second antigen binding domains binds an antigen of interest expressed on a target cell.

In one embodiment, a multispecific protein is monomeric. In one embodiment a multispecific protein is a dimer, e.g. a heterodimer, trimer or tetramer. In one embodiment, the protein is a heterodimer, heterotrimer or a tetramer comprising a first polypeptide chain comprising a VH and a VL domain of an ABD that binds NKp46 (a VH and VL disclosed herein) separated by a linker peptide, and optionally an Fc domain, and a second polypeptide chain comprising one or more variable regions or antigen binding domains that bind an antigen of interest, and optionally an Fc domain. In one embodiment, both a first and a second polypeptide chain comprise an Fc domain, and the protein comprises a dimeric Fc domain, optionally wherein the Fc domain is capable of binding to human CD16. In one embodiment, the monomeric or dimeric protein comprises a protein with a domain structure in which an Fc domain is interposed between the antigen binding domain (ABD) that binds to NKp46 and the antigen binding domain that binds an antigen of interest. In one embodiment the multispecific Fc-derived polypeptide is a bispecific antibody.

In one embodiment of any of the protein herein, the antigen binding domain of a multispecific protein that binds to an antigen of interest binds to an antigen (e.g. polypeptide) expressed by a target cell which sought to be lysed by an NK cell. Optionally such an antigen is expressed by a cancer cell, a tumor associated immune cell (e.g. an immune suppressor or regulatory cell), a virally infected cell, or a cell that contributes to an autoimmunity or inflammatory disease. Optionally, the antigen of interest is a cancer antigen known to be capable of undergoing intracellular internalization when contacted with a full length human IgG1 antibody that binds specifically thereto.

In one aspect of any of the embodiments herein, provided is a recombinant nucleic acid encoding a VH and/or a VL, an antibody heavy and/or light chain, a single chain antigen binding domain, a first, second, third or further polypeptide chain of any of the proteins of the disclosure. In one aspect of any of the embodiments herein, provided is a recombinant host cell comprising a nucleic acid of the disclosure.

Any of the methods can further be characterized as comprising any step described in the application, including notably in the "Detailed Description of the Invention"). The invention further relates to methods of identifying, testing and/or making proteins described herein. The invention further relates to a multispecific protein obtainable by any of present methods. The disclosure further relates to pharmaceutical or diagnostic formulations of the multispecific protein disclosed herein. The disclosure further relates to methods of using the multispecific protein in methods of treatment or diagnosis.

These and additional advantageous aspects and features of the invention may be further described elsewhere herein.

BRIEF DESCRIPTION OF THE FIGURES

FIG. 1 shows that Anti-CD19-F1-Anti-CD3 does not cause T/B cell aggregation in the presence of B221 (CD19) or JURKAT (CD3) cell lines when separate, but it does cause aggregation of cells when both B221 and JURKAT cells are co-incubated.

FIGS. 2A to 2F show different domain arrangements of bispecific proteins produced.

FIG. 4A (top panel CD107, bottom panel CD69) shows bispecific antibodies having NKp46 and CD19 binding regions in an F2 format protein do not activate resting NK cells in the absence of target cells, however full length anti-NKp46 antibodies as well as positive control alemtuzumab did activate NK cells. FIG. 4B shows that in presence of Daudi target cells, bispecific anti-NKp46×anti-CD19 antibodies (including each of the NKp46-1, NKp46-2, NKp46-3 or NKp46-4 binding domains) activated resting NK cells (top panel CD107, bottom panel CD69), while full-length anti-CD19 showed at best only very low activation of NK cells. Neither full-length anti-NKp46 antibodies or alemtuzumab showed substantial increase in activation beyond what was observed in presence of NK cells alone.

DETAILED DESCRIPTION OF THE INVENTION

Figure 2A:
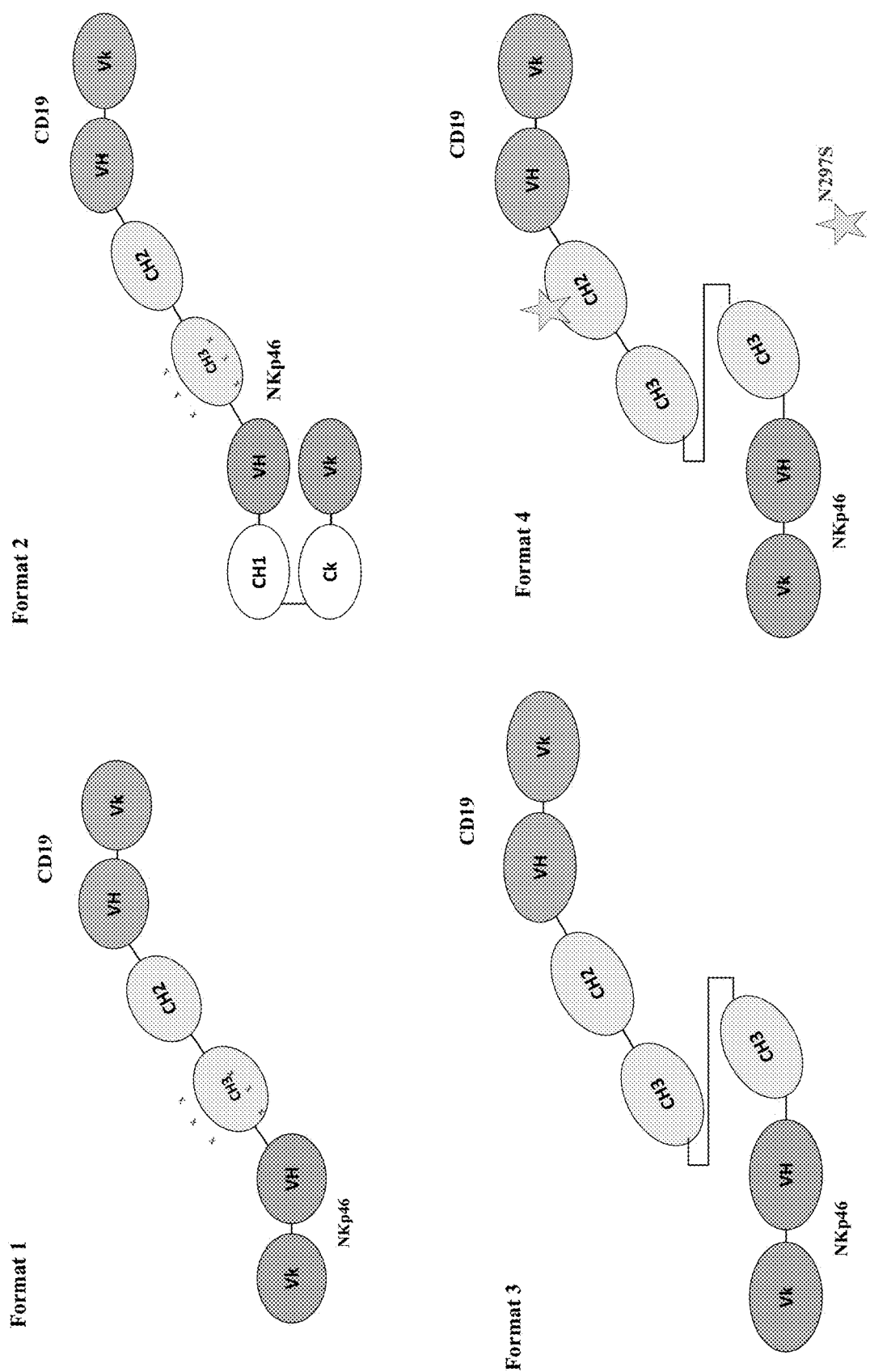

As used in the specification, "a" or "an" may mean one or more. As used in the claim(s), when used in conjunction with the word "comprising", the words "a" or "an" may mean one or more than one.

Where "comprising" is used, this can optionally be replaced by "consisting essentially of", more optionally by "consisting of".

As used herein, the term "antigen binding domain" refers to a domain comprising a three-dimensional structure capable of immunospecifically binding to an epitope. Thus, in one embodiment, said domain can comprise a hypervariable region, optionally a VH and/or VL domain of an antibody chain, optionally at least a VH domain. In another embodiment, the binding domain may comprise at least one complementarity determining region (CDR) of an antibody chain. In another embodiment, the binding domain may comprise a polypeptide domain from a non-immunoglobulin scaffold.

The term "antibody" herein is used in the broadest sense and specifically includes full-length monoclonal antibodies, polyclonal antibodies, multispecific antibodies (e.g., bispecific antibodies), and antibody fragments and derivatives, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988). An "antibody fragment" comprises a portion of a full-length antibody, e.g. antigen-binding or variable regions thereof. Examples of antibody fragments include Fab, Fab', F(ab)$_2$, F(ab)$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, e.g. comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

By "constant region" as defined herein is meant an antibody-derived constant region that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index (Kabat et al., 1991, Sequences of Proteins of Immunological Interest, 5th Ed., United States Public Health Service, National Institutes of Health, Bethesda). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "Fab" or "Fab region" as used herein is meant the polypeptide that comprises the VH, CH1, VL, and CL immunoglobulin domains. Fab may refer to this region in isolation, or this region in the context of a polypeptide, multispecific polypeptide or ABD, or any other embodiments as outlined herein.

By "single-chain Fv" or "scFv" as used herein are meant antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. Methods for producing scFvs are well known in the art. For a review of methods for producing scFvs see Pluckthun in The Pharmacology of Monoclonal Antibodies, vol. 113, Rosenburg and Moore eds. Springer-Verlag, New York, pp. 269-315 (1994).

By "Fv" or "Fv fragment" or "Fv region" as used herein is meant a polypeptide that comprises the VL and VH domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 (CH2) and Cγ3 (CH3) and the hinge between Cγ1 and Cγ2. Although the boundaries of the Fc region may vary, the human IgG heavy chain Fc region is usually defined to comprise residues at least C226, P230 or A231 to its carboxyl-terminus, wherein the numbering is according to the EU index. Fc may refer to this region in isolation, or this region in the context of an Fc polypeptide, as described below. By "Fc polypeptide" or "Fc-derived polypeptide" as used herein is meant a polypeptide that comprises all or part of an Fc region. Fc polypeptides include but is not limited to antibodies, Fc fusions and Fc fragments.

By "variable region" as used herein is meant the region of an antibody that comprises one or more Ig domains substantially encoded by any of the VL (including Vkappa (VK) and Vlambda) and/or VH genes that make up the light chain (including kappa and lambda) and heavy chain immunoglobulin genetic loci respectively. A light or heavy chain variable region (VL or VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

The term "specifically binds to" means that an antibody or polypeptide can bind preferably in a competitive binding assay to the binding partner, e.g. NKp46, as assessed using either recombinant forms of the proteins, epitopes therein, or native proteins present on the surface of isolated target cells. Competitive binding assays and other methods for determining specific binding are further described below and are well known in the art.

When an antibody or polypeptide is said to "compete with" a particular monoclonal antibody (e.g. NKp46-1, -2, -4, -6 or -9 in the context of an anti-NKp46 mono- or bi-specific antibody), it means that the antibody or polypeptide competes with the monoclonal antibody in a binding assay using either recombinant target (e.g. NKp46) molecules or surface expressed target (e.g. NKp46) molecules. For example, if a test antibody reduces the binding of NKp46-1, -2, -4, -6 or -9 to a NKp46 polypeptide or NKp46-expressing cell in a binding assay, the antibody is said to "compete" respectively with NKp46-1, -2, -4, -6 or -9.

The term "affinity", as used herein, means the strength of the binding of an antibody or polypeptide to an epitope. The affinity of an antibody is given by the dissociation constant $K_D$, defined as $[Ab] \times [Ag]/[Ab-Ag]$, where $[Ab-Ag]$ is the molar concentration of the antibody-antigen complex, $[Ab]$ is the molar concentration of the unbound antibody and $[Ag]$ is the molar concentration of the unbound antigen. The affinity constant $K_A$ is defined by $1/K_D$. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of surface plasmon resonance (SPR) screening (such as by analysis with a BIAcore™ SPR analytical device).

Within the context of this invention a "determinant" designates a site of interaction or binding on a polypeptide.

The term "epitope" refers to an antigenic determinant, and is the area or region on an antigen to which an antibody or polypeptide binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

By "amino acid modification" herein is meant an amino acid substitution, insertion, and/or deletion in a polypeptide sequence. An example of amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of a polypeptide will exhibit 98%, 98%, or 99% homogeneity for polypeptides in the context of all present peptide species in the composition or at least with respect to substantially active peptide species in the context of proposed use.

In the context herein, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

As used herein, "NK cells" refers to a sub-population of lymphocytes that is involved in non-conventional immunity. NK cells can be identified by virtue of certain characteristics and biological properties, such as the expression of specific surface antigens including CD56 and/or NKp46 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art. Any subpopulation of NK cells will also be encompassed by the term NK cells. Within the context herein "active" NK cells designate biologically active NK cells, including NK cells having the capacity of lysing target cells or enhancing the immune function of other cells. NK cells can be obtained by various techniques known in the art, such as isolation from blood samples, cytapheresis, tissue or cell collections, etc. Useful protocols for assays involving NK cells can be found in Natural Killer Cells Protocols (edited by Campbell K S and Colonna M). Human Press. pp. 219-238 (2000).

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" comprises events wherein intracellular internalization is initiated and/or the rate and/or extent of intracellular internalization is increased.

As used herein, an agent that has "agonist" activity at Nkp46 is an agent that can cause or increase "NKp46 signaling". "Nkp46 signaling" refers to an ability of a NKp46 polypeptide to activate or transduce an intracellular signaling pathway. Changes in NKp46 signaling activity can be measured, for example, by assays designed to measure changes in NKp46 signaling pathways, e.g. by monitoring phosphorylation of signal transduction components, assays to measure the association of certain signal transduction components with other proteins or intracellular structures, or in the biochemical activity of components such as kinases, or assays designed to measure expression of reporter genes under control of NKp46-sensitive promoters and enhancers, or indirectly by a downstream effect mediated by the NKp46 polypeptide (e.g. activation of specific cytolytic machinery in NK cells). Reporter genes can be naturally occurring genes (e.g. monitoring cytokine production) or they can be genes artificially introduced into a cell. Other genes can be placed under the control of such regulatory elements and thus serve to report the level of NKp46 signaling.

"NKp46" refers to a protein or polypeptide encoded by the Ncr1 gene or by a cDNA prepared from such a gene. Any naturally occurring isoform, allele or variant is encompassed by the term NKp46 polypeptide (e.g., an NKp46 polypeptide 90%, 95%, 98% or 99% identical to SEQ ID NO 1, or a contiguous sequence of at least 20, 30, 50, 100 or 200 amino acid residues thereof). The 304 amino acid residue sequence of human NKp46 (isoform a) is shown as follows:

```
                                          (SEQ ID NO: 1)
MSSTLPALLC VGLCLSQRIS AQQQTLPKPF IWAEPHFMVP

KEKQVTICCQ GNYGAVEYQL HFEGSLFAVD RPKPPERINK

VKFYIPDMNS RMAGQYSCIY RVGELWSEPS NLLDLVVTEM

YDTPTLSVHP GPEVISGEKV TFYCRLDTAT SMFLLLKEGR

SSHVQRGYGK VQAEFPLGPV TTAHRGTYRC FGSYNNHAWS

FPSEPVKLLV TGDIENTSLA PEDPTFPADT WGTYLLTTET

GLQKDHALWD HTAQNLLRMG LAFLVLVALV WFLVEDWLSR

KRTRERASRA STWEGRRRLN TQTL.
```

SEQ ID NO: 1 corresponds to NCBI accession number NP_004820, the disclosure of which is incorporated herein by reference. The human NKp46 mRNA sequence is described in NCBI accession number NM_004829, the disclosure of which is incorporated herein by reference. The amino acid residue sequence of the extracellular domain of the *Macaca fascicularis* (cynomolgus) NKp46 polypeptide is shown as follows:

```
MSSTLRALLCLGLCLSQRISAPKQTLPKPIIRAESTYMVPKEKQA

TLCCQGSYGAVEYQLHFEGSLFAVERPKPPERINGVKFHIPDMNSRKAGR

YSCIYRVGELWSERSDLLDLVVTEMYDTPTLSVHPGPEVTSGEKVTFYCR

LDTATSMFLLLKEGRSRDVQRSYGKVQAEFPMGPVTTAHRGSYRCFGSYN

NYAWSFPSEPVKLLVTGDIENTSLAPTDPTFPDSWDTCLLTRETGLQKDL

ALWDHTAQN.
```

Producing Anti-NKp46 Antibodies

The anti-NKp46 antigen binding domains bind an extracellular portion of human NKp46 polypeptide. In one aspect, the protein that comprises a VH and VL of the disclosure is a humanized antibody or comprises an antigen binding fragment thereof. In one aspect, the antibody comprises a constant domain selected from a human IgG1, IgG2, IgG3 and IgG4 constant domain, optionally comprising one or more amino acid modifications. In one aspect, anti-NKp46 antibody comprises an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect, the anti-NKp46 antibody comprises a synthetic or semisynthetic antibody-derived molecule selected from a scFV, a dsFV, a minibody, a diabody, a triabody, a kappa body, an IgNAR; and a multispecific antibody. The agent can optionally further comprise an Fc domain. In one aspect, the antibody is in at least partially purified form. In one aspect, the antibody is in essentially isolated form.

Antibodies may be produced by a variety of techniques known in the art. Immunological screening assays in which antibody competition can be assessed can be used to select for antibodies that will bind the same epitope on NKp46 as antigen binding domains herein can be assessed, e.g. as described in for example, in PCT application number PCT/EP2016/064537, filed 23 Jun. 2016 (Innate Pharma), the disclosure of which is incorporated herein by reference.

Typically, an anti-NKp46 antibody or NKp46 binding protein provided herein has an affinity for a NKp46 polypeptide (e.g., a NKp46 polypeptide as produced in the Examples herein) in the range of about $10^4$ to about $10^{11}$ $M^{-1}$ (e.g., about $10^8$ to about $10^{10}$ $M^{-1}$). For example, in a particular aspect the disclosure provides Anti-NKp46 antibody or NKp46 binding protein that has an average disassociation constant ($K_D$) of less than $1\times10^{-9}$ M with respect to NKp46, as determined by, e.g., surface plasmon resonance (SPR) screening (such as by analysis with a BIAcore™ SPR analytical device). In a more particular exemplary aspect, the disclosure provides anti-NKp46 antibodies or NKp46 binding proteins that have a KD of about $1\times10^{-8}$ M to about $1\times10^{-10}$ M, or about $1\times10^{-9}$ M to about $1\times10^{-11}$ M, for human or cynomolgus NKp46 protein. In one embodiment, the NKp46 antibodies or NKp46 binding proteins have a disassociation constant ($K_D$) for human and cynomolgus NKp46 protein that differs by no more than 1- or 2-log.

Antibodies or NKp46 binding proteins can be characterized for example by a mean KD of no more than about (i.e. better affinity than) 100, 60, 10, 5, or 1 nanomolar, preferably sub-nanomolar or optionally no more than about 500, 200, 100 or 10 picomolar. KD can be determined for example for example by immobilizing recombinantly produced human NKp46 proteins on a chip surface, followed by application of the antibody to be tested in solution.

DNA encoding an antibody or other NKp46 binding proteins that binds an epitope present on NKp46 polypeptides is isolated and placed in an appropriate expression vector for transfection into an appropriate host. The host is then used for the recombinant production of the antibody or other NKp46 binding proteins. For example, DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired proteins in the recombinant host cells.

In one embodiment, the proteins and antibodies herein bind the D1 domain of NKp46, the D2 domain of NKp46, or to a region spanning both the D1 and D2 domains (at the border of the D1 and D2 domains, the D1/D2 junction), of the NKp46 polypeptide of SEQ ID NO: 1. In one embodiment, the proteins or antibodies have an affinity for human NKp46 characterized by a $K_D$ of less than $10^{-8}$ M, less than $10^{-9}$ M, or less than $10^{-19}$ M.

In another embodiment, the proteins or antibodies bind NKp46 at substantially the same epitope on NKp46 as antibody NKp46-1, NKp46-2, NKp46-3 or NKp46-4. In another embodiment, the antibodies at least partially overlaps, or includes at least one residue in the segment bound by NKp46-1, NKp46-2, NKp46-3 or NKp46-4. In one embodiment, all key residues of the epitope are in a segment corresponding to domain D1 or D2. In one embodiment, the antibody binds a residue present in the D1 domain as well as a residue present in in the D2 domain. In one embodiment, the antibodies or proteins bind an epitope comprising 1, 2, 3, 4, 5, 6, 7 or more residues in the segment corresponding to domain D1 or D2 of the NKp46 polypeptide of SEQ ID NO: 1. In one embodiment, the antibodies or proteins bind domain D1 and bind an epitope comprising 1, 2, 3, or 4 of the residues R101, V102, E104 and/or L105. In one embodiment, the antibodies or proteins bind domain D1/D2 junction and bind an epitope comprising 1, 2, 3, 4 or 5 of the residues K41, E42, E119, Y121 and/or Y194. In one embodiment, the antibodies bind domain D2 and bind an epitope comprising 1, 2, 3, or 4 of the residues P132, E133, 1135, and/or S136.

The Examples section herein describes the construction of a series of mutant human NKp46 polypeptides. Binding of anti-NKp46 antibody or proteins to cells transfected with the NKp46 mutants was measured and compared to the ability of anti-NKp46 antibody or protein to bind wild-type NKp46 polypeptide (SEQ ID NO:1). A reduction in binding between an anti-NKp46 antibody or protein and a mutant NKp46 polypeptide as used herein means that there is a reduction in binding affinity (e.g., as measured by known methods such FACS testing of cells expressing a particular mutant, or by Biacore testing of binding to mutant polypeptides) and/or a reduction in the total binding capacity of the anti-NKp46 antibody or protein (e.g., as evidenced by a decrease in Bmax in a plot of anti-NKp46 antibody concentration versus polypeptide concentration). A significant reduction in binding indicates that the mutated residue is directly involved in binding to the anti-NKp46 antibody or protein or is in close proximity to the binding protein when the anti-NKp46 antibody or protein is bound to NKp46. An epitope will thus preferably include such residue and may include additional residues adjacent to such residue.

In some embodiments, a significant reduction in binding means that the binding affinity and/or capacity between an anti-NKp46 antibody or protein and a mutant NKp46 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody or protein and a wild type NKp46 polypeptide (e.g., the polypeptide shown in SEQ ID NO:1). In certain embodiments, binding is reduced below detectable limits. In some embodiments, a significant reduction in binding is evidenced when binding of an anti-NKp46 antibody to a mutant NKp46 polypeptide is less than 50% (e.g., less than 45%, 40%, 35%, 30%, 25%, 20%, 15% or 10%) of the binding observed between the anti-NKp46 antibody and a wild-type NKp46 polypeptide (e.g., the polypeptide shown in SEQ ID NO: 1 (or the extracellular domain thereof)). Such binding measurements can be made using a variety of binding assays known in the art. A specific example of one such assay is described in the Example section.

In some embodiments, anti-NKp46 antibodies or proteins are provided that exhibit significantly lower binding for a mutant NKp46 polypeptide in which a residue in a wild-type NKp46 polypeptide (e.g., SEQ ID NO:1) is substituted. In the shorthand notation used here, the format is: Wild type residue: Position in polypeptide: Mutant residue, with the numbering of the residues as indicated in SEQ ID NO: 1.

In some embodiments, an anti-NKp46 antibody or protein binds a wild-type NKp46 polypeptide but has decreased binding to a mutant NKp46 polypeptide having a mutation (e.g., an alanine substitution) any one or more of the residues R101, V102, E104 and/or L105 (with reference to SEQ ID NO:1) compared to binding to the wild-type NKp46).

In some embodiments, an anti-NKp46 antibody or protein binds a wild-type NKp46 polypeptide but has decreased binding to a mutant NKp46 polypeptide having a mutation (e.g., an alanine substitution) any one or more of the residues K41, E42, E119, Y121 and/or Y194 (with reference to SEQ ID NO:1) compared to binding to the wild-type NKp46).

In some embodiments, an anti-NKp46 antibody or protein binds a wild-type NKp46 polypeptide but has decreased binding to a mutant NKp46 polypeptide having a mutation (e.g., an alanine substitution) any one or more of the residues P132, E133, 1135, and/or S136 (with reference to SEQ ID NO:1) compared to binding to the wild-type NKp46).

The amino acid sequence of the heavy and light chain variable region of parental antibodies NKp46-1, NKp46-2, NKp46-3 and NKp46-4 are listed herein in Table B. Amino acid sequence of the heavy and light chain variable region of humanized antibodies NKp46-1, NKp46-2, NKp46-3, NKp46-4 and NKp46-9 that displayed high binding affinity for both human and non-human primate NKp46 are listed herein in Table C.

A heavy chain variable region of a NKp46-1, NKp46-2, NKp46-3, NKp-46-4, NKp46-6 or NKp46-9 antibody may comprise, for the respective antibody: a human heavy chain FR1 framework region; a HCDR1 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a human heavy chain FR2 framework region; a HCDR2 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a human heavy chain FR3 framework region; and a HCDR3 region comprising an amino acid sequence as set forth in as set forth in Table A, or a sequence of at least 4, 5, 6, 7, 8, 9 or 10 contiguous amino acids thereof, wherein one or more of these amino acids may be substituted by a different amino acid. Optionally, the variable region further comprises a human heavy chain FR4 framework region.

A light chain variable region of a NKp46-1, NKp46-2, NKp46-3, NKp-46-4, NKp46-6 or NKp46-9 antibody may comprise, for the respective antibody: a human light chain FR1 framework region; a LCDR1 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a human light chain FR2 framework region; a LCDR2 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a human light chain FR3 framework region; and a LCDR3 region comprising an amino acid sequence as set forth in Table A, or a sequence of at least 4, 5, 6, 7, 8, 9 or 10 contiguous amino acids thereof, wherein one or more of these amino acids may be deleted or substituted by a different amino acid. Optionally, the variable region further comprises a human light chain FR4 framework region.

Examples of VH and VL combinations include:
(a) a VH comprising a CDR1, 2 and 3 of SEQ ID NO: 3 and a FR1, 2 and 3 of a human IGHV1-69 gene segment, and a VL comprising a CDR1, 2 and 3 of SEQ ID NO: 4 and a FR1, 2 and 3 of a human IGKV1-33 gene segment;
(b) a VH comprising a CDR1, 2 and 3 of SEQ ID NO: 5 and a FR1, 2 and 3 of a human IGHV4-30-4 gene segment, and a VL comprising a CDR1, 2 and 3 of SEQ ID NO: 6 and a FR1, 2 and 3 of a human IGKV1-39 gene segment;
(c) a VH comprising a CDR1, 2 and 3 of SEQ ID NO: 7 and a FR1, 2 and 3 of a human IGHV1-69 gene segment, and a VL comprising a CDR1, 2 and 3 of SEQ ID NO: 8 and a FR1, 2 and 3 of a human IGKV3-11 and/or IGKV3-15 gene segment;
(d) a VH comprising a CDR1, 2 and 3 of SEQ ID NO: 9 and a FR1, 2 and 3 of a human IGHV1-46 and/or a IGHV1-69 gene segment, and a VL comprising a CDR1, 2 and 3 of SEQ ID NO: 10 and a FR1, 2 and 3 of a human IGKV1-NL1 gene segment; or
(e) a VH comprising a CDR1, 2 and 3 of SEQ ID NO: 13 and a FR1, 2 and 3 of a human IGHV4-30-4 gene segment, and a VL comprising a CDR1, 2 and 3 of SEQ ID NO: 14 and a FR1, 2 and 3 of a human IGKV1-39 gene segment.

In another aspect, examples of VH and VL combinations include:
(a) a VH comprising an amino acid sequence at least 70%, 80%, 90%, 95% or 98% identical to the amino acid sequence of the NKp46-1 H1 or H3 variable domain, and a VL comprising an amino acid sequence at least 70%, 80%, 90%, 95% or 98% identical to the amino acid sequence of the NKp46-1 L1 variable domain;
(b) a VH comprising an amino acid sequence at least 70%, 80%, 90%, 95% or 98% identical to the amino acid sequence of the NKp46-2 H1, H2 or H3 variable domain, and a VL comprising an amino acid sequence at least 70%, 80%, 90%, 95% or 98% identical to the amino acid sequence of the NKp46-2 L1 variable domain;
(c) a VH comprising an amino acid sequence at least 70%, 80%, 90%, 95% or 98% identical to the amino acid sequence of the NKp46-3 H1, H3 or H4 variable domain, and a VL comprising an amino acid sequence at least 70%, 80%, 90%, 95% or 98% identical to the amino acid sequence of the NKp46-3 L1 variable domain;
(d) a VH comprising an amino acid sequence at least 70%, 80%, 90%, 95% or 98% identical to the amino acid sequence of the NKp46-4 H1 variable domain, and a VL comprising an amino acid sequence at least 70%, 80%, 90%, 95% or 98% identical to the amino acid sequence of the NKp46-4 L2 variable domain;
(e) a VH comprising an amino acid sequence at least 70%, 80%, 90%, 95% or 98% identical to the amino acid sequence of the NKp46-9 H2 variable domain, and a VL comprising an amino acid sequence at least 70%, 80%, 90%, 95% or 98% identical to the amino acid sequence of the NKp46-9 L1 or L2 variable domain; or
(f) a VH comprising an amino acid sequence at least 70%, 80%, 90%, 95% or 98% identical to the amino acid sequence of the NKp46-9 H3 variable domain, and a VL comprising an amino acid sequence at least 70%, 80%, 90%, 95% or 98% identical to the amino acid sequence of the NKp46-9 L1 or L2 variable domain.

In one embodiment, the aforementioned CDRs are according to Kabat, e.g. as shown in Table A. In one embodiment, the aforementioned CDRs are according to Chotia numbering, e.g. as shown in Table A. In one embodiment, the aforementioned CDRs are according to IMGT numbering, e.g. as shown in Table A.

In one embodiment, the particular VH or VL comprises an amino acid substitution in a human framework (e.g. a back-mutation) at a Kabat position shown in Example 1; optionally the amino acid residue substituted in Example 1 at the corresponding Kabat position can be specified as being present at the particular position.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO or Table A.

The sequences of the CDRs, according to IMGT, Kabat and Chothia definitions systems, have been summarized in Table A below. The sequences of the variable chains of the antibodies according to the invention are listed in Table B below. In any embodiment herein, a VL or VH sequence can be specified or numbered so as to contain or lack a signal peptide or any part thereof.

TABLE A

| mAb | CDR definition | HCDR1 SEQ ID | Sequence | HCDR2 SEQ ID | Sequence | HCDR3 SEQ ID | Sequence |
|---|---|---|---|---|---|---|---|
| NKp46-1 | Kabat | 15 | DYVIN | 18 | EIYPGSGTNYYNEKFKA | 21 | RGRYGLYAMDY |
| | Chotia | 16 | GYTFTDY | 19 | PGSG | 22 | GRYGLYAMD |
| | IMGT | 17 | GYTFTDYV | 20 | GYTFTDYVIYPGSGTN | 23 | ARRGRYGLYAMDY |
| NKp46-2 | Kabat | 31 | SDYAWN | 34 | YITYSGSTSYNPSLES | 36 | GGYYGSSWGVFAY |
| | Chotia | 32 | GYSITSDY | | YSG | 37 | GYYGSSWGVFA |
| | IMGT | 33 | GYSITSDYA | 35 | ITYSGST | 38 | ARGGYYGSSWGVFAY |
| NKp46-3 | Kabat | 46 | EYTMH | 49 | GISPNIGGTSYNQKFKG | 51 | RGGSFDY |
| | Chotia | 47 | GYTFTEY | | PNIG | 52 | GGSFD |
| | IMGT | 48 | GYTFTEYT | 50 | ISPNIGGT | 53 | ARRGGSFDY |

TABLE A-continued

| mAb | CDR definition | SEQ ID | Sequence | SEQ ID | Sequence | SEQ ID | Sequence |
|---|---|---|---|---|---|---|---|
| NKp46-4 | Kabat | 60 | SFTMH | 63 | YINPSSGYTEYNQKFKD | 65 | GSSRGFDY |
|  | Chotia | 61 | GYTFTSF |  | PSSG | 66 | SSRGFD |
|  | IMGT | 62 | GYTFTSFT | 64 | INPSSGYT | 67 | VRGSSRGFDY |
| NKp46-6 | Kabat | 73 | SSWMH | 76 | HIHPNSGISNYNEKFKG | 78 | GGRFDD |
|  | Chotia | 74 | GYTFTSS |  | PNSG |  | GRFD |
|  | IMGT | 75 | GYTFTSSW | 77 | IHPNSGIS | 79 | ARGGRFDD |
| NKp46-9 | Kabat | 85 | SDYAWN | 88 | YITYSGSTNYNPSLKS | 89 | CWDYALYAMDC |
|  | Chotia | 86 | GYSITSDY |  | YSG | 90 | WDYALYAMD |
|  | IMGT | 87 | GYSITSDYA | 35 | ITYSGST | 91 | ARCWDYALYAMDC |
| Bab281 | Kabat | 97 | NYGMN | 100 | WINTNTGEPTYAEEFKG | 102 | DYLYYFDY |
|  | Chotia | 98 | GYTFTNY |  | TNTG | 103 | YLYYFD |
|  | IMGT | 99 | GYTFTNYG | 101 | INTNTGEP | 104 | ARDYLYYFDY |

| mAb | CDR definition | LCDR1 SEQ ID | Sequence | LCDR2 SEQ ID | Sequence | LCDR3 SEQ ID | Sequence |
|---|---|---|---|---|---|---|---|
| NKp46-1 | Kabat | 24 | RASQDISNYLN | 27 | YTSRLHS | 28 | QQGNTRPWT |
|  | Chotia | 25 | SQDISNY |  | YTS | 29 | YTSGNTRPW |
|  | IMGT | 26 | QDISNY |  | YTS | 30 | YTSQQGNTRPWT |
| NKp46-2 | Kabat | 39 | RVSENIYSYLA | 42 | NAKTLAE | 43 | QHHYGTPWT |
|  | Chotia | 40 | SENIYSY |  | NAK | 44 | HYGTPW |
|  | IMGT | 41 | ENIYSY |  | NAK | 45 | QHHYGTPWT |
| NKp46-3 | Kabat | 54 | RASQSISDYLH | 57 | YASQSIS | 58 | QNGHSFPLT |
|  | Chotia | 55 | SQSISDY |  | YAS | 59 | GHSFPL |
|  | IMGT | 56 | QSISDY |  | YAS |  | QNGHSFPLT |
| NKp46-4 | Kabat | 68 | RASENIYSNLA | 70 | AATNLAD | 71 | QHFWGTPRT |
|  | Chotia |  | SENIYSN |  | AAT | 72 | FWGTPR |
|  | IMGT | 69 | ENIYSN |  | AAT |  | QHFWGTPRT |
| NKp46-6 | Kabat | 80 | RASQSISDYLH |  | YASQSIS | 82 | QNGHSFLMYT |
|  | Chotia | 81 | GRFDSQSISDY |  | YAS | 83 | GHSFLMY |
|  | IMGT |  | QSISDY |  | YAS | 84 | YASQNGHSFLMYT |
| NKp46-9 | Kabat | 92 | RTSENIYSYLA | 93 | NAKTLAE | 94 | QHHYDTPLT |
|  | Chotia |  | SENIYSY |  | NAK | 95 | NAKHYDTPL |
|  | IMGT |  | ENIYSY |  | NAK | 96 | QHHYDTPLT |
| Bab281 | Kabat | 105 | KASENVVTYVS | 108 | GASNRYT | 109 | GQGYSYPYT |
|  | Chotia | 106 | SENVVTY |  | GAS | 110 | GYSYPY |
|  | IMGT | 107 | ENVVTY |  | GAS | 111 | GQGYSYPYT |

TABLE B

| Antibody | SEQ ID NO | Amino acid sequence |
|---|---|---|
| NKp46-1 VH | 3 | QVQLQQSGPELVKPGASVKMSCKASGYTFTDYVINWKQRSGQGLEWIGEIYPGSGTNYYNEKFKAKATLTADKSSNIAYMQLSSLTSEDSAVYFCARRGRYGLYAMDYWGQGTSVTVSS |
| NKp46-1 VL | 4 | DIQMTQTTSSLSASLGDRVTISCRASQDISNYLNWYQQKPDGTVKLLIYYTSRLHSGVPSRFSGSGSGTDYSLTINNLEQEDIATYFCQQGNTRPWTFGGGTKLEIK |
| NKp46-2 VH | 5 | EVQLQESGPGLVKPSQSLSLTCTVTGYSITSDYAWNWIRQFPGNKLEWMGYITYSGSTSYNPSLESRISITRDTSTNQFFLQLNSVTTEDTATYYCARGGYYGSSWGVFAYWGQGTLVTVSA |
| NKp46-2 VL | 6 | DIQMTQSPASLSASVGETVTITCRVSENIYSYLAWYQQKQGKSPQLLVYNAKTLAEGVPSRESGSGSGTQFSLKINSLQPEDFGSYYCQHHYGTPWTFGGGTKLEIK |
| NKp46-3 VH | 7 | EVQLQQSGPELVKPGASVKISCKTSGYTFTEYTMHWVKQSHGKSLEWIGGISPNIGGTSYNQKFKGKATLTVDKSSSTAYMELRSLTSEDSAVYYCARRGGSFDYWGQGTTLTVSS |
| NKp46-3 VL | 8 | DIVMTQSPATLSVTPGDRVSLSCRASQSISDYLHWYQQKSHESPRLLIKYASQSISGIPSRFSGSGSGSDFTLSINSVEPEDVGVYYCQNGHSFPLTFGAGTKLELK |

TABLE B-continued

| Antibody | SEQ ID NO | Amino acid sequence |
|---|---|---|
| NKp46-4 VH | 9 | QVQLQQSAVELARPGASVKMSCKASGYTFTSFTMHWVKQRPGQGLEWIGYI NPSSGYTEYNQKFKDKTTLTADKSSSTAYMQLDSLTSDDSAVYYCVRGSSR GFDYWGQGTLVTVSA |
| NKp46-4 VL | 10 | DIQMIQSPASLSVSVGETVTITCRASENIYSNLAWFQQKQGKSPQLLVYAA TNLADGVPSRFSGSGSGTQYSLKINSLQSEDFGIYYCQHEWGTPRTFGGGT KLEIK |
| NKp46-6 VH | 11 | QVQLQQPGSVLVRPGASVKLSCKASGYTFTSSWMHWAKQRPGQGLEWIGHI HPNSGISNYNEKFKGKATLTVDTSSSTAYVDLSSLTSEDSAVYYCARGGRF DDWGAGTTVTVSS |
| NKp46-6 VL | 12 | DIVMTQSPATLSVTPGDRVSLSCRASQSISDYLHWYQQKSHESPRLLIKYA SQSISGIPSRESGSGSGSDFTLSINSVEPEDVGVYYCQNGHSFLMYTFGGG TKLEIK |
| NKp46-9 VH | 13 | DVQLQESGPGLVKPSQSLSLTCTVTGYSITSDYAWNWIRQFPGNKLEWMGY ITYSGSTNYNPSLKSRISITRDTSKNQFFLQLNSVTTEDTATYYCARCWDY ALYAMDCWGQGTSVTVSS |
| NKp46-9 VL | 14 | DIQMTQSPASLSASVGETVTITCRTSENIYSYLAWCQQKQGKSPQLLVYNA KTLAEGVPSRESGSGSGTHFSLKINSLQPEDFGIYYCQHHYDTPLTFGAGT KLELK |

TABLE C

| Antibody | VH (SEQ ID NO) | VL (SEQ ID NO) |
|---|---|---|
| NKp46-1 H1L1 | 199 | 201 |
| NKp46-1 H3L1 | 200 | 201 |
| NKp46-2 H1L1 | 202 | 205 |
| NKp46-2 H2L1 | 203 | 205 |
| NKp46-2 H3L1 | 204 | 205 |
| NKp46-3 H1L1 | 206 | 209 |
| NKp46-3 H3L1 | 207 | 209 |
| NKp46-3 H4L1 | 208 | 209 |
| NKp46-4 H1L2 | 210 | 213 |
| NKp46-4 H2L2 | 211 | 213 |
| NKp46-4 H3L2 | 212 | 213 |
| NKp46-9 H2L1 | 215 | 217 |
| NKp46-9 H2L2 | 215 | 218 |
| NKp46-9 H3L1 | 216 | 217 |
| NKp46-9 H3L2 | 216 | 218 |

Multi-Specific Antibodies and Polypeptides

Antigen binding domains (ABDs) that bind NKp46 can be derived from the anti-NKp46 CDR, VH and VL sequences provided herein (see section "Anti-NKp46 variable domains"). The antigen binding domains can be arranged one the same or on separate polypeptides, such that they form an antigen binding domain capable of binding NKp46 (e.g. human NKp46 as expressed at the surface of a cell). The ABDs can be produced, for example, as an scFv, a tandem scFv, a Bite, a DART, a Fab, a F(ab)$_2$, an antibody, a bispecific antibody, or a monomeric or multimeric Fc protein.

For the construction of multi-specific proteins (e.g. antibodies, tandem scFv, BiTe, DART, Fc proteins), antigen binding domains that bind an antigen of interest (other than NKp46) can be readily derived a variety of immunoglobulin or non-immunoglobulin scaffolds, for example affibodies based on the Z-domain of staphylococcal protein A, engineered Kunitz domains, monobodies or adnectins based on the 10th extracellular domain of human fibronectin Ill, anticalins derived from lipocalins, DARPins (designed ankyrin repeat domains, multimerized LDLR-A module, avimers or cysteine-rich knottin peptides. See, e.g., Gebauer and Skerra (2009) Current Opinion in Chemical Biology 13:245-255, the disclosure of which is incorporated herein by reference.

Variable domains that bind an antigen of interest (other than NKp46) can be derived from an antibody, for example in the form of associated VL and VH domains found on two polypeptide chains, or single chain antigen binding domains such as scFv, a $V_H$ domain, a $V_L$ domain, a dAb, a V-NAR domain or a $V_H$H domain. The an antigen binding domain (e.g, $ABD_1$ and $ABD_2$) can also be readily derived from antibodies as a Fab.

Typically, antibodies are initially obtained by immunization of a non-human animal, e.g., a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, N.Y. (1988), the entire disclosure of which is herein incorporated by reference).

Antigen binding domains (ABDs) that bind antigens of interest (other than NKp46) for use in a multispecific polypeptide can be selected based on the desired cellular target, and may include for example cancer antigens, bacterial or viral antigens, etc. As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. In some embodiments the bacterial antigen is derived from a bacterium selected from the group consisting of *Helicobacter* species, in particular *Helicobacter pyloris; Borelia* species, in particular *Borelia burgdorferi; Legionella* species, in particular *Legionella pneumophilia; Mycobacteria* species, in particular *M. tuberculosis, M. avium, M. intracellulare, M. kansasii, M. gordonae; Staphylococcus* species, in particular *Staphylococcus aureus*; *Neisseria* species, in particular *N. gonorrhoeae, N. meningitidis*; *Listeria* species, in particular *Listeria monocytogenes*; *Streptococcus* species, in particular *S. pyogenes, S. agalactiae; S. faecalis; S. bovis, S. pneumonias*; anaerobic *Streptococcus* species; pathogenic *Campylobacter* species; *Enterococcus* species; *Haemophilus* species, in particular *Haemophilus influenzue*; *Bacillus* species, in particular *Bacillus anthracis*; *Corynebacterium* species, in particular *Corynebacterium diphtheriae*; *Erysipelothrix* species, in particular Erysipelothrix rhusiopathiae; *Clostridium* species, in particular *C. perfringens, C. tetani; Enterobacter* species, in particular *Enterobacter aerogenes, Klebsiella* species, in particular *Klebsiella 1S pneumoniae, Pasteurella* species, in particular *Pasteurella multocida, Bacteroides* species; *Fusobacterium* species, in particular *Fusobacterium nucleatum; Streptobacillus* species, in particular *Streptobacillus moniliformis; Treponema* species, in particular *Treponema pertenue; Leptospira*; pathogenic *Escherichia* species; and *Actinomyces* species, in particular *Actinomyces israelli*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papavaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses). Alternatively, a viral antigen may be produced recombinantly.

As used herein, the terms "cancer antigen" and "tumor antigen" are used interchangeably and refer to antigens (other than NKp46) that are differentially expressed by cancer cells or are expressed by non-tumoral cells (e.g. immune cells) having a pro-tumoral effect (e.g. an immunosuppressive effect), and can thereby be exploited in order to target cancer cells. Cancer antigens are antigens which can potentially stimulate apparently tumor-specific immune responses. Some of these antigens are encoded, although not necessarily expressed, or expressed at lower levels or less frequently, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Still other cancer antigens can be expressed on immune cells capable of mediating a pro-tumoral effect, e.g. a monocyte or a macrophage, optionally a suppressor T cell, regulatory T cell, or myeloid-derived suppressor cell.

The cancer antigens are usually normal cell surface antigens which are either over-expressed or expressed at abnormal times, or are expressed by a targeted population of cells. Ideally the target antigen is expressed only on proliferative cells (e.g., tumor cells) or pro-tumoral cells (e.g. immune cells having an immunosuppressive effect), however this is rarely observed in practice. As a result, target antigens are in many cases selected on the basis of differential expression between proliferative/disease tissue and healthy tissue. Example of cancer antigens include: Receptor Tyrosine Kinase-like Orphan Receptor 1 (ROR1), Cripto, CD4, CD20, CD30, CD19, CD38, CD47, Glycoprotein NMB, CanAg, Her2 (ErbB2/Neu), a Siglec family member, for example CD22 (Siglec2) or CD33 (Siglec3), CD79, CD138, CD171, PSCA, L1-CAM, PSMA (prostate specific membrane antigen), BCMA, CD52, CD56, CD80, CD70, E-selectin, EphB2, Melanotransferin, Mud 6 and TMEFF2. Examples of cancer antigens also include Immunoglobulin immunoglobulin superfamily (IgSF) such as cytokine receptors, Killer-Ig Like Receptor, CD28 family proteins, for example, Killer-Ig Like Receptor 3DL2 (KIR3DL2), B7-H3, B7-H4, B7-H6, PD-L1, IL-6 receptor. Examples also include MAGE, MART-1/Melan-A, gp100, major histocompatibility complex class I-related chain A and B polypeptides (MICA and MICB), adenosine deaminase-binding protein (ADAbp), cyclophilin b, colorectal associated antigen (CRC)-0017-1A/GA733, protein tyrosine kinase 7 (PTK7), receptor protein tyrosine kinase 3 (TYRO-3), nectins (e.g. nectin-4), major histocompatibility complex class I-related chain A and B polypeptides (MICA and MICB), proteins of the UL16-binding protein (ULBP) family, proteins of the retinoic acid early transcript-1 (RAET1) family, carcinoembryonic antigen (CEA) and its immunogenic epitopes CAP-1 and CAP-2, etv6, am11, prostate specific antigen (PSA), T-cell receptor/CD3-zeta chain, MAGE-family of tumor antigens, GAGE-family of tumor antigens, anti-Mullerian hormone Type II receptor, delta-like ligand 4 (DLL4), DRS, ROR1 (also known as Receptor Tyrosine Kinase-Like Orphan Receptor 1 or NTRKR1 (EC 2.7.10.1), BAGE, RAGE, LAGE-1, NAG, GnT-V, MUM-1, CDK4, MUC family, VEGF, VEGF receptors, Angiopoietin-2, PDGF, TGF-alpha, EGF, EGF receptor, members of the human EGF-like receptor family, e.g., HER-2/neu, HER-3, HER-4 or a heterodimeric receptor comprised of at least one HER subunit, gastrin releasing peptide receptor antigen, Muc-1, CA125, integrin receptors, $\alpha v \beta 3$ integrins, $\alpha 5 \beta 1$ integrins, $\alpha IIb \beta 3$-integrins, PDGF beta receptor, SVE-cadherin, IL-8 receptor, hCG, IL-6 receptor, CSF1R (tumor-associated monocytes and macrophages), $\alpha$-fetoprotein, E-cadherin, $\alpha$-catenin, $\beta$-catenin and $\gamma$-catenin, p120ctn, PRAME, NY-ESO-1, cdc27, adenomatous polyposis *coli* protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive. In one aspect, the antigen of interest is an antigen (e.g. any one of the antigens listed above) capable of undergoing intracellular internalization, for example when bound by an conventional human IgG1 antibody, either in the presence of absence of Fcγ receptor cells. In one aspect, the antigen of interest is a CD19 polypeptide; in one aspect, the multispecific protein comprises an scFv that binds CD19 comprising an amino acid sequence which is at least 60%, 70%, 80%, 85%, 90% or 95% identical to the sequence of the anti-CD19 scFv of the Examples herein, or that comprises the heavy and light chain CDR1, -2 and -3 of the anti-CD19 heavy and light chain variable regions shown herein.

In one embodiment, the ABD that binds an antigen of interest is derived from (e.g. comprises the hypervariable region of, or comprises the CDRs of) a parental antibody that binds an antigen of interest (e.g. a murine antibody, a human antibody) which, when bound to its antigenic target (the antigen of interest on cells), increases or induces down-modulation or intracellular internalization of the antigen of interest. In one embodiment, the antigen of interest is a cancer antigen, e.g. one of the cancer antigens listed above known to internalize (e.g. Immunoglobulin immunoglobulin superfamily (IgSF) members, for example cytokine receptor alpha or beta chains, Killer-Ig Like Receptors, CD28 family proteins, B7-H3, B7-H4, B7-H6, KIR3DL2, PTK7, ROR1, L1-CAM, Siglec family members, EGF receptor and EGF-like receptor family members, EGFR, HER-2, integrins, anti-Mullerian hormone Type II receptor, CSF-1R, and others) In one embodiment, the antigen target is a polypeptide present on an immune cell capable of mediating a pro-tumoral effect, e.g. a monocyte or a macrophage, optionally a suppressor T cell, regulatory T cell, or myeloid-derived suppressor cell.

In one embodiment, the non-NKp46 ABD binds to a cancer antigen, a viral antigen, a microbial antigen, or an antigen present on an infected cell (e.g. virally infected) or on a pro-inflammatory immune cell.

Once appropriate antigen binding domains having desired specificity and/or activity are identified, DNA encoding each of the or ABD can be separately placed, in suitable arrangements, in an appropriate expression vector, together with DNA encoding any elements such as an enzymatic recognition tag, CH1, Cκ, CH2 and/or CH3 domains and any other optional elements (e.g. DNA encoding a hinge region) for transfection into an appropriate host. ABDs will be arranged in an expression vector, or in separate vectors as a function of which type of polypeptide is to be produced, so as to produce the Fc-polypeptides having the desired domains operably linked to one another. The host is then used for the recombinant production of the multispecific polypeptide.

For example, a polypeptide fusion product can be produced from a vector in which the first of the two ABD is operably linked (e.g. directly, via a heavy or light chain CH1, CK or Cλ constant region and/or hinge region) to the N-terminus of a CH2 domain, and the CH2 domain is operably linked at its C-terminus to the N-terminus a CH3 domain. The second of the two ABD can be linked to the polypeptide at either terminus, or can be on a second polypeptide chain that forms a dimer, e.g. heterodimer, with the polypeptide comprising the first ABD. The polypeptide may comprise a full length Fc domain.

The multispecific polypeptide can then be produced in an appropriate host cell or by any suitable synthetic process. A host cell chosen for expression of the multispecific polypeptide is an important contributor to the final composition, including, without limitation, the variation in composition of the oligosaccharide moieties decorating the protein in the immunoglobulin CH2 domain. The host cell may, for example, be of mammalian origin or may be selected from COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof.

A range of different protein formats can be prepared using the NKp46-binding VH-VL pairs of the disclosure, including monomeric, heterodimeric, hetertrimeric and tetrameric multispecific proteins. Included, without limitation, are any of a variety of formats described in for example, in PCT application number PCT/EP2016/064537, filed 23 Jun. 2016 (Innate Pharma), the disclosure of which is incorporated herein by reference.

Monomeric Proteins

In one example, a multispecific protein comprises, in a single polypeptide chain, a first antigen binding domain that binds to NKp46 (e.g. an ABD comprising a VH and a VL disclosed herein, separated by a (poly)peptide linker) and a second antigen binding domain that binds an antigen other than NKp46. In one embodiment, the protein or polypeptide is or comprises an scFv comprising the anti-NKp46 VH and VL of the disclosure, or a tandem scFv comprising the scFv that binds NKp46 and a second scFv that binds NKp46 or an antigen of interest other than NKp46, linked by a (poly) peptide linker optionally fused to another polypeptide or amino acid sequence.

Examples of such single chain antigen binding proteins include BiTE and DART protein formats. An scFv-based bispecific antibody construct, known as BITE® (Bispecific T-cell Engager) employs a single polypeptide containing two antigen-binding domains, each contributed by a pair of VH and VL, linked in tandem via a flexible linker (see, e.g., Nagorsen et al., 2009, Leukemia & Lymphoma 50:886-91; Amann et al., 2009, J Immunother 32:453-64; Baeuerle and Reinhardt, 2009, Cancer Res 69:4941-44). Another bispecific antibody called DART® (Dual-Affinity Re-Targeting) utilizes a disulfide-stabilized diabody design (see, e.g., Moore et al., 2011, Blood 117:4542-51; Veri et al., 2010, Arthritis Rheum 62:1933-43).

In one embodiment, the single polypeptide chain further comprises an Fc domain (e.g. a full length Fc domain or a portion thereof), optionally wherein the Fc domain is interposed between the first and second antigen binding domains.

In one aspect of any embodiment, the first antigen binding domain and/or the second antigen binding domain comprise a scFv, optionally where the scFv comprises human framework amino acid sequences. In one embodiment, provided is a monomeric bispecific Fc-derived polypeptide comprising: (a) a first scFv that binds to NKp46; (b) a second scFv that binds an antigen other than NKp46; and, optionally, (c) at least a portion of a human Fc domain. Optionally the Fc domain (i) does not dimerize with another Fc-derived polypeptide and (ii) is capable of binding to human FcRn. Optionally, the Fc domain is interposed between the first and second scFv.

When the polypeptide fusion product comprising the two ABDs and at least a portion of an Fc domain is a monomer, the CH3 domains may be arranged and/or comprise amino acid modification to prevent CH3-CH3 dimerization. In one embodiment, the CH3 domain comprises mutations in the dimer interface to prevent interchain CH3-CH3 dimerization. In another embodiment, the CH3 domain is a tandem CH3 domain (or the Fc domain comprises a tandem CH3 domain) to prevent interchain CH3-CH3 dimerization. Such monomers will retain partial FcRn binding (compared, e.g., to a wild type full length human IgG1 antibody). Optionally the monomeric polypeptide is capable of binding to human FcRn with intermediate affinity, e.g. retains binding to FcRn but has decreased binding to a human FcRn receptor compared to a full-length wild type human IgG1 antibody. The Fc moiety may further comprise one or more amino acid modifications, e.g. in the CH2 domain, that further decreases or substantially abolishes binding to one or more Fcγ receptors.

In one configuration, the monomeric Fc-derived polypeptides that have at least a portion of a human Fc domain can advantageously comprise a CH2 domain and a CH3 domain, wherein said CH3 domain comprises a modified CH3 dimer interface (e.g. a mutations in the CH3 dimer interface) to prevent dimerization with another Fc-derived polypeptide. See e.g. format 1 and 2 in FIG. 2A). In one embodiment of any of the polypeptides or methods herein, the CH3 domain comprises an amino acid substitution at 1, 2, 3, 4, 5, 6 or 7 of the positions L351, T366, L368, P395, F405, T407 (or Y407) and/or K409 (EU numbering as in Kabat).

Another configuration for a CH3 domain that can be used in a monomeric multispecific protein is a tandem CH3 domain (see e.g. format 3 and 4 in FIG. 2A). A tandem CH3 domain comprises a first and a second CH3 domain, wherein the two CH3 domains associate with one another via non-covalent interactions. In one embodiment, the two CH3 domains associate with one another via the CH3 dimerization interface of each CH3 domain. In one embodiment, the polypeptide chain does not dimerize with another polypeptide chain comprising an Fc domain. An Fc domain that comprise a tandem CH3 domain will interact with neonatal Fc receptor (FcRn) but will have low or no binding to human FCγ receptors, notably CD16.

Multimeric Proteins

Multimeric bispecific proteins such as heterodimers, heterotrimers and tetramers (the latter including for example antibodies with two heavy chains and two light chains) that comprise an ABD that binds NKp46 (e.g. an ABD comprising a VH and a VL disclosed herein) can be produced according to a variety of formats.

In one embodiment, a multimeric protein or polypeptide is a tetrameric antibody made up of two heavy chains comprising variable regions (or 1, 2 or 3 CDRs thereof) derived from two different parental antibodies, and two light chains comprising variable regions (or 1, 2 or 3 CDRs thereof) derived from two different parental antibodies. Such a tetramer may comprise (a) two heavy chains each comprising a variable region, a CH1 domain, hinge and an Fc domain, and (b) two antibody light chains each comprising a light chain variable region and a Cκ domain, wherein one heavy chain variable region together with a light chain variable region binds to NKp46 and the other heavy chain variable region together with a light chain variable region bind an antigen of interest.

One advantageous way of making multimeric proteins is through the assembly of different polypeptide chains that each comprise at least one heavy or light chain variable domain fused to a human CH1 or Cκ constant domain (a V—(CH1/Cκ) unit), wherein the protein chains undergo CH1-Cκ dimerization and are bound to one another by non-covalent bonds and optionally further by disulfide bonds formed between respective CH1 and Cκ domain. In one embodiment, provided is an isolated or purified heterodimeric or heterotrimeric protein that binds a first and second antigen, wherein the protein comprises at least two or three polypeptide chains each comprising a V—(CH1/Cκ) unit, whereby the chains are bound to one another by non-covalent bonds and optionally further by disulfide bonds between CH1 and Cκ domains, optionally, whereby the chains are further bound by non-covalent bonds between respective variable regions and CH3 domains of the Fc portion.

The variable and constant regions can be selected and configured such that each chain will preferentially associate with its desired complementary partner chain. The resulting multimeric protein will therefore be simple to produce using conventional production methods using recombinant host cells. The choice of which VH, VL to associate with a CH1 and Cκ in a unit is based on affinity between the units to be paired so as to drive the formation of the desired multimer. The resulting multimer will be bound by non-covalent bonds between complementary VH and VL domains, by non-covalent bonds between complementary CH1 and Cκ domains, and optionally by disulfide bonding between complementary CH1 and Cκ domains and/or optionally further by disulfide bonds between complementary hinge domains). VH-VL associations are stronger than VH-VH or VL-VL, consequently, as shown herein, one can place a VH or a VL next to either a CH1 or a Cκ, and the resulting V—C unit will partner preferably with its V—C counterpart. For example VH-Cκ will pair with VL-CH1 preferentially over VH-CH1. Additionally, by including an Fc domain, preferred chain pairing is further improved, as the two Fc-containing chains will be bound by non-covalent bonds between CH3 domains of the Fc domains. The different V—C combinations, optionally further combined with Fc pairing thereby provides tools to make heteromultimeric proteins.

In one embodiment, a heteromultimeric polypeptide or protein comprises a monomeric Fc domain (e.g. the second polypeptide does not comprise an Fc domain), optionally wherein the Fc domain comprises a CH3 domain with an amino acid mutation to prevent CH3-CH3 dimerization or a tandem CH3 domain.

In another embodiment, the above heteromultimeric polypeptide or protein comprises a dimeric Fc domain capable of binding to human CD16, e.g. a human Fc domain comprising N-linked glycosylation at amino acid residue N297 (Kabat EU numbering).

A heterodimer can for example have the configuration as follows (see also Examples of such proteins shown as formats 2, 11 and 12 shown in FIGS. 2A and 2C):

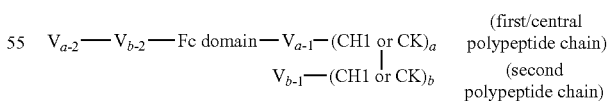

wherein one of $V_{a\text{-}1}$ of the first polypeptide chain and $V_{b\text{-}1}$ of the second polypeptide chain is a light chain variable domain and the other is a heavy chain variable domain, and wherein one of $V_{a\text{-}2}$ and $V_{b\text{-}2}$ is a light chain variable domain and the other is a heavy chain variable domain.

The heterodimer can in another example have the configuration as follows (see also Examples of such proteins shown as format 10 shown in FIG. 2B):

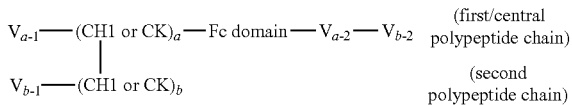
(first/central polypeptide chain)
(second polypeptide chain)

wherein one of $V_{a-1}$ of the first polypeptide chain and $V_{b-1}$ of the second polypeptide chain is a light chain variable domain and the other is a heavy chain variable domain, and wherein one of $V_{a-2}$ and $V_{b-2}$ is a light chain variable domain and the other is a heavy chain variable domain.

The resulting heterodimer can in another example have the configuration as follows (see also Examples of such proteins shown as formats 13 and 14 shown in FIGS. 2D and 2E):

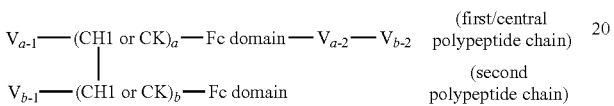
(first/central polypeptide chain)
(second polypeptide chain)

wherein one of $V_{a-1}$ of the first polypeptide chain and $V_{b-1}$ of the second polypeptide chain is a light chain variable domain and the other is a heavy chain variable domain, and wherein one of $V_{a-2}$ and $V_{b-2}$ is a light chain variable domain and the other is a heavy chain variable domain.

Heterotrimeric proteins can for example be formed by using a central (first) polypeptide chain comprising a first variable domain (V) fused to a first CH1 or CK constant region, a second variable domain (V) fused to a second CH1 or CK constant region, and an Fc domain or portion thereof interposed between the first and second variable domains (i.e. the Fc domain is interposed between the first and second (V—(CH1/CK) units. For example, a central polypeptide chain for use in a heterotrimeric protein can have the domain arrangements (N- to C-terminal) as follows:

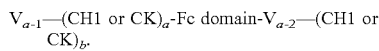

A second polypeptide can then comprise a domain arrangement (N- to C-terminal):

or

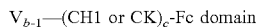

such that the $(CH1\ or\ CK)_c$ dimerizes with the $(CH1\ or\ CK)_a$ on the central chain, and the $V_{a-1}$ and $V_{b-1}$ form an antigen binding domain.

A third polypeptide chain can then comprise a domain arrangement (N- to C-terminal):

such that the $(CH1\ or\ CK)_d$ dimerizes with the $(CH1\ or\ CK)_b$ unit on the central chain, and the $V_{a-2}$ and $V_{b-2}$ form an antigen binding domain.

An example of a configuration of a resulting heterotrimer with a dimeric Fc domain (also shown as formats 5, 6, 7 and 16 in FIGS. 2D and 2E) has a domain arrangement:

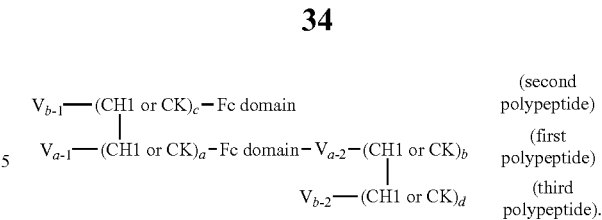

An example of a configuration of a resulting heterotrimer with a monomeric Fc domain (also shown as formats 8, 9 and 17 in FIGS. 2B and 2C) has a domain arrangement:

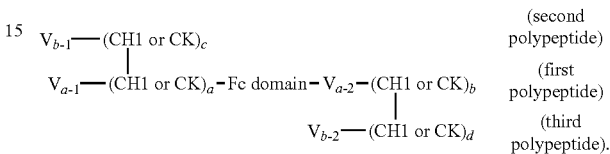

Thus, in a configuration of a trimer polypeptide, the first polypeptide can have two variable domains that each form an antigen binding domain with a variable domain on a separate polypeptide chain (i.e. the variable domain of the second and third chains), the second polypeptide chain has one variable domain, and the third polypeptide has one variable domain.

A trimeric polypeptide may comprise:
(a) a first polypeptide chain comprising a first variable domain (V) fused to a first CH1 of CK constant region, a second variable domain (V) fused to a second CH1 of CK constant region, and an Fc domain or portion thereof interposed between the first and second variable domains;
(b) a second polypeptide chain comprising a variable domain fused at its C-terminus to a CH1 or CK constant region selected to be complementary to the first CH1 or CK constant region of the first polypeptide chain such that the first and second polypeptides form a CH1-CK heterodimer, and optionally an Fc domain; and
(c) a third polypeptide chain comprising a variable domain fused (e.g. at its C-terminus) to a CH1 or CK constant region, wherein the variable domain and the constant region are selected to be complementary to the second variable domain and second CH1 or CK constant region of the first polypeptide chain such that the first and third polypeptides form a CH1-CK heterodimer bound by non-covalent bonds and optionally further by disulfide bond(s) formed between the CH1 or CK constant region of the third polypeptide and the second CH1 or CK constant region of the first polypeptide, but not between the CH1 or CK constant region of the third polypeptide and the first CH1 or CK constant region of the first polypeptide;
wherein the first, second and third polypeptides form a CH1-CK heterotrimer, and wherein the first variable domain of the first polypeptide chain and the variable domain of the second polypeptide chain form an antigen binding domain specific for a first antigen of interest, and the second variable domain of the first polypeptide chain and the variable domain on the third polypeptide chain form an antigen binding domain specific for a second antigen of interest. One of the two antigens of interest will be NKp46, and the ABD that binds NKp46 comprises a VH-VL variable domain pair of the disclosure.

Examples of domain arrangement for the trimeric bispecific polypeptide formed from include but are not limited to:

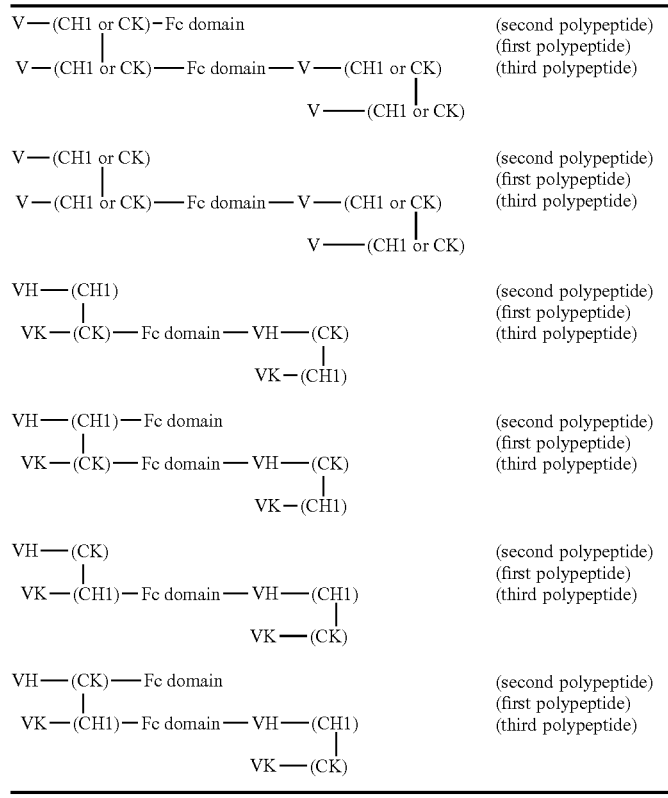

In any of the domain arrangements, the Fc domain may comprise a CH2-CH3 unit (a full length CH2 and CH3 domain or a fragment thereof). In heterodimers or heterotrimers comprising two chains with Fc domains (a dimeric Fc domain), the CH3 domain will be capable of CH3-CH3 dimerization (e.g. a wild-type CH3 domain). In heterodimers or heterotrimers comprising only one chain with an Fc domain (monomeric Fc domain), the Fc domain will be incapable of CH3-CH3 dimerization; for example the CH3 domain(s) will have amino acid modification(s) in the CH3 dimer interface or the Fc domain will comprise a tandem CH3 domain incapable of CH3-CH3 dimerization.

In some exemplary configurations, the multispecific protein can be tetramers, e.g. heterodimeric tetramers with two light chains and two different heavy chains, wherein the heavy chains are engineered for heterodimerization. Such proteins can be prepared as described, for example, in PCT application number PCT/EP2016/064537, filed 23 Jun. 2016 (Innate Pharma), the disclosure of which is incorporated herein by reference.

In any protein of the disclosure, a hinge region will typically be present on a polypeptide chain between a CH1 domain and a CH2 domain, and/or can be present between a CK domain and a CH2 domain. A hinge region can optionally be replaced for example by a suitable linker peptide.

The proteins domains described in the present disclosure can optionally be specified as being from N- to C-terminal. Protein arrangements of the disclosure for purposes of illustration are shown from N-terminus (on the left) to C-terminus. Domains can be referred to as fused to one another (e.g. a domain can be said to be fused to the C-terminus of the domain on its left, and/or a domain can be said to be fused to the N-terminus of the domain on its right).

The proteins domains described in the present disclosure can be fused to one another directly or via intervening amino acid sequences. For example, a CH1 or CK domain will be fused to an Fc domain (or CH2 or CH3 domain thereof) via a linker peptide, optionally a hinge region or a fragment thereof. In another example, a VH or VK domain will be fused to a CH3 domain via a linker peptide. VH and VL domains linked to another in tandem will be fused via a linker peptide (e.g. as an scFv). VH and VL domains linked to an Fc domain will be fused via a linker peptide. Two polypeptide chains will be bound to one another (indicated by "|") by non-covalent bonds and optionally further by interchain disulfide bonds formed between cysteine residues within complementary CH1 and CK domains.

Linkers and Fc domains are described in more detail, for example, in PCT application number PCT/EP2016/064537, filed 23 Jun. 2016 (Innate Pharma), the disclosure of which is incorporated herein by reference.

Once the multispecific protein is produced it can be assessed for biological activity.

In one aspect of any embodiment herein, a multispecific protein is capable of inducing activation of an NKp46-expressing cell (e.g. an NK cell, a reporter cell) when the protein is incubated in the presence of the NKp46-expressing cell (e.g. purified NK cells) and a target cell that expresses the antigen of interest).

In one aspect of any embodiment herein, a multispecific protein is capable of inducing NKp46 signaling in an NKp46-expressing cell (e.g. an NK cell, a reporter cell) when the protein is incubated in the presence of the NKp46-expressing cell (e.g. purified NK cells) and a target cell that expresses the antigen of interest).

Optionally, NK cell activation or signaling in characterized by increased expression of a cell surface marker of activation, e.g. CD107, CD69, etc.

Activity can be measured for example by bringing target cells and NKp46-expressing cells into contact with one another, in presence of the multispecific polypeptide. In one example, aggregation of target cells and NK cells is measured. In another example, the multispecific protein may, for example, be assessed for the ability to cause a measurable increase in any property or activity known in the art as associated with NK cell activity, respectively, such as marker of cytotoxicity (CD107) or cytokine production (for example IFN-γ or TNF-α), increases in intracellular free calcium levels, the ability to lyse target cells in a redirected killing assay, etc. Assays for activity are further described in more detail, for example, in PCT application number PCT/EP2016/064537, filed 23 Jun. 2016 (Innate Pharma), the disclosure of which is incorporated herein by reference.

Uses of Compounds

Compounds according to the disclosure that comprise an antigen binding domain that binds NKp46 can be used in a variety of applications, including, e.g. to bind, detect, eliminate, purify or modulate the activity of NKp46 polypeptides and/or cells that express NKp46 polypeptide (e.g. NK cells).

In one aspect, provided are the use of any of the compounds defined herein for the manufacture of a pharmaceutical preparation for the treatment or diagnosis of a mammal in need thereof. Provided also are the use any of the compounds defined above as a medicament or an active component or active substance in a medicament. In a further aspect provided is a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one aspect, provided is a method to treat, prevent or more generally affect a predefined condition by exerting a certain effect, or detect a certain condition using a multispecific protein described herein, or a (pharmaceutical) composition comprising such.

For example, in one aspect, the invention provides a method of restoring or potentiating the activity of NKp46+ NK cells in a patient in need thereof (e.g. a patient having a cancer, or a viral or bacterial infection), comprising the step of administering a multispecific protein described herein to said patient. In one embodiment, the method is directed at increasing the activity of NKp46+ lymphocytes in patients having a disease in which increased lymphocyte (e.g. NK cell) activity is beneficial or which is caused or characterized by insufficient NK cell activity, such as a cancer, or a viral or microbial/bacterial infection.

The polypeptides described herein can be used to prevent or treat disorders that can be treated with antibodies, such as cancers, solid and non-solid tumors, hematological malignancies, infections such as viral infections, and inflammatory or autoimmune disorders.

In one embodiment, the antigen of interest (the non-NKp46 antigen) is an antigen expressed on the surface of a malignant cell of a type of cancer selected from the group consisting of: carcinoma, including that of the bladder, head and neck, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

In one embodiment, polypeptides described herein can be used to prevent or treat a cancer selected from the group consisting of: carcinoma, including that of the bladder, head and neck, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma. Other exemplary disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

In one example, the tumor antigen is an antigen expressed on the surface of a lymphoma cell or a leukemia cell, and the multispecific protein is administered to, and/or used for the treatment of, an individual having a lymphoma or a leukemia. Optionally, the tumor antigen is selected from CD19, CD20, CD22, CD30 or CD33.

In one aspect, the methods of treatment comprise administering to an individual a multispecific protein described herein in a therapeutically effective amount, e.g., for the treatment of a disease as disclosed herein, for example a cancer selected from the group above. A therapeutically effective amount may be any amount that has a therapeutic effect in a patient having a disease or disorder (or promotes, enhances, and/or induces such an effect in at least a substantial proportion of patients with the disease or disorder and substantially similar characteristics as the patient).

In one embodiment, the multispecific protein described herein may be used as monotherapy (without other therapeutic agents), or in combined treatments with one or more other therapeutic agents, including agents normally utilized for the particular therapeutic purpose for which the antibody is being administered. The additional therapeutic agent will normally be administered in amounts and treatment regimens typically used for that agent in a monotherapy for the particular disease or condition being treated. Such therapeutic agents when used in the treatment of cancer, include, but are not limited to anti-cancer agents and chemotherapeutic agents; in the treatment of infectious disease, include, but are not limited to anti-viral agents and anti-biotics.

The proteins and/or polypeptides disclosed herein can be included in kits. The kits may optionally further contain any number of polypeptides and/or other compounds, e.g., 1, 2, 3, 4, or any other number of proteins and/or polypeptides and/or other compounds. It will be appreciated that this description of the contents of the kits is not limiting in any way. For example, the kit may contain other types of therapeutic compounds. Optionally, the kits also include instructions for using the proteins and/or polypeptides, e.g., detailing the herein-described methods.

Also provided are pharmaceutical compositions comprising the compounds as defined above. A compound may be administered in purified form together with a pharmaceutical carrier as a pharmaceutical composition. The form depends on the intended mode of administration and therapeutic or diagnostic application. The pharmaceutical carrier can be any compatible, nontoxic substance suitable to deliver the compounds to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids A pharmaceutically acceptable carrier may further contain physiologically acceptable compounds that act for example to stabilize or to increase the absorption of the compounds Such physiologically acceptable compounds include, for example, carbohydrates, such as glucose, sucrose or dextrans, antioxidants, such as ascorbic acid or glutathione, chelating agents, low molecular weight proteins or other stabilizers or excipients One skilled in the art would know that the choice of a pharmaceutically acceptable carrier, including a physiologically acceptable compound, depends, for example, on the route of administration of the composition Pharmaceutically acceptable adjuvants, buffering agents, dispersing agents, and the like, may also be incorporated into the pharmaceutical compositions.

The compounds can be administered parenterally. Preparations of the compounds for parenteral administration must be sterile. Sterilization is readily accomplished by filtration through sterile filtration membranes, optionally prior to or following lyophilization and reconstitution. The parenteral route for administration of compounds is in accord with known methods, e.g. injection or infusion by intravenous, intraperitoneal, intramuscular, intraarterial, or intralesional routes. The compounds may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound, depending on the particular type of compound and its required dosing regimen. Methods for preparing parenterally administrable compositions are well known in the art.

EXAMPLES

Example 1

Generation of Anti-huNKp46 Antibodies

Part A: Generation of Anti-huNKp46 Antibodies

Balb/c mice were immunized with a recombinant human NKp46 extracellular domain recombinant-Fc protein. Mice received one primo-immunization with an emulsion of 50 µg NKp46 protein and Complete Freund Adjuvant, intraperitoneally, a 2nd immunization with an emulsion of 50 µg NKp46 protein and Incomplete Freund Adjuvant, intraperitoneally, and finally a boost with 10 µg NKp46 protein, intravenously. Immune spleen cells were fused 3 days after the boost with X63.Ag8.653 immortalized B cells, and cultured in the presence of irradiated spleen cells.

Primary screen: Supernatant (SN) of growing clones were tested in a primary screen by flow cytometry using a cell line expressing the human NKp46 construct at the cell surface. Briefly, for FACS screening, the presence of reacting antibodies in supernanants was revealed by Goat anti-mouse polyclonal antibody (pAb) labeled with PE.

A selection of antibodies that bound NKp46 were selected, produced as full-length human IgG antibodies and as bispecific antibodies. Among the variable regions evaluated for their activity in the context of a bispecific molecule in Examples 2-13 were antibodies NKp46-1, -2, -3, -4, -6 and -9 having the respective variable regions shown in Table B herein.

Part B: Generation of Humanized Anti-Human/Anti-Cynomologus NKp46 Antibodies

Antibodies NKp46-1, -2, -3 and -4 having the respective variable regions shown in Table B herein were produced as humanized antibodies by complementary determining region (CDR) grafting of heavy and light chains having the amino acid sequence shown below. Antibodies were produced using CHO cells and tested for binding to human NKp46.

Each of the CDR-grafted antibodies bound with good affinity to human NKp46. However, none of the CDR-grafted antibodies bound to cynomologus NKp46. Epitopes on human NKp46 were determined (see Example 13); in view of the possibility that modifications that affect the conformation of the antibody variable regions or positioning of the CDRs may permit an epitope shared on cynomolgus NKp46 to be recognized, multiple variants were prepared for each of the CDR-grafted antibodies for NKp46-1, -2, -3, -4, and -9 were prepared and produced using CHO cells, and tested for binding to cynomolgus NKp46. For each of antibody NKp46-1, -2, -3, -4, and -9, one more variants were identified that permitted the recognition with good affinity of an epitope shared by human and cynomolgus NKp46 binding. Based on 3D modelling studies, different heavy and light chain variable regions were designed that included NKp46-1 CDRs and human frameworks, produced as human IgG1 antibodies, and tested for binding to cynomolgus NKp46.

Antibody NKp46-1

Based on 3D modelling studies, different heavy and light chain variable regions were designed that included NKp46-1 CDRs and human frameworks, produced as human IgG1 antibodies, and tested for binding to cynomolgus NKp46. Two combinations of heavy and light chains were able to bind to both human and cynomolgus NKp46: the heavy chain variable region "H1" and the heavy chain "H3", in each case combined with the light chain "L1". These cross-binding variable regions included, for the heavy chain variable region: the NKp46-1 heavy chain CDRs (shown below, underlined), human IGHV1-69*06 gene framework 1, 2 and 3 regions and a human IGHJ6*01 gene framework 4 region. The light chain variable region: the NKp46-1 light chain CDRs (shown below, underlined), human IGKV1-33*01 gene framework 1, 2 and 3 regions and a human IGKJ4*01 gene framework 4 region. CDRs were chosen according to Kabat numbering. The H1, H3 and L1 chain had the specific amino acid substitutions (shown in bold and underlining below). L1 had a phenylalanine at Kabat light chain residue 87. H1 had a tyrosine at Kabat heavy chain residue 27 and a lysine and alanine at Kabat residues 66 and 67, respectively. H3 additionally had a glycine at Kabat residue 37, an isoleucine at Kabat residue 48, and a phenylalanine at Kabat residue 91.

NKp46-1: "H1" Heavy Chain Variable Region (SEQ ID NO: 199)
QVQLVQSGAEVKKPGSSVKVSCKASGYTFSDYVINWVRQAPGQGLEWMG

EIYPGSGTNYYNEKFKAKATITADKSTSTAYMELSSLRSEDTAVYYCAR

RGRYGLYAMDYWGQGTTVTVSS

NKp46-1: "H3" Heavy Chain Variable Region (SEQ ID NO: 200)
QVQLVQSGAEVKKPGSSVKVSCKASGYTFTDYVINWGRQAPGQGLEWIG

EIYPGSGTNYYNEKFKAKATITADKSTSTAYMELSSLRSEDTAVYFCAR

RGRYGLYAMDYWGQGTTVTVSS

NKp46-1: "L1" Light Chain Variable Region (SEQ ID NO: 201)
DIQMTQSPSSLSASVGDRVTITC<u>RASQDISNYLN</u>WYQQKPGKAPKLLIY <u>YTSRLHS</u>GVPSRFSGSGSGTDFTFTISSLQPEDIATYFC<u>QQGNTRPWT</u>F

GGGTKVEIK

Antibody NKp46-2

Based on 3D modelling studies, different heavy and light chain variable regions were designed that included NKp46-2 CDRs and human frameworks, produced as human IgG1 antibodies, and tested for binding to cynomolgus NKp46. Three combinations of heavy and light chains were able to bind to both human and cynomolgus NKp46: the heavy chain variable regions "H1", "H2 and "H3", in each case combined with the light chain "L1". Interestingly, the H1L1 furthermore had an improved binding affinity compared to the parental NKp46-2 antibody having the VH and VL of SEQ ID NOS: 5 and 6. These cross-binding variable regions included, for the heavy chain variable region: the NKp46-2 heavy chain CDRs (shown below, underlined), human IGHV4-30-4*01 gene framework 1, 2 and 3 regions and a human IGHJ1*01 gene framework 4 region. The light chain variable region: the NKp46-2 light chain CDRs (shown below, underlined), human IGKV1-39*01 gene framework 1, 2 and 3 regions and a human IGKJ4*01 gene framework 4 region. CDRs were chosen according to Kabat numbering. The L1, H1, H2 and H3 chains had the specific amino acid substitutions (shown in bold and underlining below). L1 had a valine at Kabat light chain residue 48. H1 had a tyrosine at Kabat heavy chain residue 27 and an arginine at Kabat residue 71. H2 additionally had a methionine at Kabat residue 48 and an isoleucine at Kabat residue 67. H3 additionally had a threonine at Kabat residue 31.

NKp46-2: "H1" Heavy Chain Variable Region (SEQ ID NO: 202)
QVQLQESGPGLVKPSQTLSLTCTVSGYSISS<u>DYAWN</u>WIRQPPGKGLEWI G<u>YITYSGSTSYNPSLES</u>RVTISRDTSKNQFSLKLSSVTAADTAVYYCAR <u>GGYYGSSWGVFAY</u>WGQGTLVTVSS NKp46-2: "H2" Heavy Chain Variable Region (SEQ ID NO: 203)
QVQLQESGPGLVKPSQTLSLTCTVSGYSISS<u>DYAWN</u>WIRQPPGKGLEWM

G<u>YITYSGSTSYNPSLES</u>RITISRDTSKNQFSLKLSSVTAADTAVYYCAR

<u>GGYYGSSWGVFAY</u>WGQGTLVTVSS

NKp46-2: "H3" Heavy Chain Variable Region (SEQ ID NO: 204)
QVQLQESGPGLVKPSQTLSLTCTVSGYSITS<u>DYAWN</u>WIRQPPGKGLEWMG <u>YITYSGSTSYNPSLES</u>RITISRDTSKNQFSLKLSSVTAADTAVYYCAR<u>GG</u>

<u>YYGSSWGVFAY</u>WGQGTLVTVSS

NKp46-2: "L1" Light Chain Variable Region (SEQ ID NO: 205)
DIQMTQSPSSLSASVGDRVTITC<u>RVSENTYSYLA</u>WYQQKPGKAPKLLVY <u>NAKTLAE</u>GVPSRFSGSGSGTDFTLTISSLQPEDFATYYC<u>QHHYGTPWT</u>F

GGGTKVEIK

Antibody NKp46-3

Based on 3D modelling studies, different heavy and light chain variable regions were designed that included NKp46-3 CDRs and human frameworks, produced as human IgG1 antibodies, and tested for binding to cynomolgus NKp46. Three combinations of heavy and light chains were able to bind to both human and cynomolgus NKp46: the heavy chain variable regions "H1", "H3 and "H4", in each case combined with the light chain "L1". Interestingly, the H3L1 furthermore had an improved binding affinity compared to the parental NKp46-3 antibody having the VH and VL of SEQ ID NOS: 7 and 8. These cross-binding variable regions included, for the heavy chain variable region: the NKp46-3 heavy chain CDRs (shown below, underlined), human IGHV1-69*02 gene framework 1, 2 and 3 regions and a human IGHJ6*01 gene framework 4 region. The light chain variable region: the NKp46-3 light chain CDRs (shown below, underlined), framework 1, 2 and 3 regions created by a mosaic approach using FR1 and FR2 from IGKV3-15 and FR3 from IGKV3-11, and a human IGKJ2*01 gene framework 4 region. CDRs were chosen according to Kabat numbering. The L1, H1, H3 and H4 chains had the specific amino acid substitutions (shown in bold and underlining below). L1 had a lysine at Kabat light chain residue 49. H1 had a tyrosine at Kabat heavy chain residue 27. H3 additionally had a isoleucine at Kabat residue 48 and an alanine at Kabat residue 67. H4 additionally had a leucine at Kabat residue 69.

NKp46-3: "H1" Heavy Chain Variable Region (SEQ ID NO: 206)
QVQLVQSGAEVKKPGSSVKVSCKASGYTFSEYTMHWVRQAPGQGLEWMG

GISPNIGGTSYNQKFKGRVTITADKSTSTAYMELSSLRSEDTAVYYCAR

RGGSFDYWGQGTTVTVSS

NKp46-3: "H3" Heavy Chain Variable Region (SEQ ID NO: 207)
QVQLVQSGAEVKKPGSSVKVSCKASGYTFSEYTMHWVRQAPGQGLEWIG

GISPNIGGTSYNQKFKGRATITADKSTSTAYMELSSLRSEDTAVYYCAR

RGGSFDYWGQGTTVTVSS

NKp46-3: "H4" Heavy Chain Variable Region (SEQ ID NO: 208)
QVQLVQSGAEVKKPGSSVKVSCKASGYTFSEYTMHWVRQAPGQGLEWIG

GISPNIGGTSYNQKFKGRATL**TADKSTSTAYMELSSLRSEDTAVYYCAR

RGGSFDYWGQGTTVTVSS

NKp46-3: "L1" Light Chain Variable Region (SEQ ID NO: 209)
EIVMTQSPATLSVSPGERATLSCRASQSISDYLHWYQQKPGQAPRLLI

KYASQSISGIPARFSGSGSGTDFTLTISSLEPEDFAVYYCQNGHSFPL

TFGQGTKLEIK

Antibody NKp46-4

Based on 3D modelling studies, different heavy and light chain variable regions were designed that included NKp46-4 CDRs and human frameworks, produced as human IgG1 antibodies, and tested for binding to cynomolgus NKp46. The heavy chain variable region "H1" combined with the light chain "L2" was able to bind to both human and cynomolgus NKp46 as well as the parental antibody. Two other antigen binding regions (one composed of "L2" and "H2", and one composed of "L2" and "H3") were able to bind cynomolgus NKp46 at intermediate levels, although with an affinity that was 10-fold lower that for human NKp46. These cross-binding variable regions included, for the heavy chain variable region: the NKp46-4 heavy chain CDRs (shown below, underlined), human framework 1, 2 and 3 regions designed using a mosaic approach using FR1 from IGHV1646,0 FR3 from IGHV1-69, and a common FR2 (IGHV1-46 and IGHV1-69 share the same FR2), and a human IGHJ6*01 gene framework 4 region. The light chain variable region: the NKp46-4 light chain CDRs (shown below, underlined), framework 1, 2 and 3 regions from IGKV1-NL1, and a human IGKJ4*01 gene framework 4 region. CDRs were chosen according to Kabat numbering. The L2, H1, H2 and H3 chains had the specific amino acid substitutions (shown in bold and underlining below). L2 had a phenylalanine at Kabat light chain residue 36 and a valine at Kabat residue 48. H1 had a threonine at Kabat heavy chain residue 30 and an isoleucine at Kabat residue 48 and a valine at Kabat residue 93. H2 additionally had a threonine at Kabat residue 67. H3 additionally had a leucine at Kabat residue 69.

NKp46-4: "H1" Heavy Chain Variable Region (SEQ ID NO: 210)
QVQLVQSGAEVKKPGASVKVSCKASGYTFTSFTMHWVRQAPGQGLEWIG

YINPSSGYTEYNQKFKDRVTITADKSTSTAYMELSSLRSEDTAVYYCVR

GSSRGFDYWGQGTLVTVSS

NKp46-4: "H2" Heavy Chain Variable Region (SEQ ID NO: 211)
QVQLVQSGAEVKKPGASVKVSCKASGYTFTSFTMHWVRQAPGQGLEWIG

YINPSSGYTEYNQKFKDRTTITADKSTSTAYMELSSLRSEDTAVYYCVR

GSSRGFDYWGQGTLVTVSS

NKp46-4: "H3" Heavy Chain Variable Region (SEQ ID NO: 212)
QVQLVQSGAEVKKPGASVKVSCKASGYTFTSFTMHWVRQAPGQGLEWIG

YINPSSGYTEYNQKFKDRTTLTADKSTSTAYMELSSLRSEDTAVYYCV**R

GSSRGFDYWGQGTLVTVSS

NKp46-4: "L2" Light Chain Variable Region (SEQ ID NO: 213)
DIQMTQSPSSLSASVGDRVTITCRASENTYSNLAWFQQKPGKAPKLLV**Y

AATNLADGVPSRFSGSGSGTDYTLTISSLQPEDFATYYCQHFWGTPRTF

GGGTKVEIK

Antibody NKp46-9

Based on 3D modelling studies, different heavy and light chain variable regions were designed that included NKp46-9 CDRs and human frameworks, produced as human IgG1 antibodies, and tested for binding to cynomolgus NKp46. Heavy chain variable region "H2", when combined with either light chain variable region "L1" or "L2", and heavy chain variable region "H3" when combined with either light chain variable region "L1" or "L2", were able to bind to both human and cynomolgus NKp46 with greater affinity that the parental antibody (having the VH and VL of SEQ ID NOS: 13 and 14. The "H1" chain was not able to bind cynomolgus NKp46 with any of the light chains tested but bound well to human NKp46. These cross-binding variable regions included, for the heavy chain variable region: the NKp46-9 heavy chain CDRs (shown below, underlined), human framework 1, 2 and 3 regions from IGHV4-30-4*01, and a human IGHJ6*01 gene framework 4 region. The light chain variable region: the NKp46-9 light chain CDRs (shown below, underlined), framework 1, 2 and 3 regions from IGKV1-39*01, and a human IGKJ2*01 gene framework 4 region. CDRs were chosen according to Kabat numbering. The L1, L2, H1, H2 and H3 chains had the specific amino acid substitutions (shown in bold and underlining below). L1 had a cysteine at Kabat light chain residue 36. L2 additionally had a valine at Kabat residue 48. H1 had an arginine at Kabat heavy chain residue 71. H2 additionally had a tyrosine at Kabat residue 27. H3 additionally had a methionine at Kabat residue 48 and an isoleucine at Kabat residue 67.

NKp46-9: "H1" Heavy Chain Variable Region (SEQ ID NO: 214)
QVQLQESGPGLVKPSQTLSLTCTVSGGSISSDYAWNWIRQPPGKGLEWIG

YITYSGSTNYNPSLKSRVTISRDTSKNQFSLKLSSVTAADTAVYYCARCW

DYALYAMDCWGQGTTVTVSS

NKp46-9: "H2" Heavy Chain Variable Region (SEQ ID NO: 215)
QVQLQESGPGLVKPSQTLSLTCTVSGYSISSDYAWNWIRQPPGKGLEWIG

YITYSGSTNYNPSLKSRVTISRDTSKNQFSLKLSSVTAADTAVYYCARCW

DYALYAMDCWGQGTTVTVSS

NKp46-9: "H3" Heavy Chain Variable Region (SEQ ID NO: 216)
QVQLQESGPGLVKPSQTLSLTCTVSGYSISSDYAWNWIRQPPGKGLEWMG

YITYSGSTNYNPSLKSRITISRDTSKNQFSLKLSSVTAADTAVYYCARCW

DYALYAMDCWGQGTTVTVSS

NKp46-9: "L1" Light Chain Variable Region (SEQ ID NO: 217)
DIQMTQSPSSLSASVGDRVTITCRTSENTYSYLAWCQQKPGKAPKLLIY

NAKTLAEGVPSRFSGSGSGTDFTLTISSLQPEDFATYYCQHHYDTPLTF

GQGTKLEIK

NKp46-9: "L2" Light Chain Variable Region (SEQ ID NO: 218)
DIQMTQSPSSLSASVGDRVTITCRTSENTYSYLAWCQQKPGKAPKLLVY

NAKTLAEGVPSRFSGSGSGTDFTLTISSLQPEDFATYYCQHHYDTPLTF

GQGTKLEIK

Example 2

Identification of a Bispecific Antibody Format that Binds FcRn but not FcγR for Targeting Effector Cell Receptors The aim of this experiment was to develop a new bispecific protein format that places an Fc domain on a polypeptide together with an anti-NKp46 binding domain and an anti-target antigen binding domain. The bispecific protein binds to NKp46 monovalently via its anti-NKp46 binding domain. The monomeric Fc domain retains at least partial binding to the human neonatal Fc receptor (FcRn), yet does not substantially bind human CD16 and/or other human Fcγ receptors. Consequently, the bispecific protein will not induce Fcγ-mediated (e.g. CD16-mediated) target cell lysis.

Example 2-1 Construction and Binding Analysis of Anti-CD19-IgG1-Fcmono-Anti-CD3

Since no anti-NKp46 bispecific antibody has been produced that could indicate whether such a protein could be functional, CD3 was used as a model antigen in place of NKp46 in order to investigate the functionality of a new monovalent bispecific protein format prior to targeting NK cells via NKp46.

A bispecific Fc-based on a scFv specific for tumor antigen CD19 (anti-CD19 scFv) and a scFV specific for activating receptor CD3 on a T cell (anti-CD3 scFv) was used to assess FcRn binding and CD19-binding functions of a new monomeric bispecific polypeptide format. The domain arrangement of the final polypeptide is referred to as the "F1" format (the star in the CH2 domain indicates an optional N297S mutation, not included in the polypeptide tested here).

A bispecific monomeric Fc-containing polypeptide was constructed based on an scFv specific for the tumor antigen CD19 (anti-CD19 scFv) and an scFV specific for an activating receptor CD3 on a T cell (anti-CD3 scFv). The CH3 domain incorporated the mutations (EU numbering) L351K, T366S, P395V, F405R, T407A and K409Y. The polypeptide has domains arranged as follows: anti-CD19-CH2-CH3-anti-CD3. DNA sequence coding for a CH3/VH linker peptide having the amino acid sequence STGS was designed in order to insert a specific SalI restriction site at the CH3-VH junction.

The CH3 domain incorporated the mutations (EU numbering) L351K, T366S, P395V, F405R, T407A and K409Y. The CH2 domain was a wild-type CH2. DNA and amino acid sequences for the monomeric CH2-CH3 Fc portion and the anti-CD19 are shown below.

The light chain and heavy chain DNA and amino acid sequences corresponding to the anti-CD19 scFv were as follows:

| Sequence | SEQ ID NO |
|---|---|
| Anti-CD19-VK DNA | 113 |
| Anti-CD19-VK amino acid | 114 |
| Anti-CD19-VH DNA | 115 |
| Anti-CD19-VH amino acid | 116 |

The DNA sequences for the monomeric CH2-CH3 Fc portion and final bispecific IgG1-Fcmono polypeptide (the last K was removed in that construct) is shown in SEQ ID NO: 117. The amino acid sequence is shown in SEQ ID NO: 2. The Anti-CD19-F1-Anti-CD3 complete sequence (mature protein) is shown in SEQ ID NO: 118.

Cloning and Production of the Recombinant Proteins

Coding sequences were generated by direct synthesis and/or by PCR. PCR were performed using the PrimeSTAR MAX DNA polymerase (Takara, #R045A) and PCR products were purified from 1% agarose gel using the NucleoSpin gel and PCR clean-up kit (Macherey-Nagel, #740609.250). Once purified the PCR product were quantified prior to the In-Fusion ligation reaction performed as described in the manufacturer's protocol (ClonTech, #ST0345). The plasmids were obtained after a miniprep preparation run on an EVO200 (Tecan) using the Nucleospin 96 plasmid kit (Macherey-Nagel, #740625.4). Plasmids were then sequenced for sequences confirmation before to transfecting the CHO cell line.

CHO cells were grown in the CD-CHO medium (Invitrogen) complemented with phenol red and 6 mM GlutaMax. The day before the transfection, cells are counted and seeded at 175.000 cells/ml. For the transfection, cells (200.000 cells/transfection) are prepared as described in the AMAXA SF cell line kit (AMAXA, #V4XC-2032) and nucleofected using the DS137 protocol with the Nucleofector 4D device.

All the tranfections were performed using 300 ng of verified plasmids. After transfection, cells are seeded into 24 well plates in pre-warmed culture medium. After 24H, hygromycine B was added in the culture medium (200 µg/ml). Protein expression is monitored after one week in culture. Cells expressing the proteins are then sub-cloned to obtain the best producers. Sub-cloning was performed using 96 flat-bottom well plates in which the cells are seeded at one cell per well into 200 µl of culture medium complemented with 200 µg/ml of hygromycine B. Cells were left for three weeks before to test the clone's productivity.

Recombinant proteins which contain a IgG1-Fc fragment are purified using Protein-A beads (-rProteinA Sepharose fast flow, GE Healthcare, ref.: 17-1279-03). Briefly, cell culture supernatants were concentrated, clarified by centrifugation and injected onto Protein-A columns to capture the recombinant Fc containing proteins. Proteins were eluted at acidic pH (citric acid 0.1M pH3), immediately neutralized using TRIS-HCL pH8.5 and dialyzed against 1×PBS. Recombinant scFv which contain a "six his" tag were purified by affinity chromatography using Cobalt resin. Other recombinant scFv were purified by size exclusion chromatography (SEC).

Example 2-2: Binding Analysis of Anti-CD19-IgG1-Fcmono-Anti-CD3 to B221, JURKAT, HUT78 and CHO Cell Lines Cells were harvested and stained with the cell supernatant of the anti-CD19-F1-anti-CD3 producing cells during 1 H at 4° C. After two washes in staining buffer (PBS1X/BSA 0.2%/EDTA 2 mM), cells were stained for 30 min at 4° C. with goat anti-human (Fc)-PE antibody (IM0550 Beckman Coulter—1/200). After two washes, stainings were acquired on a BD FACS Canto II and analyzed using the FlowJo software.

CD3 and CD19 expression were also controlled by flow cytometry: Cells were harvested and stained in PBS1X/BSA 0.2%/EDTA 2 mM buffer during 30 min at 4° C. using 5 µl of the anti-CD3-APC and 5 µl of the anti-CD19-FITC antibodies. After two washes, stainings were acquired on a BD FACS Canto II and analyzed using the FlowJo software.

The Anti-CD19-F1-Anti-CD3 protein binds to the CD3 cell lines (HUT78 and JURKAT cell lines) and the CD19 cell line (B221 cell line) but not to the CHO cell line used as a negative control.

Example 2-3

T- and B-Cell Aggregation by Purified Anti-CD19-F1-Anti-CD3

Purified Anti-CD19-F1-Anti-CD3 was tested in a T/B cell aggregation assay to evaluate whether the antibody is functional in bringing together CD19 and CD3 expressing cells.

Results are shown in FIG. 1. The top panel shows that Anti-CD19-F1-Anti-CD3 does not cause aggregation in the presence of B221 (CD19) or JURKAT (CD3) cell lines, but it does cause aggregation of cells when both B221 and JURKAT cells are co-incubated, illustrating that the bispecific antibody is functional. The lower panel shows control without antibody.

Example 2-4

Binding of Bispecific Monomeric Fc Polypeptide to FcRn

Affinity Study by Surface Plasmon Resonance (SPR)
Biacore T100 General Procedure and Reagents SPR measurements were performed on a Biacore T100 apparatus (Biacore GE Healthcare) at 25° C. In all Biacore experiments Acetate Buffer (50 mM Acetate pH5.6, 150 mM NaCl, 0.1% surfactant p20) and HBS-EP+ (Biacore GE Healthcare) served as running buffer and regeneration buffer respectively. Sensorgrams were analyzed with Biacore T100 Evaluation software. Recombinant mouse FcRn was purchase from R&D Systems.

Immobilization of FcRn

Recombinant FcRn proteins were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). FcRn proteins were diluted to 10 µg/ml in coupling buffer (10 mM acetate, pH 5.6) and injected until the appropriate immobilization level was reached (i.e. 2500 RU). Deactivation of the remaining activated groups was performed using 100 mM ethanolamine pH 8 (Biacore GE Healthcare).

Affinity Study

Monovalent affinity study was done following the Single Cycle Kinetic (SCK) protocol. Five serial dilutions of soluble analytes (antibodies and bi-specific molecules) ranging from 41.5 to 660 nM were injected over the FcRn (without regeneration) and allowed to dissociate for 10 min before regeneration. For each analyte, the entire sensorgram was fitted using the 1:1 SCK binding model.

Results

Anti-CD19-F1-Anti-CD3 having its CH2-CH3 domains placed between two antigen binding domains, here two scFv, was evaluated to assess whether such bispecific monomeric Fc protein could retain binding to FcRn and thereby have improved in vivo half-lives compared to convention bispecific antibodies. Results showed that FcRn binding was retained, the model suggesting 1:1 ratio (1 FcRn for each monomeric Fc) instead of 2:1 ration (2 FcRn for each antibody) for a regular IgG.

Affinity was evaluated using SPR, in comparison to a chimeric full length antibody having human IgG1 constant regions. The monomeric Fc retained significant monomeric binding to FcRn (monomeric Fc: affinity of KD=194 nM; full length antibody with bivalent binding: avidity of KD=15.4 nM).

Example 3

Construction of Anti-CD19×Anti-NKp46 Bispecific Monomeric Fc Domain Polypeptides It was unknown what activating receptors on NK cells would contribute to the lysis of target cells, and moreover since anti-NKp46 antibodies may block NKp46, it was further unknown whether cytotoxicity could be mediated by NKp46. We therefore investigated whether the bispecific protein format could induce NKp46 triggering, and whether it would induce NKp46 agonism in the absence of target cells, which could lead to inappropriate NK activation distant from the target and/or decreased overall activity toward target cells.

A new bispecific protein format was developed as a single chain protein which binds to FcRn but not FcγR. Additionally, multimeric proteins that comprise two or three polypeptide chains, wherein the Fc domain remains monomeric, were developed that are compatible for use with antibody variable regions that do not maintain binding to their target when converted to scFv format. The latter formats can be used conveniently for antibody screening; by incorporating at least one binding region as a F(ab) structure, any anti-target (e.g. anti-tumor) antibody variable region can be directly expressed in a bispecific construct as the F(ab) format within the bispecific protein and tested, irrespective of whether the antibody would retain binding as an scFv, thereby simplifying screening and enhancing the number of antibodies available. These formats in which the Fc domain remains monomeric have the advantage of maintaining maximum conformational flexibility and as shown infra may permit optimal binding to NKp46 or target antigens.

Different constructs were made for use in the preparation of bispecific antibodies using the variable domains from the scFv specific for tumor antigen CD19 described in Example 2-1, and different variable regions from antibodies specific for the NKp46 receptor identified in Example 1. A construct was also made using as the anti-NKp46 the variable regions from a commercially available antibody Bab281 (mIgG1, available commercially from Beckman Coulter, Inc. (Brea, Calif., USA) (see also Pessino et al, *J. Exp. Med,* 1998, 188 (5): 953-960 and Sivori et al, *Eur J Immunol,* 1999. 29:1656-1666) specific for the NKp46 receptor.

In order for the Fc domain to remain monomeric in single chain polypeptides or in multimers in which only one chain had an Fc domain, CH3-CH3 dimerization was prevented through two different strategies: (1) through the use of CH3 domain incorporating specific mutations (EU numbering), i.e., L351K, T366S, P395V, F405R, T407A and K409Y; or (2) through the use of a tandem CH3 domain in which the tandem CH3 domains are separated by a flexible linker associated with one another, which prevents interchain CH3-CH3 dimerization. The DNA and amino acid sequences for the monomeric CH2-CH3 Fc portion containing the above-identified point mutations were the same as in Example 2-1. The DNA and amino acid sequences for the monomeric CH2-CH3-linker-CH3 Fc portion with tandem CH3 domains are shown in FIGS. 2A-2D.

The light chain and heavy chain DNA and amino acid sequences for the anti-CD19 scFv were also the same as in Example 2-1. Proteins were cloned, produced and purified as in Example 2-1. Shown below are the light chain and heavy chain DNA and amino acid sequences for different anti-NKp46 scFvs.

TABLE 1

Amino acid sequences of different anti-NKp46 scFvs

| scFv anti-NKp46 | scFV sequence (VHVK)/-stop |
|---|---|
| NKp46-1 | STGSQVQLQQSGPELVKPGASVKMSCKASGYTFTDYVINWGKQRSGQ GLEWIGEIYPGSGTNYYNEKFKAKATLTADKSSNIAYMQLSSLTSEDSAV YFCARRGRYGLYAMDYWGQGTSVTVSSVEGGSGGSGGSGGSGGVDD IQMTQTTSSLSASLGDRVTISCRASQDISNYLNWYQQKPDGTVKLLIYYT SRLHSGVPSRFSGSGSGTDYSLTINNLEQEDIATYFCQQGNTRPWTFG GGTKLEIK- (SEQ ID NO: 119) |
| NKp46-2 | STGSEVQLQESGPGLVKPSQSLSLTCTVTGYSITSDYAWNWIRQFPGNK LEWMGYITYSGSTSYNPSLESRISITRDTSTNQFFLQLNSVTTEDTATYY CARGGYYGSSWGVFAYWGQGTLVTVSAVEGGSGGSGGSGGSGGVD DIQMTQSPASLSASVGETVTITCRVSENIYSYLAWYQQKQGKSPQLLVY NAKTLAEGVPSRFSGSGSGTQFSLKINSLQPEDFGSYYCQHHYGTPWT FGGGTKLEIK- (SEQ ID NO: 120) |
| NKp46-3 | STGSEVQLQQSGPELVKPGASVKISCKTSGYTFTEYTMHWVKQSHGKS LEWIGGISPNIGGTSYNQKFKGKATLTVDKSSSTAYMELRSLTSEDSAVY YCARRGGSFDYWGQGTTLTVSSVEGGSGGSGGSGGSGGVDDIVMTQ SPATLSVTPGDRVSLSCRASQSISDYLHWYQQKSHESPRLLIKYASQSIS GIPSRFSGSGSGSDFTLSINSVEPEDVGVYYCQNGHSFPLTFGAGTKLE LK- (SEQ ID NO: 121) |
| NKp46-4 | STGSQVQLQQSAVELARPGASVKMSCKASGYTFTSFTMHWVKQRPGQ GLEWIGYINPSSGYTEYNQKFKDKTTLTADKSSSTAYMQLDSLTSDDSA VYYCVRGSSRGFDYWGQGTLVTVSAVEGGSGGSGGSGGSGGVDDIQ MIQSPASLSVSVGETVTITCRASENIYSNLAWFQQKQGKSPQLLVYAATN LADGVPSRFSGSGSGTQYSLKINSLQSEDFGIYYCQHFWGTPRTFGGG TKLEIK- (SEQ ID NO: 122) |
| NKp46-6 | STGSQVQLQQPGSVLVRPGASVKLSCKASGYTFTSSWMHWAKQRPGQ GLEWIGHIHPNSGISNYNEKFKGKATLTVDTSSSTAYVDLSSLTSEDSAV YYCARGGRFDDWGAGTTVTVSSVEGGSGGSGGSGGSGGVDDIVMTQ SPATLSVTPGDRVSLSCRASQSISDYLHWYQQKSHESPRLLIKYASQSIS GIPSRFSGSGSGSDFTLSINSVEPEDVGVYYCQNGHSFLMYTFGGGTKL EIK- (SEQ ID NO: 123) |
| NKp46-9 | STGSDVQLQESGPGLVKPSQSLSLTCTVTGYSITSDYAWNWIRQFPGNK LEWMGYITYSGSTNYNPSLKSRISITRDTSKNQFFLQLNSVTTEDTATYY CARCWDYALYAMDCWGQGTSVTVSSVEGGSGGSGGSGGSGGVDDIQ MTQSPASLSASVGETVTITCRTSENIYSYLAWCQQKQGKSPQLLVYNAK TLAEGVPSRFSGSGSGTHFSLKINSLQPEDFGIYYCQHHYDTPLTFGAG TKLELK- (SEQ ID NO: 124) |
| Bab281 | STGSQIQLVQSGPELQKPGETVKISCKASGYTFTNYGMNWVKQAPGKG LKWMGWINTNTGEPTYAEEFKGRFAFSLETSASTAYLQINNLKNEDTAT YFCARDYLYYFDYWGQGTTLTVSSVEGGSGGSGGSGGSGGVDNIVMT QSPKSMSMSVGERVTLTCKASENVVTYVSWYQQKPEQSPKLLIYGASN |

TABLE 1-continued

Amino acid sequences of different anti-NKp46 scFvs scFv
anti-NKp46 scFV sequence (VHVK)/-stop

RYTGVPDRFTGSGSATDFTLTISSVQAEDLADYHCGQGYSYPYTFGGG
TKLEIK- (SEQ ID NO: 125)

TABLE 2A

DNA sequences corresponding to different anti-NKp46 scFvs

| scFv anti-NKp46 | scFV sequences |
|---|---|
| NKp46-1 | SEQ ID NO: 126 |
| NKp46-2 | SEQ ID NO: 127 |
| NKp46-3 | SEQ ID NO: 128 |
| NKp46-4 | SEQ ID NO: 129 |
| NKp46-6 | SEQ ID NO: 130 |
| NKp46-9 | SEQ ID NO: 131 |
| Bab281 | SEQ ID NO: 132 |

Format 1 (F1) (Anti-CD19-IgG1-Fcmono-Anti-NKp46 (scFv))

The domain structure of Format 1 (F1) is shown in FIG. 2A. A bispecific Fc-containing polypeptide was constructed based on a scFv specific for the tumor antigen CD19 (anti-CD19 scFv) and an scFV specific for the NKp46 receptor. The polypeptide is a single chain polypeptide having domains arranged (N- to C-termini) as follows: $(V_K-V_H)^{anti-CD19}$ CH2-CH3-$(V_H-V_K)^{anti-NKp46}$ A DNA sequence coding for a CH3/VH linker peptide having the amino acid sequence STGS was designed in order to insert a specific SalI restriction site at the CH3-$V_H$ junction. The domain arrangement of the final polypeptide in shown in FIG. 2 (the star in the CH2 domain indicates an optional N297S mutation), where the anti-CD3 scFv is replaced by an anti-NKp46 scFv. The $(V_K-V_H)$ units include a linker between the $V_H$ and $V_K$ domains. Proteins were cloned, produced and purified as in Example 2-1. The amino acid sequences of the bispecific polypeptides (complete sequence (mature protein)) are shown in the corresponding SEQ ID NOS listed in the Table 2B below.

TABLE 2B

| Sequence | SEQ ID NO |
|---|---|
| CD19-F1-NKp46-1 | 133 |
| CD19-F1-NKp46-2 | 134 |
| CD19-F1-NKp46-3 | 135 |
| CD19-F1-NKp46-4 | 136 |
| CD19-F1-NKp46-6 | 137 |
| CD19-F1-NKp46-9 | 138 |
| CD19-F1-Bab281 | 139 |

Format 2 (F2): CD19-F2-NKp46-3

The domain structure of F2 polypeptides is shown in FIG. 2A. The DNA and amino acid sequences for the monomeric CH2-CH3 Fc portion were as in Example 2-1 and it similarly contains CH3 domain mutations (the mutations (EU numbering) L351K, T366S, P395V, F405R, T407A and K409Y. The heterodimer is made up of:

(1) a first (central) polypeptide chain having domains arranged as follows (N- to C-termini):

$(V_K-V_H)^{anti-CD19}$CH2-CH3-$V_H^{anti-NKp46}$—CH1 and (2) a second polypeptide chain having domains arranged as follows (N- to C-termini): $VK^{anti-NIKP46}$-CK.

The $(V_K-V_H)$ unit was made up of a $V_H$ domain, a linker and a $V_K$ cunit (i.e. an scFv). As with other formats of the inventive bispecific polypeptides, the DNA sequence coded for a CH3/VH linker peptide having the amino acid sequence STGS designed in order to insert a specific SalI restriction site at the CH3-VH junction. Proteins were cloned, produced and purified as in Example 2-1. The amino acid sequences for the first and second chains of the F2 protein are shown in SEQ ID NO: 140 and 141.

Format 3 (F3): CD19-F3-NKp46-3

The domain structure of F3 polypeptides is shown in FIG. 2A. The DNA and amino acid sequences for the CH2-CH3 Fc portion comprised a tandem CH3 domain in which the two CH3 domains on the same polypeptide chain associated with one another, thereby preventing dimerization between different bispecific proteins.

The single chain polypeptide has domains arranged (N- to C-termini) as follows: $(V_K-V_H)^{anti-CD19}$ CH2-CH3-CH3-$(V_H-V_K)^{anti-NKp46}$.

The $(V_K-V_H)$ units were made up of a $V_H$ domain, a linker and a $V_K$ unit (scFv). Proteins were cloned, produced and purified as in Example 2-1. Bispecific protein was purified from cell culture supernatant by affinity chromatography using prot-A beads and analyzed and purified by SEC. The protein showed a high production yield of 3.4 mg/L and the purified proteins exhibited a simple SEC profile. The amino acid sequence for the F3 protein is shown in SEQ ID NO: 142.

Format 4 (F4): CD19-F4-NKp46-3

The domain structure of F4 polypeptides is shown in FIG. 2A. The DNA and amino acid sequences for the CH2-CH3 Fc portion comprised a tandem CH3 domain as in Format F3, and additionally comprise a N297S mutation which prevents N-linked glycosylation and abolishes FcγR binding. Proteins were cloned, produced and purified as in Example 2-1. Bispecific proteins was purified from cell culture supernatant by affinity chromatography using prot-A beads and analyzed and purified by SEC. The protein showed a good production yield of 1 mg/L and the purified proteins exhibited a simple SEC profile. The amino acid sequence for the F4 protein with NKp46-3 variable domains is shown in SEQ ID NO: 143.

Format 8 (F8)

Figure 2B:
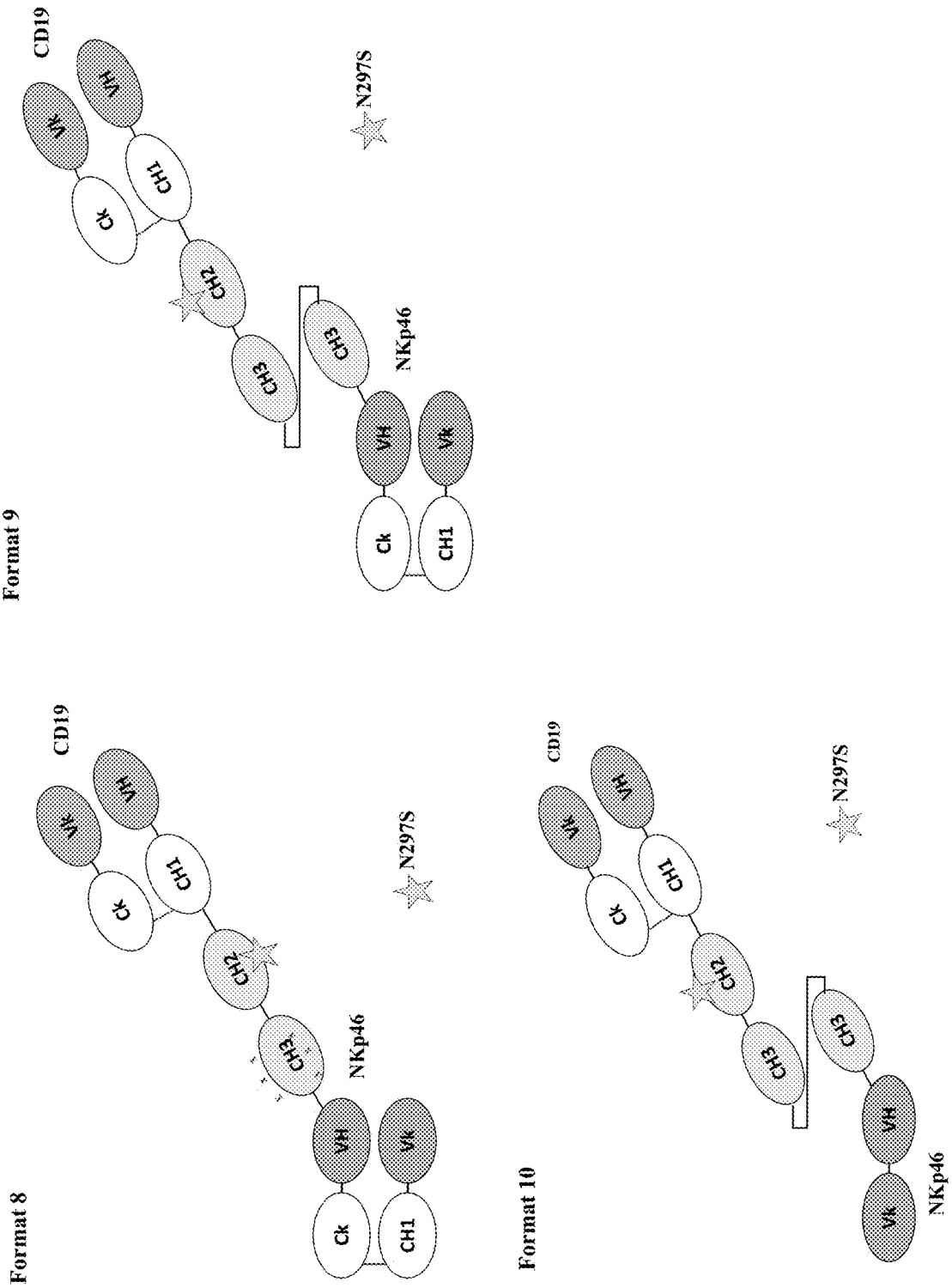

The domain structure of F8 polypeptides is shown in FIG. 2B. The DNA and amino acid sequences for the monomeric CH2-CH3 Fc portion were as in Format F2 and it similarly contains CH3 domain mutations (the mutations (EU numbering) L351K, T366S, P395V, F405R, T407A and K409Y, as well as a N297S mutation which prevents N-linked glycosylation and moreover abolishes FcγR binding. Three variants of F8 proteins were produced: (a) one wherein the cysteine residues in the hinge region were left intact (wild-type, referred to as F8A), (b) a second wherein the cysteine residues in the hinge region were replaced by serine residues (F8B), and (c) a third including a linker sequence GGGSS replacing residues DKTHTCPPCP in the hinge (F8C). Variants F8B and F8C provided production advantages as these versions avoided the formation of homodimers of the central chain. This heterotrimer is made up of;

(1) a first (central) polypeptide chain having domains arranged as follows (N- to C-termini):

$V_H^{anti-CD19}$-CH1-CH2-CH3-$VH^{anti-NKP46}$-$C_K$;

and (2) a second polypeptide chain having domains arranged as follows (N- to C-termini): $VK^{anti-NKp46}$-CH1;

and (3) a third polypeptide chain having domains arranged as follows (N- to C-termini):

$V_K^{anti-CD19}$-$C_K$.

Proteins were cloned, produced and purified as in Example 2-1. Bispecific proteins was purified from cell culture supernatant by affinity chromatography using prot-A beads and analyzed and purified by SEC. The protein showed a high production yield of 3.7 mg/L (F8C) and the purified proteins again exhibited a simple SEC profile. The amino acid sequences of the three chains of the F8 protein (C variant) with NKp46-3 variable regions are shown in SEQ ID NOS: 144, 145 and 146.

Format 9 (F9): CD19-F9-NKp46-3

The F9 polypeptide is a trimeric polypeptide having a central polypeptide chain and two polypeptide chains each of which associate with the central chain via CH1-CK dimerization. The domain structure of the trimeric F9 protein is shown in FIG. 2B, wherein the bonds between the CH1 and CK domains are interchain disulfide bonds. The two antigen binding domains have a F(ab) structure permitting the use of these antibodies irrespective of whether they remain functional in a scFv format. The DNA and amino acid sequences for the CH2-CH3 Fc portion comprise a tandem CH3 domain as in Format F4 and comprise a CH2 domain comprising a N297S substitution. Three variants of F9 proteins were produced: (a) a first wherein the cysteine residues in the hinge region left intact (wild-type, referred to as F9A), (b) a second wherein the cysteine residues in the hinge region were replaced by serine residues (F9B), and (c) a third containing a linker sequence GGGSS which replaces residues DKTHTCPPCP in the hinge (F9C). Variants F9B and F9C provided advantages in production by avoiding the formation of homodimers of the central chain. The heterotrimer is made up of:

(1) a first (central) polypeptide chain having domains arranged as follows (N- to C-termini):

$V_H^{anti-CD19}$-CH1-CH2-CH3-CH3-$V_H^{anti-NKp46}$-$C_K$ and (2) a second polypeptide chain having domains arranged as follows (N- to C-termini): $V_K^{anti-N\backslash1"46}$-CH1 and (3) a third polypeptide chain having domains arranged as follows (N- to C-termini):

$V_K^{anti-CD19}$-$C_K$.

Proteins were cloned, produced and purified as in Example 2-1. Bispecific proteins was purified from cell culture supernatant by affinity chromatography using prot-A beads and analyzed and purified by SEC. The protein showed a high production yield of 8.7 mg/L (F9A) and 3.0 mg/L (F9B), and the purified proteins again exhibited a simple SEC profile.

The amino acid sequences of the three chains of the F9 protein variant F9A are shown in the SEQ ID NOS: 147, 148 and 149. The amino acid sequences of the three chains of the F9 protein variant F9B are shown in the SEQ ID NOS: 150, 151 and 152. The amino acid sequences of the three chains of the F9 protein variant F9C are shown in the SEQ ID NOS: 153, 154 and 155.

Format 10 (F10): CD19-F10-NKp46-3

The F10 polypeptide is a dimeric protein having a central polypeptide chain and a second polypeptide chain which associates with the central chain via CH1-CK dimerization. The domain structure of the dimeric F10 protein is shown in FIG. 2B wherein the bonds between the CH1 and CK domains are interchain disulfide bonds. One of the two antigen binding domains has a Fab structure, and the other is a scFv. The DNA and amino acid sequences for the CH2-CH3 Fc portion comprise a tandem CH3 domain as shown in Format F4 and comprise a CH2 domain containing a N297S substitution. Three variants of F10 proteins were also produced: (a) a first wherein the cysteine residues in the hinge region were left intact (wild-type, referred to as F10A), (b) a second wherein the cysteine residues in the hinge region were replaced by serine residues (F10B), and (c) a third containing a linker sequence GGGSS replacing residues DKTHTCPPCP in the hinge (F100). Variants F10B and F100 provided advantages in production as they avoid the formation of homodimers of the central chain. The ($V_K$-$V_H$) unit was made up of a $V_H$ domain, a linker and a $V_K$ unit (scFv). The heterodimer is made up of:

(1) a first (central) polypeptide chain having domains arranged as follows (N- to C-termini):

$V_H^{anti-CD19}$-CH1-CH2-CH3-CH3-$(V_H$-$V_K)^{anti-NKp46}$ and (2) a second polypeptide chain having domains arranged as follows (N- to C-termini): $V_K^{anti-CD19}$-$C_K$.

These proteins were cloned, produced and purified as in Example 2-1. Bispecific proteins was purified from cell culture supernatant by affinity chromatography using prot-A beads and analyzed and purified by SEC. The protein showed a good production yield of 2 mg/L (F10A) and the purified proteins again exhibited a simple SEC profile. The amino acid sequences of the two chains of the F10A protein variant are shown in SEQ ID NOS: 156 (second chain) and 157 (first chain). The amino acid sequences of the two chains of the F10B protein variant are shown in SEQ ID NOS: 158 (second chain) and 159 (first chain). The amino acid sequences of the two chains of the F10C protein variant are shown in the SEQ ID NOS: 160 (second chain) and 161 (first chain).

Format 11 (F11): CD19-F11-NKp46-3

The domain structure of F11 polypeptides is shown in FIG. 2C. The heterodimeric protein is similar to F10 except that the structures of the antigen binding domains are reversed. One of the two antigen binding domains has a Fab-like structure, and the other is a scFv. The heterodimer is made up of:

(1) a first (central) polypeptide chain having domains arranged as follows (N- to C-termini):

$(V_K$-$V_H)^{anti-CD19}$-CH2-CH3-CH3-$VH^{anti-NKp46}$-$C_K$ and (2) a second polypeptide chain having domains arranged as follows (N- to C-termini): $V_K^{anti-NKp46}$-CH1.

Proteins were cloned, produced and purified as in Example 2-1. Bispecific proteins was purified from cell culture supernatant by affinity chromatography using prot-A beads and analyzed and purified by SEC. The protein showed a good production yield of 2 mg/L and the purified proteins similarly exhibited a simple SEC profile. The amino acid sequences of the two chains of the F11 protein are shown in SEQ ID NO: 162 (chain 1) and SEQ ID NO: 163 (chain 2).

Format 12 (F12): CD19-F12-NKp46-3

The domain structure of the dimeric F12 polypeptides is shown in FIG. 2C, wherein the bonds between the CH1 and CK domains are disulfide bonds. The heterodimeric protein is similar to F11 but the CH1 and CK domains within the F(ab) structure are inversed. The heterodimer is made up of:

(1) a first (central) polypeptide chain having domains arranged as follows (N- to C-termini):

$(V_K-V_H)^{anti-CD19}$CH2-CH3-CH3-$V_H^{anti-NKp46}$—CH1 and (2) a second polypeptide chain having domains arranged as follows (N- to C-termini): $V_K^{anti-NKp46}$-CK.

Proteins were cloned, produced and purified as in Example 2-1. Bispecific proteins were purified from the cell culture supernatant by affinity chromatography using prot-A beads and analyzed and purified by SEC. The protein showed a good production yield of 2.8 mg/L and the purified proteins similarly exhibited a simple SEC profile. The amino acid sequences of the two chains of the F12 protein are shown in SEQ ID NO: 164 (chain 1) and SEQ ID NO: 165 (chain 2).

Format 17 (F17): CD19-F17-NKp46-3

The domain structure of the trimeric F17 polypeptides is shown in FIG. 2C, wherein the bonds between the CH1 and CK domains are disulfide bonds. The heterodimeric protein is similar to F9 but the $V_H$ and $V_K$ domains, and the CH1 and CK, domains within the C-terminal F(ab) structure are each respectively inversed with their partner. The heterotrimer is made up of:

(1) a first (central) polypeptide chain having domains arranged as follows (N- to C-termini):

$V_H^{anti-CD19}$-CH1-CH2-CH3-CH3-$V_K^{anti-NKp46}$-CH1;

and (2) a second polypeptide chain having domains arranged as follows (N- to C-termini): $V_H^{anti-NKp46}$-CK;

and (3) a third polypeptide chain having domains arranged as follows (N- to C-termini):

$V_K^{anti-CD19}$-CK.

Additionally, three variants of F17 proteins were produced: (a) a first where the cysteine residues in the hinge region were left intact (wild-type, referred to as F17A), (b) a second wherein the cysteine residues in the hinge region were replaced by serine residues (F10B, and (c) a third containing a linker sequence GGGSS which replaces residues DKTHTCPPCP in the hinge (F17C). Proteins were cloned, produced and purified as in Example 2-1. The amino acid sequences of the three chains of the F17B protein are shown in SEQ ID NOS: 166, 167 and 168.

Example 4

Bispecific NKp46 Antibody Formats with Dimeric Fc Domains

New protein constructions with dimeric Fc domains were developed that share many of the advantages of the monomeric Fc domain proteins of Example 3 but bind to FcRn with greater affinity. Different protein formats were produced that either had low or substantially lack of binding to FcγR (including CD16) or which had binding to FcγRs (including CD16), e.g. the binding affinity to human CD16 was within 1-log of that of wild-type human IgG1 antibodies, as assessed by SPR (e.g. see methods of Example 16. The different polypeptide formats were tested and compared to investigate the functionality of heterodimeric proteins comprising a central chain with a ($V_H$-(CH1/CK)-CH2-CH3-) unit or a ($V_K$-(CH1 or CK)-CH2-CH3-) unit. One of both of the CH3 domains are fused, optionally via intervening amino acid sequences or domains, to a variable domain(s) (a single variable domain that associates with a variable domain on a separated polypeptide chain, a tandem variable domain (e.g., an scFv), or a single variable domain that is capable of binding antigen as a single variable domain). The two chains associate by CH1-CK dimerization to form disulfide linked dimers, or if associated with a third chain, to form trimers.

Different constructs were made for use in the preparation of a bispecific antibody using the variable domains DNA and amino acid sequences derived from the scFv specific for tumor antigen CD19 described in Example 2-1 and different variable regions from antibodies specific for NKp46 identified in Example 1. Proteins were cloned, produced and purified as in Example 2-1. Domains structures are shown in FIGS. 2A-6D.

Format 5 (F5): CD19-F5-NKp46-3

The domain structure of the trimeric F5 polypeptide is shown in FIG. 2D, wherein the interchain bonds between hinge domains (indicated in the figures between CH1/CK and CH2 domains on a chain) and interchain bonds between the CH1 and CK domains are interchain disulfide bonds. The heterotrimer is made up of:

(1) a first (central) polypeptide chain having domains arranged as follows (N- to C-termini):

$V_H^{anti-CD19}$-CH1-CH2-CH3-$V_H^{anti-NKp46}$-CK;

and (2) a second polypeptide chain having domains arranged as follows (N- to C-termini): $V_K^{anti-CD19}$-CK-CH2-CH3;

and (3) a third polypeptide chain having domains arranged as follows (N- to C-termini):

$V_K^{anti-NKp46}$-CH1.

Proteins were cloned, produced and purified as in Example 2-1. Bispecific proteins was purified from cell culture supernatant by affinity chromatography using prot-A beads and analyzed and purified by SEC. The protein showed a high production yield of 37 mg/L and the purified proteins again exhibited a simple SEC profile. The amino acid sequences of the three polypeptide chains are shown in SEQ ID NOS 169 (second chain), 170 (first chain) and 171 (third chain).

Format 6 (F6): CD19-F6-NKp46-3

The domain structure of heterotrimeric F6 polypeptides is shown in FIG. 2D. The F6 protein is the same as F5, but contains a N297S substitution to avoid N-linked glycosylation. Proteins were cloned, produced and purified as in Example 2-1. Bispecific proteins were purified from cell culture supernatant by affinity chromatography using prot-A beads and analyzed and purified by SEC. The protein showed a high production yield of 12 mg/L and the purified proteins exhibited a simple SEC profile. The amino acid sequences of the three polypeptide chains are shown in SEQ ID NOS: 172 (second chain), 173 (first chain) and 174 (third chain).

Format 7 (F7): CD19-F7-NKp46-3

The domain structure of heterotrimeric F7 polypeptides is shown in FIG. 2D. The F7 protein is the same as F6, except for cysteine to serine substitutions in the CH1 and CK domains that are linked at their C-termini to Fc domains, in order to prevent formation of a minor population of dimeric species of the central chain with the VK$^{anti-NKp46}$-CH1 chain. Proteins were cloned, produced and purified as in Example 2-1. Bispecific proteins were purified from the cell culture supernatant by affinity chromatography using prot-A beads and analyzed and purified by SEC. The protein showed a high production yield of 11 mg/L and the purified proteins exhibited a simple SEC profile. The amino acid sequences of the three polypeptide chains are shown in SEQ ID NOS: 175 (second chain), 176 (first chain) and 177 (third chain).

Format 13 (F13): CD19-F13-NKp46-3

The domain structure of the dimeric F13 polypeptide is shown in FIG. 2D, wherein the interchain bonds between hinge domains (indicated between CH1/CK and CH2 domains on a chain) and interchain bonds between the CH1 and CK domains are interchain disulfide bonds. The heterodimer is made up of:

(1) a first (central) polypeptide chain having domains arranged as follows (N- to C-termini):

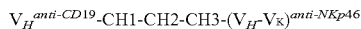

V$_H$$^{anti-CD19}$-CH1-CH2-CH3-(V$_H$-VK)$^{anti-NKp46}$ and (2) a second polypeptide chain having domains arranged as follows (N- to C-termini): VK$^{anti-CD19}$-CK-CH2-CH3.

The (V$_H$-VK) unit was made up of a V$_H$ domain, a linker and a VK unit (scFv).

Proteins were cloned, produced and purified as in Example 2-1. Bispecific proteins were purified from the cell culture supernatant by affinity chromatography using prot-A beads and analyzed and purified by SEC. The protein showed a high production yield of 6.4 mg/L and the purified proteins exhibited a simple SEC profile. The amino acid sequences of the two polypeptide chains are shown in SEQ ID NOS: 178 (second chain) and 179 (first chain).

Format 14 (F14): CD19-F14-NKp46-3

The domain structure of the dimeric F14 polypeptide is shown in FIG. 2E. The F14 polypeptide is a dimeric polypeptide which shares the structure of the F13 format, but instead of a wild-type Fc domain (CH2-CH3), the F14 bispecific format has CH2 domain mutations N297S to abolish N-linked glycosylation. Proteins were cloned, produced and purified as in Example 2-1. Bispecific proteins were purified from cell culture supernatant by affinity chromatography using prot-A beads and analyzed and purified by SEC. The protein showed a high production yield of 2.4 mg/L and the purified proteins exhibited a simple SEC profile. The amino acid sequences of the two polypeptide chains are shown in SEQ ID NOS: 180 (second chain) and 181 (first chain).

Format 15 (F15): CD19-F15-NKp46-3

The domain structure of the trimeric F15 polypeptides is shown in FIG. 2E. The F15 polypeptide is a dimeric polypeptide which shares the structure of the F6 format, but differs by inversion of the N-terminal V$_H$-CH1 and VK-CK units between the central and second chains. Proteins were cloned, produced and purified as in Example 2-1. Bispecific proteins were purified from the cell culture supernatant by affinity chromatography using prot-A beads and analyzed and purified by SEC. The protein showed a good production yield of 0.9 mg/L and the purified proteins possessed a simple SEC profile. The amino acid sequences of the three polypeptide chains are shown in SEQ ID NOS: 182 (second chain), 183 (first chain) and 184 (third chain).

Format 16 (F16): CD19-F16-NKp46-3

The domain structure of the trimeric F16 polypeptide is shown in FIG. 2E. The F16 polypeptide is a dimeric polypeptide which shares the structure of the F6 format, but differs by inversion of the C-terminal V$_H$-CK and VK-CH1 units between the central and second chains. Proteins were cloned, produced and purified as in Example 2-1. The amino acid sequences of the three polypeptide chains are shown in SEQ ID NOS: 185 (second chain), 186 (first chain) and 187 (third chain).

Format T5 (T5)

Figure 2F:
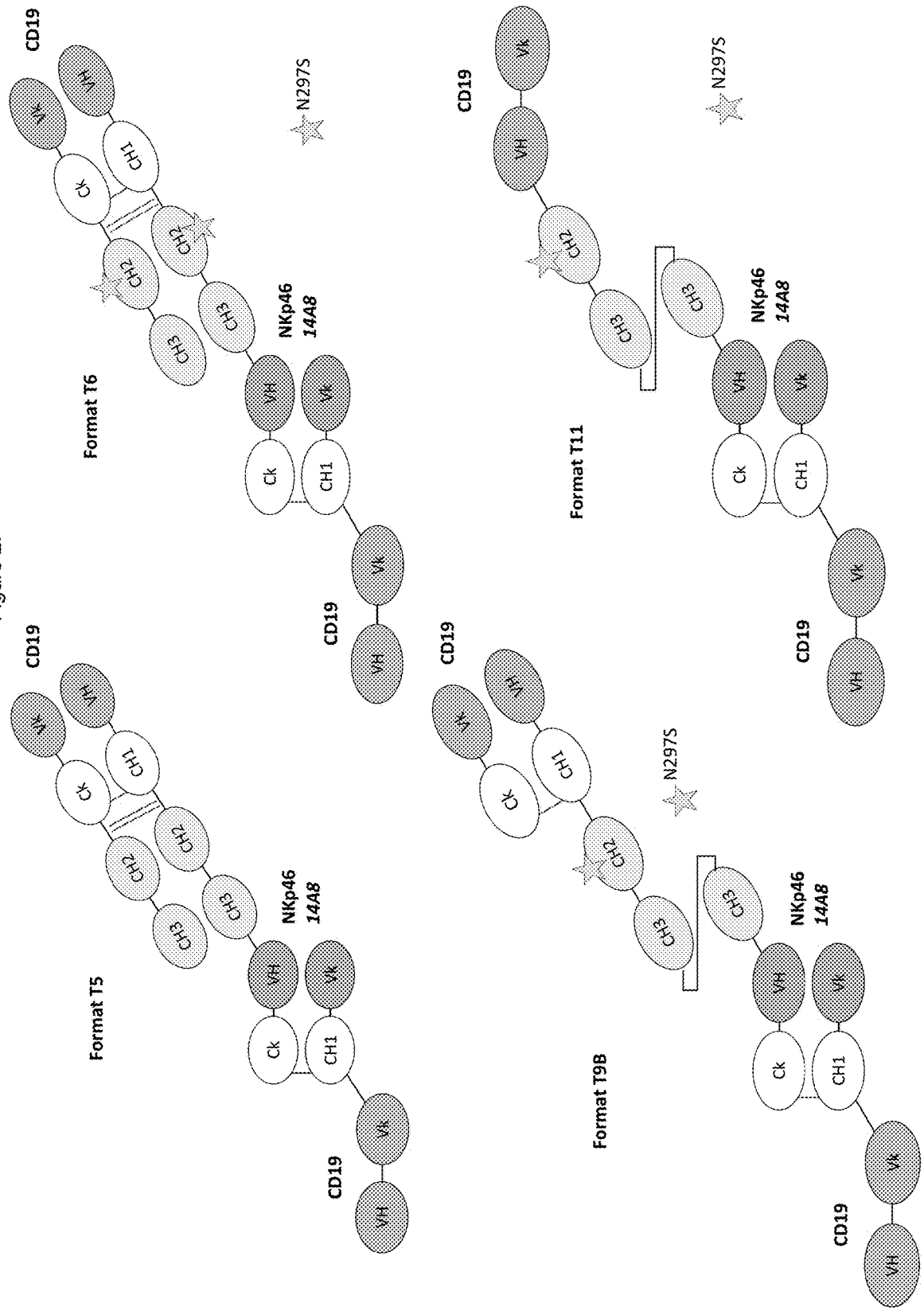

The domain structure of a trimeric T5 polypeptide is shown in FIG. 2F. The T5 polypeptide is a trimeric polypeptide which shares the structure of the F5 format, but differs by fusion of an scFv unit at the C-terminus of the third chain (the chain lacking the Fc domain). This protein will therefore have two antigen binding domains for antigens of interest, and one for NKp46, and will bind CD16 via its Fc domain. Proteins were cloned, produced and purified as in Example 2-1. The T5 protein had two antigen binding domains that bind human CD20, originating from different antibodies (and binding to different epitopes on CD20). The first anti-CD20 ABD contained the V$_H$ and V$_L$ of the parent antibody GA101 (GAZYVA®, Gazyvaro®, obinutuzumab, Roche Pharmaceuticals). The second anti-CD20 ABD contained the V$_H$ and V$_L$ of the parent antibody rituximab (Rituxan®, Mabthera®, Roche Pharmaceuticals). The third antigen binding domain binds human NKp46. The amino acid sequences of the three chains of the T5 protein are shown below (Rituximab sequences are in bold and underlined, anti-GA101 sequences are underlined, anti-NKp46 sequences are in italics).

GA101-T5-Ritux-NKp46

```
Polypeptide 1
                                      (SEQ ID NO: 188)
QVQLVQSGAEVKKPGSSVKVSCKASGYAFSYSWINWVRQAPGQGLEWMGR

IFPGDGDTDYNGKFKGRVTITADKSTSTAYMELSSLRSEDTAVYYCARNV

FDGYWLVYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGST

GSQVQLQQPGAELVKPGASVKMSCKASGYTFTSYNMHWVKQTPGRGLEWI

GAIYPGNGDTSYNQKFKGKATLTADKSSSTAYMQLSSLTSEDSAVYYCAR

STYYGGDWYFNVWGAGTTVTVSARTVAAPSVFIFPPSDEQLKSGTASVVC

LLNNFYPREAKVQWKVDNALQSGNSQESVTEQDSKDSTYSLSSTLTLSKA

DYEKHKVYACEVTHQGLSSPVTKSFNRGEC-
```

Polypeptide 2
(SEQ ID NO: 189)
DIVMTQTPLSLPVTPGEPASISCRSSKSLLHSNGITYLYWYLQKPGQSPQ

LLIYQMSNLVSGVPDRFSGSGSGTDFTLKISRVEAEDVGVYYCAQNLELP

YTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGECDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK-

Polypeptide 3:
(SEQ ID NO: 190)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKRVEPKSCDKTHGGSS*SEVQLQQSGPELVKPGASVKISCKTSGYTFTEY*

*TMHWVKQSHGKSLEWIGGISPNIGGTSYNQKFKGKATLTVDKSSSTAYME*

*LRSLTSEDSAVYYCARRGGSFDYWGQGTTLTVSS*VEGGSGGSGGSGGSGG

*VDDIVMTQSPATLSVTPGDRVSLSCRASQSISDYLHWYQQKSHESPRLLI*

*KYASQSISGIPSRFSGSGSGSDFTLSINSVEPEDVGVYYCQNGHSFPLTF*

*GAGTKLELK-*

Format T6 (T6)

The domain structure of the trimeric T6 polypeptide is shown in FIG. 2F. The T6 polypeptide is a trimeric polypeptide which shares the structure of the F6 format, but differs by the fusion of an scFv unit at the C-terminus of the third chain (the chain lacking the Fc domain). This trimeric protein contains two antigen binding domains for antigens of interest, and one for NKp46, and does not bind CD16 via its Fc domain due to the N297 substitution. Proteins were cloned, produced and purified as in Example 2-1. The T6 protein contains two antigen binding domains that bind human CD20. The first anti-CD20 ABD comprises the $V_H$ and $V_L$ of the parent antibody GA101 and the second anti-CD20 ABD comprises the $V_H$ and $V_L$ of rituximab. The amino acid sequences of the three chains of the T6 proteins are shown in SEQ ID NOS: 191, 192 and 193.

Format T98 (T98)

The domain structure of the trimeric T9B polypeptide is shown in FIG. 2F. The T9B polypeptide is a trimeric polypeptide which shares the structure of the F9 format (F9B variant), but differs by the fusion of an scFv unit at the C-terminus of the free CH1 domain (on the third chain). This protein contains two antigen binding domains for antigen of interest, and one for NKp46, but will not bind CD16 via its Fc domain due to the monomeric Fc domain and/or the N297 substitution. Trimeric proteins as above described were cloned, produced and purified as in Example 2-1. The T9B protein had two antigen binding domains that bind human CD20. The first anti-CD20 ABD contained the $V_H$ and $V_L$ of the parent antibody GA101 and the second anti-CD20 ABD contained the $V_H$ and $V_L$ of the parent antibody rituximab. The amino acid sequences of the three chains of the T9B proteins are shown below.

GA101-T9B-Ritux-NKp46

Polypeptide 2:
(SEQ ID NO: 195)
DIVMTQTPLSLPVTPGEPASISCRSSKSLLHSNGITYLYWYLQKPGQSPQ

LLIYQMSNLVSGVPDRFSGSGSGTDFTLKISRVEAEDVGVYYCAQNLELP

YTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC-

Polypeptide 1:
(SEQ ID NO: 194)
QVQLVQSGAEVKKPGSSVKVSCKASGYAFSYSWINWVRQAPGQGLEWMGR

IFPGDGDTDYNGKFKGRVTITADKSTSTAYMELSSLRSEDTAVYYCARNV

FDGYWLVYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTSPPSPAPELLGGPSVFLFPPKPK

DTLMISRTPEVTCVVVDVSHEDPEVKFNWYVDGVEVHNAKTKPREEQYSS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGGG

GGSGGGGSGGGGSGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGSTGSQVQLQQPGAELVKPGASVKMSCKASGY

TFTSYNMHWVKQTPGRGLEWIGAIYPGNGDTSYNQKFKGKATLTADKSSS

TAYMQLSSLTSEDSAVYYCARSTYYGGDWYFNVWGAGTTVTVSARTVAAP

SVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGE

C-

Polypeptide 3 (SEQ ID NO: 196):
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKRVEPKSCDKTHGGSSSEVQLQQSGPELVKPGASVKISCKTSGYTFTEY

TMHWVKQSHGKSLEWIGGISPNIGGTSYNQKFKGKATLTVDKSSSTAYME

LRSLTSEDSAVYYCARRGGSFDYWGQGTTLTVSSVEGGSGGSGGSGGSGG

VDDIVMTQSPATLSVTPGDRVSLSCRASQSISDYLHWYQQKSHESPRLLI

KYASQSISGIPSRFSGSGSGSDFTLSINSVEPEDVGVYYCQNGHSFPLTF

GAGTKLELK-

Format T11 (T1): CD19-T11-NKp46-3

The domain structure of the dimeric T11 polypeptide is shown in FIG. 2F. The T11 polypeptide is a trimeric polypeptide which shares the structure of the F11 format, but differs by the fusion of an scFv unit at the C-terminus of the free CH1 domain. This dimeric protein contains two antigen binding domains for antigen of interest, and one for NKp46, and does not bind CD16 via its Fc domain due to the monomeric Fc domain and/or the N297 substitution. Proteins were cloned, produced and purified as in Example 2-1. The T11 protein contains two antigen binding domains that bind human CD20. The first anti-CD20 ABD contained the $V_H$ and $V_L$ of the parent antibody GA101 and the second anti-CD20 ABD contained the $V_H$ and $V_L$ of rituximab. The amino acid sequences of the two chains of the T11 protein are shown below.

GA101-T11-Ritux-NKp46

```
Polypeptide 1 (SEQ ID NO: 197):
DIVMTQTPLSLPVTPGEPASISCRSSKSLLHSNGITYLYWYLQKPGQSPQ

LLIYQMSNLVSGVPDRFSGSGSGTDFTLKISRVEAEDVGVYYCAQNLELP

YTFGGGTKVEIKGGGGSGGGGSGGGGSQVQLVQSGAEVKKPGSSVKVSCK

ASGYAFSYSWINWVROAPGQGLEWMGRIFPGDGDTDYNGKFKGRVTITAD

KSTSTAYMELSSLRSEDTAVYYCARNVFDGYWLVYWGQGTLVTVSSASTK

GPSVFPLAPSSKSTSGGTAALGCLVKDYFPEPVTVSWNSGALTSGVHTFP

AVLQSSGLYSLSSVVTVPSSSLGTQTYICNVNHKPSNTKVDKRVEPKSCD

KTHTSPPSPAPELLGGPSVFLFPPKPKDTLMISRTPEVTCVVVDVSHEDP

EVKFNWYVDGVEVHNAKTKPREEQYSSTYRVVSVLTVLHQDWLNGKEYKC

KVSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQGN

VFSCSVMHEALHNHYTQKSLSLSPGGGGSGGGGSGGGGSGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGSTGS

QVQLQQPGAELVKPGASVKMSCKASGYTFTSYNMHWVKQTPGRGLEWIGA

IYPGNGDTSYNQKFKGKATLTADKSSTAYMQLSSLTSEDSAVYYCARST

YYGGDWYFNVWGAGTTVTVSARTVAAPSVFIFPPSDEQLKSGTASVVCLL

NNFYPREAKVQWKVDNALQSGNSQESVTEQDSKDSTYSLSSTLTLSKADY

EKHKVYACEVTHQGLSSPVTKSFNRGEC-

Polypeptide 2 (SEQ ID NO: 198):
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKRVEPKSCDKTHGGSSSEVQLQQSGPELVKPGASVKISCKTSGYTFTEY

TMHWVKQSHGKSLEWIGGISPNIGGTSYNQKFKGKATLTVDKSSSTAYME

LRSLTSEDSAVYYCARRGGSFDYWGQGTTLTVSSVEGGSGGSGGSGGSGG

VDDIVMTQSPATLSVTPGDRVSLSCRASQSISDYLHWYQQKSHESPRLLI

KYASQSISGIPSRFSGSGSGSDFTLSINSVEPEDVGVYYCQNGHSFPLTF

GAGTKLELK-
```

Example 5

NKp46 Binding Affinity by Bispecific Proteins by Surface Plasmon Resonance (SPR)

Biacore T100 General Procedure and Reagents

SPR measurements were performed on a Biacore T100 apparatus (Biacore GE Healthcare) at 25° C. In all Biacore experiments HBS-EP+(Biacore GE Healthcare) and NaOH 10 mM served as running buffer and regeneration buffer respectively. Sensorgrams were analyzed with Biacore T100 Evaluation software. Protein-A was purchase from (GE Healthcare). Human NKp46 recombinant proteins were cloned, produced and purified at Innate Pharma.

Immobilization of Protein-A

Protein-A proteins were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). Protein-A was diluted to 10 µg/ml in coupling buffer (10 mM acetate, pH 5.6) and injected until the appropriate immobilization level was reached (i.e. 2000 RU). Deactivation of the remaining activated groups was performed using 100 mM ethanolamine pH 8 (Biacore GE Healthcare).

Binding Study

The bispecific proteins were first tested in Format F1 described in Example 2 having different anti-NKp46 variable regions from NKp46-1, NKp46-2, NKp46-3 or NKp46-4 antibodies. Antibodies were next tested as different formats F3, F4, F5, F6, F9, F10, F11, F13, F14 having the anti-NKp46 variable regions from the NKp46-3 antibody, and compared to the NKp46-3 antibody as a full-length human IgG1.

Bispecific proteins at 1 µg/mL were captured onto Protein-A chip and recombinant human NKp46 proteins were injected at 5 µg/mL over captured bispecific antibodies. For blank subtraction, cycles were performed again replacing NKp46 proteins with running buffer.

The Bab281 antibody was separately tested for binding to NKp46 by SPR, and additionally by flow cytometry using a cell line expressing the human NKp46 construct at the cell surface. For FACS screening, the presence of reacting antibodies in supernanants was revealed by Goat anti-mouse polyclonal antibody (pAb) labeled with PE. SPC and FACS results showed that the Bab281 based antibody did not bind the NKp46 cell line or NKp46-Fc proteins. Bab281 lost binding to its target when presented in the bispecific format.

Affinity Study

Monovalent affinity study was done following a regular Capture-Kinetic protocol recommended by the manufacturer (Biacore GE Healthcare kinetic wizard). Seven serial dilutions of human NKp46 recombinant proteins, ranging from 6.25 to 400 nM were sequentially injected over the captured Bi-Specific antibodies and allowed to dissociate for 10 min before regeneration. The entire sensorgram sets were fitted using the 1:1 kinetic binding model.

Results

SPR showed that the bispecific polypeptides of format F1 having the NKp46-1, 2, 3 and 4 scFv binding domains bound to NKp46, while other bispecific polypeptides having the scFv of other anti-NK46 antibodies did not retain NKp46 binding. The binding domains that did not retain binding in monomeric bispecific format initially bound to NKp46 but lost binding upon conversion to the bispecific format. All of the bispecific polypeptides of formats F1, F2 F3, F4, F5, F6, F9, F10, F11, F13, F14 retained binding to NKp46 when using the NKp46-3 variable regions. Monovalent affinities and kinetic association and dissociation rate constants are shown below in the Table 3 below.

TABLE 3

| Bispecific mAb | ka (1/Ms) | kd (1/s) | KD (M) |
| --- | --- | --- | --- |
| CD19-F1-Bab281 | n/a | n/a | n/a (loss of binding) |
| CD19-F1-NKp46-1 | 1.23E+05 | 0.001337 | 1.09E−08 |
| CD19-F1-NKp46-2 | 1.62E+05 | 0.001445 | 8.93E−09 |
| CD19-F1-NKp46-3 | 7.05E+04 | 6.44E−04 | 9.14E−09 |
| CD19-F1-NKp46-4 | 1.35E+05 | 6.53E−04 | 4.85E−09 |
| CD19-F3-NKp46-3 | 3.905E+5 | 0.01117 | 28E−09 |
| CD19-F4-NKp46-3 | 3.678E+5 | 0.01100 | 30E−09 |
| CD19-F5-NKp46-3 | 7.555E+4 | 0.00510 | 67E−09 |
| CD19-F6-NKp46-3 | 7.934E+4 | 0.00503 | 63E−09 |
| CD19-F9A-NKp46-3 | 2.070E+5 | 0.00669 | 32E−09 |
| CD19-F10A-NKp46-3 | 2.607E+5 | 0.00754 | 29E−09 |
| CD19-F11A-NKp46-3 | 3.388E+5 | 0.01044 | 30E−09 |
| CD19-F13-NKp46-3 | 8.300E+4 | 0.00565 | 68E−09 |
| CD19-F14-NKp46-3 | 8.826E+4 | 0.00546 | 62E−09 |
| NKp46-3 IgG1 | 2.224E+5 | 0.00433 | 20E−09 |

Example 6

Engagement of NK Cells Against Daudi Tumor Target with Fc-Containing NKp46×CD19 Bispecific Protein Bispecific antibodies having a monomeric Fc domain and a domain arrangement according to the single chain F1 or dimeric F2 formats described in Example 3, and a NKp46 binding region based on NKp46-1, NKp46-2, NKp46-3 or NKp46-4 were tested for functional ability to direct NK cells to lyse CD19-positive tumor target cells (Daudi, a well characterized B lymphoblast cell line). The F2 proteins additionally included NKp46-9 variable regions which lost binding to NKp46 in the scFv format but which retained binding in the F(ab)-like format of F2.

Briefly, the cytolytic activity of each of (a) resting human NK cells, and (b) human NK cell line KHYG-1 transfected with human NKp46, was assessed in a classical 4-h $^{51}$Cr-release assay in U-bottom 96 well plates. Daudi cells were labelled with $^{51}$Cr (50 μCi (1.85 MBq)/1×10$^6$ cells), then mixed with KHYG-1 transfected with hNKp46 at an effector/target ratio equal to 50 for KHYG-1, and 10 (for F1 proteins) or 8.8 (for F2 proteins) for resting NK cells, in the presence of monomeric bi-specific antibodies at different concentrations. After brief centrifugation and 4 hours of incubation at 37° C., samples of supernatant were removed and transferred into a LumaPlate (Perkin Elmer Life Sciences, Boston, Mass.), and $^{51}$Cr release was measured with a TopCount NXT beta detector (PerkinElmer Life Sciences, Boston, Mass.). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Results

In the KHYG-1 hNKp46 NK experimental model, each bi-specific antibody NKp46-1, NKp46-2, NKp46-3, NKp46-4 or NKp46-9 induced specific lysis of Daudi cells by human KHYG-1 hNKp46 NK cell line compared to negative controls (Human IgG1 isotype control (IC) and CD19/CD3 bi-specific antibodies), thereby showing that these antibodies induce Daudi target cell lysis by KHYG-1 hNKp46 through CD19/NKp46 cross-linking.

Figure 3A:
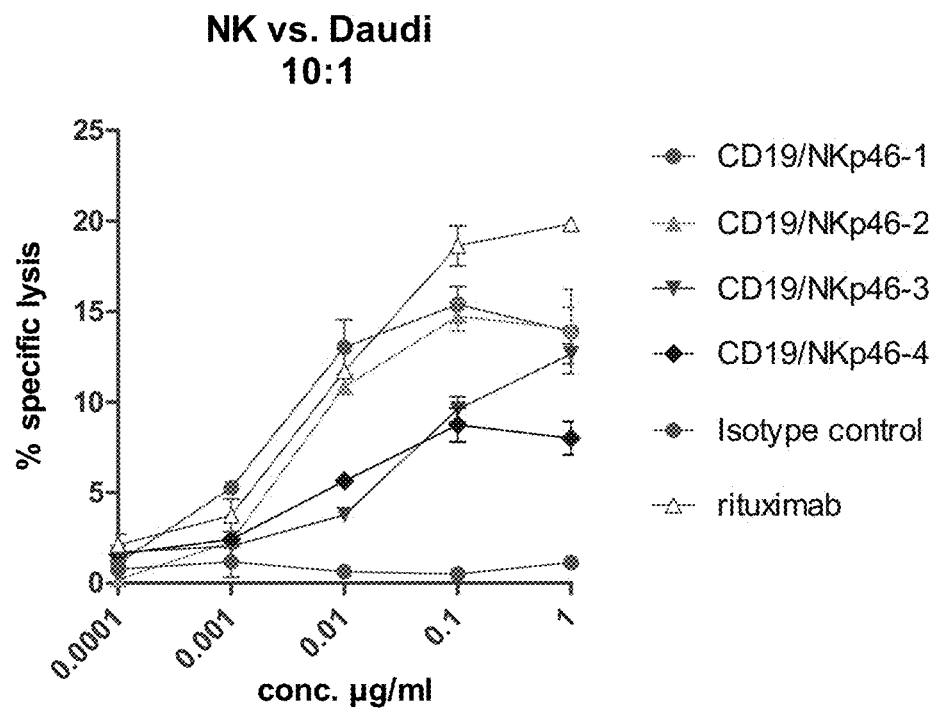
FIGS. 3A and 3B show respectively bispecific F1 and F2 antibodies having NKp46 binding region based on NKp46-1, NKp46-2, NKp46-3 or NKp46-4 are able to direct resting NK cells to their CD19-positive Daudi tumor target cells, while isotype control antibody did not lead to elimination of the Daudi cells. Rituximab (RTX) served as positive control of ADCC, where the maximal response obtained with RTX (at 10 μg/ml in this assay) was 21.6% specific lysis.
Figure 3B:
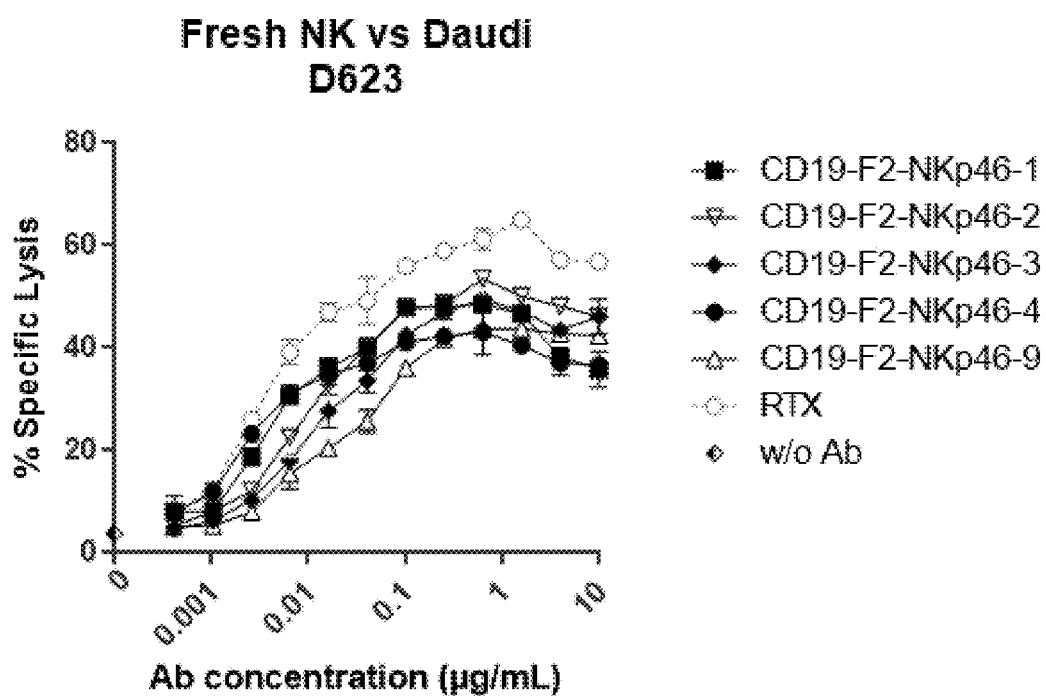

When resting NK cells were used as effectors, each bi-specific antibody NKp46-1, NKp46-2, NKp46-3, NKp46-4 or NKp46-9 again induced specific lysis of Daudi cells by human NK cells compared to negative control (Human IgG1 isotype control (IC) antibody), thereby showing that these antibodies induce Daudi target cell lysis by human NK cells through CD19/NKp46 cross-linking. Rituximab (RTX, chimeric IgG1) was used as a positive control of ADCC (Antibody-Dependent Cell Cytotoxicity) by resting human NK cells. The maximal response obtained with RTX (at 10 μg/ml in this assay) was 21.6% specific lysis illustrating that the bispecific antibodies have high target cell lysis activity. Results for experiments with resting NK cells are shown in FIG. 3A for the single chain F1 proteins and 3B for the dimeric F2 proteins.

Example 7

Comparison with Full Length Anti-NKp46 mAbs and Depleting Anti-Tumor mAbs: Only NKp46×CD19 Bispecific Proteins Prevent Non-Specific NK Activation These studies aimed to investigate whether bispecific antibodies can mediate NKp46-mediated NK activation toward cancer target cells without triggering non-specific NK cell activation.

NKp46×CD19 bispecific proteins having an arrangement according to the F2 format described in Example 3 with anti-NKp46 variable domains from NKp46-1, NKp46-2, NKp46-3, NKp46-4 or NKp46-9 were compared to:
  (a) full-length monospecific anti-NKp46 antibodies (NKp46-3 as human IgG1), and
  (b) the anti-CD19 antibody as a full-length human IgG1 as ADCC inducing antibody comparator.
The experiments further included as controls: rituximab, an anti-CD20 ADCC inducing antibody control for a target antigen with high expression levels; anti-CD52 antibody alemtuzumab, a human IgG1, binds CD52 target present on both targets and NK cells; and negative control isotype control therapeutic antibody (a human IgG1 that does not bind a target present on the target cells (HUG1-IC).

The different proteins were tested for functional effect on NK cell activation in the presence of CD19-positive tumor target cells (Daudi cells), in the presence of CD19-negative, CD16-positive target cells (HUT78 T-lymphoma cells), and in the absence of target cells.

Briefly, NK activation was tested by assessing CD69 and CD107 expression on NK cells by flow cytometry. The assay was carried out in 96 U well plates in completed RPM1, 150 μL final/well. Effector cells were fresh NK cells purified from donors. Target cells were Daudi (CD19-positive), HUT78 (CD19-negative) or K562 (NK activation control cell line). In addition to K562 positive control, three conditions were tested, as follows:
  NK cell alone
  NK cells vs Daudi (CD19+)
  NK cells vs HUT78 (CD19−)

Effector:Target (E:T) ratio was 2.5:1 (50 000 E:20 000 T), with an antibody dilution range starting to 10 µg/mL with 1/4 dilution (n=8 concentrations). Antibodies, target cells and effector cells were mixed; spun 1 min at 300 g; incubated 4 h at 37° C.; spun 3 min at 500 g; washed twice with Staining Buffer (SB); added 50 µL of staining Ab mix; incubated 30 min at 300 g; washed twice with SB resuspended pellet with CellFix; stored overnight at 4° C.; and fluorescence revealed with Canto II (HTS).

Results

1. NK Cells Alone

Results are shown in FIG. 4A. In the absence of target-antigen expressing cells, none of the bispecific anti-NKp46× anti-CD19 antibody (including each of the NKp46-1, NKp46-2, NKp46-3, NKp46-4 and NKp46-9 variable regions) activated NK cells as assessed by CD69 or CD107 expression. Full-length anti-CD19 also did not activate NK cells. However, the full-length anti-NKp46 antibodies caused detectable activation of NK cells. Alemtuzumab also induced activation of NK cells, at a very high level. Isotype control antibody did not induce activation.

2. NK Cells vs Daudi (CD19+)

Results are shown in FIG. 4B. In the presence of target-antigen expressing cells, each of the bispecific anti-NKp46× anti-CD19 antibodies (including each of the NKp46-1, NKp46-2, NKp46-3, NKp46-4 and NKp46-9 binding domains) activated NK cells. Full-length anti-CD19 showed at best only very low activation of NK cells. Neither full-length anti-NKp46 antibodies or alemtuzumab showed substantial increase in activation beyond what was observed in presence of NK cells alone. FIG. 4 shows full-length anti-NKp46 antibodies showed a similar level of baseline activation observed in presence of NK cells alone. Alemtuzumab also induced activation of NK cells a similar level of activation observed in presence of NK cells alone, and at higher antibody concentrations in this setting (ET 2.5:1) the activation was greater than with the bispecific anti-NKp46×anti-CD19 antibody. Isotype control antibody did not induce activation.

3. NK Cells vs HUT78 (CD19−)

Figure 4C:
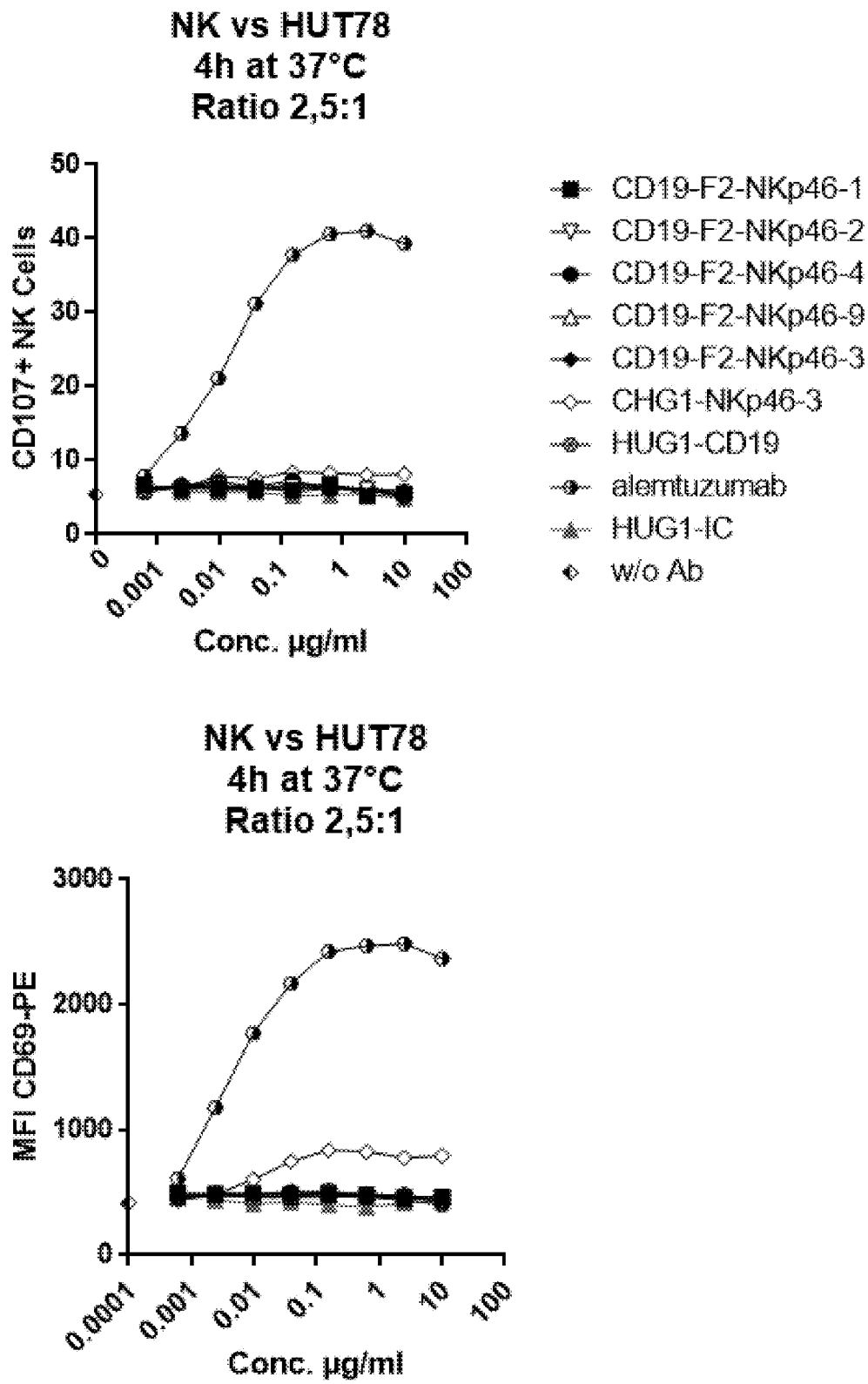
FIG. 4C (top panel CD107, bottom panel CD69) shows that in the presence of CD19-negative HUT78 cells, none of the bispecific anti-NKp46×anti-CD19 antibody (including each of the NKp46-1, NKp46-2, NKp46-3 or NKp46-4 variable regions) activated NK cells. However, the full-length anti-NKp46 antibodies and alemtuzumab caused detectable activation of NK cells at a similar level observed in presence of NK cells alone. Isotype control antibody did not induce activation.

Results are shown in FIG. 4C. In the presence of target-antigen-negative HUT78 cells, none of the bispecific anti-NKp46×anti-CD19 antibody (including each of the NKp46-1, NKp46-2, NKp46-3, NKp46-4 and NKp46-9 variable regions) activated NK cells. However, the full-length anti-NKp46 antibodies and alemtuzumab caused detectable activation of NK cells at a similar level observed in presence of NK cells alone. Isotype control antibody did not induce activation.

In conclusion, the bispecific anti-NKp46 proteins are able to activate NK cells in a target-cell specific manner, unlike full-length monospecific anti-NKp46 antibodies and full-length antibodies of depleting IgG isotypes which also activate NK cells in the absence of target cells. The NK cell activation achieved with anti-NKp46 bispecific proteins was higher than that observed with full length anti-CD19 IgG1 antibodies.

Example 8

Comparative Efficacy with Depleting Anti-Tumor mAbs: NKp46×CD19 Bispecific Proteins at Low ET Ratio These studies aimed to investigate whether bispecific antibodies can mediate NKp46-mediated NK cell activation toward cancer target cells at lower effector:target ratios. The ET ratio used in this Example was 1:1 which is believed to be closer to the setting that would be encountered in vivo than the 2.5:1 ET ratio used in Example 7 or the 10:1 ET ratio of Example 6.

NKp46×CD19 bispecific proteins having an arrangement according to the F2 format described in Example 3 with anti-NKp46 variable domains from NKp46-1, NKp46-2, NKp46-3, NKp46-4 or NKp46-9 were compared to:
  (a) full-length monospecific anti-NKp46 antibodies (NKp46-3 as human IgG1), and
  (b) the anti-CD19 antibody as a full-length human IgG1 as ADCC inducing antibody control comparator.

The experiments further included as controls: rituximab (an anti-CD20 ADCC inducing antibody control for a target antigen with high expression levels); anti-CD52 antibody alemtuzumab (a human IgG1, binds CD52 target present on both targets and NK cells), and negative control isotype control therapeutic antibody (a human IgG1 that does not bind a target present on the target cells (HUG1-IC). The different proteins were tested for functional effect on NK cell activation as assessed by CD69 or CD107 expression in the presence of CD19-positive tumor target cells (Daudi cells), in the presence of CD19-negative, CD16-positive target cells (HUT78 T-lymphoma cells), and in the absence of target cells. The experiments were carried out as in Example 7 except that the ET ratio was 1:1.

Results

Figure 5A:
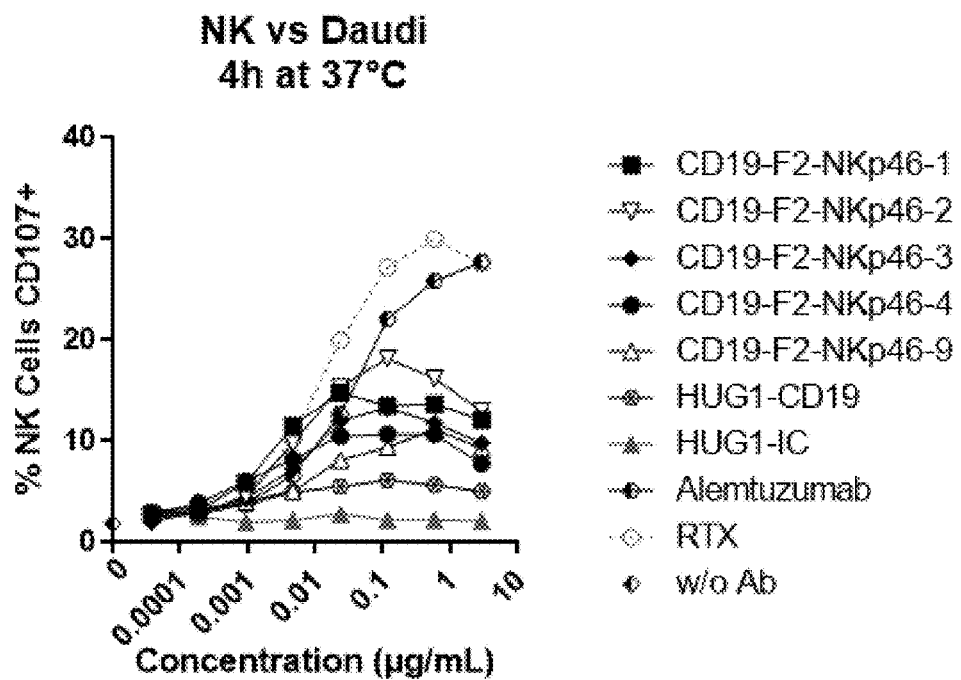
FIGS. 5A and 5B show that at low effector:target ratio of 1:1 each of the bispecific anti-NKp46×anti-CD19 antibody activated NK cells in the presence of Daudi cells, and that bispecific anti-NKp46×anti-CD19 were far more potent than the anti-CD19 antibody as a full-length human IgG1 as ADCC inducing antibody. Top panel is CD107 (FIG. 5A) and bottom panel shows CD69 (FIG. 5B).
Figure 5B:
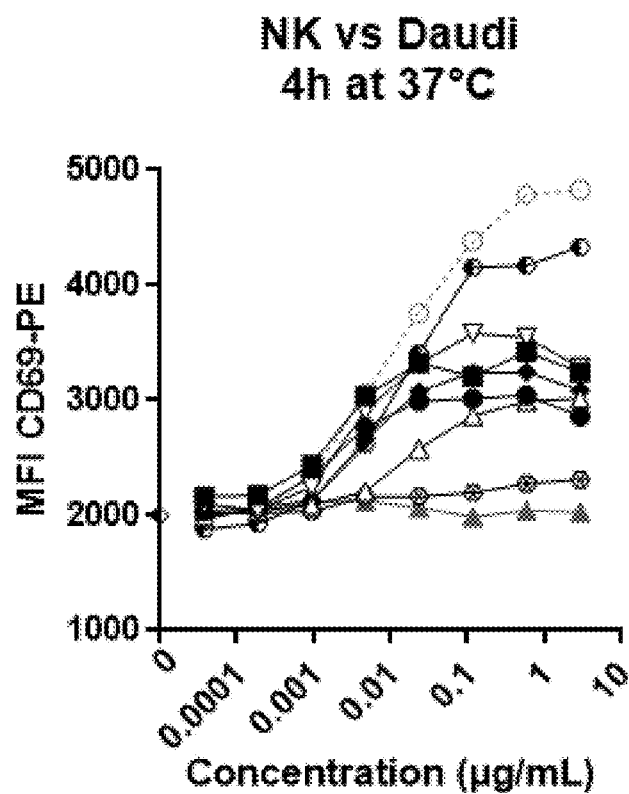

Results are shown in FIG. 5 (5A: CD107 and 5B: CD69). In the presence of target-antigen expressing cells, each of the bispecific anti-NKp46×anti-CD19 antibody (including each of the NKp46-1, NKp46-2, NKp46-3, NKp46-4 and NKp46-9 variable regions) activated NK cells in the presence of Daudi cells.

The activation induced by bispecific anti-NKp46×anti-CD19 antibody in the presence of Daudi cells was far more potent than the full-length human IgG1 anti-CD19 antibody as ADCC inducing antibody which had low activity in this setting. Furthermore, in this low E:T ratio setting the activation induced by bispecific anti-NKp46×anti-CD19 antibody was as potent as anti-CD20 antibody rituximab, with a difference being observed only at the highest concentrations that were 10 fold higher than concentrations in which differences were observed at the 2.5:1 ET ratio.

In the absence of target cells or in the in the presence of target antigen-negative HUT78 cells, full-length anti-NKp46 antibodies and alemtuzumab showed a similar level of baseline activation observed in the presence of Daudi cells. Anti-NKp46×anti-CD19 antibody did not activate NK cells in presence of HUT78 cells.

In conclusion, the bispecific anti-NKp46 proteins are able to activate NK cells in a target-cell specific manner and at lower effector:target ratio are more effective in mediating NK cell activation that traditional human IgG1 antibodies.

Example 9

NKp46 Mechanism of Action

NKp46×CD19 bispecific proteins having an arrangement according to the F2, F3, F5 or F6 formats described in Examples 3 or 4 with anti-NKp46 variable domains from NKp46-3 were compared to rituximab (anti-CD20 ADCC inducing antibody), and a human IgG1 isotype control antibody for functional ability to direct CD16-/NKp46+NK cell lines to lyse CD19-positive tumor target cells.

Briefly, the cytolytic activity of the CD16-/NKp46+ human NK cell line KHYG-1 was assessed in a classical 4-h $^{51}$Cr-release assay in U-bottom 96 well plates. Daudi or B221 cells were labelled with $^{51}$Cr (50 µCi (1.85 MBq)/1×10$^6$ cells), then mixed with KHYG-1 at an effector/target ratio equal to 50:1, in the presence of test antibodies at dilution range starting from 10$^{-7}$ mol/L with 1/5 dilution (n=8 concentrations).

After brief centrifugation and 4 hours of incubation at 37° C., 50 µL of supernatant were removed and transferred into a LumaPlate (Perkin Elmer Life Sciences, Boston, Mass.), and $^{51}$Cr release was measured with a TopCount NXT beta detector (PerkinElmer Life Sciences, Boston, Mass.). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Results

Figure 6A:
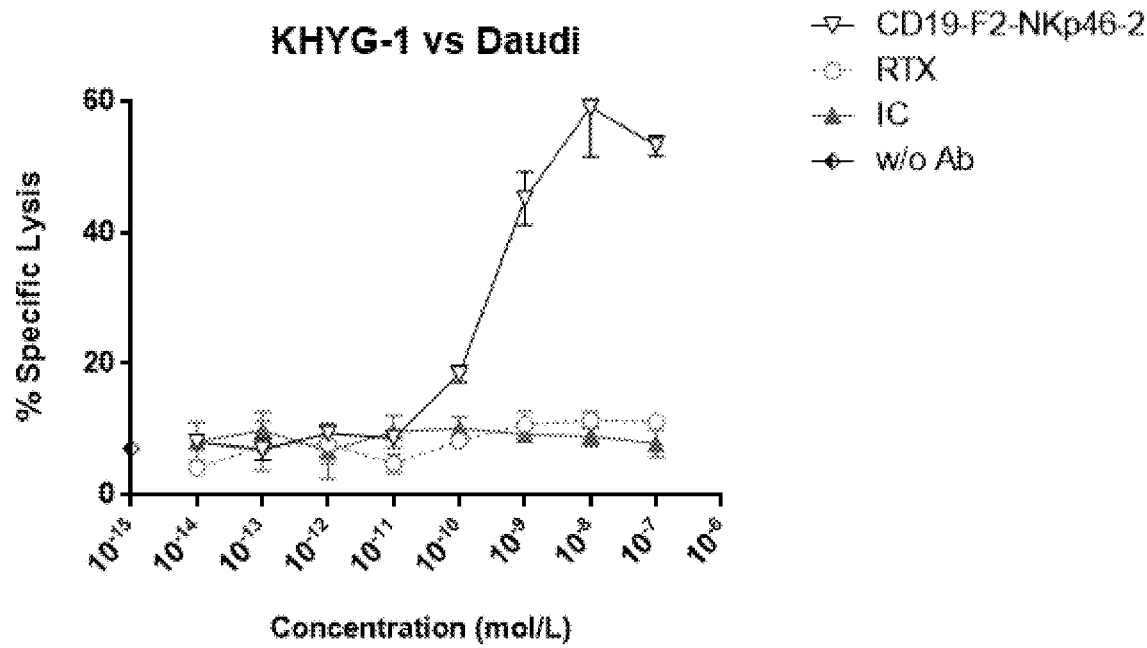
FIGS. 6A and 6B show that each NKp46×CD19 bispecific protein (single chain format F3, and multimeric formats F5 and F6) induced specific lysis of Daudi (FIG. 6A) or B221 (FIG. 6B) cells by human KHYG-1 CD16-negative hNKp46-positive NK cell line, while rituximab and human IgG1 isotype control (IC) antibodies did not.
Figure 6B:
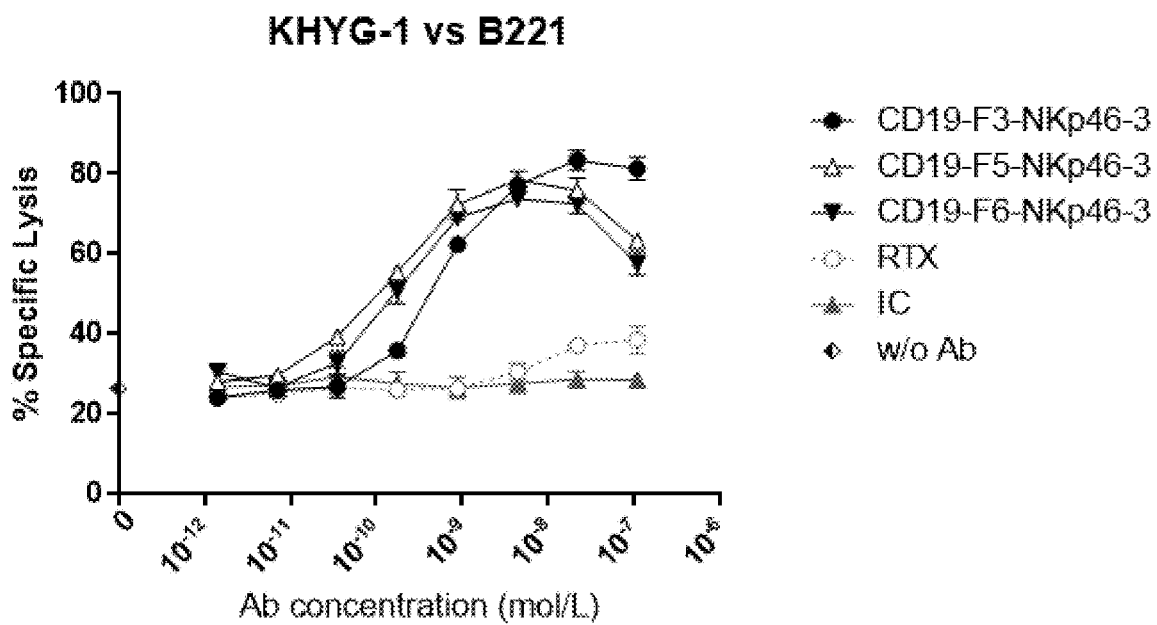

Results are shown in FIG. 6A (KHYG-1 vs Daudi) and FIG. 6B (KHYG-1 vs B221). In the KHYG-1 hNKp46 NK experimental model, each NKp46×CD19 bispecific protein (Format F2, F3, F5 and F6) induced specific lysis of Daudi or B221 cells by human KHYG-1 hNKp46 NK cell line, while rituximab and human IgG1 isotype control (IC) antibodies did not.

Example 10

Comparative Efficacy of Bispecific and Conventional IgG Antibody Using Fresh Human NK Cells NKp46×CD19 bispecific proteins that bind human CD16 having an arrangement according to the F5 format with anti-NKp46 variable domains from NKp46-3 were compared to the same bispecific antibody as a F6 format (which lacks CD16 binding), and to a human IgG1 isotype anti-CD19 antibody, as well as a human IgG1 isotype control antibody for functional ability to direct purified NK cells to lyse CD19-positive Daudi tumor target cells.

Briefly, the cytolytic activity of fresh human purified NK cells from EFS Buffy Coat was assessed in a classical 4-h $^{51}$Cr-release assay in U-bottom 96 well plates. Daudi or HUT78 cells (negative control cells that do not express CD19) were labelled with $^{51}$Cr and then mixed with NK cells at an effector/target ratio equal to 10:1, in the presence of test antibodies at dilution range starting from 10 µg/ml with 1/10 dilution (n=8 concentrations).

After brief centrifugation and 4 hours of incubation at 37° C., 50 µL of supernatant were removed and transferred into a LumaPlate (Perkin Elmer Life Sciences, Boston, Mass.), and $^{51}$Cr release was measured with a TopCount NXT beta detector (PerkinElmer Life Sciences, Boston, Mass.). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Figure 7:
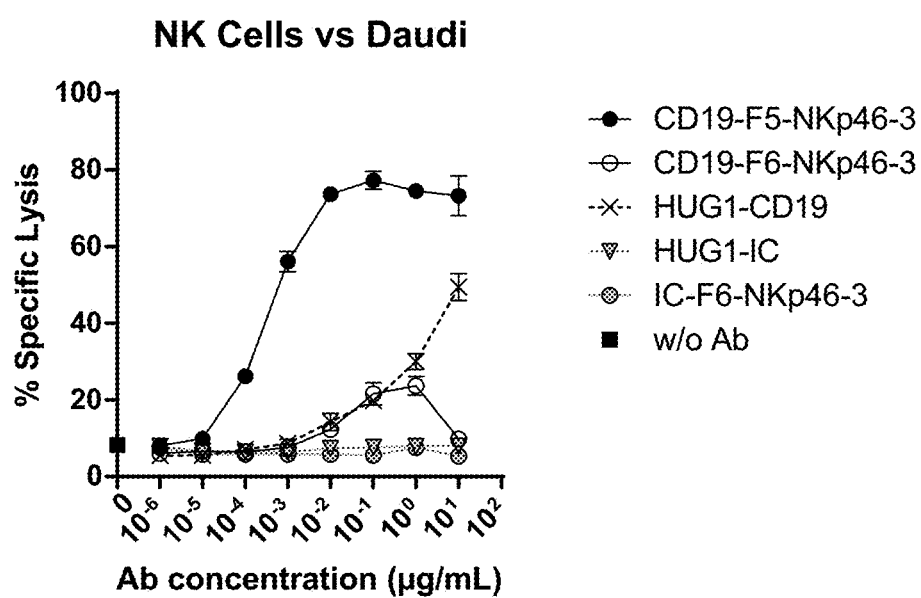
FIG. 7 shows the NKp46×CD19 bispecific protein in F5 format whose Fc domain binds CD16 is far more potent in mediating Daudi target cell lysis that the full-length IgG1 anti-CD19 antibody or the F6 format bispecific protein. The bispecific anti-CD19 in F6 format whose Fc domain does not bind CD16 was as potent in mediating NK cell lysis of Daudi target cells as the full-length IgG1 anti-CD19 antibody, which is remarkable considering that the control IgG1 anti-CD19 antibody binds CD19 bivalently.

Results are shown in FIG. 7. The CD19-F6-NKp46 (bispecific protein in F6 format) whose Fc domain does not bind CD16 due to a N297 substitution was as potent in mediating NK cell lysis of Daudi target cells as the full-length IgG1 anti-CD19 antibody, which is remarkable considering that the control IgG1 anti-CD19 antibody binds CD19 bivalently and that the anti-CD19 is bound by CD16. Surprisingly, the CD19-F6-NKp46 (F5 format protein) whose Fc domain additionally binds CD16 is far more potent in mediating Daudi target cell lysis that the full-length IgG1 anti-CD19 antibody or the F6 format bispecific protein. At comparable levels of target cell lysis, the CD19-F6-NKp46 was at least 1000 times more potent than the full-length anti-CD19 IgG1.

Example 11

Binding of Different Bispecific Formats to FcRn

Affinity of different antibody formats for human FcRn was studied by Surface Plasmon Resonance (SPR) by immobilizing recombinant FcRn proteins covalently to carboxyl groups in the dextran layer on a Sensor Chip CM5, as described in Example 2-6.

A chimeric full length anti-CD19 antibody having human IgG1 constant regions and NKp46×CD19 bispecific proteins having an arrangement according to the F3, F4, F5, F6, F9, F10, F11, F13 or F14 formats described in Examples 3 or 4 with anti-NKp46 variable domains from NKp46-3 (NKp46-2 for F2) were tested; for each analyte, the entire sensorgram was fitted using the steady state or 1:1 SCK binding model.

Results are shown in Table 4 below. The bispecific proteins having dimeric Fc domains (formats F5, F6, F13, F14) bound to FcRn with affinity similar to that of the full-length IgG1 antibody. The bispecific proteins with monomeric Fc domains (F3, F4, F9, F10, F11) also displayed binding to FcRn, however with lower affinity that the bispecific proteins having dimeric Fc domains.

TABLE 4

| Antibody/Bispecific | SPR method | KD nM |
|---|---|---|
| Human IgG1/K Anti-CD19 | SCK/Two state reaction | 7.8 |
| CD19-F5-NKp46-3 | SCK/Two state reaction | 2.6 |
| CD19-F6-NKp46-3 | SCK/Two state reaction | 6.0 |
| CD19-F13-NKp46-3 | SCK/Two state reaction | 15.2 |
| CD19-F14-NKp46-3 | SCK/Two state reaction | 14.0 |
| CD19-F3-NKp46-3 | Steady State | 474.4 |
| CD19-F4-NKp46-3 | Steady State | 711.7 |
| CD19-F9A-NKp46-3 | Steady State | 858.5 |
| CD19-F10A-NKp46-3 | Steady State | 432.8 |
| CD19-F11-NKp46-3 | Steady State | 595.5 |

Example 12

Binding to FcγR

Different multimeric Fc proteins were evaluated to assess whether such bispecific monomeric Fc protein could retain binding to Fcγ receptors.

SPR measurements were performed on a Biacore T100 apparatus (Biacore GE Healthcare) at 25° C. In all Biacore experiments HBS-EP+(Biacore GE Healthcare) and 10 mM NaOH, 500 mM NaCl served as running buffer and regeneration buffer respectively. Sensorgrams were analyzed with Biacore T100 Evaluation software. Recombinant human FcRs (CD64, CD32a, CD32b, CD16a and CD16b) were cloned, produced and purified.

F5 and F6 bispecific antibodies CD19-F5-NKp46-3 or CD19-F6-NKp46-3 were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). Bispecific antibodies were diluted to 10 µg/ml in coupling buffer (10 mM acetate, pH 5.6) and injected until the appropriate immobilization level was reached (i.e. 800 to 900 RU). Deactivation of the remaining activated groups was performed using 100 mM ethanolamine pH 8 (Biacore GE Healthcare).

Monovalent affinity study was assessed following a classical kinetic wizard (as recommended by the manufacturer). Serial dilutions of soluble analytes (FcRs) ranging from 0.7 to 60 nM for CD64 and from 60 to 5000 nM for all the other FcRs were injected over the immobilized bispecific antibodies and allowed to dissociate for 10 min before regeneration. The entire sensorgram sets were fitted using the 1:1 kinetic binding model for CD64 and with the Steady State Affinity model for all the other FcRs.

While full length wild type human IgG1 bound to all cynomolgus and human Fcγ receptors, the CD19-F6-NKp46-3 bi-specific antibodies did not bind to any of the receptors. The CD19-F5-NKp46-3, on the other hand, bound to each of the human receptors CD64 (KD=0.7 nM), CD32a (KD=846 nM), CD32b (KD=1850 nM), CD16a (KD=1098 nM) and CD16b (KD=2426 nM). Convention human anti-IgG1 antibodies has comparable binding to the Fc receptors (KD shown in the table below).

| Human Fcγ receptor | CD19-F5-NKp46-3 KD (nM) | Full length human IgG1 antibody KD (nM) |
|---|---|---|
| CD64 | 0.7 | 0.24 |
| CD32a | 846 | 379 |
| CD32b | 1850 | 1180 |
| CD16a | 1098 | 630 |
| CD16b | 2426 | 2410 |

Example 13

Epitope Mapping of Anti-NKp46 Antibodies

A. Competition Assays

Competition assays were conducted by Surface Plasmon Resonance (SPR according to the methods described below.

SPR measurements were performed on a Biacore T100 apparatus (Biacore GE Healthcare) at 25° C. In all Biacore experiments HBS-EP+(Biacore GE Healthcare) and NaOH 10 mM NaCl 500 mM served as running buffer and regeneration buffer respectively. Sensorgrams were analyzed with Biacore T100 Evaluation software. Anti-6×His tag antibody was purchased from QIAGEN. Human 6×His tagged NKp46 recombinant proteins (NKp46-His) were cloned, produced and purified at Innate Pharma.

Anti-His antibodies were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). Protein-A and Anti-His antibodies were diluted to 10 µg/ml in coupling buffer (10 mM acetate, pH 5.6) and injected until the appropriate immobilization level was reached (i.e. 2000 to 2500 RU). Deactivation of the remaining activated groups was performed using 100 mM ethanolamine pH 8 (Biacore GE Healthcare).

Parental regular human IgG1 chimeric antibodies having NKp46 binding region corresponding to NKp46-1, NKp46-2, NKp46-3 or NKp46-4 were used for the competition study which has been performed using an Anti-6×His tag antibody chip.

Bispecific antibodies having NKp46 binding region based on NKp46-1, NKp46-2, NKp46-3 or NKp46-4 at 1 µg/mL were captured onto Protein-A chip and recombinant human NKp46 proteins were injected at 5 µg/mL together with a second test bispecific antibody of the NKp46-1, NKp46-2, NKp46-3 or NKp46-4 group.

None of NKp46-1, NKp46-2, NKp46-3 or NKp46-4 competed with one another for binding to NKp46, these antibodies each representing a different epitope.

B. Binding to NKp46 Mutants

In order to define the epitopes of anti NKp46 antibodies, we designed NKp46 mutants defined by one, two or three substitutions of amino acids exposed at the molecular surface over the 2 domains of NKp46. This approach led to the generation of 42 mutants transfected in Hek-293T cells, as shown in the table below. The targeted amino acid mutations in the table 5 below are shown both using numbering of SEQ ID NO: 1 (also corresponding to the numbering used in Jaron-Mendelson et al. (2012) J. Immunol. 88(12):6165-74.

TABLE 5

| Mutant | Substitution (Numbering according to: Jaron-Mendelson and SEQ ID NO 1) | | |
|---|---|---|---|
| 1 | P40A | K43S | Q44A |
| 2 | K41S | E42A | E119A |
| 3 | P86A | D87A | |
| 4 | N89A | R91A | |
| 5 | K80A | K82A | |
| 5bis | E34A | T46A | |
| 6 | R101A | V102A | |
| 7 | N52A | Y53A | |
| 8 | V56A | P75A | E76A |
| 9 | R77A | I78A | |
| 10 | S97A | I99A | |
| 10bis | Q59A | H61A | |
| 11 | L66A | V69A | |
| 12 | E108A | | |
| 13 | N111A | L112A | |
| 14 | D114A | | |
| 15 | T125A | R145S | D147A |
| 16 | S127A | Y143A | |
| 17 | H129A | K139A | |
| 18 | K170A | V172A | |
| 19 | I135A | S136A | |
| 19bis | T182A | R185A | |
| 20 | R160A | | |
| 21 | K207A | | |
| 22 | M152A | R166A | |
| 23 | N195A | N196A | |
| Stalk1 | D213A | I214A | T217A |
| Stalk2 | F226A | T233A | |
| Stalk3 | L236A | T240A | |
| Supp1 | F30A | W32A | |
| Supp2 | F62A | F67A | |
| Supp3 | E63A | Q95A | |
| Supp4 | R71A | K73A | |
| Supp5 | Y84A | | |
| Supp6 | E104A | L105A | |
| Supp7 | Y121A | Y194A | |
| Supp8 | P132A | E133A | |
| Supp9 | S151A | Y168A | |
| Supp10 | S162A | H163A | |
| Supp11 | E174A | P176A | |
| Supp12 | P179A | H184A | |
| Supp13 | R189A | E204A | P205A |

Generation of Mutants

NKp46 mutants were generated by PCR. The sequences amplified were run on agarose gel and purified using the Macherey Nagel PCR Clean-Up Gel Extraction kit (reference 740609). The two or three purified PCR products generated for each mutant were then ligated into an expression vector, with the ClonTech InFusion system. The vectors containing the mutated sequences were prepared as Miniprep and sequenced. After sequencing, the vectors containing the mutated sequences were prepared as Midiprep using the Promega PureYield™ Plasmid Midiprep System. HEK293T cells were grown in DMEM medium (Invitrogen), transfected with vectors using Invitrogen's Lipofectamine 2000 and incubated at 37° C. in a CO2 incubator for 24 hours prior to testing for transgene expression.

Flow Cytometry Analysis of Anti-NKp46 Binding to the HEK293T Transfected Cells

All the anti-NKp46 antibodies were tested for their binding to each mutant by flow cytometry. A first experiment was performed to determine antibodies that lose their binding to one or several mutants at one concentration (10 µg/ml). To confirm a loss of binding, titration of antibodies was done on antibodies for which binding seemed to be affected by the NKp46 mutations (1-0.1-0.01-0.001 µg/ml).

Results

Antibody NKp46-1 had decreased binding to the mutant 2 (having a mutation at residues K41, E42 and E119 (numbering in NKp46 wild-type) compared to wild-type NK46. Similarly, NKp46-1 also had decreased binding to the supplementary mutant Supp7 (having a mutation at residues Y121 and Y194.

Antibody NKp46-3 had decreased binding to the mutant 19 (having a mutation at residues I135, and S136. Similarly, NKp46-1 also had decreased binding to the supplementary mutant Supp8 (having a mutation at residues P132 and E133.

Antibody NKp46-4 had decreased binding to the mutant 6 (having a mutation at residues R101, and V102. Similarly, NKp46-1 also had decreased binding to the supplementary mutant Supp6 having a mutation at residues E104 and L105.

In this study, we identified epitopes for anti-NKp46 antibodies (NKp46-1, NKp46-3 and NKp46-4). Epitopes of NKp46-4, NKp46-3 and NKp46-1 are on NKp46 D1 domain, D2 domain and D1/D2 junction, respectively. R101, V102, E104 and L105 are essential residues for NKp46-4 binding and defined a part of NKp46-4 epitope. The epitope of NKp46-1 epitope includes K41, E42, E119, Y121 and Y194 residues. The epitope of NKp46-3 includes P132, E133, 1135, and S136 residues.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate). All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

We claim:

1. An isolated nucleic acid encoding a heavy chain variable region (VH) and/or a light chain variable region (VL) selected from the group consisting of:
   (a) a VH comprising an amino acid sequence of SEQ ID NOS: 199 or 200 (NKp46-1 H1 or H3 variable domain), and a VL comprising an amino acid sequence of the amino acid sequence of SEQ ID NO: 201 (NKp46-1 L1 variable domain);
   (b) a VH comprising an amino acid sequence of SEQ ID NOS: 202, 203 or 204 (NKp46-2 H1, H2 or H3 variable domain), and a VL comprising an amino acid sequence of SEQ ID NO: 205 (NKp46-2 L1 variable domain);
   (c) a VH comprising an amino acid sequence of SEQ ID NOS: 206, 207 or 208 (NKp46-3 H1, H3 or H4 variable domain), and a VL comprising an amino acid sequence of SEQ ID NO: 209 (NKp46-3 L1 variable domain);
   (d) a VH comprising an amino acid sequence of SEQ ID NOS: 210, 211 or 212 (NKp46-4 H1 variable domain), and a VL comprising an amino acid sequence of SEQ ID NO: 213 (NKp46-4 L2 variable domain);
   (e) a VH comprising an amino acid sequence of SEQ ID NO: 215 (NKp46-9 H2 variable domain), and a VL comprising an amino acid sequence of SEQ ID NOS: 217 or 218 (NKp46-9 L1 or L2 variable domain); or
   (f) a VH comprising an amino acid sequence of SEQ ID NO: 216 (NKp46-9 H3 variable domain), and a VL comprising an amino acid sequence of SEQ ID NOS: 217 or 218 (NKp46-9 L1 or L2 variable domain).

2. A recombinant host cell comprising a nucleic acid according to claim 1.

3. A method of producing a protein comprising culturing a cell of claim 2 under conditions suitable for expression of the protein and recovering the protein.

4. The nucleic acid according to claim 1, wherein said nucleic acid encodes a VH comprising SEQ ID NOS: 199 or 200.

5. The nucleic acid according to claim 1, wherein said nucleic acid encodes a VL comprising SEQ ID NO: 201.

6. The nucleic acid according to claim 1, wherein said nucleic acid encodes a VH comprising SEQ ID NOS: 202, 203 or 204.

7. The nucleic acid according to claim 1, wherein said nucleic acid encodes a VL comprising SEQ ID NO: 205.

8. The nucleic acid according to claim 1, wherein said nucleic acid encodes a VH comprising SEQ ID NOS: 206, 207 or 208.

9. The nucleic acid according to claim 1, wherein said nucleic acid encodes a VL comprising SEQ ID NO: 209.

10. The nucleic acid according to claim 1, wherein said nucleic acid encodes a VH comprising SEQ ID NOS: 210, 211 or 212.

11. The nucleic acid according to claim 1, wherein said nucleic acid encodes a VL comprising SEQ ID NO: 213.

12. The nucleic acid according to claim 1, wherein said nucleic acid encodes a VH comprising SEQ ID NO: 215.

13. The nucleic acid according to claim 1, wherein said nucleic acid encodes a VL comprising SEQ ID NOS: 217 or 218.

14. The nucleic acid according to claim 1, wherein said nucleic acid encodes a VH comprising SEQ ID NO: 216.

15. The nucleic acid according to claim 1, wherein said nucleic acid encodes a VL comprising SEQ ID NOS: 217 or 218.

* * * * *

UNITED STATES PATENT AND TRADEMARK OFFICE
CERTIFICATE OF CORRECTION

PATENT NO. : 11,891,444 B2
APPLICATION NO. : 17/315547
DATED : February 6, 2024
INVENTOR(S) : Laurent Gauthier et al.

It is certified that error appears in the above-identified patent and that said Letters Patent is hereby corrected as shown below:

In the Specification

Column 1,
Line 20, "entitled "NKp46-7-PCT_ST25.bd"," should read --entitled "NKp46-7-PCT_ST25.txt--.

Column 2,
Line 21, "Fcy-positive." should read --Fcγ-positive.--.

Column 11,
Line 65, "F(ab)$_2$, F(ab)$_3$" should read --F(ab')$_2$, F(ab)$_3$--.

Column 19,
Line 25, "1135" should read --I135--.

Column 20,
Line 24, "1135" should read --I135--.

Column 24,
Line 66, SEQ ID NO: 8, "CONGH" should read --CQNGH--.

Column 25,
Line 16, SEQ ID NO: 12, "SRE" should read --SRF--.
Line 23, SEQ ID NO: 14, "SRE" should read --SRF--.
Line 64, "I11" should read --III--.

Column 26,
Line 10, SEQ ID NO: 10, "HEWG" should read --HFWG--.

Column 28,
Line 46, "am11" should read --amI1--.

Signed and Sealed this
Fourteenth Day of October, 2025

John A. Squires
*Director of the United States Patent and Trademark Office*

CERTIFICATE OF CORRECTION (continued)
U.S. Pat. No. 11,891,444 B2

Line 50, "DRS" should read --DR5--.

Column 42,
Line 41, "SENTY" should read --SENIY--.

Column 45,
Line 30, "SENTY" should read --SENIY--.
Line 39, "SENTY" should read --SENIY--.

Column 52,
Line 12, "VK$^{anti\text{-}NIKP46}$–CK" should read --VK$^{anti\text{-}NKp46}$–CK--.

Column 53,
Line 55, "V$_K^{anti\text{-}1/1"46}$–CH1" should read --V$_K^{anti\text{-}NKp46}$–CK1--.

Column 54,
Line 25, "(F100)" should read --(F10C)--.
Line 26, "F100" should read --F10C--.

Column 71,
Line 30, "1135" should read --I135--.
Line 46, "1135" should read --I135--.

SEQUENCE LISTING

```
<160> NUMBER OF SEQ ID NOS: 218

<210> SEQ ID NO 1
<211> LENGTH: 304
<212> TYPE: PRT
<213> ORGANISM: homo sapiens

<400> SEQUENCE: 1

Met Ser Ser Thr Leu Pro Ala Leu Leu Cys Val Gly Leu Cys Leu Ser
1               5                   10                  15

Gln Arg Ile Ser Ala Gln Gln Gln Thr Leu Pro Lys Pro Phe Ile Trp
            20                  25                  30
```

Ala Glu Pro His Phe Met Val Pro Lys Glu Lys Gln Val Thr Ile Cys
             35                  40                  45

Cys Gln Gly Asn Tyr Gly Ala Val Glu Tyr Gln Leu His Phe Glu Gly
 50                  55                  60

Ser Leu Phe Ala Val Asp Arg Pro Lys Pro Glu Arg Ile Asn Lys
 65                  70                  75                  80

Val Lys Phe Tyr Ile Pro Asp Met Asn Ser Arg Met Ala Gly Gln Tyr
                 85                  90                  95

Ser Cys Ile Tyr Arg Val Gly Glu Leu Trp Ser Glu Pro Ser Asn Leu
                100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
    130                 135                 140

Arg Leu Asp Thr Ala Thr Ser Met Phe Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
                245                 250                 255

Leu Arg Met Gly Leu Ala Phe Leu Val Leu Val Ala Leu Val Trp Phe
                260                 265                 270

Leu Val Glu Asp Trp Leu Ser Arg Lys Arg Thr Arg Glu Arg Ala Ser
            275                 280                 285

Arg Ala Ser Thr Trp Glu Gly Arg Arg Arg Leu Asn Thr Gln Thr Leu
    290                 295                 300

<210> SEQ ID NO 2
<211> LENGTH: 216
<212> TYPE: PRT
<213> ORGANISM: homo sapiens

<400> SEQUENCE: 2

Ala Pro Glu Leu Leu Gly Gly Pro Ser Val Phe Leu Phe Pro Pro Lys
1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Thr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 3
<211> LENGTH: 120
<212> TYPE: PRT
<213> ORGANISM: Mus musculus

<400> SEQUENCE: 3

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Gly Lys Gln Arg Ser Gly Gln Gly Leu Glu Trp Ile
        35                  40                  45

Gly Glu Ile Tyr Pro Gly Ser Gly Thr Asn Tyr Tyr Asn Glu Lys Phe
    50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95

Ala Arg Arg Gly Arg Tyr Gly Leu Tyr Ala Met Asp Tyr Trp Gly Gln
            100                 105                 110

Gly Thr Ser Val Thr Val Ser Ser
        115                 120

<210> SEQ ID NO 4
<211> LENGTH: 107
<212> TYPE: PRT
<213> ORGANISM: Mus musculus

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Arg Pro Trp
                85                  90                  95
```

```
Thr Phe Gly Gly Gly Thr Lys Leu Glu Ile Lys
                100                 105
```

```
<210> SEQ ID NO 5
<211> LENGTH: 122
<212> TYPE: PRT
<213> ORGANISM: Mus musculus

<400> SEQUENCE: 5

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Ser Thr Ser Tyr Asn Pro Ser Leu
    50                  55                  60

Glu Ser Arg Ile Ser Ile Thr Arg Asp Thr Ser Thr Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Tyr Tyr Gly Ser Ser Trp Gly Val Phe Ala Tyr Trp
            100                 105                 110

Gly Gln Gly Thr Leu Val Thr Val Ser Ala
        115                 120
```

```
<210> SEQ ID NO 6
<211> LENGTH: 107
<212> TYPE: PRT
<213> ORGANISM: Mus musculus

<400> SEQUENCE: 6

Asp Ile Gln Met Thr Gln Ser Pro Ala Ser Leu Ser Ala Ser Val Gly
1               5                   10                  15

Glu Thr Val Thr Ile Thr Cys Arg Val Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Trp
                85                  90                  95

Thr Phe Gly Gly Gly Thr Lys Leu Glu Ile Lys
            100                 105
```

```
<210> SEQ ID NO 7
<211> LENGTH: 116
<212> TYPE: PRT
<213> ORGANISM: Mus musculus

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30
```

Thr Met His Trp Val Lys Gln Ser His Gly Lys Ser Leu Glu Trp Ile
            35                  40                  45

Gly Gly Ile Ser Pro Asn Ile Gly Gly Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Arg Gly Gly Ser Phe Asp Tyr Trp Gly Gln Gly Thr Thr Leu
                100                 105                 110

Thr Val Ser Ser
            115

<210> SEQ ID NO 8
<211> LENGTH: 107
<212> TYPE: PRT
<213> ORGANISM: Mus musculus

<400> SEQUENCE: 8

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
                 20                  25                  30

Leu His Trp Tyr Gln Gln Lys Ser His Glu Ser Pro Arg Leu Leu Ile
             35                  40                  45

Lys Tyr Ala Ser Gln Ser Ile Ser Gly Ile Pro Ser Arg Phe Ser Gly
 50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys
                100                 105

<210> SEQ ID NO 9
<211> LENGTH: 117
<212> TYPE: PRT
<213> ORGANISM: Mus musculus

<400> SEQUENCE: 9

Gln Val Gln Leu Gln Gln Ser Ala Val Glu Leu Ala Arg Pro Gly Ala
 1               5                  10                  15

Ser Val Lys Met Ser Cys Lys Ala Ser Gly Tyr Thr Phe Thr Ser Phe
                 20                  25                  30

Thr Met His Trp Val Lys Gln Arg Pro Gly Gln Gly Leu Glu Trp Ile
             35                  40                  45

Gly Tyr Ile Asn Pro Ser Ser Gly Tyr Thr Glu Tyr Asn Gln Lys Phe
 50                  55                  60

Lys Asp Lys Thr Thr Leu Thr Ala Asp Lys Ser Ser Ser Thr Ala Tyr
 65                  70                  75                  80

Met Gln Leu Asp Ser Leu Thr Ser Asp Asp Ser Ala Val Tyr Tyr Cys
                 85                  90                  95

Val Arg Gly Ser Ser Arg Gly Phe Asp Tyr Trp Gly Gln Gly Thr Leu
                100                 105                 110

Val Thr Val Ser Ala
            115

<210> SEQ ID NO 10
<211> LENGTH: 107
<212> TYPE: PRT
<213> ORGANISM: Mus musculus

<400> SEQUENCE: 10

Asp Ile Gln Met Ile Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Phe Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ile Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 11
<211> LENGTH: 115
<212> TYPE: PRT
<213> ORGANISM: Mus musculus

<400> SEQUENCE: 11

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Met His Trp Ala Lys Gln Arg Pro Gly Gln Gly Leu Glu Trp Ile
        35                  40                  45

Gly His Ile His Pro Asn Ser Gly Ile Ser Asn Tyr Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Gly Gly Arg Phe Asp Asp Trp Gly Ala Gly Thr Thr Val Thr
            100                 105                 110

Val Ser Ser
        115

<210> SEQ ID NO 12
<211> LENGTH: 107
<212> TYPE: PRT
<213> ORGANISM: Mus musculus

<400> SEQUENCE: 12

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly

```
                    50                  55                  60
Ser Arg Ser Gly Ser Asp Tyr Ser Leu Thr Ile Ser Ser Leu Glu Ser
 65                  70                  75                  80

Glu Asp Phe Val Asp Tyr Tyr Cys Leu Gln Tyr Ala Ser Ser Pro Trp
                     85                  90                  95

Thr Phe Gly Gly Gly Thr Lys Leu Glu Ile Lys
                100                 105
```

<210> SEQ ID NO 13
<211> LENGTH: 120
<212> TYPE: PRT
<213> ORGANISM: Mus musculus

<400> SEQUENCE: 13

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
             35                  40                  45

Met Gly Tyr Ile Thr Tyr Ser Gly Ser Thr Asn Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Cys Trp Asp Tyr Ala Leu Tyr Ala Met Asp Cys Trp Gly Gln
                100                 105                 110

Gly Thr Ser Val Thr Val Ser Ser
            115                 120
```

<210> SEQ ID NO 14
<211> LENGTH: 107
<212> TYPE: PRT
<213> ORGANISM: Mus musculus

<400> SEQUENCE: 14

```
Asp Ile Gln Met Thr Gln Ser Pro Ala Ser Leu Ser Ala Ser Val Gly
 1               5                  10                  15

Glu Thr Val Thr Ile Thr Cys Arg Thr Ser Glu Asn Ile Tyr Ser Tyr
                20                  25                  30

Leu Ala Trp Cys Gln Gln Lys Gln Gly Lys Ser Pro Gln Leu Leu Val
             35                  40                  45

Tyr Asn Ala Lys Thr Leu Ala Glu Gly Val Pro Ser Arg Phe Ser Gly
 50                  55                  60

Ser Gly Ser Gly Thr His Phe Ser Leu Lys Ile Asn Ser Leu Gln Pro
 65                  70                  75                  80

Glu Asp Phe Gly Ile Tyr Tyr Cys Gln His His Tyr Asp Thr Pro Leu
                 85                  90                  95

Thr Phe Gly Ala Gly Thr Lys Leu Glu Leu Lys
                100                 105
```

<210> SEQ ID NO 15
<211> LENGTH: 5
<212> TYPE: PRT
<213> ORGANISM: mus musculus

<400> SEQUENCE: 15

```
Asp Tyr Val Ile Asn
1               5

<210> SEQ ID NO 16
<211> LENGTH: 7
<212> TYPE: PRT
<213> ORGANISM: mus musculus

<400> SEQUENCE: 16

Gly Tyr Thr Phe Thr Asp Tyr
1               5

<210> SEQ ID NO 17
<211> LENGTH: 8
<212> TYPE: PRT
<213> ORGANISM: mus musculus

<400> SEQUENCE: 17

Gly Tyr Thr Phe Thr Asp Tyr Val
1               5

<210> SEQ ID NO 18
<211> LENGTH: 17
<212> TYPE: PRT
<213> ORGANISM: mus musculus

<400> SEQUENCE: 18

Glu Ile Tyr Pro Gly Ser Gly Thr Asn Tyr Tyr Asn Glu Lys Phe Lys
1               5                   10                  15

Ala

<210> SEQ ID NO 19
<211> LENGTH: 4
<212> TYPE: PRT
<213> ORGANISM: mus musculus

<400> SEQUENCE: 19

Pro Gly Ser Gly
1

<210> SEQ ID NO 20
<211> LENGTH: 16
<212> TYPE: PRT
<213> ORGANISM: mus musculus

<400> SEQUENCE: 20

Gly Tyr Thr Phe Thr Asp Tyr Val Ile Tyr Pro Gly Ser Gly Thr Asn
1               5                   10                  15

<210> SEQ ID NO 21
<211> LENGTH: 11
<212> TYPE: PRT
<213> ORGANISM: mus musculus

<400> SEQUENCE: 21

Arg Gly Arg Tyr Gly Leu Tyr Ala Met Asp Tyr
1               5                   10

<210> SEQ ID NO 22
<211> LENGTH: 9
<212> TYPE: PRT
<213> ORGANISM: mus musculus

<400> SEQUENCE: 22
```

```
Gly Arg Tyr Gly Leu Tyr Ala Met Asp
1               5

<210> SEQ ID NO 23
<211> LENGTH: 13
<212> TYPE: PRT
<213> ORGANISM: mus musculus

<400> SEQUENCE: 23

Ala Arg Arg Gly Arg Tyr Gly Leu Tyr Ala Met Asp Tyr
1               5                   10

<210> SEQ ID NO 24
<211> LENGTH: 11
<212> TYPE: PRT
<213> ORGANISM: mus musculus

<400> SEQUENCE: 24

Arg Ala Ser Gln Asp Ile Ser Asn Tyr Leu Asn
1               5                   10

<210> SEQ ID NO 25
<211> LENGTH: 7
<212> TYPE: PRT
<213> ORGANISM: Mus musculus

<400> SEQUENCE: 25

Ser Gln Asp Ile Ser Asn Tyr
1               5

<210> SEQ ID NO 26
<211> LENGTH: 6
<212> TYPE: PRT
<213> ORGANISM: mus musculus

<400> SEQUENCE: 26

Gln Asp Ile Ser Asn Tyr
1               5

<210> SEQ ID NO 27
<211> LENGTH: 7
<212> TYPE: PRT
<213> ORGANISM: Mus musculus

<400> SEQUENCE: 27

Tyr Thr Ser Arg Leu His Ser
1               5

<210> SEQ ID NO 28
<211> LENGTH: 9
<212> TYPE: PRT
<213> ORGANISM: mus musculus

<400> SEQUENCE: 28

Gln Gln Gly Asn Thr Arg Pro Trp Thr
1               5

<210> SEQ ID NO 29
<211> LENGTH: 9
<212> TYPE: PRT
<213> ORGANISM: Mus musculus

<400> SEQUENCE: 29

Tyr Thr Ser Gly Asn Thr Arg Pro Trp
```

<210> SEQ ID NO 30
<211> LENGTH: 12
<212> TYPE: PRT
<213> ORGANISM: Mus musculus

<400> SEQUENCE: 30

Tyr Thr Ser Gln Gln Gly Asn Thr Arg Pro Trp Thr
1               5                   10

<210> SEQ ID NO 31
<211> LENGTH: 6
<212> TYPE: PRT
<213> ORGANISM: Mus musculus

<400> SEQUENCE: 31

Ser Asp Tyr Ala Trp Asn
1               5

<210> SEQ ID NO 32
<211> LENGTH: 8
<212> TYPE: PRT
<213> ORGANISM: Mus musculus

<400> SEQUENCE: 32

Gly Tyr Ser Ile Thr Ser Asp Tyr
1               5

<210> SEQ ID NO 33
<211> LENGTH: 9
<212> TYPE: PRT
<213> ORGANISM: Mus musculus

<400> SEQUENCE: 33

Gly Tyr Ser Ile Thr Ser Asp Tyr Ala
1               5

<210> SEQ ID NO 34
<211> LENGTH: 16
<212> TYPE: PRT
<213> ORGANISM: Mus musculus

<400> SEQUENCE: 34

Tyr Ile Thr Tyr Ser Gly Ser Thr Ser Tyr Asn Pro Ser Leu Glu Ser
1               5                   10                  15

<210> SEQ ID NO 35
<211> LENGTH: 7
<212> TYPE: PRT
<213> ORGANISM: Mus musculus

<400> SEQUENCE: 35

Ile Thr Tyr Ser Gly Ser Thr
1               5

<210> SEQ ID NO 36
<211> LENGTH: 13
<212> TYPE: PRT
<213> ORGANISM: Mus musculus

<400> SEQUENCE: 36

Gly Gly Tyr Tyr Gly Ser Ser Trp Gly Val Phe Ala Tyr
1               5                   10

```
<210> SEQ ID NO 37
<211> LENGTH: 11
<212> TYPE: PRT
<213> ORGANISM: Mus musculus

<400> SEQUENCE: 37

Gly Tyr Tyr Gly Ser Ser Trp Gly Val Phe Ala
1               5                   10

<210> SEQ ID NO 38
<211> LENGTH: 15
<212> TYPE: PRT
<213> ORGANISM: Mus musculus

<400> SEQUENCE: 38

Ala Arg Gly Gly Tyr Tyr Gly Ser Ser Trp Gly Val Phe Ala Tyr
1               5                   10                  15

<210> SEQ ID NO 39
<211> LENGTH: 11
<212> TYPE: PRT
<213> ORGANISM: Mus musculus

<400> SEQUENCE: 39

Arg Val Ser Glu Asn Ile Tyr Ser Tyr Leu Ala
1               5                   10

<210> SEQ ID NO 40
<211> LENGTH: 7
<212> TYPE: PRT
<213> ORGANISM: Mus musculus

<400> SEQUENCE: 40

Ser Glu Asn Ile Tyr Ser Tyr
1               5

<210> SEQ ID NO 41
<211> LENGTH: 6
<212> TYPE: PRT
<213> ORGANISM: Mus musculus

<400> SEQUENCE: 41

Glu Asn Ile Tyr Ser Tyr
1               5

<210> SEQ ID NO 42
<211> LENGTH: 7
<212> TYPE: PRT
<213> ORGANISM: Mus musculus

<400> SEQUENCE: 42

Asn Ala Lys Thr Leu Ala Glu
1               5

<210> SEQ ID NO 43
<211> LENGTH: 9
<212> TYPE: PRT
<213> ORGANISM: Mus musculus

<400> SEQUENCE: 43

Gln His His Tyr Gly Thr Pro Trp Thr
1               5

<210> SEQ ID NO 44
```

```
<211> LENGTH: 6
<212> TYPE: PRT
<213> ORGANISM: Mus musculus

<400> SEQUENCE: 44

His Tyr Gly Thr Pro Trp
1               5

<210> SEQ ID NO 45
<211> LENGTH: 9
<212> TYPE: PRT
<213> ORGANISM: mus musculus

<400> SEQUENCE: 45

Gln His His Tyr Gly Thr Pro Trp Thr
1               5

<210> SEQ ID NO 46
<211> LENGTH: 5
<212> TYPE: PRT
<213> ORGANISM: Mus musculus

<400> SEQUENCE: 46

Glu Tyr Thr Met His
1               5

<210> SEQ ID NO 47
<211> LENGTH: 7
<212> TYPE: PRT
<213> ORGANISM: Mus musculus

<400> SEQUENCE: 47

Gly Tyr Thr Phe Thr Glu Tyr
1               5

<210> SEQ ID NO 48
<211> LENGTH: 8
<212> TYPE: PRT
<213> ORGANISM: Mus musculus

<400> SEQUENCE: 48

Gly Tyr Thr Phe Thr Glu Tyr Thr
1               5

<210> SEQ ID NO 49
<211> LENGTH: 17
<212> TYPE: PRT
<213> ORGANISM: Mus musculus

<400> SEQUENCE: 49

Gly Ile Ser Pro Asn Ile Gly Gly Thr Ser Tyr Asn Gln Lys Phe Lys
1               5                   10                  15

Gly

<210> SEQ ID NO 50
<211> LENGTH: 8
<212> TYPE: PRT
<213> ORGANISM: Mus musculus

<400> SEQUENCE: 50

Ile Ser Pro Asn Ile Gly Gly Thr
1               5

<210> SEQ ID NO 51
```

```
<211> LENGTH: 7
<212> TYPE: PRT
<213> ORGANISM: Mus musculus

<400> SEQUENCE: 51

Arg Gly Gly Ser Phe Asp Tyr
1               5

<210> SEQ ID NO 52
<211> LENGTH: 5
<212> TYPE: PRT
<213> ORGANISM: Mus musculus

<400> SEQUENCE: 52

Gly Gly Ser Phe Asp
1               5

<210> SEQ ID NO 53
<211> LENGTH: 9
<212> TYPE: PRT
<213> ORGANISM: Mus musculus

<400> SEQUENCE: 53

Ala Arg Arg Gly Gly Ser Phe Asp Tyr
1               5

<210> SEQ ID NO 54
<211> LENGTH: 11
<212> TYPE: PRT
<213> ORGANISM: Mus musculus

<400> SEQUENCE: 54

Arg Ala Ser Gln Ser Ile Ser Asp Tyr Leu His
1               5                   10

<210> SEQ ID NO 55
<211> LENGTH: 7
<212> TYPE: PRT
<213> ORGANISM: Mus musculus

<400> SEQUENCE: 55

Ser Gln Ser Ile Ser Asp Tyr
1               5

<210> SEQ ID NO 56
<211> LENGTH: 6
<212> TYPE: PRT
<213> ORGANISM: Mus musculus

<400> SEQUENCE: 56

Gln Ser Ile Ser Asp Tyr
1               5

<210> SEQ ID NO 57
<211> LENGTH: 7
<212> TYPE: PRT
<213> ORGANISM: Mus musculus

<400> SEQUENCE: 57

Tyr Ala Ser Gln Ser Ile Ser
1               5

<210> SEQ ID NO 58
<211> LENGTH: 9
<212> TYPE: PRT
```

```
<213> ORGANISM: Mus musculus

<400> SEQUENCE: 58

Gln Asn Gly His Ser Phe Pro Leu Thr
1               5

<210> SEQ ID NO 59
<211> LENGTH: 6
<212> TYPE: PRT
<213> ORGANISM: Mus musculus

<400> SEQUENCE: 59

Gly His Ser Phe Pro Leu
1               5

<210> SEQ ID NO 60
<211> LENGTH: 5
<212> TYPE: PRT
<213> ORGANISM: Mus musculus

<400> SEQUENCE: 60

Ser Phe Thr Met His
1               5

<210> SEQ ID NO 61
<211> LENGTH: 7
<212> TYPE: PRT
<213> ORGANISM: Mus musculus

<400> SEQUENCE: 61

Gly Tyr Thr Phe Thr Ser Phe
1               5

<210> SEQ ID NO 62
<211> LENGTH: 8
<212> TYPE: PRT
<213> ORGANISM: Mus musculus

<400> SEQUENCE: 62

Gly Tyr Thr Phe Thr Ser Phe Thr
1               5

<210> SEQ ID NO 63
<211> LENGTH: 17
<212> TYPE: PRT
<213> ORGANISM: Mus musculus

<400> SEQUENCE: 63

Tyr Ile Asn Pro Ser Ser Gly Tyr Thr Glu Tyr Asn Gln Lys Phe Lys
1               5                   10                  15

Asp

<210> SEQ ID NO 64
<211> LENGTH: 8
<212> TYPE: PRT
<213> ORGANISM: Mus musculus

<400> SEQUENCE: 64

Ile Asn Pro Ser Ser Gly Tyr Thr
1               5

<210> SEQ ID NO 65
<211> LENGTH: 8
<212> TYPE: PRT
```

```
<213> ORGANISM: Mus musculus

<400> SEQUENCE: 65

Gly Ser Ser Arg Gly Phe Asp Tyr
1               5

<210> SEQ ID NO 66
<211> LENGTH: 6
<212> TYPE: PRT
<213> ORGANISM: Mus musculus

<400> SEQUENCE: 66

Ser Ser Arg Gly Phe Asp
1               5

<210> SEQ ID NO 67
<211> LENGTH: 10
<212> TYPE: PRT
<213> ORGANISM: Mus musculus

<400> SEQUENCE: 67

Val Arg Gly Ser Ser Arg Gly Phe Asp Tyr
1               5                   10

<210> SEQ ID NO 68
<211> LENGTH: 11
<212> TYPE: PRT
<213> ORGANISM: Mus musculus

<400> SEQUENCE: 68

Arg Ala Ser Glu Asn Ile Tyr Ser Asn Leu Ala
1               5                   10

<210> SEQ ID NO 69
<211> LENGTH: 6
<212> TYPE: PRT
<213> ORGANISM: Mus musculur

<400> SEQUENCE: 69

Glu Asn Ile Tyr Ser Asn
1               5

<210> SEQ ID NO 70
<211> LENGTH: 7
<212> TYPE: PRT
<213> ORGANISM: mus musculur

<400> SEQUENCE: 70

Ala Ala Thr Asn Leu Ala Asp
1               5

<210> SEQ ID NO 71
<211> LENGTH: 9
<212> TYPE: PRT
<213> ORGANISM: Mus musculus

<400> SEQUENCE: 71

Gln His Phe Trp Gly Thr Pro Arg Thr
1               5

<210> SEQ ID NO 72
<211> LENGTH: 6
<212> TYPE: PRT
<213> ORGANISM: Mus musculus
```

```
<400> SEQUENCE: 72

Phe Trp Gly Thr Pro Arg
1               5

<210> SEQ ID NO 73
<211> LENGTH: 5
<212> TYPE: PRT
<213> ORGANISM: Mus musculus

<400> SEQUENCE: 73

Ser Ser Trp Met His
1               5

<210> SEQ ID NO 74
<211> LENGTH: 7
<212> TYPE: PRT
<213> ORGANISM: Mus musculus

<400> SEQUENCE: 74

Gly Tyr Thr Phe Thr Ser Ser
1               5

<210> SEQ ID NO 75
<211> LENGTH: 8
<212> TYPE: PRT
<213> ORGANISM: Mus musculus

<400> SEQUENCE: 75

Gly Tyr Thr Phe Thr Ser Ser Trp
1               5

<210> SEQ ID NO 76
<211> LENGTH: 17
<212> TYPE: PRT
<213> ORGANISM: Mus musculus

<400> SEQUENCE: 76

His Ile His Pro Asn Ser Gly Ile Ser Asn Tyr Asn Glu Lys Phe Lys
1               5                   10                  15

Gly

<210> SEQ ID NO 77
<211> LENGTH: 8
<212> TYPE: PRT
<213> ORGANISM: Mus musculus

<400> SEQUENCE: 77

Ile His Pro Asn Ser Gly Ile Ser
1               5

<210> SEQ ID NO 78
<211> LENGTH: 6
<212> TYPE: PRT
<213> ORGANISM: Mus musculus

<400> SEQUENCE: 78

Gly Gly Arg Phe Asp Asp
1               5

<210> SEQ ID NO 79
<211> LENGTH: 8
<212> TYPE: PRT
<213> ORGANISM: Mus musculus
```

```
<400> SEQUENCE: 79

Ala Arg Gly Gly Arg Phe Asp Asp
1               5

<210> SEQ ID NO 80
<211> LENGTH: 11
<212> TYPE: PRT
<213> ORGANISM: Mus musculus

<400> SEQUENCE: 80

Arg Ala Ser Gln Ser Ile Ser Asp Tyr Leu His
1               5                   10

<210> SEQ ID NO 81
<211> LENGTH: 11
<212> TYPE: PRT
<213> ORGANISM: Mus musculus

<400> SEQUENCE: 81

Gly Arg Phe Asp Ser Gln Ser Ile Ser Asp Tyr
1               5                   10

<210> SEQ ID NO 82
<211> LENGTH: 10
<212> TYPE: PRT
<213> ORGANISM: Mus musculus

<400> SEQUENCE: 82

Gln Asn Gly His Ser Phe Leu Met Tyr Thr
1               5                   10

<210> SEQ ID NO 83
<211> LENGTH: 7
<212> TYPE: PRT
<213> ORGANISM: Mus musculus

<400> SEQUENCE: 83

Gly His Ser Phe Leu Met Tyr
1               5

<210> SEQ ID NO 84
<211> LENGTH: 13
<212> TYPE: PRT
<213> ORGANISM: Mus musculus

<400> SEQUENCE: 84

Tyr Ala Ser Gln Asn Gly His Ser Phe Leu Met Tyr Thr
1               5                   10

<210> SEQ ID NO 85
<211> LENGTH: 6
<212> TYPE: PRT
<213> ORGANISM: mus musculus

<400> SEQUENCE: 85

Ser Asp Tyr Ala Trp Asn
1               5

<210> SEQ ID NO 86
<211> LENGTH: 8
<212> TYPE: PRT
<213> ORGANISM: Mus musculus

<400> SEQUENCE: 86
```

-continued

Gly Tyr Ser Ile Thr Ser Asp Tyr
1               5

<210> SEQ ID NO 87
<211> LENGTH: 9
<212> TYPE: PRT
<213> ORGANISM: Mus musculus

<400> SEQUENCE: 87

Gly Tyr Ser Ile Thr Ser Asp Tyr Ala
1               5

<210> SEQ ID NO 88
<211> LENGTH: 16
<212> TYPE: PRT
<213> ORGANISM: Mus musculus

<400> SEQUENCE: 88

Tyr Ile Thr Tyr Ser Gly Ser Thr Asn Tyr Asn Pro Ser Leu Lys Ser
1               5                   10                  15

<210> SEQ ID NO 89
<211> LENGTH: 11
<212> TYPE: PRT
<213> ORGANISM: Mus musculus

<400> SEQUENCE: 89

Cys Trp Asp Tyr Ala Leu Tyr Ala Met Asp Cys
1               5                   10

<210> SEQ ID NO 90
<211> LENGTH: 9
<212> TYPE: PRT
<213> ORGANISM: mus musculus

<400> SEQUENCE: 90

Trp Asp Tyr Ala Leu Tyr Ala Met Asp
1               5

<210> SEQ ID NO 91
<211> LENGTH: 13
<212> TYPE: PRT
<213> ORGANISM: Mus musculus

<400> SEQUENCE: 91

Ala Arg Cys Trp Asp Tyr Ala Leu Tyr Ala Met Asp Cys
1               5                   10

<210> SEQ ID NO 92
<211> LENGTH: 11
<212> TYPE: PRT
<213> ORGANISM: Mus musculus

<400> SEQUENCE: 92

Arg Thr Ser Glu Asn Ile Tyr Ser Tyr Leu Ala
1               5                   10

<210> SEQ ID NO 93
<211> LENGTH: 7
<212> TYPE: PRT
<213> ORGANISM: Mus musculus

<400> SEQUENCE: 93

Asn Ala Lys Thr Leu Ala Glu
1               5

<210> SEQ ID NO 94
<211> LENGTH: 9
<212> TYPE: PRT
<213> ORGANISM: Mus musculus

<400> SEQUENCE: 94

Gln His His Tyr Asp Thr Pro Leu Thr
1               5

<210> SEQ ID NO 95
<211> LENGTH: 9
<212> TYPE: PRT
<213> ORGANISM: mus musculus

<400> SEQUENCE: 95

Asn Ala Lys His Tyr Asp Thr Pro Leu
1               5

<210> SEQ ID NO 96
<211> LENGTH: 9
<212> TYPE: PRT
<213> ORGANISM: Mus musculus

<400> SEQUENCE: 96

Gln His His Tyr Asp Thr Pro Leu Thr
1               5

<210> SEQ ID NO 97
<211> LENGTH: 5
<212> TYPE: PRT
<213> ORGANISM: Mus musculus

<400> SEQUENCE: 97

Asn Tyr Gly Met Asn
1               5

<210> SEQ ID NO 98
<211> LENGTH: 7
<212> TYPE: PRT
<213> ORGANISM: mus musculus

<400> SEQUENCE: 98

Gly Tyr Thr Phe Thr Asn Tyr
1               5

<210> SEQ ID NO 99
<211> LENGTH: 8
<212> TYPE: PRT
<213> ORGANISM: mus musculus

<400> SEQUENCE: 99

Gly Tyr Thr Phe Thr Asn Tyr Gly
1               5

<210> SEQ ID NO 100
<211> LENGTH: 17
<212> TYPE: PRT
<213> ORGANISM: mus musculus

<400> SEQUENCE: 100

Trp Ile Asn Thr Asn Thr Gly Glu Pro Thr Tyr Ala Glu Glu Phe Lys
1               5                   10                  15

Gly

-continued

```
<210> SEQ ID NO 101
<211> LENGTH: 8
<212> TYPE: PRT
<213> ORGANISM: Mus musculus

<400> SEQUENCE: 101

Ile Asn Thr Asn Thr Gly Glu Pro
1               5

<210> SEQ ID NO 102
<211> LENGTH: 8
<212> TYPE: PRT
<213> ORGANISM: Mus musculus

<400> SEQUENCE: 102

Asp Tyr Leu Tyr Tyr Phe Asp Tyr
1               5

<210> SEQ ID NO 103
<211> LENGTH: 6
<212> TYPE: PRT
<213> ORGANISM: mus musculus

<400> SEQUENCE: 103

Tyr Leu Tyr Tyr Phe Asp
1               5

<210> SEQ ID NO 104
<211> LENGTH: 10
<212> TYPE: PRT
<213> ORGANISM: Mus musculus

<400> SEQUENCE: 104

Ala Arg Asp Tyr Leu Tyr Tyr Phe Asp Tyr
1               5                   10

<210> SEQ ID NO 105
<211> LENGTH: 11
<212> TYPE: PRT
<213> ORGANISM: Mus musculus

<400> SEQUENCE: 105

Lys Ala Ser Glu Asn Val Val Thr Tyr Val Ser
1               5                   10

<210> SEQ ID NO 106
<211> LENGTH: 7
<212> TYPE: PRT
<213> ORGANISM: Mus musculus

<400> SEQUENCE: 106

Ser Glu Asn Val Val Thr Tyr
1               5

<210> SEQ ID NO 107
<211> LENGTH: 6
<212> TYPE: PRT
<213> ORGANISM: Mus musculus

<400> SEQUENCE: 107

Glu Asn Val Val Thr Tyr
1               5
```

<210> SEQ ID NO 108
<211> LENGTH: 7
<212> TYPE: PRT
<213> ORGANISM: Mus musculus

<400> SEQUENCE: 108

Gly Ala Ser Asn Arg Tyr Thr
1               5

<210> SEQ ID NO 109
<211> LENGTH: 9
<212> TYPE: PRT
<213> ORGANISM: mus musculus

<400> SEQUENCE: 109

Gly Gln Gly Tyr Ser Tyr Pro Tyr Thr
1               5

<210> SEQ ID NO 110
<211> LENGTH: 6
<212> TYPE: PRT
<213> ORGANISM: mus musculus

<400> SEQUENCE: 110

Gly Tyr Ser Tyr Pro Tyr
1               5

<210> SEQ ID NO 111
<211> LENGTH: 9
<212> TYPE: PRT
<213> ORGANISM: mus musculus

<400> SEQUENCE: 111

Gly Gln Gly Tyr Ser Tyr Pro Tyr Thr
1               5

<210> SEQ ID NO 112
<211> LENGTH: 227
<212> TYPE: PRT
<213> ORGANISM: homo sapiens

<400> SEQUENCE: 112

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Gly Gly Gly Ser Gly
                100                 105                 110

Gly Gly Gly Ser Gly Gly Gly Ser Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val

-continued

```
            145                 150                 155                 160
Glu Trp Glu Ser Asn Gly Gln Pro Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
210                 215                 220

Ser Pro Gly
225
```

<210> SEQ ID NO 113
<211> LENGTH: 333
<212> TYPE: DNA
<213> ORGANISM: mus musculus

<400> SEQUENCE: 113

```
gacattcagc tgacccaatc tccagcttct ttggctgtgt ctctagggca gagggccacc    60
atctcctgca aggccagcca aagtgttgat tatgatggtg atagttattt gaactggtac   120
caacagatac caggacagcc acccaaactc ctcatctatg atgcatccaa tctagtatct   180
gggattccac ccaggtttag tggcagtggg tctgggacag acttcaccct caacatccat   240
cctgtggaga aggtggatgc tgcaacctat cactgtcagc aaagtactga ggacccttgg   300
acgttcggtg aggcaccaa gctggaaatc aaa                                  333
```

<210> SEQ ID NO 114
<211> LENGTH: 111
<212> TYPE: PRT
<213> ORGANISM: mus musculus

<400> SEQUENCE: 114

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110
```

<210> SEQ ID NO 115
<211> LENGTH: 372
<212> TYPE: DNA
<213> ORGANISM: mus musculus

<400> SEQUENCE: 115

```
caggttcagc tgcagcagtc tggggctgag ctggtgcggc ctgggtcctc agtgaagatt    60
tcctgcaaag catctggcta cgcattcagt agctactgga tgaactgggt gaagcagagg   120
cctggacagg gtcttgagtg gattggacag atttggcctg agatggtga tactaactac   180
```

```
aacggaaagt tcaagggcaa ggccacactg actgcagacg aatcctccag cacagcctac      240
atgcagctca gcagcctggc ctctgaggac tctgcggtct atttctgtgc aagacgagaa      300
acgaccactg tcgggcgtta ttactatgct atggactact ggggtcaagg aaccacagtc      360
accgtctcct ca                                                          372
```

<210> SEQ ID NO 116
<211> LENGTH: 124
<212> TYPE: PRT
<213> ORGANISM: Mus musculus

<400> SEQUENCE: 116

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 117
<211> LENGTH: 648
<212> TYPE: DNA
<213> ORGANISM: homo sapiens

<400> SEQUENCE: 117

```
gcacctgaac tcctggggg accgtcagtc ttcctcttcc ccccaaaacc caaggacacc       60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcgggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
cccatcgaga aaaccatctc caaagccaaa gggcagcccc gagaaccaca ggtgtacacc     360 aagccccat cccgggagga tgaccaag aaccaggtca gcctgtcctg cctggtcaaa        420
ggcttctatc ccagcgacat cgccgtggag tgggagagca atgggcagcc ggagaacaac     480
tacaagacca cggttcccgt gctggactcc gacggctcct tccgcctcgc tagctacctc     540
accgtggaca agagcaggtg gcagcagggg aacgtcttct catgctccgt gatgcatgag     600
gctctgcaca accactacac gcagaagagc ctctcccctgt ccccgggg               648
```

<210> SEQ ID NO 118
<211> LENGTH: 718
<212> TYPE: PRT
<213> ORGANISM: Artificial
<220> FEATURE:
<223> OTHER INFORMATION: Chimeric homo sapiens mus musculus

```
<400> SEQUENCE: 118

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
    195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
            245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
    355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415
```

```
Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly Ser Thr Gly Ser Asp Ile Lys Leu Gln
465                 470                 475                 480

Gln Ser Gly Ala Glu Leu Ala Arg Pro Gly Ala Ser Val Lys Met Ser
            485                 490                 495

Cys Lys Thr Ser Gly Tyr Thr Phe Thr Arg Tyr Thr Met His Trp Val
            500                 505                 510

Lys Gln Arg Pro Gly Gln Gly Leu Glu Trp Ile Gly Tyr Ile Asn Pro
            515                 520                 525

Ser Arg Gly Tyr Thr Asn Tyr Asn Gln Lys Phe Lys Asp Lys Ala Thr
            530                 535                 540

Leu Thr Thr Asp Lys Ser Ser Ser Thr Ala Tyr Met Gln Leu Ser Ser
545                 550                 555                 560

Leu Thr Ser Glu Asp Ser Ala Val Tyr Tyr Cys Ala Arg Tyr Tyr Asp
            565                 570                 575

Asp His Tyr Cys Leu Asp Tyr Trp Gly Gln Gly Thr Thr Leu Thr Val
            580                 585                 590

Ser Ser Val Glu Gly Gly Ser Gly Gly Ser Gly Gly Ser Gly Gly Ser
            595                 600                 605

Gly Gly Val Asp Asp Ile Gln Leu Thr Gln Ser Pro Ala Ile Met Ser
            610                 615                 620

Ala Ser Pro Gly Glu Lys Val Thr Met Thr Cys Arg Ala Ser Ser Ser
625                 630                 635                 640

Val Ser Tyr Met Asn Trp Tyr Gln Gln Lys Ser Gly Thr Ser Pro Lys
            645                 650                 655

Arg Trp Ile Tyr Asp Thr Ser Lys Val Ala Ser Gly Val Pro Tyr Arg
            660                 665                 670

Phe Ser Gly Ser Gly Ser Gly Thr Ser Tyr Ser Leu Thr Ile Ser Ser
            675                 680                 685

Met Glu Ala Glu Asp Ala Ala Thr Tyr Tyr Cys Gln Gln Trp Ser Ser
            690                 695                 700

Asn Pro Leu Thr Phe Gly Ala Gly Thr Lys Leu Glu Leu Lys
705                 710                 715

<210> SEQ ID NO 119
<211> LENGTH: 249
<212> TYPE: PRT
<213> ORGANISM: mus musculus

<400> SEQUENCE: 119

Ser Thr Gly Ser Gln Val Gln Leu Gln Gln Ser Gly Pro Glu Leu Val
1               5                   10                  15

Lys Pro Gly Ala Ser Val Lys Met Ser Cys Lys Ala Ser Gly Tyr Thr
            20                  25                  30

Phe Thr Asp Tyr Val Ile Asn Trp Gly Lys Gln Arg Ser Gly Gln Gly
            35                  40                  45

Leu Glu Trp Ile Gly Glu Ile Tyr Pro Gly Ser Gly Thr Asn Tyr Tyr
        50                  55                  60

Asn Glu Lys Phe Lys Ala Lys Ala Thr Leu Thr Ala Asp Lys Ser Ser
```

Asn Ile Ala Tyr Met Gln Leu Ser Ser Leu Thr Ser Glu Asp Ser Ala
 65                  70                  75                  80

Val Tyr Phe Cys Ala Arg Arg Gly Arg Tyr Gly Leu Tyr Ala Met Asp
             85                  90                  95

Tyr Trp Gly Gln Gly Thr Ser Val Thr Val Ser Ser Val Glu Gly Gly
            100                 105                 110

Ser Gly Ser Gly Gly Ser Gly Gly Ser Gly Val Asp Asp Ile
        115                 120                 125

Ser Gly Ser Gly Gly Ser Gly Gly Ser Gly Val Asp Asp Ile
    130                 135                 140

Gln Met Thr Gln Thr Thr Ser Ser Leu Ser Ala Ser Leu Gly Asp Arg
145                 150                 155                 160

Val Thr Ile Ser Cys Arg Ala Ser Gln Asp Ile Ser Asn Tyr Leu Asn
                165                 170                 175

Trp Tyr Gln Gln Lys Pro Asp Gly Thr Val Lys Leu Leu Ile Tyr Tyr
            180                 185                 190

Thr Ser Arg Leu His Ser Gly Val Pro Ser Arg Phe Ser Gly Ser Gly
            195                 200                 205

Ser Gly Thr Asp Tyr Ser Leu Thr Ile Asn Asn Leu Glu Gln Glu Asp
    210                 215                 220

Ile Ala Thr Tyr Phe Cys Gln Gln Gly Asn Thr Arg Pro Trp Thr Phe
225                 230                 235                 240

Gly Gly Gly Thr Lys Leu Glu Ile Lys
                245

<210> SEQ ID NO 120
<211> LENGTH: 251
<212> TYPE: PRT
<213> ORGANISM: mus musculus

<400> SEQUENCE: 120

Ser Thr Gly Ser Glu Val Gln Leu Gln Glu Ser Gly Pro Gly Leu Val
1               5                   10                  15

Lys Pro Ser Gln Ser Leu Ser Leu Thr Cys Thr Val Thr Gly Tyr Ser
            20                  25                  30

Ile Thr Ser Asp Tyr Ala Trp Asn Trp Ile Arg Gln Phe Pro Gly Asn
        35                  40                  45

Lys Leu Glu Trp Met Gly Tyr Ile Thr Tyr Ser Gly Ser Thr Ser Tyr
    50                  55                  60

Asn Pro Ser Leu Glu Ser Arg Ile Ser Ile Thr Arg Asp Thr Ser Thr
65                  70                  75                  80

Asn Gln Phe Phe Leu Gln Leu Asn Ser Val Thr Thr Glu Asp Thr Ala
            85                  90                  95

Thr Tyr Tyr Cys Ala Arg Gly Gly Tyr Tyr Gly Ser Ser Trp Gly Val
            100                 105                 110

Phe Ala Tyr Trp Gly Gln Gly Thr Leu Val Thr Val Ser Ala Val Glu
        115                 120                 125

Gly Gly Ser Gly Gly Ser Gly Gly Ser Gly Gly Ser Gly Val Asp
    130                 135                 140

Asp Ile Gln Met Thr Gln Ser Pro Ala Ser Leu Ser Ala Ser Val Gly
145                 150                 155                 160

Glu Thr Val Thr Ile Thr Cys Arg Val Ser Glu Asn Ile Tyr Ser Tyr
                165                 170                 175

Leu Ala Trp Tyr Gln Gln Lys Gln Gly Lys Ser Pro Gln Leu Leu Val
            180                 185                 190

Tyr Asn Ala Lys Thr Leu Ala Glu Gly Val Pro Ser Arg Phe Ser Gly
            195                 200                 205

Ser Gly Ser Gly Thr Gln Phe Ser Leu Lys Ile Asn Ser Leu Gln Pro
    210                 215                 220

Glu Asp Phe Gly Ser Tyr Tyr Cys Gln His His Tyr Gly Thr Pro Trp
225                 230                 235                 240

Thr Phe Gly Gly Gly Thr Lys Leu Glu Ile Lys
                245                 250

<210> SEQ ID NO 121
<211> LENGTH: 245
<212> TYPE: PRT
<213> ORGANISM: mus musculus

<400> SEQUENCE: 121

Ser Thr Gly Ser Glu Val Gln Leu Gln Gln Ser Gly Pro Glu Leu Val
1               5                   10                  15

Lys Pro Gly Ala Ser Val Lys Ile Ser Cys Lys Thr Ser Gly Tyr Thr
            20                  25                  30

Phe Thr Glu Tyr Thr Met His Trp Val Lys Gln Ser His Gly Lys Ser
        35                  40                  45

Leu Glu Trp Ile Gly Gly Ile Ser Pro Asn Ile Gly Gly Thr Ser Tyr
    50                  55                  60

Asn Gln Lys Phe Lys Gly Lys Ala Thr Leu Thr Val Asp Lys Ser Ser
65                  70                  75                  80

Ser Thr Ala Tyr Met Glu Leu Arg Ser Leu Thr Ser Glu Asp Ser Ala
                85                  90                  95

Val Tyr Tyr Cys Ala Arg Arg Gly Gly Ser Phe Asp Tyr Trp Gly Gln
            100                 105                 110

Gly Thr Thr Leu Thr Val Ser Ser Val Glu Gly Gly Ser Gly Gly Ser
        115                 120                 125

Gly Gly Ser Gly Gly Ser Gly Gly Val Asp Asp Ile Val Met Thr Gln
    130                 135                 140

Ser Pro Ala Thr Leu Ser Val Thr Pro Gly Asp Arg Val Ser Leu Ser
145                 150                 155                 160

Cys Arg Ala Ser Gln Ser Ile Ser Asp Tyr Leu His Trp Tyr Gln Gln
                165                 170                 175

Lys Ser His Glu Ser Pro Arg Leu Leu Ile Lys Tyr Ala Ser Gln Ser
            180                 185                 190

Ile Ser Gly Ile Pro Ser Arg Phe Ser Gly Ser Gly Ser Gly Ser Asp
        195                 200                 205

Phe Thr Leu Ser Ile Asn Ser Val Glu Pro Glu Asp Val Gly Val Tyr
    210                 215                 220

Tyr Cys Gln Asn Gly His Ser Phe Pro Leu Thr Phe Gly Ala Gly Thr
225                 230                 235                 240

Lys Leu Glu Leu Lys
                245

<210> SEQ ID NO 122
<211> LENGTH: 246
<212> TYPE: PRT
<213> ORGANISM: Mus musculus

<400> SEQUENCE: 122

Ser Thr Gly Ser Gln Val Gln Leu Gln Gln Ser Ala Val Glu Leu Ala
1               5                   10                  15

Arg Pro Gly Ala Ser Val Lys Met Ser Cys Lys Ala Ser Gly Tyr Thr
            20                  25                  30

Phe Thr Ser Phe Thr Met His Trp Val Lys Gln Arg Pro Gly Gln Gly
            35                  40                  45

Leu Glu Trp Ile Gly Tyr Ile Asn Pro Ser Ser Gly Tyr Thr Glu Tyr
        50                  55                  60

Asn Gln Lys Phe Lys Asp Lys Thr Thr Leu Thr Ala Asp Lys Ser Ser
65                  70                  75                  80

Ser Thr Ala Tyr Met Gln Leu Asp Ser Leu Thr Ser Asp Asp Ser Ala
                85                  90                  95

Val Tyr Tyr Cys Val Arg Gly Ser Ser Arg Gly Phe Asp Tyr Trp Gly
            100                 105                 110

Gln Gly Thr Leu Val Thr Val Ser Ala Val Glu Gly Gly Ser Gly Gly
            115                 120                 125

Ser Gly Gly Ser Gly Gly Ser Gly Gly Val Asp Asp Ile Gln Met Ile
        130                 135                 140

Gln Ser Pro Ala Ser Leu Ser Val Ser Val Gly Glu Thr Val Thr Ile
145                 150                 155                 160

Thr Cys Arg Ala Ser Glu Asn Ile Tyr Ser Asn Leu Ala Trp Phe Gln
                165                 170                 175

Gln Lys Gln Gly Lys Ser Pro Gln Leu Leu Val Tyr Ala Ala Thr Asn
            180                 185                 190

Leu Ala Asp Gly Val Pro Ser Arg Phe Ser Gly Ser Gly Ser Gly Thr
            195                 200                 205

Gln Tyr Ser Leu Lys Ile Asn Ser Leu Gln Ser Glu Asp Phe Gly Ile
        210                 215                 220

Tyr Tyr Cys Gln His Phe Trp Gly Thr Pro Arg Thr Phe Gly Gly Gly
225                 230                 235                 240

Thr Lys Leu Glu Ile Lys
                245

<210> SEQ ID NO 123
<211> LENGTH: 245
<212> TYPE: PRT
<213> ORGANISM: Mus musculus

<400> SEQUENCE: 123

Ser Thr Gly Ser Gln Val Gln Leu Gln Gln Pro Gly Ser Val Leu Val
1               5                   10                  15

Arg Pro Gly Ala Ser Val Lys Leu Ser Cys Lys Ala Ser Gly Tyr Thr
            20                  25                  30

Phe Thr Ser Ser Trp Met His Trp Ala Lys Gln Arg Pro Gly Gln Gly
            35                  40                  45

Leu Glu Trp Ile Gly His Ile His Pro Asn Ser Gly Ile Ser Asn Tyr
        50                  55                  60

Asn Glu Lys Phe Lys Gly Lys Ala Thr Leu Thr Val Asp Thr Ser Ser
65                  70                  75                  80

Ser Thr Ala Tyr Val Asp Leu Ser Ser Leu Thr Ser Glu Asp Ser Ala
                85                  90                  95

Val Tyr Tyr Cys Ala Arg Gly Gly Arg Phe Asp Asp Trp Gly Ala Gly
            100                 105                 110

Thr Thr Val Thr Val Ser Ser Val Glu Gly Gly Ser Gly Gly Ser Gly
            115                 120                 125

Gly Ser Gly Gly Ser Gly Gly Val Asp Asp Ile Val Met Thr Gln Ser
        130                 135                 140

```
Pro Ala Thr Leu Ser Val Thr Pro Gly Asp Arg Val Ser Leu Ser Cys
145                 150                 155                 160

Arg Ala Ser Gln Ser Ile Ser Asp Tyr Leu His Trp Tyr Gln Gln Lys
                165                 170                 175

Ser His Glu Ser Pro Arg Leu Leu Ile Lys Tyr Ala Ser Gln Ser Ile
            180                 185                 190

Ser Gly Ile Pro Ser Arg Phe Ser Gly Ser Gly Ser Gly Ser Asp Phe
        195                 200                 205

Thr Leu Ser Ile Asn Ser Val Glu Pro Glu Asp Val Gly Val Tyr Tyr
    210                 215                 220

Cys Gln Asn Gly His Ser Phe Leu Met Tyr Thr Phe Gly Gly Gly Thr
225                 230                 235                 240

Lys Leu Glu Ile Lys
                245

<210> SEQ ID NO 124
<211> LENGTH: 249
<212> TYPE: PRT
<213> ORGANISM: Mus musculus

<400> SEQUENCE: 124

Ser Thr Gly Ser Asp Val Gln Leu Gln Glu Ser Gly Pro Gly Leu Val
1               5                   10                  15

Lys Pro Ser Gln Ser Leu Ser Leu Thr Cys Thr Val Thr Gly Tyr Ser
            20                  25                  30

Ile Thr Ser Asp Tyr Ala Trp Asn Trp Ile Arg Gln Phe Pro Gly Asn
        35                  40                  45

Lys Leu Glu Trp Met Gly Tyr Ile Thr Tyr Ser Gly Ser Thr Asn Tyr
    50                  55                  60

Asn Pro Ser Leu Lys Ser Arg Ile Ser Ile Thr Arg Asp Thr Ser Lys
65                  70                  75                  80

Asn Gln Phe Phe Leu Gln Leu Asn Ser Val Thr Thr Glu Asp Thr Ala
                85                  90                  95

Thr Tyr Tyr Cys Ala Arg Cys Trp Asp Tyr Ala Leu Tyr Ala Met Asp
            100                 105                 110

Cys Trp Gly Gln Gly Thr Ser Val Thr Val Ser Ser Val Glu Gly Gly
        115                 120                 125

Ser Gly Gly Ser Gly Gly Ser Gly Gly Ser Gly Gly Val Asp Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Thr Ser Glu Asn Ile Tyr Ser Tyr Leu Ala
                165                 170                 175

Trp Cys Gln Gln Lys Gln Gly Lys Ser Pro Gln Leu Leu Val Tyr Asn
            180                 185                 190

Ala Lys Thr Leu Ala Glu Gly Val Pro Ser Arg Phe Ser Gly Ser Gly
        195                 200                 205

Ser Gly Thr His Phe Ser Leu Lys Ile Asn Ser Leu Gln Pro Glu Asp
    210                 215                 220

Phe Gly Ile Tyr Tyr Cys Gln His His Tyr Asp Thr Pro Leu Thr Phe
225                 230                 235                 240

Gly Ala Gly Thr Lys Leu Glu Leu Lys
                245
```

<210> SEQ ID NO 125
<211> LENGTH: 246
<212> TYPE: PRT
<213> ORGANISM: Mus musculus

<400> SEQUENCE: 125

Ser Thr Gly Ser Gln Ile Gln Leu Val Gln Ser Gly Pro Glu Leu Gln
1               5                   10                  15

Lys Pro Gly Glu Thr Val Lys Ile Ser Cys Lys Ala Ser Gly Tyr Thr
            20                  25                  30

Phe Thr Asn Tyr Gly Met Asn Trp Val Lys Gln Ala Pro Gly Lys Gly
        35                  40                  45

Leu Lys Trp Met Gly Trp Ile Asn Thr Asn Thr Gly Glu Pro Thr Tyr
    50                  55                  60

Ala Glu Glu Phe Lys Gly Arg Phe Ala Phe Ser Leu Glu Thr Ser Ala
65                  70                  75                  80

Ser Thr Ala Tyr Leu Gln Ile Asn Asn Leu Lys Asn Glu Asp Thr Ala
                85                  90                  95

Thr Tyr Phe Cys Ala Arg Asp Tyr Leu Tyr Tyr Phe Asp Tyr Trp Gly
            100                 105                 110

Gln Gly Thr Thr Leu Thr Val Ser Ser Val Glu Gly Gly Ser Gly Gly
        115                 120                 125

Ser Gly Gly Ser Gly Gly Ser Gly Gly Val Asp Asn Ile Val Met Thr
    130                 135                 140

Gln Ser Pro Lys Ser Met Ser Met Ser Val Gly Glu Arg Val Thr Leu
145                 150                 155                 160

Thr Cys Lys Ala Ser Glu Asn Val Val Thr Tyr Val Ser Trp Tyr Gln
                165                 170                 175

Gln Lys Pro Glu Gln Ser Pro Lys Leu Leu Ile Tyr Gly Ala Ser Asn
            180                 185                 190

Arg Tyr Thr Gly Val Pro Asp Arg Phe Thr Gly Ser Gly Ser Ala Thr
        195                 200                 205

Asp Phe Thr Leu Thr Ile Ser Ser Val Gln Ala Glu Asp Leu Ala Asp
    210                 215                 220

Tyr His Cys Gly Gln Gly Tyr Ser Tyr Pro Tyr Thr Phe Gly Gly Gly
225                 230                 235                 240

Thr Lys Leu Glu Ile Lys
                245

<210> SEQ ID NO 126
<211> LENGTH: 751
<212> TYPE: DNA
<213> ORGANISM: mus musculus

<400> SEQUENCE: 126
gtcgactgga agccaggtac agctgcagca gtctggccct gaactcgtca aaccaggagc      60
ttccgtgaag atgtcctgca aggcttcagg gtacacgttt accgactatg tgatcaattg     120
gggtaagcag cgctctgggc aaggcttgga gtggattggc gagatctatc ctgggagtgg     180
gaccaactat tacaacgaga gttcaaggc caaagccact ttgactgcag acaagagctc     240
aaacattgcc tacatgcaac tgagctccct gacatcagag gattctgctg tgtacttctg     300
tgcacgtaga ggtcggtacg gtctgtatgc catggactat ggggccaag gcacttccgt     360 gacagtcagc tctgtggaag gaggaagtgg cggttcagga ggtagcggag ggtccggagg     420
agtggatgac attcagatga cacagaccac ttctagcctc tccgcatccc ttggggatag     480

```
ggtcaccatc agttgtaggg ctagccagga catttccaat tacctgaact ggtatcagca        540
gaaacccgat ggcacagtta agcttctgat ctactacaca agcagactgc actcaggggt        600
tccatctcgg tttagtggaa gtggctctgg taccgactat tccctgacca tcaacaatct        660
ggaacaggaa gatatcgcca cctacttctg ccaacagggc aatactcgac cctggacatt        720
tggtggcggc acgaaactcg agataaaata a                                        751

<210> SEQ ID NO 127
<211> LENGTH: 757
<212> TYPE: DNA
<213> ORGANISM: Mus musculus

<400> SEQUENCE: 127
gtcgactgga tccgaggtac agttgcagga gagtgggcct ggactggtca aaccctccca         60
atctctgagc ttgacatgca cagtcacagg ctacagcatc acctccgact acgcttggaa        120
ttggattcga cagtttcccg gcaacaagct ggaatggatg gctacatca cctatagtgg        180 tagcacttcc tataatccct cacttgagag ccggatttcc atcactaggg atacgagcac        240
caaccagttc ttcctgcagc tgaatagcgt caccaccgaa gatactgcca cctattactg        300
cgcaagaggc ggttactatg gcagttcatg gggtgtattc gcctattggg gacagggggac       360 acttgtgaca gtgtctgctg ttgaaggtgg atccggcgga tcaggaggga gtggtggcag        420
tggaggtgtt gacgacattc agatgaccca atcccctgct tctctctcag cctctgtggg        480
agagactgtg accataacct gtcgtgttag cgagaacatc tactcctatc tcgcctggta        540
tcagcagaaa caggggaaat ccccacaact gctcgtgtac aatgccaaga ctctggcaga        600
aggagtgcca agccgctttt ccgggtctgg gtctgggaca cagttctcac tgaagatcaa        660
ctctttgcaa cctgaggatt ttggctctta ctactgtcag catcactatg gcacaccatg        720
gacgtttggt ggcggcacta agctggagat taagtaa                                 757

<210> SEQ ID NO 128
<211> LENGTH: 739
<212> TYPE: DNA
<213> ORGANISM: Mus musculus

<400> SEQUENCE: 128
gtcgactggg tccgaagtgc aactgcaaca gtctggccct gagctggtca aaccccggtgc        60 ttcagtgaag atctcctgca agacatccgg ctacaccttc actgagtaca ccatgcactg       120
ggtcaaacag tctcacgtta agagcctgga gtggataggc ggaatttcac ccaacattgg       180
agggacctcc tataaccaga gttcaagggg caaagccacc cttacagttg acaagagcag       240
ttcaactgcc tacatggaac tgcgctcatt gacctccgag gattcagccg tgtattactg       300
cgctagaagg ggaggatcct tcgattattg gggccaaggc actacgctta ccgtgagcag       360
cgttgaaggt ggttctggcg gctctggtgg aagtggaggg agtggcgggg tagacgacat       420
cgtgatgact cagagtccag caactctgtc cgttacacct ggagatcgag tgtctctgag       480
ttgtcgtgca agccagtcta tctctgacta tctgcactgg tatcagcaga agagccatga       540
gtcacctagg ctgttgatca agtacgcctc tcagtccatt agcgggattc catcccggtt       600
tagtggctct ggctccggta gtgacttcac actcagcatc aatagcgtcg aaccagagga       660 tgtagggggtg tactactgtc agaatgggca ttcctttccc ctcacatttg gagctggtac       720
caaactcgag ctgaaataa                                                     739
```

<210> SEQ ID NO 129
<211> LENGTH: 742
<212> TYPE: DNA
<213> ORGANISM: Mus musculus

<400> SEQUENCE: 129

| | | | | | |
|---|---|---|---|---|---|
| gtcgactggc | tcccaagtac | agcttcagca | gtctgccgtc | gaacttgctc | gaccaggagc | 60 |
| ttcagtgaag | atgagctgca | aagcctctgg | ttacaccttc | acgtccttta | ccatgcattg | 120 |
| ggtgaagcag | cgtcctggcc | aaggcctgga | gtggattggc | tacatcaatc | cctccagcgg | 180 |
| gtataccgag | tacaaccaga | agttcaagga | caaaacaacc | ctgactgccg | ataagtcaag | 240 |
| tagcacagcc | tatatgcagc | tggattccct | gacatcagac | gatagcgctg | tgtattactg | 300 |
| cgttaggggc | tctagcagag | ggttcgacta | ttggggtcaa | ggcacactgg | tcacggttag | 360 |
| tgccgttgaa | ggaggctctg | aggcagtgg | aggttctgga | gggtcaggcg | gtgtggatga | 420 |
| cattcagatg | attcagagtc | ccgctagctt | gagtgtaagc | gtcggtgaga | cagtgaccat | 480 |
| cacttgtcgc | gcatccgaaa | acatctactc | caatctcgca | tggttccagc | agaaacaggg | 540 |
| caaatcaccc | caattgctcg | tgtatgccgc | aactaatctg | gctgatggtg | tgccttccag | 600 |
| gtttagcggg | tctggatctg | ggactcagta | ctccctgaag | atcaactccc | tccagtctga | 660 |
| ggacttcggg | atctattact | gtcagcactt | ttggggaact | ccacggacct | ttggaggcgg | 720 |
| gaccaaactg | gagataaagt | aa | | | | 742 |

<210> SEQ ID NO 130
<211> LENGTH: 696
<212> TYPE: DNA
<213> ORGANISM: Mus musculus

<400> SEQUENCE: 130

| | | | | | |
|---|---|---|---|---|---|
| ctggtgaggc | caggtgcatc | tgtgaagctg | tcatgcaaag | catccgggta | cacgttcacc | 60 |
| tcttcatgga | tgcattgggc | caaacagcgt | ccaggccagg | ccttgagtg | gattggacac | 120 |
| attcacccca | atagcggcat | atccaactac | aacgagaagt | tcaagggcaa | agccacactg | 180 |
| acagtggata | cttccagctc | tacagcctat | gtggacctta | gtagcttgac | cagtgaggat | 240 |
| tctgccgtat | actactgtgc | tagaggtggg | cggtttgacg | attggggtgc | tgggaccaca | 300 |
| gtcaccgtga | gcagtgtcga | aggtggatca | ggtggatctg | gaggctcagg | cggttctggc | 360 |
| ggtgttgacg | acatcgtgat | gactcaaagc | cctgctactc | tctctgtcac | acccggagat | 420 |
| agggtaagcc | tcagttgtcg | agcaagccag | tcaatcagcg | actatctgca | ctggtatcag | 480 |
| cagaagtccc | atgaatcccc | acgcttgctc | atcaagtacg | ccagtcagtc | catcagtggc | 540 |
| attccttccc | ggttttctgg | gtctggatcc | gggtcagact | tcactctgag | cattaactcc | 600 |
| gtcgaacccg | aggatgttgg | cgtgtattat | tgccagaatg | acattccctt | cctgatgtac | 660 |
| acctttggcg | agggaccaa | actggagatc | aagtaa | | | 696 |

<210> SEQ ID NO 131
<211> LENGTH: 751
<212> TYPE: DNA
<213> ORGANISM: Mus musculus

<400> SEQUENCE: 131

| | | | | | |
|---|---|---|---|---|---|
| gtcgactggg | tctgatgtgc | agttgcagga | gtcaggacct | gggcttgtca | agccaagcca | 60 |
| gagcctcagt | ctcacttgca | ctgtcacagg | ctatagcatc | acatccgact | atgcttggaa | 120 |
| ttggattagg | cagtttcctg | gcaataagct | ggaatggatg | gggtacatca | cctattccgg | 180 |

```
cagtaccaac tacaatccca gcttgaaatc tcggatttcc ataacacgcg atactagcaa    240
gaaccagttc ttccttcagc tgaactctgt gacaacagag gataccgcta cgtactattg    300
cgccagatgc tgggattacg ccctgtatgc catggactgt tggggtcaag gtaccagcgt    360
tactgtgtct agcgtcgaag gcggaagtgg cggctcagga gggtcaggag gctcaggcgg    420
agtggatgac attcagatga cccaatctcc cgcatccctg tccgcatcag taggggagac    480
agtgaccatt acctgtcgta cttccgagaa catctactcc tatcttgcct ggtgtcaaca    540
gaaacagggg aaaagtccac agctgctggt gtataacgcc aagaccttgg cagaaggtgt    600
tcccagtcga ttctctggtt ccggatccgg tacacacttc agcctgaaga tcaattctct    660
gcaaccagag gactttggaa tctactactg ccagcatcac tacgacactc ctctgacgtt    720
tggcgctggt accaagctcg aactgaaata a                                   751

<210> SEQ ID NO 132
<211> LENGTH: 742
<212> TYPE: DNA
<213> ORGANISM: Mus musculus

<400> SEQUENCE: 132
gtcgactggt agccagatac agctggtaca gtcaggacca gagctgcaga aacctggaga     60
gacagtgaag atcagctgca aggctagcgg gtacaccttc acgaattacg ggatgaactg    120
ggtcaagcag gctccaggca aagggctgaa gtggatgggc tggattaaca ccaatactgg    180
ggaaccaacc tatgccgagg aattcaaggg gagatttgcc ttttccctcg aaaccagcgc    240
ctcaaccgcc tatctccaga tcaacaacct gaagaatgag gataccgcta cctacttctg    300
tgcaagggac tacctctact acttcgacta ttggggccaa ggtacgactc ttacagtctc    360
tagtgttgag ggagggagtg gaggttctgg aggctctggt ggctctggag gcgttgacaa    420
catcgtgatg actcagtctc ccaaaagcat gagtatgagt gtgggtgaac gagttacctt    480
gacatgcaaa gcctccgaga atgtcgtgac atacgtgtcc tggtatcagc agaaacccga    540
gcaatcccct aagctgctga tctatggcgc tagcaatcgc tatactggcg tacctgatcg    600
gttcacagga tcaggctcag ccactgactt tactcttacc atttcctccg tgcaggcaga    660
agatttggca gattaccact gtgggcaagg ttactcttat ccctatacat ttggaggcgg    720
cacaaagctg gagattaagt aa                                             742

<210> SEQ ID NO 133
<211> LENGTH: 720
<212> TYPE: PRT
<213> ORGANISM: Artificial
<220> FEATURE:
<223> OTHER INFORMATION: Chimeric homo sapiens mus musculus

<400> SEQUENCE: 133

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Asn Ile His
65                  70                  75                  80
```

-continued

```
Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
    370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Gln Val Gln Leu Gln
465                 470                 475                 480

Gln Ser Gly Pro Glu Leu Val Lys Pro Gly Ala Ser Val Lys Met Ser
                485                 490                 495

Cys Lys Ala Ser Gly Tyr Thr Phe Thr Asp Tyr Val Ile Asn Trp Gly
```

```
                500             505             510
Lys Gln Arg Ser Gly Gln Gly Leu Glu Trp Ile Gly Glu Ile Tyr Pro
            515                 520                 525
Gly Ser Gly Thr Asn Tyr Tyr Asn Glu Lys Phe Lys Ala Lys Ala Thr
        530                 535                 540
Leu Thr Ala Asp Lys Ser Ser Asn Ile Ala Tyr Met Gln Leu Ser Ser
545                 550                 555                 560
Leu Thr Ser Glu Asp Ser Ala Val Tyr Phe Cys Ala Arg Arg Gly Arg
                565                 570                 575
Tyr Gly Leu Tyr Ala Met Asp Tyr Trp Gly Gln Gly Thr Ser Val Thr
            580                 585                 590
Val Ser Ser Val Glu Gly Gly Ser Gly Gly Ser Gly Gly Ser Gly Gly
        595                 600                 605
Ser Gly Gly Val Asp Asp Ile Gln Met Thr Gln Thr Thr Ser Ser Leu
            610                 615                 620
Ser Ala Ser Leu Gly Asp Arg Val Thr Ile Ser Cys Arg Ala Ser Gln
625                 630                 635                 640
Asp Ile Ser Asn Tyr Leu Asn Trp Tyr Gln Gln Lys Pro Asp Gly Thr
                645                 650                 655
Val Lys Leu Leu Ile Tyr Tyr Thr Ser Arg Leu His Ser Gly Val Pro
            660                 665                 670
Ser Arg Phe Ser Gly Ser Gly Ser Gly Thr Asp Tyr Ser Leu Thr Ile
        675                 680                 685
Asn Asn Leu Glu Gln Glu Asp Ile Ala Thr Tyr Phe Cys Gln Gln Gly
            690                 695                 700
Asn Thr Arg Pro Trp Thr Phe Gly Gly Gly Thr Lys Leu Glu Ile Lys
705                 710                 715                 720

<210> SEQ ID NO 134
<211> LENGTH: 722
<212> TYPE: PRT
<213> ORGANISM: Artificial
<220> FEATURE:
<223> OTHER INFORMATION: Chimeric homo sapiens mus musculus

<400> SEQUENCE: 134

Asp Ile Gln Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
            20                  25                  30
Gly Asp Ser Tyr Leu Asn Trp Tyr Gln Gln Ile Pro Gly Gln Pro Pro
        35                  40                  45
Lys Leu Leu Ile Tyr Asp Ala Ser Asn Leu Val Ser Gly Ile Pro Pro
    50                  55                  60
Arg Phe Ser Gly Ser Gly Ser Gly Thr Asp Phe Thr Leu Asn Ile His
65                  70                  75                  80
Pro Val Glu Lys Val Asp Ala Ala Thr Tyr His Cys Gln Gln Ser Thr
                85                  90                  95
Glu Asp Pro Trp Thr Phe Gly Gly Gly Thr Lys Leu Glu Ile Lys Gly
            100                 105                 110
Gly Gly Gly Ser Gly Gly Gly Gly Ser Gly Gly Gly Gly Ser Gln Val
        115                 120                 125
Gln Leu Gln Gln Ser Gly Ala Glu Leu Val Arg Pro Gly Ser Ser Val
    130                 135                 140
Lys Ile Ser Cys Lys Ala Ser Gly Tyr Ala Phe Ser Ser Tyr Trp Met
```

```
              145                 150                 155                 160
Asn Trp Val Lys Gln Arg Pro Gly Gln Gly Leu Glu Trp Ile Gly Gln
                    165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
                195                 200                 205

Leu Ser Ser Leu Ala Ser Glu Asp Ser Ala Val Tyr Phe Cys Ala Arg
            210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Ser Ser Ala
                    245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                    325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Lys Pro Pro Ser Arg Glu Glu Met Thr
                370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                    405                 410                 415

Lys Thr Thr Val Pro Val Leu Asp Ser Asp Gly Ser Phe Arg Leu Ala
                420                 425                 430

Ser Tyr Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Ser Thr Gly Ser Glu Val Gln Leu Gln
465                 470                 475                 480

Glu Ser Gly Pro Gly Leu Val Lys Pro Ser Gln Ser Leu Ser Leu Thr
                    485                 490                 495

Cys Thr Val Thr Gly Tyr Ser Ile Thr Ser Asp Tyr Ala Trp Asn Trp
                500                 505                 510

Ile Arg Gln Phe Pro Gly Asn Lys Leu Glu Trp Met Gly Tyr Ile Thr
                515                 520                 525

Tyr Ser Gly Ser Thr Ser Tyr Asn Pro Ser Leu Glu Ser Arg Ile Ser
                530                 535                 540

Ile Thr Arg Asp Thr Ser Thr Asn Gln Phe Phe Leu Gln Leu Asn Ser
545                 550                 555                 560

Val Thr Thr Glu Asp Thr Ala Thr Tyr Tyr Cys Ala Arg Gly Gly Tyr
                    565                 570                 575
```

-continued

```
Tyr Gly Ser Ser Trp Gly Val Phe Ala Tyr Trp Gln Gly Thr Leu
            580                 585                 590

Val Thr Val Ser Ala Val Glu Gly Ser Gly Ser Gly Gly Ser
        595                 600                 605

Gly Gly Ser Gly Gly Val Asp Asp Ile Gln Met Thr Gln Ser Pro Ala
    610                 615                 620

Ser Leu Ser Ala Ser Val Gly Glu Thr Val Thr Ile Thr Cys Arg Val
625                 630                 635                 640

Ser Glu Asn Ile Tyr Ser Tyr Leu Ala Trp Tyr Gln Lys Gln Gly
            645                 650                 655

Lys Ser Pro Gln Leu Leu Val Tyr Asn Ala Lys Thr Leu Ala Glu Gly
            660                 665                 670

Val Pro Ser Arg Phe Ser Gly Ser Gly Ser Gly Thr Gln Phe Ser Leu
        675                 680                 685

Lys Ile Asn Ser Leu Gln Pro Glu Asp Phe Gly Ser Tyr Tyr Cys Gln
        690                 695                 700

His His Tyr Gly Thr Pro Trp Thr Phe Gly Gly Gly Thr Lys Leu Glu
705                 710                 715                 720

Ile Lys

<210> SEQ ID NO 135
<211> LENGTH: 716
<212> TYPE: PRT
<213> ORGANISM: Artificial
<220> FEATURE:
<223> OTHER INFORMATION: Chimeric homo sapiens mus musculus

<400> SEQUENCE: 135

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205
```

-continued

```
Leu Ser Ser Leu Ala Ser Glu Asp Ser Ala Val Tyr Phe Cys Ala Arg
    210             215                 220
Arg Glu Thr Thr Thr Val Gly Arg Tyr Tyr Ala Met Asp Tyr Trp
225                 230                 235                 240
Gly Gln Gly Thr Thr Val Thr Val Ser Ser Gly Gly Ser Ser Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Lys Pro Pro Ser Arg Glu Glu Met Thr
370                 375                 380
Lys Asn Gln Val Ser Leu Ser Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Val Pro Val Leu Asp Ser Asp Gly Ser Phe Arg Leu Ala
            420                 425                 430
Ser Tyr Leu Thr Val Asp Lys Ser Arg Trp Gln Gln Gly Asn Val Phe
            435                 440                 445
Ser Cys Ser Val Met His Glu Ala Leu His Asn His Tyr Thr Gln Lys
450                 455                 460
Ser Leu Ser Leu Ser Pro Gly Ser Thr Gly Ser Glu Val Gln Leu Gln
465                 470                 475                 480
Gln Ser Gly Pro Glu Leu Val Lys Pro Gly Ala Ser Val Lys Ile Ser
                485                 490                 495
Cys Lys Thr Ser Gly Tyr Thr Phe Thr Glu Tyr Thr Met His Trp Val
            500                 505                 510
Lys Gln Ser His Gly Lys Ser Leu Glu Trp Ile Gly Gly Ile Ser Pro
            515                 520                 525
Asn Ile Gly Gly Thr Ser Tyr Asn Gln Lys Phe Lys Gly Lys Ala Thr
530                 535                 540
Leu Thr Val Asp Lys Ser Ser Thr Ala Tyr Met Glu Leu Arg Ser
545                 550                 555                 560
Leu Thr Ser Glu Asp Ser Ala Val Tyr Tyr Cys Ala Arg Arg Gly Gly
                565                 570                 575
Ser Phe Asp Tyr Trp Gly Gln Gly Thr Thr Leu Thr Val Ser Ser Val
            580                 585                 590
Glu Gly Gly Ser Gly Gly Ser Gly Gly Ser Gly Gly Ser Gly Gly Val
            595                 600                 605
Asp Asp Ile Val Met Thr Gln Ser Pro Ala Thr Leu Ser Val Thr Pro
610                 615                 620
Gly Asp Arg Val Ser Leu Ser Cys Arg Ala Ser Gln Ser Ile Ser Asp
```

```
                625                 630                 635                 640
Tyr Leu His Trp Tyr Gln Gln Lys Ser His Glu Ser Pro Arg Leu Leu
                    645                 650                 655

Ile Lys Tyr Ala Ser Gln Ser Ile Ser Gly Ile Pro Ser Arg Phe Ser
                660                 665                 670

Gly Ser Gly Ser Gly Ser Asp Phe Thr Leu Ser Ile Asn Ser Val Glu
                675                 680                 685

Pro Glu Asp Val Gly Val Tyr Tyr Cys Gln Asn Gly His Ser Phe Pro
            690                 695                 700

Leu Thr Phe Gly Ala Gly Thr Lys Leu Glu Leu Lys
705                 710                 715

<210> SEQ ID NO 136
<211> LENGTH: 717
<212> TYPE: PRT
<213> ORGANISM: Artificial
<220> FEATURE:
<223> OTHER INFORMATION: Chimeric homo sapiens mus musculus

<400> SEQUENCE: 136

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
```

```
            275                 280                 285
Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Gln Val Gln Leu Gln
465                 470                 475                 480

Gln Ser Ala Val Glu Leu Ala Arg Pro Gly Ala Ser Val Lys Met Ser
                485                 490                 495

Cys Lys Ala Ser Gly Tyr Thr Phe Thr Ser Phe Thr Met His Trp Val
            500                 505                 510

Lys Gln Arg Pro Gly Gln Gly Leu Glu Trp Ile Gly Tyr Ile Asn Pro
        515                 520                 525

Ser Ser Gly Tyr Thr Glu Tyr Asn Gln Lys Phe Lys Asp Lys Thr Thr
    530                 535                 540

Leu Thr Ala Asp Lys Ser Ser Ser Thr Ala Tyr Met Gln Leu Asp Ser
545                 550                 555                 560

Leu Thr Ser Asp Asp Ser Ala Val Tyr Tyr Cys Val Arg Gly Ser Ser
                565                 570                 575

Arg Gly Phe Asp Tyr Trp Gly Gln Gly Thr Leu Val Thr Val Ser Ala
            580                 585                 590

Val Glu Gly Gly Ser Gly Gly Ser Gly Gly Ser Gly Gly Ser Gly Gly
        595                 600                 605

Val Asp Asp Ile Gln Met Ile Gln Ser Pro Ala Ser Leu Ser Val Ser
    610                 615                 620

Val Gly Glu Thr Val Thr Ile Thr Cys Arg Ala Ser Glu Asn Ile Tyr
625                 630                 635                 640

Ser Asn Leu Ala Trp Phe Gln Gln Lys Gln Gly Lys Ser Pro Gln Leu
                645                 650                 655

Leu Val Tyr Ala Ala Thr Asn Leu Ala Asp Gly Val Pro Ser Arg Phe
            660                 665                 670

Ser Gly Ser Gly Ser Gly Thr Gln Tyr Ser Leu Lys Ile Asn Ser Leu
        675                 680                 685

Gln Ser Glu Asp Phe Gly Ile Tyr Tyr Cys Gln His Phe Trp Gly Thr
    690                 695                 700
```

```
Pro Arg Thr Phe Gly Gly Gly Thr Lys Leu Glu Ile Lys
705                 710                 715

<210> SEQ ID NO 137
<211> LENGTH: 716
<212> TYPE: PRT
<213> ORGANISM: Artificial
<220> FEATURE:
<223> OTHER INFORMATION: Chimeric homo sapiens mus musculus

<400> SEQUENCE: 137

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350
```

-continued

```
Leu Pro Ala Pro Ile Glu Lys Thr Ile Ser Lys Ala Lys Gly Gln Pro
            355                 360                 365

Arg Glu Pro Gln Val Tyr Thr Lys Pro Pro Ser Arg Glu Glu Met Thr
        370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gly Asn Val Phe
        435                 440                 445

Ser Cys Ser Val Met His Glu Ala Leu His Asn His Tyr Thr Gln Lys
        450                 455                 460

Ser Leu Ser Leu Ser Pro Gly Ser Thr Gly Ser Gln Val Gln Leu Gln
465                 470                 475                 480

Gln Pro Gly Ser Val Leu Val Arg Pro Gly Ala Ser Val Lys Leu Ser
                485                 490                 495

Cys Lys Ala Ser Gly Tyr Thr Phe Thr Ser Ser Trp Met His Trp Ala
            500                 505                 510

Lys Gln Arg Pro Gly Gln Gly Leu Glu Trp Ile Gly His Ile His Pro
        515                 520                 525

Asn Ser Gly Ile Ser Asn Tyr Asn Glu Lys Phe Lys Gly Lys Ala Thr
    530                 535                 540

Leu Thr Val Asp Thr Ser Ser Thr Ala Tyr Val Asp Leu Ser Ser
545                 550                 555                 560

Leu Thr Ser Glu Asp Ser Ala Val Tyr Tyr Cys Ala Arg Gly Gly Arg
                565                 570                 575

Phe Asp Asp Trp Gly Ala Gly Thr Thr Val Thr Val Ser Ser Val Glu
            580                 585                 590

Gly Gly Ser Gly Gly Ser Gly Gly Ser Gly Gly Ser Gly Gly Val Asp
        595                 600                 605

Asp Ile Val Met Thr Gln Ser Pro Ala Thr Leu Ser Val Thr Pro Gly
    610                 615                 620

Asp Arg Val Ser Leu Ser Cys Arg Ala Ser Gln Ser Ile Ser Asp Tyr
625                 630                 635                 640

Leu His Trp Tyr Gln Gln Lys Ser His Glu Ser Pro Arg Leu Leu Ile
                645                 650                 655

Lys Tyr Ala Ser Gln Ser Ile Ser Gly Ile Pro Ser Arg Phe Ser Gly
            660                 665                 670

Ser Gly Ser Gly Ser Asp Phe Thr Leu Ser Ile Asn Ser Val Glu Pro
        675                 680                 685

Glu Asp Val Gly Val Tyr Tyr Cys Gln Asn Gly His Ser Phe Leu Met
    690                 695                 700

Tyr Thr Phe Gly Gly Gly Thr Lys Leu Glu Ile Lys
705                 710                 715
```

<210> SEQ ID NO 138
<211> LENGTH: 720
<212> TYPE: PRT
<213> ORGANISM: Artificial
<220> FEATURE:
<223> OTHER INFORMATION: Chimeric homo sapiens mus musculus

<400> SEQUENCE: 138

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Thr Lys Leu Glu Ile Lys Gly
            100                 105                 110

Gly Gly Gly Ser Gly Gly Gly Ser Gly Gly Gly Ser Gln Val
            115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415
```

```
Lys Thr Thr Val Pro Val Leu Asp Ser Asp Gly Ser Phe Arg Leu Ala
                420                 425                 430

Ser Tyr Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Ser Thr Gly Ser Asp Val Gln Leu Gln
465                 470                 475                 480

Glu Ser Gly Pro Gly Leu Val Lys Pro Ser Gln Ser Leu Ser Leu Thr
                485                 490                 495

Cys Thr Val Thr Gly Tyr Ser Ile Thr Ser Asp Tyr Ala Trp Asn Trp
            500                 505                 510

Ile Arg Gln Phe Pro Gly Asn Lys Leu Glu Trp Met Gly Tyr Ile Thr
        515                 520                 525

Tyr Ser Gly Ser Thr Asn Tyr Asn Pro Ser Leu Lys Ser Arg Ile Ser
    530                 535                 540

Ile Thr Arg Asp Thr Ser Lys Asn Gln Phe Phe Leu Gln Leu Asn Ser
545                 550                 555                 560

Val Thr Thr Glu Asp Thr Ala Thr Tyr Tyr Cys Ala Arg Cys Trp Asp
                565                 570                 575

Tyr Ala Leu Tyr Ala Met Asp Cys Trp Gly Gln Gly Thr Ser Val Thr
            580                 585                 590

Val Ser Ser Val Glu Gly Gly Ser Gly Gly Ser Gly Gly Ser Gly Gly
        595                 600                 605

Ser Gly Gly Val Asp Asp Ile Gln Met Thr Gln Ser Pro Ala Ser Leu
    610                 615                 620

Ser Ala Ser Val Gly Glu Thr Val Thr Ile Thr Cys Arg Thr Ser Glu
625                 630                 635                 640

Asn Ile Tyr Ser Tyr Leu Ala Trp Cys Gln Gln Lys Gln Gly Lys Ser
                645                 650                 655

Pro Gln Leu Leu Val Tyr Asn Ala Lys Thr Leu Ala Glu Gly Val Pro
            660                 665                 670

Ser Arg Phe Ser Gly Ser Gly Ser Gly Thr His Phe Ser Leu Lys Ile
        675                 680                 685

Asn Ser Leu Gln Pro Glu Asp Phe Gly Ile Tyr Tyr Cys Gln His His
    690                 695                 700

Tyr Asp Thr Pro Leu Thr Phe Gly Ala Gly Thr Lys Leu Glu Leu Lys
705                 710                 715                 720

<210> SEQ ID NO 139
<211> LENGTH: 717
<212> TYPE: PRT
<213> ORGANISM: Artificial
<220> FEATURE:
<223> OTHER INFORMATION: Chimeric homo sapiens mus musculus

<400> SEQUENCE: 139

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60
```

```
Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Ser Thr Gly Ser Gln Ile Gln Leu Val
465                 470                 475                 480

Gln Ser Gly Pro Glu Leu Gln Lys Pro Gly Glu Thr Val Lys Ile Ser
```

```
            485                 490                 495
Cys Lys Ala Ser Gly Tyr Thr Phe Thr Asn Tyr Gly Met Asn Trp Val
            500                 505                 510

Lys Gln Ala Pro Gly Lys Gly Leu Lys Trp Met Gly Trp Ile Asn Thr
            515                 520                 525

Asn Thr Gly Glu Pro Thr Tyr Ala Glu Glu Phe Lys Gly Arg Phe Ala
            530                 535                 540

Phe Ser Leu Glu Thr Ser Ala Ser Thr Ala Tyr Leu Gln Ile Asn Asn
545                 550                 555                 560

Leu Lys Asn Glu Asp Thr Ala Thr Tyr Phe Cys Ala Arg Asp Tyr Leu
            565                 570                 575

Tyr Tyr Phe Asp Tyr Trp Gly Gln Gly Thr Thr Leu Thr Val Ser Ser
            580                 585                 590

Val Glu Gly Gly Ser Gly Gly Ser Gly Gly Ser Gly Gly Ser Gly Gly
            595                 600                 605

Val Asp Asn Ile Val Met Thr Gln Ser Pro Lys Ser Met Ser Met Ser
            610                 615                 620

Val Gly Glu Arg Val Thr Leu Thr Cys Lys Ala Ser Glu Asn Val Val
625                 630                 635                 640

Thr Tyr Val Ser Trp Tyr Gln Gln Lys Pro Glu Gln Ser Pro Lys Leu
            645                 650                 655

Leu Ile Tyr Gly Ala Ser Asn Arg Tyr Thr Gly Val Pro Asp Arg Phe
            660                 665                 670

Thr Gly Ser Gly Ser Ala Thr Asp Phe Thr Leu Thr Ile Ser Ser Val
            675                 680                 685

Gln Ala Glu Asp Leu Ala Asp Tyr His Cys Gly Gln Gly Tyr Ser Tyr
            690                 695                 700

Pro Tyr Thr Phe Gly Gly Gly Thr Lys Leu Glu Ile Lys
705                 710                 715

<210> SEQ ID NO 140
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 140

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
            85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
```

```
            130                 135                 140
Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
            195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
            245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Lys Pro Pro Ser Arg Glu Glu Met Thr
    370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Glu Val Gln Leu Gln
465                 470                 475                 480

Gln Ser Gly Pro Glu Leu Val Lys Pro Gly Ala Ser Val Lys Ile Ser
            485                 490                 495

Cys Lys Thr Ser Gly Tyr Thr Phe Thr Glu Tyr Thr Met His Trp Val
            500                 505                 510

Lys Gln Ser His Gly Lys Ser Leu Glu Trp Ile Gly Gly Ile Ser Pro
            515                 520                 525

Asn Ile Gly Gly Thr Ser Tyr Asn Gln Lys Phe Lys Gly Lys Ala Thr
            530                 535                 540

Leu Thr Val Asp Lys Ser Ser Ser Thr Ala Tyr Met Glu Leu Arg Ser
545                 550                 555                 560
```

```
Leu Thr Ser Glu Asp Ser Ala Val Tyr Tyr Cys Ala Arg Arg Gly Gly
                565                 570                 575

Ser Phe Asp Tyr Trp Gly Gln Gly Thr Thr Leu Thr Val Ser Ser Ala
            580                 585                 590

Ser Thr Lys Gly Pro Ser Val Phe Pro Leu Ala Pro Ser Ser Lys Ser
        595                 600                 605

Thr Ser Gly Gly Thr Ala Ala Leu Gly Cys Leu Val Lys Asp Tyr Phe
    610                 615                 620

Pro Glu Pro Val Thr Val Ser Trp Asn Ser Gly Ala Leu Thr Ser Gly
625                 630                 635                 640

Val His Thr Phe Pro Ala Val Leu Gln Ser Ser Gly Leu Tyr Ser Leu
            645                 650                 655

Ser Ser Val Val Thr Val Pro Ser Ser Ser Leu Gly Thr Gln Thr Tyr
            660                 665                 670

Ile Cys Asn Val Asn His Lys Pro Ser Asn Thr Lys Val Asp Lys Arg
        675                 680                 685

Val Glu Pro Lys Ser Cys Asp Lys Thr His
    690                 695

<210> SEQ ID NO 141
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 141

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 142
<211> LENGTH: 837
<212> TYPE: PRT
<213> ORGANISM: Artificial
<220> FEATURE:
<223> OTHER INFORMATION: Chimeric homo sapiens mus musculus

<400> SEQUENCE: 142

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

```
Arg Glu Pro Gln Val Tyr Thr Leu Pro Pro Ser Arg Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly Gly Gly Gly Ser Gly Gly Gly Gly
465                 470                 475                 480

Ser Gly Gly Gly Gly Ser Gly Gln Pro Arg Glu Pro Gln Val Tyr Thr
                485                 490                 495

Leu Pro Pro Ser Arg Glu Met Thr Lys Asn Gln Val Ser Leu Thr
                500                 505                 510

Cys Leu Val Lys Gly Phe Tyr Pro Ser Asp Ile Ala Val Glu Trp Glu
            515                 520                 525

Ser Asn Gly Gln Pro Glu Asn Asn Tyr Lys Thr Thr Pro Pro Val Leu
530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
                580                 585                 590

Ser Thr Gly Ser Glu Val Gln Leu Gln Gln Ser Gly Pro Glu Leu Val
            595                 600                 605

Lys Pro Gly Ala Ser Val Lys Ile Ser Cys Lys Thr Ser Gly Tyr Thr
            610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
                660                 665                 670

Ser Thr Ala Tyr Met Glu Leu Arg Ser Leu Thr Ser Glu Asp Ser Ala
            675                 680                 685

Val Tyr Tyr Cys Ala Arg Arg Gly Gly Ser Phe Asp Tyr Trp Gly Gln
            690                 695                 700

Gly Thr Thr Leu Thr Val Ser Ser Val Glu Gly Gly Ser Gly Gly Ser
705                 710                 715                 720

Gly Gly Ser Gly Gly Ser Gly Gly Val Asp Asp Ile Val Met Thr Gln
                725                 730                 735

Ser Pro Ala Thr Leu Ser Val Thr Pro Gly Asp Arg Val Ser Leu Ser
                740                 745                 750

Cys Arg Ala Ser Gln Ser Ile Ser Asp Tyr Leu His Trp Tyr Gln Gln
            755                 760                 765

Lys Ser His Glu Ser Pro Arg Leu Leu Ile Lys Tyr Ala Ser Gln Ser
770                 775                 780
```

```
Ile Ser Gly Ile Pro Ser Arg Phe Ser Gly Ser Gly Ser Asp
785                 790                 795                 800

Phe Thr Leu Ser Ile Asn Ser Val Glu Pro Glu Asp Val Gly Val Tyr
                805                 810                 815

Tyr Cys Gln Asn Gly His Ser Phe Pro Leu Thr Phe Gly Ala Gly Thr
            820                 825                 830

Lys Leu Glu Leu Lys
        835

<210> SEQ ID NO 143
<211> LENGTH: 837
<212> TYPE: PRT
<213> ORGANISM: Artificial
<220> FEATURE:
<223> OTHER INFORMATION: Chimeric homo sapiens mus musculus

<400> SEQUENCE: 143

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300
```

-continued

Asp Gly Val Glu Val His Asn Ala Lys Thr Lys Pro Arg Glu Glu Gln
305                 310                 315                 320

Tyr Ser Ser Thr Tyr Arg Val Ser Val Leu Thr Val Leu His Gln
            325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Gly Gly Gly Ser Gly Gly Gly Gly
465                 470                 475                 480

Ser Gly Gly Gly Gly Ser Gly Gln Pro Arg Glu Pro Gln Val Tyr Thr
                485                 490                 495

Leu Pro Pro Ser Arg Glu Glu Met Thr Lys Asn Gln Val Ser Leu Thr
            500                 505                 510

Cys Leu Val Lys Gly Phe Tyr Pro Ser Asp Ile Ala Val Glu Trp Glu
            515                 520                 525

Ser Asn Gly Gln Pro Glu Asn Asn Tyr Lys Thr Thr Pro Pro Val Leu
530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
            580                 585                 590

Ser Thr Gly Ser Glu Val Gln Leu Gln Gln Ser Gly Pro Glu Leu Val
            595                 600                 605

Lys Pro Gly Ala Ser Val Lys Ile Ser Cys Lys Thr Ser Gly Tyr Thr
610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
            660                 665                 670

Ser Thr Ala Tyr Met Glu Leu Arg Ser Leu Thr Ser Glu Asp Ser Ala
            675                 680                 685

Val Tyr Tyr Cys Ala Arg Arg Gly Gly Ser Phe Asp Tyr Trp Gly Gln
            690                 695                 700

Gly Thr Thr Leu Thr Val Ser Ser Val Glu Gly Gly Ser Gly Gly Ser
705                 710                 715                 720

Gly Gly Ser Gly Gly Ser Gly Gly Val Asp Asp Ile Val Met Thr Gln

```
                    725                 730                 735
Ser Pro Ala Thr Leu Ser Val Thr Pro Gly Asp Arg Val Ser Leu Ser
                740                 745                 750

Cys Arg Ala Ser Gln Ser Ile Ser Asp Tyr Leu His Trp Tyr Gln Gln
            755                 760                 765

Lys Ser His Glu Ser Pro Arg Leu Leu Ile Lys Tyr Ala Ser Gln Ser
        770                 775                 780

Ile Ser Gly Ile Pro Ser Arg Phe Ser Gly Ser Gly Ser Gly Ser Asp
785                 790                 795                 800

Phe Thr Leu Ser Ile Asn Ser Val Glu Pro Glu Asp Val Gly Val Tyr
                805                 810                 815

Tyr Cys Gln Asn Gly His Ser Phe Pro Leu Thr Phe Gly Ala Gly Thr
            820                 825                 830

Lys Leu Glu Leu Lys
        835

<210> SEQ ID NO 144
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 144

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 145
<211> LENGTH: 675
<212> TYPE: PRT
```

<213> ORGANISM: Artificial
<220> FEATURE:
<223> OTHER INFORMATION: Chimeric homo sapiens mus musculus

<400> SEQUENCE: 145

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Gly Gly Gly Ser Ser Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ser Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Lys Pro Pro Ser Arg Glu Glu Met Thr Lys Asn Gln Val Ser Leu Ser
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Val Pro Val Leu
```

```
385                 390                 395                 400
Asp Ser Asp Gly Ser Phe Arg Leu Ala Ser Tyr Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Ser Thr Gly Ser Glu Val Gln Leu Gln Gln Ser Gly Pro Glu Leu Val
            450                 455                 460

Lys Pro Gly Ala Ser Val Lys Ile Ser Cys Lys Thr Ser Gly Tyr Thr
465                 470                 475                 480

Phe Thr Glu Tyr Thr Met His Trp Val Lys Gln Ser His Gly Lys Ser
                485                 490                 495

Leu Glu Trp Ile Gly Gly Ile Ser Pro Asn Ile Gly Gly Thr Ser Tyr
                500                 505                 510

Asn Gln Lys Phe Lys Gly Lys Ala Thr Leu Thr Val Asp Lys Ser Ser
            515                 520                 525

Ser Thr Ala Tyr Met Glu Leu Arg Ser Leu Thr Ser Glu Asp Ser Ala
530                 535                 540

Val Tyr Tyr Cys Ala Arg Arg Gly Gly Ser Phe Asp Tyr Trp Gly Gln
545                 550                 555                 560

Gly Thr Thr Leu Thr Val Ser Ser Arg Thr Val Ala Ala Pro Ser Val
                565                 570                 575

Phe Ile Phe Pro Pro Ser Asp Glu Gln Leu Lys Ser Gly Thr Ala Ser
                580                 585                 590

Val Val Cys Leu Leu Asn Asn Phe Tyr Pro Arg Glu Ala Lys Val Gln
            595                 600                 605

Trp Lys Val Asp Asn Ala Leu Gln Ser Gly Asn Ser Gln Glu Ser Val
            610                 615                 620

Thr Glu Gln Asp Ser Lys Asp Ser Thr Tyr Ser Leu Ser Ser Thr Leu
625                 630                 635                 640

Thr Leu Ser Lys Ala Asp Tyr Glu Lys His Lys Val Tyr Ala Cys Glu
                645                 650                 655

Val Thr His Gln Gly Leu Ser Ser Pro Val Thr Lys Ser Phe Asn Arg
                660                 665                 670

Gly Glu Cys
        675

<210> SEQ ID NO 146
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 146

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
```

```
                65                  70                  75                  80
Glu Asp Val Gly Val Tyr Tyr Cys Gln Asn Gly His Ser Phe Pro Leu
                    85                  90                  95

Thr Phe Gly Ala Gly Thr Lys Leu Glu Leu Lys Ala Ser Thr Lys Gly
                100                 105                 110

Pro Ser Val Phe Pro Leu Ala Pro Ser Ser Lys Ser Thr Ser Gly Gly
                115                 120                 125

Thr Ala Ala Leu Gly Cys Leu Val Lys Asp Tyr Phe Pro Glu Pro Val
            130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
                180                 185                 190

Asn His Lys Pro Ser Asn Thr Lys Val Asp Lys Arg Val Glu Pro Lys
                195                 200                 205

Ser Cys Asp Lys Thr His
            210

<210> SEQ ID NO 147
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 147

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
```

210                 215

<210> SEQ ID NO 148
<211> LENGTH: 801
<212> TYPE: PRT
<213> ORGANISM: Artificial
<220> FEATURE:
<223> OTHER INFORMATION: Chimeric homo sapiens mus musculus

<400> SEQUENCE: 148

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn

```
            355                 360                 365
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Gly Gly Gly Ser Gly Gly Gly Gly Ser Gly
    450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
        595                 600                 605

Glu Tyr Thr Met His Trp Val Lys Gln Ser His Gly Lys Ser Leu Glu
    610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
        675                 680                 685

Thr Leu Thr Val Ser Ser Arg Thr Val Ala Ala Pro Ser Val Phe Ile
    690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
                725                 730                 735

Val Asp Asn Ala Leu Gln Ser Gly Asn Ser Gln Glu Ser Val Thr Glu
            740                 745                 750

Gln Asp Ser Lys Asp Ser Thr Tyr Ser Leu Ser Ser Thr Leu Thr Leu
        755                 760                 765

Ser Lys Ala Asp Tyr Glu Lys His Lys Val Tyr Ala Cys Glu Val Thr
    770                 775                 780
```

His Gln Gly Leu Ser Ser Pro Val Thr Lys Ser Phe Asn Arg Gly Glu
785                 790                 795                 800

Cys

<210> SEQ ID NO 149
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 149

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 150
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 150

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

```
Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 151
<211> LENGTH: 801
<212> TYPE: PRT
<213> ORGANISM: Artificial
<220> FEATURE:
<223> OTHER INFORMATION: Chimeric homo sapiens mus musculus

<400> SEQUENCE: 151

```
Gln Val Gln Leu Gln Gln Ser Gly Ala Glu Leu Val Arg Pro Gly Ser
  1               5                  10                  15

Ser Val Lys Ile Ser Cys Lys Ala Ser Gly Tyr Ala Phe Ser Ser Tyr
                 20                  25                  30

Trp Met Asn Trp Val Lys Gln Arg Pro Gly Gln Gly Leu Glu Trp Ile
             35                  40                  45

Gly Gln Ile Trp Pro Gly Asp Gly Asp Thr Asn Tyr Asn Gly Lys Phe
     50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205
```

```
Val Asn His Lys Pro Ser Asn Thr Lys Val Asp Lys Arg Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Ser
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
            435                 440                 445
Ser Leu Ser Pro Gly Gly Gly Gly Ser Gly Gly Gly Gly Ser Gly
    450                 455                 460
Gly Gly Gly Ser Gly Gln Pro Arg Glu Pro Gln Val Tyr Thr Leu Pro
465                 470                 475                 480
Pro Ser Arg Glu Glu Met Thr Lys Asn Gln Val Ser Leu Thr Cys Leu
                485                 490                 495
Val Lys Gly Phe Tyr Pro Ser Asp Ile Ala Val Glu Trp Glu Ser Asn
            500                 505                 510
Gly Gln Pro Glu Asn Asn Tyr Lys Thr Thr Pro Pro Val Leu Asp Ser
    515                 520                 525
Asp Gly Ser Phe Phe Leu Tyr Ser Lys Leu Thr Val Asp Lys Ser Arg
530                 535                 540
Trp Gln Gln Gly Asn Val Phe Ser Cys Ser Val Met His Glu Ala Leu
545                 550                 555                 560
His Asn His Tyr Thr Gln Lys Ser Leu Ser Leu Ser Pro Gly Ser Thr
                565                 570                 575
Gly Ser Glu Val Gln Leu Gln Gln Ser Gly Pro Glu Leu Val Lys Pro
            580                 585                 590
Gly Ala Ser Val Lys Ile Ser Cys Lys Thr Ser Gly Tyr Thr Phe Thr
    595                 600                 605
Glu Tyr Thr Met His Trp Val Lys Gln Ser His Gly Lys Ser Leu Glu
    610                 615                 620
```

```
Trp Ile Gly Gly Ile Ser Pro Asn Ile Gly Thr Ser Tyr Asn Gln
625                 630                 635                 640

Lys Phe Lys Gly Lys Ala Thr Leu Thr Val Asp Lys Ser Ser Thr
            645                 650                 655

Ala Tyr Met Glu Leu Arg Ser Leu Thr Ser Glu Asp Ser Ala Val Tyr
                660                 665                 670

Tyr Cys Ala Arg Arg Gly Gly Ser Phe Asp Tyr Trp Gly Gln Gly Thr
            675                 680                 685

Thr Leu Thr Val Ser Ser Arg Thr Val Ala Ala Pro Ser Val Phe Ile
        690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
                725                 730                 735

Val Asp Asn Ala Leu Gln Ser Gly Asn Ser Gln Glu Ser Val Thr Glu
                740                 745                 750

Gln Asp Ser Lys Asp Ser Thr Tyr Ser Leu Ser Ser Thr Leu Thr Leu
            755                 760                 765

Ser Lys Ala Asp Tyr Glu Lys His Lys Val Tyr Ala Cys Glu Val Thr
        770                 775                 780

His Gln Gly Leu Ser Ser Pro Val Thr Lys Ser Phe Asn Arg Gly Glu
785                 790                 795                 800

Cys

<210> SEQ ID NO 152
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 152

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
```

-continued

```
            180                 185                 190
Asn His Lys Pro Ser Asn Thr Lys Val Asp Lys Arg Val Glu Pro Lys
        195                 200                 205

Ser Cys Asp Lys Thr His
        210

<210> SEQ ID NO 153
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 153

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 154
<211> LENGTH: 796
<212> TYPE: PRT
<213> ORGANISM: Artificial
<220> FEATURE:
<223> OTHER INFORMATION: Chimeric homo sapiens mus musculus

<400> SEQUENCE: 154

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45
```

```
Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Thr Ala Tyr
 65              70                  75                  80

Met Gln Leu Ser Ser Leu Ala Ser Glu Asp Ser Ala Val Tyr Phe Cys
             85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
210                 215                 220

Lys Ser Cys Gly Gly Gly Ser Ser Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Gly Gly Gly Gly Ser Gly Gly Gly Ser Gly Gly Gly Ser Gly
450                 455                 460

Gln Pro Arg Glu Pro Gln Val Tyr Thr Leu Pro Pro Ser Arg Glu Glu
```

```
              465                 470                 475                 480
        Met Thr Lys Asn Gln Val Ser Leu Thr Cys Leu Val Lys Gly Phe Tyr
                        485                 490                 495

Pro Ser Asp Ile Ala Val Glu Trp Glu Ser Asn Gly Gln Pro Glu Asn
                        500                 505                 510

Asn Tyr Lys Thr Thr Pro Pro Val Leu Asp Ser Asp Gly Ser Phe Phe
                        515                 520                 525

Leu Tyr Ser Lys Leu Thr Val Asp Lys Ser Arg Trp Gln Gln Gly Asn
                        530                 535                 540

Val Phe Ser Cys Ser Val Met His Glu Ala Leu His Asn His Tyr Thr
        545                 550                 555                 560

Gln Lys Ser Leu Ser Leu Ser Pro Gly Ser Thr Gly Ser Glu Val Gln
                        565                 570                 575

Leu Gln Gln Ser Gly Pro Glu Leu Val Lys Pro Gly Ala Ser Val Lys
                        580                 585                 590

Ile Ser Cys Lys Thr Ser Gly Tyr Thr Phe Thr Glu Tyr Thr Met His
                        595                 600                 605

Trp Val Lys Gln Ser His Gly Lys Ser Leu Glu Trp Ile Gly Gly Ile
                        610                 615                 620

Ser Pro Asn Ile Gly Gly Thr Ser Tyr Asn Gln Lys Phe Lys Gly Lys
        625                 630                 635                 640

Ala Thr Leu Thr Val Asp Lys Ser Ser Thr Ala Tyr Met Glu Leu
                        645                 650                 655

Arg Ser Leu Thr Ser Glu Asp Ser Ala Val Tyr Tyr Cys Ala Arg Arg
                        660                 665                 670

Gly Gly Ser Phe Asp Tyr Trp Gly Gln Gly Thr Thr Leu Thr Val Ser
                        675                 680                 685

Ser Arg Thr Val Ala Ala Pro Ser Val Phe Ile Phe Pro Pro Ser Asp
                        690                 695                 700

Glu Gln Leu Lys Ser Gly Thr Ala Ser Val Val Cys Leu Leu Asn Asn
        705                 710                 715                 720

Phe Tyr Pro Arg Glu Ala Lys Val Gln Trp Lys Val Asp Asn Ala Leu
                        725                 730                 735

Gln Ser Gly Asn Ser Gln Glu Ser Val Thr Glu Gln Asp Ser Lys Asp
                        740                 745                 750

Ser Thr Tyr Ser Leu Ser Ser Thr Leu Thr Leu Ser Lys Ala Asp Tyr
                        755                 760                 765

Glu Lys His Lys Val Tyr Ala Cys Glu Val Thr His Gln Gly Leu Ser
                        770                 775                 780

Ser Pro Val Thr Lys Ser Phe Asn Arg Gly Glu Cys
        785                 790                 795

<210> SEQ ID NO 155
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 155

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
```

```
                35                  40                  45
Lys Tyr Ala Ser Gln Ser Ile Ser Gly Ile Pro Ser Arg Phe Ser Gly
 50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 156
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 156

Asp Ile Gln Leu Thr Gln Ser Pro Ala Ser Leu Ala Val Ser Leu Gly
  1               5                  10                  15

Gln Arg Ala Thr Ile Ser Cys Lys Ala Ser Gln Ser Val Asp Tyr Asp
             20                  25                  30

Gly Asp Ser Tyr Leu Asn Trp Tyr Gln Gln Ile Pro Gly Gln Pro Pro
         35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
```

```
            180             185             190
His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 157
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 157

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
```

-continued

```
            325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
            370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
                435                 440                 445
Ser Leu Ser Pro Gly Gly Gly Gly Ser Gly Gly Gly Gly Ser Gly
            450                 455                 460
Gly Gly Ser Gly Gln Pro Arg Glu Pro Gln Val Tyr Thr Leu Pro
465                 470                 475                 480
Pro Ser Arg Glu Glu Met Thr Lys Asn Gln Val Ser Leu Thr Cys Leu
                485                 490                 495
Val Lys Gly Phe Tyr Pro Ser Asp Ile Ala Val Glu Trp Glu Ser Asn
            500                 505                 510
Gly Gln Pro Glu Asn Asn Tyr Lys Thr Thr Pro Pro Val Leu Asp Ser
            515                 520                 525
Asp Gly Ser Phe Phe Leu Tyr Ser Lys Leu Thr Val Asp Lys Ser Arg
            530                 535                 540
Trp Gln Gln Gly Asn Val Phe Ser Cys Ser Val Met His Glu Ala Leu
545                 550                 555                 560
His Asn His Tyr Thr Gln Lys Ser Leu Ser Leu Ser Pro Gly Ser Thr
                565                 570                 575
Gly Ser Glu Val Gln Leu Gln Gln Ser Gly Pro Glu Leu Val Lys Pro
            580                 585                 590
Gly Ala Ser Val Lys Ile Ser Cys Lys Thr Ser Gly Tyr Thr Phe Thr
            595                 600                 605
Glu Tyr Thr Met His Trp Val Lys Gln Ser His Gly Lys Ser Leu Glu
            610                 615                 620
Trp Ile Gly Gly Ile Ser Pro Asn Ile Gly Gly Thr Ser Tyr Asn Gln
625                 630                 635                 640
Lys Phe Lys Gly Lys Ala Thr Leu Thr Val Asp Lys Ser Ser Ser Thr
                645                 650                 655
Ala Tyr Met Glu Leu Arg Ser Leu Thr Ser Glu Asp Ser Ala Val Tyr
                660                 665                 670
Tyr Cys Ala Arg Arg Gly Gly Ser Phe Asp Tyr Trp Gly Gln Gly Thr
                675                 680                 685
Thr Leu Thr Val Ser Ser Val Glu Gly Gly Ser Gly Gly Ser Gly Gly
            690                 695                 700
Ser Gly Gly Ser Gly Gly Val Asp Asp Ile Val Met Thr Gln Ser Pro
705                 710                 715                 720
Ala Thr Leu Ser Val Thr Pro Gly Asp Arg Val Ser Leu Ser Cys Arg
                725                 730                 735
Ala Ser Gln Ser Ile Ser Asp Tyr Leu His Trp Tyr Gln Gln Lys Ser
                740                 745                 750
```

His Glu Ser Pro Arg Leu Leu Ile Lys Tyr Ala Ser Gln Ser Ile Ser
            755                 760                 765

Gly Ile Pro Ser Arg Phe Ser Gly Ser Gly Ser Asp Phe Thr
            770                 775                 780

Leu Ser Ile Asn Ser Val Glu Pro Glu Asp Val Gly Val Tyr Tyr Cys
785                 790                 795                 800

Gln Asn Gly His Ser Phe Pro Leu Thr Phe Gly Ala Gly Thr Lys Leu
            805                 810                 815

Glu Leu Lys

<210> SEQ ID NO 158
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 158

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 159
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 159

Gln Val Gln Leu Gln Gln Ser Gly Ala Glu Leu Val Arg Pro Gly Ser
1               5                   10                  15

```
Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Ser Pro Pro Ser Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430
```

Ser Val Met His Glu Ala Leu His Asn His Tyr Thr Gln Lys Ser Leu
            435                 440                 445

Ser Leu Ser Pro Gly Gly Gly Gly Ser Gly Gly Gly Ser Gly
450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
        595                 600                 605

Glu Tyr Thr Met His Trp Val Lys Gln Ser His Gly Lys Ser Leu Glu
    610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
        675                 680                 685

Thr Leu Thr Val Ser Ser Val Glu Gly Gly Ser Gly Gly Ser Gly Gly
    690                 695                 700

Ser Gly Gly Ser Gly Gly Val Asp Asp Ile Val Met Thr Gln Ser Pro
705                 710                 715                 720

Ala Thr Leu Ser Val Thr Pro Gly Asp Arg Val Ser Leu Ser Cys Arg
                725                 730                 735

Ala Ser Gln Ser Ile Ser Asp Tyr Leu His Trp Tyr Gln Gln Lys Ser
            740                 745                 750

His Glu Ser Pro Arg Leu Leu Ile Lys Tyr Ala Ser Gln Ser Ile Ser
        755                 760                 765

Gly Ile Pro Ser Arg Phe Ser Gly Ser Gly Ser Asp Phe Thr
    770                 775                 780

Leu Ser Ile Asn Ser Val Glu Pro Glu Asp Val Gly Val Tyr Tyr Cys
785                 790                 795                 800

Gln Asn Gly His Ser Phe Pro Leu Thr Phe Gly Ala Gly Thr Lys Leu
                805                 810                 815

Glu Leu Lys

<210> SEQ ID NO 160
<211> LENGTH: 218
<212> TYPE: PRT
<213> ORGANISM: Artificial

```
<220> FEATURE:
<223> OTHER INFORMATION: Chimeric homo sapiens mus musculus

<400> SEQUENCE: 160

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 161
<211> LENGTH: 815
<212> TYPE: PRT
<213> ORGANISM: Artificial
<220> FEATURE:
<223> OTHER INFORMATION: Chimeric homo sapiens mus musculus

<400> SEQUENCE: 161

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
```

```
            115                 120                 125
Gly Pro Ser Val Phe Pro Leu Ala Pro Ser Ser Lys Ser Thr Ser Gly
            130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
            165                 170                 175
Phe Pro Ala Val Leu Gln Ser Ser Gly Leu Tyr Ser Leu Ser Ser Val
            180                 185                 190
Val Thr Val Pro Ser Ser Leu Gly Thr Gln Thr Tyr Ile Cys Asn
            195                 200                 205
Val Asn His Lys Pro Ser Asn Thr Lys Val Asp Lys Arg Val Glu Pro
            210                 215                 220
Lys Ser Cys Gly Gly Gly Ser Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Ser Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Gly Gly Gly Gly Ser Gly Gly Gly Ser Gly Gly Gly Gly Ser
            450                 455                 460
Gly Gln Pro Arg Glu Pro Gln Val Tyr Thr Leu Pro Pro Ser Arg Glu
465                 470                 475                 480
Glu Met Thr Lys Asn Gln Val Ser Leu Thr Cys Leu Val Lys Gly Phe
            485                 490                 495
Tyr Pro Ser Asp Ile Ala Val Glu Trp Glu Ser Asn Gly Gln Pro Glu
            500                 505                 510
Asn Asn Tyr Lys Thr Thr Pro Pro Val Leu Asp Ser Asp Gly Ser Phe
            515                 520                 525
Phe Leu Tyr Ser Lys Leu Thr Val Asp Lys Ser Arg Trp Gln Gln Gly
            530                 535                 540
```

Asn Val Phe Ser Cys Ser Val Met His Glu Ala Leu His Asn His Tyr
545                 550                 555                 560

Thr Gln Lys Ser Leu Ser Leu Ser Pro Gly Ser Thr Gly Ser Glu Val
                565                 570                 575

Gln Leu Gln Gln Ser Gly Pro Glu Leu Val Lys Pro Gly Ala Ser Val
            580                 585                 590

Lys Ile Ser Cys Lys Thr Ser Gly Tyr Thr Phe Thr Glu Tyr Thr Met
        595                 600                 605

His Trp Val Lys Gln Ser His Gly Lys Ser Leu Glu Trp Ile Gly Gly
    610                 615                 620

Ile Ser Pro Asn Ile Gly Gly Thr Ser Tyr Asn Gln Lys Phe Lys Gly
625                 630                 635                 640

Lys Ala Thr Leu Thr Val Asp Lys Ser Ser Thr Ala Tyr Met Glu
                645                 650                 655

Leu Arg Ser Leu Thr Ser Glu Asp Ser Ala Val Tyr Tyr Cys Ala Arg
            660                 665                 670

Arg Gly Gly Ser Phe Asp Tyr Trp Gly Gln Gly Thr Thr Leu Thr Val
        675                 680                 685

Ser Ser Val Glu Gly Gly Ser Gly Gly Ser Gly Gly Ser
            690                 695                 700

Gly Gly Val Asp Asp Ile Val Met Thr Gln Ser Pro Ala Thr Leu Ser
705                 710                 715                 720

Val Thr Pro Gly Asp Arg Val Ser Leu Ser Cys Arg Ala Ser Gln Ser
                725                 730                 735

Ile Ser Asp Tyr Leu His Trp Tyr Gln Gln Lys Ser His Glu Ser Pro
            740                 745                 750

Arg Leu Leu Ile Lys Tyr Ala Ser Gln Ser Ile Ser Gly Ile Pro Ser
        755                 760                 765

Arg Phe Ser Gly Ser Gly Ser Gly Ser Asp Phe Thr Leu Ser Ile Asn
    770                 775                 780

Ser Val Glu Pro Glu Asp Val Gly Val Tyr Tyr Cys Gln Asn Gly His
785                 790                 795                 800

Ser Phe Pro Leu Thr Phe Gly Ala Gly Thr Lys Leu Glu Leu Lys
                805                 810                 815

<210> SEQ ID NO 162
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 162

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

```
Glu Asp Pro Trp Thr Phe Gly Gly Thr Lys Leu Glu Ile Lys Gly
                100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
            195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Ser Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
    450                 455                 460

Ser Leu Ser Leu Ser Pro Gly Gly Gly Gly Ser Gly Gly Gly Gly
465                 470                 475                 480

Ser Gly Gly Gly Gly Ser Gly Gln Pro Arg Glu Pro Gln Val Tyr Thr
                485                 490                 495

Leu Pro Pro Ser Arg Glu Glu Met Thr Lys Asn Gln Val Ser Leu Thr
            500                 505                 510
```

```
Cys Leu Val Lys Gly Phe Tyr Pro Ser Asp Ile Ala Val Glu Trp Glu
            515                 520                 525

Ser Asn Gly Gln Pro Glu Asn Asn Tyr Lys Thr Thr Pro Pro Val Leu
    530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
            580                 585                 590

Ser Thr Gly Ser Glu Val Gln Leu Gln Gln Ser Gly Pro Glu Leu Val
        595                 600                 605

Lys Pro Gly Ala Ser Val Lys Ile Ser Cys Lys Thr Ser Gly Tyr Thr
    610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
            660                 665                 670

Ser Thr Ala Tyr Met Glu Leu Arg Ser Leu Thr Ser Glu Asp Ser Ala
        675                 680                 685

Val Tyr Tyr Cys Ala Arg Arg Gly Gly Ser Phe Asp Tyr Trp Gly Gln
    690                 695                 700

Gly Thr Thr Leu Thr Val Ser Ser Arg Thr Val Ala Ala Pro Ser Val
705                 710                 715                 720

Phe Ile Phe Pro Pro Ser Asp Glu Gln Leu Lys Ser Gly Thr Ala Ser
                725                 730                 735

Val Val Cys Leu Leu Asn Asn Phe Tyr Pro Arg Glu Ala Lys Val Gln
            740                 745                 750

Trp Lys Val Asp Asn Ala Leu Gln Ser Gly Asn Ser Gln Glu Ser Val
        755                 760                 765

Thr Glu Gln Asp Ser Lys Asp Ser Thr Tyr Ser Leu Ser Ser Thr Leu
    770                 775                 780

Thr Leu Ser Lys Ala Asp Tyr Glu Lys His Lys Val Tyr Ala Cys Glu
785                 790                 795                 800

Val Thr His Gln Gly Leu Ser Ser Pro Val Thr Lys Ser Phe Asn Arg
                805                 810                 815

Gly Glu Cys

<210> SEQ ID NO 163
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 163

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
```

```
            50                  55                  60
Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
        210

<210> SEQ ID NO 164
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 164

Asp Ile Gln Leu Thr Gln Ser Pro Ala Ser Leu Ala Val Ser Leu Gly
  1               5                  10                  15

Gln Arg Ala Thr Ile Ser Cys Lys Ala Ser Gln Ser Val Asp Tyr Asp
             20                  25                  30

Gly Asp Ser Tyr Leu Asn Trp Tyr Gln Gln Ile Pro Gly Gln Pro Pro
         35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
```

-continued

```
                195                 200                 205
Leu Ser Ser Leu Ala Ser Glu Asp Ser Ala Val Tyr Phe Cys Ala Arg
    210                 215                 220
Arg Glu Thr Thr Thr Val Gly Arg Tyr Tyr Tyr Ala Met Asp Tyr Trp
225                 230                 235                 240
Gly Gln Gly Thr Thr Val Thr Val Ser Ser Gly Gly Gly Ser Ser Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
        290                 295                 300
Asp Gly Val Glu Val His Asn Ala Lys Thr Lys Pro Arg Glu Glu Gln
305                 310                 315                 320
Tyr Ser Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Leu Pro Pro Ser Arg Glu Glu Met Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
            435                 440                 445
Ser Cys Ser Val Met His Glu Ala Leu His Asn His Tyr Thr Gln Lys
450                 455                 460
Ser Leu Ser Leu Ser Pro Gly Gly Gly Gly Ser Gly Gly Gly Gly
465                 470                 475                 480
Ser Gly Gly Gly Gly Ser Gly Gln Pro Arg Glu Pro Gln Val Tyr Thr
                485                 490                 495
Leu Pro Pro Ser Arg Glu Glu Met Thr Lys Asn Gln Val Ser Leu Thr
            500                 505                 510
Cys Leu Val Lys Gly Phe Tyr Pro Ser Asp Ile Ala Val Glu Trp Glu
            515                 520                 525
Ser Asn Gly Gln Pro Glu Asn Asn Tyr Lys Thr Thr Pro Pro Val Leu
530                 535                 540
Asp Ser Asp Gly Ser Phe Phe Leu Tyr Ser Lys Leu Thr Val Asp Lys
545                 550                 555                 560
Ser Arg Trp Gln Gln Gly Asn Val Phe Ser Cys Ser Val Met His Glu
                565                 570                 575
Ala Leu His Asn His Tyr Thr Gln Lys Ser Leu Ser Leu Ser Pro Gly
            580                 585                 590
Ser Thr Gly Ser Glu Val Gln Leu Gln Gln Ser Gly Pro Glu Leu Val
            595                 600                 605
Lys Pro Gly Ala Ser Val Lys Ile Ser Cys Lys Thr Ser Gly Tyr Thr
610                 615                 620
```

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Thr Ser Tyr
            645                 650                 655

Asn Gln Lys Phe Lys Gly Lys Ala Thr Leu Thr Val Asp Lys Ser Ser
            660                 665                 670

Ser Thr Ala Tyr Met Glu Leu Arg Ser Leu Thr Ser Glu Asp Ser Ala
            675                 680                 685

Val Tyr Tyr Cys Ala Arg Arg Gly Gly Ser Phe Asp Tyr Trp Gly Gln
            690                 695                 700

Gly Thr Thr Leu Thr Val Ser Ser Ala Ser Thr Lys Gly Pro Ser Val
705                 710                 715                 720

Phe Pro Leu Ala Pro Ser Ser Lys Ser Thr Ser Gly Gly Thr Ala Ala
            725                 730                 735

Leu Gly Cys Leu Val Lys Asp Tyr Phe Pro Glu Pro Val Thr Val Ser
            740                 745                 750

Trp Asn Ser Gly Ala Leu Thr Ser Gly Val His Thr Phe Pro Ala Val
            755                 760                 765

Leu Gln Ser Ser Gly Leu Tyr Ser Leu Ser Ser Val Val Thr Val Pro
            770                 775                 780

Ser Ser Ser Leu Gly Thr Gln Thr Tyr Ile Cys Asn Val Asn His Lys
785                 790                 795                 800

Pro Ser Asn Thr Lys Val Asp Lys Arg Val Glu Pro Lys Ser Cys Asp
            805                 810                 815

Lys Thr His

<210> SEQ ID NO 165
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 165

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
            85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 166
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 166

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 167
<211> LENGTH: 792
<212> TYPE: PRT
<213> ORGANISM: Artificial
<220> FEATURE:
<223> OTHER INFORMATION: Chimeric homo sapiens mus musculus

<400> SEQUENCE: 167

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30
```

```
Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
        210                 215                 220

Lys Ser Cys Asp Lys Thr His Thr Ser Pro Pro Ser Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445
```

Ser Leu Ser Pro Gly Gly Gly Gly Ser Gly Gly Gly Ser Gly
    450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Asp Ile Val Met Thr Gln Ser Pro Ala Thr Leu Ser Val Thr
            580                 585                 590

Pro Gly Asp Arg Val Ser Leu Ser Cys Arg Ala Ser Gln Ser Ile Ser
        595                 600                 605

Asp Tyr Leu His Trp Tyr Gln Gln Lys Ser His Glu Ser Pro Arg Leu
    610                 615                 620

Leu Ile Lys Tyr Ala Ser Gln Ser Ile Ser Gly Ile Pro Ser Arg Phe
625                 630                 635                 640

Ser Gly Ser Gly Ser Gly Ser Asp Phe Thr Leu Ser Ile Asn Ser Val
                645                 650                 655

Glu Pro Glu Asp Val Gly Val Tyr Tyr Cys Gln Asn Gly His Ser Phe
            660                 665                 670

Pro Leu Thr Phe Gly Ala Gly Thr Lys Leu Glu Leu Lys Ala Ser Thr
        675                 680                 685

Lys Gly Pro Ser Val Phe Pro Leu Ala Pro Ser Ser Lys Ser Thr Ser
    690                 695                 700

Gly Gly Thr Ala Ala Leu Gly Cys Leu Val Lys Asp Tyr Phe Pro Glu
705                 710                 715                 720

Pro Val Thr Val Ser Trp Asn Ser Gly Ala Leu Thr Ser Gly Val His
                725                 730                 735

Thr Phe Pro Ala Val Leu Gln Ser Ser Gly Leu Tyr Ser Leu Ser Ser
            740                 745                 750

Val Val Thr Val Pro Ser Ser Ser Leu Gly Thr Gln Thr Tyr Ile Cys
        755                 760                 765

Asn Val Asn His Lys Pro Ser Asn Thr Lys Val Asp Lys Arg Val Glu
    770                 775                 780

Pro Lys Ser Cys Asp Lys Thr His
785                 790

<210> SEQ ID NO 168
<211> LENGTH: 223
<212> TYPE: PRT
<213> ORGANISM: Artificial
<220> FEATURE:
<223> OTHER INFORMATION: Chimeric homo sapiens mus musculus

<400> SEQUENCE: 168

Glu Val Gln Leu Gln Gln Ser Gly Pro Glu Leu Val Lys Pro Gly Ala
1               5                   10                  15

```
Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Ser Pro Asn Ile Gly Gly Thr Ser Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Gly Ser Phe Asp Tyr Trp Gly Gln Gly Thr Thr Leu
            100                 105                 110

Thr Val Ser Ser Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
210                 215                 220

<210> SEQ ID NO 169
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 169

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160
```

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 170
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 170

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

-continued

```
Met Gln Leu Ser Ser Leu Ala Ser Glu Asp Ser Ala Val Tyr Phe Cys
             85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Ser Thr Gly Ser Glu Val Gln Leu Gln Gln Ser
450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
```

```
                500             505             510
Gly Gly Thr Ser Tyr Asn Gln Lys Phe Lys Gly Lys Ala Thr Leu Thr
            515                 520             525

Val Asp Lys Ser Ser Ser Thr Ala Tyr Met Glu Leu Arg Ser Leu Thr
        530                 535             540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
                565                 570             575

Ala Ala Pro Ser Val Phe Ile Phe Pro Pro Ser Asp Glu Gln Leu Lys
            580                 585             590

Ser Gly Thr Ala Ser Val Val Cys Leu Leu Asn Asn Phe Tyr Pro Arg
        595                 600             605

Glu Ala Lys Val Gln Trp Lys Val Asp Asn Ala Leu Gln Ser Gly Asn
            610                 615             620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650             655

Val Tyr Ala Cys Glu Val Thr His Gln Gly Leu Ser Ser Pro Val Thr
            660                 665             670

Lys Ser Phe Asn Arg Gly Glu Cys
            675                 680

<210> SEQ ID NO 171
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 171

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
```

```
                180                 185                 190
Asn His Lys Pro Ser Asn Thr Lys Val Asp Lys Arg Val Glu Pro Lys
            195                 200                 205

Ser Cys Asp Lys Thr His
        210

<210> SEQ ID NO 172
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 172

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ser Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
```

```
                    325                 330                 335
Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 173
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 173

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
```

```
              245                 250                 255
Thr Leu Met Ile Ser Arg Thr Pro Glu Val Thr Cys Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Ser
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Ser Thr Gly Ser Glu Val Gln Leu Gln Gln Ser
            450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
                500                 505                 510

Gly Gly Thr Ser Tyr Asn Gln Lys Phe Lys Gly Lys Ala Thr Leu Thr
            515                 520                 525

Val Asp Lys Ser Ser Thr Ala Tyr Met Glu Leu Arg Ser Leu Thr
                535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
            565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
            595                 600                 605

Glu Ala Lys Val Gln Trp Lys Val Asp Asn Ala Leu Gln Ser Gly Asn
            610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670
```

```
Lys Ser Phe Asn Arg Gly Glu Cys
        675                 680

<210> SEQ ID NO 174
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 174

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 175
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 175

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
```

```
                65                  70                  75                  80
Pro Val Glu Lys Val Asp Ala Ala Thr Tyr His Cys Gln Gln Ser Thr
                    85                  90                  95

Glu Asp Pro Trp Thr Phe Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Ser Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Ser Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 176
<211> LENGTH: 680
<212> TYPE: PRT
<213> ORGANISM: Artificial
<220> FEATURE:
<223> OTHER INFORMATION: Chimeric homo sapiens mus musculus
```

```
<400> SEQUENCE: 176

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Ser Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415
```

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
        595                 600                 605

Glu Ala Lys Val Gln Trp Lys Val Asp Asn Ala Leu Gln Ser Gly Asn
    610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670

Lys Ser Phe Asn Arg Gly Glu Cys
        675                 680

<210> SEQ ID NO 177
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 177

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

```
Thr Phe Gly Ala Gly Thr Lys Leu Glu Leu Lys Ala Ser Thr Lys Gly
                100                 105                 110

Pro Ser Val Phe Pro Leu Ala Pro Ser Ser Lys Ser Thr Ser Gly Gly
            115                 120                 125

Thr Ala Ala Leu Gly Cys Leu Val Lys Asp Tyr Phe Pro Glu Pro Val
        130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 178
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 178

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 179
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 179

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160
```

```
Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys Gly Thr Gly Ser Glu Val Gln Leu Gln Gln Ser
450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
            485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
            515                 520                 525

Val Asp Lys Ser Ser Ser Thr Ala Tyr Met Glu Leu Arg Ser Leu Thr
            530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Leu Thr Val Ser Ser Val Glu Gly
            565                 570                 575
```

```
Gly Ser Gly Gly Ser Gly Gly Ser Gly Gly Val Asp Asp
            580             585             590

Ile Val Met Thr Gln Ser Pro Ala Thr Leu Ser Val Pro Gly Asp
        595             600             605

Arg Val Ser Leu Ser Cys Arg Ala Ser Gln Ser Ile Ser Asp Tyr Leu
        610             615             620

His Trp Tyr Gln Gln Lys Ser His Glu Ser Pro Arg Leu Leu Ile Lys
625             630             635             640

Tyr Ala Ser Gln Ser Ile Ser Gly Ile Pro Ser Arg Phe Ser Gly Ser
            645             650             655

Gly Ser Gly Ser Asp Phe Thr Leu Ser Ile Asn Ser Val Glu Pro Glu
            660             665             670

Asp Val Gly Val Tyr Tyr Cys Gln Asn Gly His Ser Phe Pro Leu Thr
            675             680             685

Phe Gly Ala Gly Thr Lys Leu Glu Leu Lys
            690             695

<210> SEQ ID NO 180
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 180

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
            245                 250                 255

Val Thr Cys Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Ser Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 181
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 181

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
    115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160
```

-continued

```
Val Thr Val Ser Trp Asn Ser Gly Ala Leu Thr Ser Gly Val His Thr
            165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
            195                 200                 205
Val Asn His Lys Pro Ser Asn Thr Lys Val Asp Lys Arg Val Glu Pro
            210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
            245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Ser
            290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
            325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
            370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
            405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
            435                 440                 445
Ser Leu Ser Pro Gly Ser Thr Gly Ser Glu Val Gln Leu Gln Gln Ser
            450                 455                 460
Gly Pro Glu Leu Val Lys Pro Gly Ala Ser Val Lys Ile Ser Cys Lys
465                 470                 475                 480
Thr Ser Gly Tyr Thr Phe Thr Glu Tyr Thr Met His Trp Val Lys Gln
            485                 490                 495
Ser His Gly Lys Ser Leu Glu Trp Ile Gly Gly Ile Ser Pro Asn Ile
            500                 505                 510
Gly Gly Thr Ser Tyr Asn Gln Lys Phe Lys Gly Lys Ala Thr Leu Thr
            515                 520                 525
Val Asp Lys Ser Ser Ser Thr Ala Tyr Met Glu Leu Arg Ser Leu Thr
            530                 535                 540
Ser Glu Asp Ser Ala Val Tyr Tyr Cys Ala Arg Arg Gly Gly Ser Phe
545                 550                 555                 560
Asp Tyr Trp Gly Gln Gly Thr Thr Leu Thr Val Ser Ser Val Glu Gly
            565                 570                 575
Gly Ser Gly Gly Ser Gly Gly Ser Gly Gly Ser Gly Gly Val Asp Asp
```

```
                580             585             590
Ile Val Met Thr Gln Ser Pro Ala Thr Leu Ser Val Thr Pro Gly Asp
            595                 600             605

Arg Val Ser Leu Ser Cys Arg Ala Ser Gln Ser Ile Ser Asp Tyr Leu
        610             615                 620

His Trp Tyr Gln Gln Lys Ser His Glu Ser Pro Arg Leu Leu Ile Lys
625                 630             635                     640

Tyr Ala Ser Gln Ser Ile Ser Gly Ile Pro Ser Arg Phe Ser Gly Ser
                645             650                 655

Gly Ser Gly Ser Asp Phe Thr Leu Ser Ile Asn Ser Val Glu Pro Glu
            660             665             670

Asp Val Gly Val Tyr Tyr Cys Gln Asn Gly His Ser Phe Pro Leu Thr
        675             680             685

Phe Gly Ala Gly Thr Lys Leu Glu Leu Lys
    690                 695

<210> SEQ ID NO 182
<211> LENGTH: 454
<212> TYPE: PRT
<213> ORGANISM: Artificial
<220> FEATURE:
<223> OTHER INFORMATION: Chimeric homo sapiens mus musculus

<400> SEQUENCE: 182

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
```

```
                   245                 250                 255
Thr Leu Met Ile Ser Arg Thr Pro Glu Val Thr Cys Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 183
<211> LENGTH: 670
<212> TYPE: PRT
<213> ORGANISM: Artificial
<220> FEATURE:
<223> OTHER INFORMATION: Chimeric homo sapiens mus musculus

<400> SEQUENCE: 183

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
```

-continued

```
                145                 150                 155                 160
Gly Asn Ser Gln Glu Ser Val Thr Glu Gln Asp Ser Lys Asp Ser Thr
                    165                 170                 175
Tyr Ser Leu Ser Ser Thr Leu Thr Leu Ser Lys Ala Asp Tyr Glu Lys
                    180                 185                 190
His Lys Val Tyr Ala Cys Glu Val Thr His Gln Gly Leu Ser Ser Pro
                    195                 200                 205
Val Thr Lys Ser Phe Asn Arg Gly Glu Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                    245                 250                 255
Val Thr Cys Val Val Val Asp Val Ser His Glu Asp Pro Glu Val Lys
                    260                 265                 270
Phe Asn Trp Tyr Val Asp Gly Val Glu Val His Asn Ala Lys Thr Lys
                    275                 280                 285
Pro Arg Glu Glu Gln Ser Ser Thr Tyr Arg Val Val Ser Val Leu Thr
                    290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                    325                 330                 335
Lys Gly Gln Pro Arg Glu Pro Gln Val Tyr Thr Leu Pro Pro Ser Arg
                    340                 345                 350
Glu Glu Met Thr Lys Asn Gln Val Ser Leu Thr Cys Leu Val Lys Gly
                    355                 360                 365
Phe Tyr Pro Ser Asp Ile Ala Val Glu Trp Ser Asn Gly Gln Pro
                    370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                    405                 410                 415
Gly Asn Val Phe Ser Cys Ser Val Met His Glu Ala Leu His Asn His
                    420                 425                 430
Tyr Thr Gln Lys Ser Leu Ser Leu Ser Pro Gly Ser Thr Gly Ser Glu
                    435                 440                 445
Val Gln Leu Gln Gln Ser Gly Pro Glu Leu Val Lys Pro Gly Ala Ser
                    450                 455                 460
Val Lys Ile Ser Cys Lys Thr Ser Gly Tyr Thr Phe Thr Glu Tyr Thr
465                 470                 475                 480
Met His Trp Val Lys Gln Ser His Gly Lys Ser Leu Glu Trp Ile Gly
                    485                 490                 495
Gly Ile Ser Pro Asn Ile Gly Gly Thr Ser Tyr Asn Gln Lys Phe Lys
                    500                 505                 510
Gly Lys Ala Thr Leu Thr Val Asp Lys Ser Ser Ser Thr Ala Tyr Met
                    515                 520                 525
Glu Leu Arg Ser Leu Thr Ser Glu Asp Ser Ala Val Tyr Tyr Cys Ala
                    530                 535                 540
Arg Arg Gly Gly Ser Phe Asp Tyr Trp Gly Gln Gly Thr Thr Leu Thr
545                 550                 555                 560
Val Ser Ser Arg Thr Val Ala Ala Pro Ser Val Phe Ile Phe Pro Pro
                    565                 570                 575
```

```
Ser Asp Glu Gln Leu Lys Ser Gly Thr Ala Ser Val Val Cys Leu Leu
            580                 585                 590

Asn Asn Phe Tyr Pro Arg Glu Ala Lys Val Gln Trp Lys Val Asp Asn
            595                 600                 605

Ala Leu Gln Ser Gly Asn Ser Gln Glu Ser Val Thr Glu Gln Asp Ser
            610                 615                 620

Lys Asp Ser Thr Tyr Ser Leu Ser Ser Thr Leu Thr Leu Ser Lys Ala
625                 630                 635                 640

Asp Tyr Glu Lys His Lys Val Tyr Ala Cys Glu Val Thr His Gln Gly
            645                 650                 655

Leu Ser Ser Pro Val Thr Lys Ser Phe Asn Arg Gly Glu Cys
            660                 665                 670

<210> SEQ ID NO 184
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 184

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 185
<211> LENGTH: 445
<212> TYPE: PRT
<213> ORGANISM: Artificial
<220> FEATURE:
<223> OTHER INFORMATION: Chimeric homo sapiens mus musculus
```

<400> SEQUENCE: 185

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ser Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 186
<211> LENGTH: 671
<212> TYPE: PRT
<213> ORGANISM: Artificial
<220> FEATURE:
<223> OTHER INFORMATION: Chimeric homo sapiens mus musculus

<400> SEQUENCE: 186

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

```
Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Ser Thr Gly Ser Asp Ile Val Met Thr Gln Ser
            450                 455                 460

Pro Ala Thr Leu Ser Val Thr Pro Gly Asp Arg Val Ser Leu Ser Cys
465                 470                 475                 480

Arg Ala Ser Gln Ser Ile Ser Asp Tyr Leu His Trp Tyr Gln Gln Lys
                485                 490                 495

Ser His Glu Ser Pro Arg Leu Leu Ile Lys Tyr Ala Ser Gln Ser Ile
            500                 505                 510

Ser Gly Ile Pro Ser Arg Phe Ser Gly Ser Gly Ser Gly Ser Asp Phe
            515                 520                 525

Thr Leu Ser Ile Asn Ser Val Glu Pro Glu Asp Val Gly Val Tyr Tyr
            530                 535                 540

Cys Gln Asn Gly His Ser Phe Pro Leu Thr Phe Gly Ala Gly Thr Lys
545                 550                 555                 560

Leu Glu Leu Lys Ala Ser Thr Lys Gly Pro Ser Val Phe Pro Leu Ala
                565                 570                 575

Pro Ser Ser Lys Ser Thr Ser Gly Gly Thr Ala Ala Leu Gly Cys Leu
                580                 585                 590

Val Lys Asp Tyr Phe Pro Glu Pro Val Thr Val Ser Trp Asn Ser Gly
                595                 600                 605

Ala Leu Thr Ser Gly Val His Thr Phe Pro Ala Val Leu Gln Ser Ser
            610                 615                 620

Gly Leu Tyr Ser Leu Ser Ser Val Val Thr Val Pro Ser Ser Ser Leu
625                 630                 635                 640

Gly Thr Gln Thr Tyr Ile Cys Asn Val Asn His Lys Pro Ser Asn Thr
                645                 650                 655

Lys Val Asp Lys Arg Val Glu Pro Lys Ser Cys Asp Lys Thr His
                660                 665                 670

<210> SEQ ID NO 187
<211> LENGTH: 223
<212> TYPE: PRT
<213> ORGANISM: Artificial
<220> FEATURE:
<223> OTHER INFORMATION: Chimeric homo sapiens mus musculus

<400> SEQUENCE: 187

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30
```

```
Thr Met His Trp Val Lys Gln Ser His Gly Lys Ser Leu Glu Trp Ile
        35                  40                  45

Gly Gly Ile Ser Pro Asn Ile Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Gly Ser Phe Asp Tyr Trp Gly Gln Gly Thr Thr Leu
            100                 105                 110

Thr Val Ser Ser Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220

<210> SEQ ID NO 188
<211> LENGTH: 680
<212> TYPE: PRT
<213> ORGANISM: Artificial
<220> FEATURE:
<223> OTHER INFORMATION: Human-mouse chimeric

<400> SEQUENCE: 188

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Thr Gly Ser Gln Val Gln Leu Gln Gln Pro Gly Ala Glu Leu Val
    450                 455                 460

Lys Pro Gly Ala Ser Val Lys Met Ser Cys Lys Ala Ser Gly Tyr Thr
465                 470                 475                 480

Phe Thr Ser Tyr Asn Met His Trp Val Lys Gln Thr Pro Gly Arg Gly
                485                 490                 495

Leu Glu Trp Ile Gly Ala Ile Tyr Pro Gly Asn Gly Asp Thr Ser Tyr
            500                 505                 510

Asn Gln Lys Phe Lys Gly Lys Ala Thr Leu Thr Ala Asp Lys Ser Ser
        515                 520                 525

Ser Thr Ala Tyr Met Gln Leu Ser Ser Leu Thr Ser Glu Asp Ser Ala
    530                 535                 540

Val Tyr Tyr Cys Ala Arg Ser Thr Tyr Tyr Gly Gly Asp Trp Tyr Phe
545                 550                 555                 560

Asn Val Trp Gly Ala Gly Thr Thr Val Thr Val Ser Ala Arg Thr Val
                565                 570                 575

Ala Ala Pro Ser Val Phe Ile Phe Pro Pro Ser Asp Glu Gln Leu Lys
            580                 585                 590
```

```
Ser Gly Thr Ala Ser Val Val Cys Leu Leu Asn Asn Phe Tyr Pro Arg
            595                 600                 605

Glu Ala Lys Val Gln Trp Lys Val Asp Asn Ala Leu Gln Ser Gly Asn
610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
                660                 665                 670

Lys Ser Phe Asn Arg Gly Glu Cys
            675                 680

<210> SEQ ID NO 189
<211> LENGTH: 446
<212> TYPE: PRT
<213> ORGANISM: Artificial
<220> FEATURE:
<223> OTHER INFORMATION: Human-mouse chimeric

<400> SEQUENCE: 189

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 190
<211> LENGTH: 459
<212> TYPE: PRT
<213> ORGANISM: Artificial
<220> FEATURE:
<223> OTHER INFORMATION: Human-mouse chimeric

<400> SEQUENCE: 190

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65              70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ala Ser Lys Gly Pro
            100                 105                 110

Ser Val Phe Pro Leu Ala Pro Ser Ser Lys Ser Thr Ser Gly Gly Thr
        115                 120                 125

Ala Ala Leu Gly Cys Leu Val Lys Asp Tyr Phe Pro Glu Pro Val Thr
    130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175

Val Pro Ser Ser Ser Leu Gly Thr Gln Thr Tyr Ile Cys Asn Val Asn
            180                 185                 190
```

His Lys Pro Ser Asn Thr Lys Val Asp Lys Arg Val Glu Pro Lys Ser
            195                 200                 205

Cys Asp Lys Thr His Gly Gly Ser Ser Glu Val Gln Leu Gln Gln
210                 215                 220

Ser Gly Pro Glu Leu Val Lys Pro Gly Ala Ser Val Lys Ile Ser Cys
225                 230                 235                 240

Lys Thr Ser Gly Tyr Thr Phe Thr Glu Tyr Thr Met His Trp Val Lys
                245                 250                 255

Gln Ser His Gly Lys Ser Leu Glu Trp Ile Gly Gly Ile Ser Pro Asn
            260                 265                 270

Ile Gly Gly Thr Ser Tyr Asn Gln Lys Phe Lys Gly Lys Ala Thr Leu
        275                 280                 285

Thr Val Asp Lys Ser Ser Ser Thr Ala Tyr Met Glu Leu Arg Ser Leu
    290                 295                 300

Thr Ser Glu Asp Ser Ala Val Tyr Tyr Cys Ala Arg Arg Gly Gly Ser
305                 310                 315                 320

Phe Asp Tyr Trp Gly Gln Gly Thr Leu Thr Val Ser Ser Val Glu
                325                 330                 335

Gly Gly Ser Gly Gly Ser Gly Gly Ser Gly Gly Ser Gly Gly Val Asp
                340                 345                 350

Asp Ile Val Met Thr Gln Ser Pro Ala Thr Leu Ser Val Thr Pro Gly
                355                 360                 365

Asp Arg Val Ser Leu Ser Cys Arg Ala Ser Gln Ser Ile Ser Asp Tyr
        370                 375                 380

Leu His Trp Tyr Gln Gln Lys Ser His Glu Ser Pro Arg Leu Leu Ile
385                 390                 395                 400

Lys Tyr Ala Ser Gln Ser Ile Ser Gly Ile Pro Ser Arg Phe Ser Gly
                405                 410                 415

Ser Gly Ser Gly Ser Asp Phe Thr Leu Ser Ile Asn Ser Val Glu Pro
            420                 425                 430

Glu Asp Val Gly Val Tyr Tyr Cys Gln Asn Gly His Ser Phe Pro Leu
        435                 440                 445

Thr Phe Gly Ala Gly Thr Lys Leu Glu Leu Lys
    450                 455

<210> SEQ ID NO 191
<211> LENGTH: 446
<212> TYPE: PRT
<213> ORGANISM: Artificial
<220> FEATURE:
<223> OTHER INFORMATION: Human-mouse chimeric

<400> SEQUENCE: 191

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

```
Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Ser Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 192
<211> LENGTH: 680
<212> TYPE: PRT
<213> ORGANISM: Artificial
<220> FEATURE:
<223> OTHER INFORMATION: Human mouse chimeric

<400> SEQUENCE: 192

Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Tyr Ala Phe Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ser Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

```
                435                 440                 445
Ser Thr Gly Ser Gln Val Gln Leu Gln Gln Pro Gly Ala Glu Leu Val
        450                 455                 460

Lys Pro Gly Ala Ser Val Lys Met Ser Cys Lys Ala Ser Gly Tyr Thr
465                 470                 475                 480

Phe Thr Ser Tyr Asn Met His Trp Val Lys Gln Thr Pro Gly Arg Gly
                485                 490                 495

Leu Glu Trp Ile Gly Ala Ile Tyr Pro Gly Asn Gly Asp Thr Ser Tyr
            500                 505                 510

Asn Gln Lys Phe Lys Gly Lys Ala Thr Leu Thr Ala Asp Lys Ser Ser
                515                 520                 525

Ser Thr Ala Tyr Met Gln Leu Ser Ser Leu Thr Ser Glu Asp Ser Ala
        530                 535                 540

Val Tyr Tyr Cys Ala Arg Ser Thr Tyr Gly Gly Asp Trp Tyr Phe
545                 550                 555                 560

Asn Val Trp Gly Ala Gly Thr Thr Val Thr Val Ser Ala Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
                595                 600                 605

Glu Ala Lys Val Gln Trp Lys Val Asp Asn Ala Leu Gln Ser Gly Asn
            610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
                660                 665                 670

Lys Ser Phe Asn Arg Gly Glu Cys
            675                 680

<210> SEQ ID NO 193
<211> LENGTH: 459
<212> TYPE: PRT
<213> ORGANISM: Artificial
<220> FEATURE:
<223> OTHER INFORMATION: Human mouse chimeric

<400> SEQUENCE: 193

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65              70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ala Ser Thr Lys Gly Pro
            100                 105                 110

Ser Val Phe Pro Leu Ala Pro Ser Ser Lys Ser Thr Ser Gly Gly Thr
```

```
            115                 120                 125
Ala Ala Leu Gly Cys Leu Val Lys Asp Tyr Phe Pro Glu Pro Val Thr
    130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175

Val Pro Ser Ser Ser Leu Gly Thr Gln Thr Tyr Ile Cys Asn Val Asn
            180                 185                 190

His Lys Pro Ser Asn Thr Lys Val Asp Lys Arg Val Glu Pro Lys Ser
        195                 200                 205

Cys Asp Lys Thr His Gly Gly Ser Ser Glu Val Gln Leu Gln Gln
    210                 215                 220

Ser Gly Pro Glu Leu Val Lys Pro Gly Ala Ser Val Lys Ile Ser Cys
225                 230                 235                 240

Lys Thr Ser Gly Tyr Thr Phe Thr Glu Tyr Thr Met His Trp Val Lys
                245                 250                 255

Gln Ser His Gly Lys Ser Leu Glu Trp Ile Gly Gly Ile Ser Pro Asn
            260                 265                 270

Ile Gly Gly Thr Ser Tyr Asn Gln Lys Phe Lys Gly Lys Ala Thr Leu
        275                 280                 285

Thr Val Asp Lys Ser Ser Ser Thr Ala Tyr Met Glu Leu Arg Ser Leu
    290                 295                 300

Thr Ser Glu Asp Ser Ala Val Tyr Tyr Cys Ala Arg Arg Gly Gly Ser
305                 310                 315                 320

Phe Asp Tyr Trp Gly Gln Gly Thr Thr Leu Thr Val Ser Ser Val Glu
                325                 330                 335

Gly Gly Ser Gly Gly Ser Gly Ser Gly Gly Ser Gly Gly Val Asp
            340                 345                 350

Asp Ile Val Met Thr Gln Ser Pro Ala Thr Leu Ser Val Thr Pro Gly
        355                 360                 365

Asp Arg Val Ser Leu Ser Cys Arg Ala Ser Gln Ser Ile Ser Asp Tyr
    370                 375                 380

Leu His Trp Tyr Gln Gln Lys Ser His Glu Ser Pro Arg Leu Leu Ile
385                 390                 395                 400

Lys Tyr Ala Ser Gln Ser Ile Ser Gly Ile Pro Ser Arg Phe Ser Gly
                405                 410                 415

Ser Gly Ser Gly Ser Asp Phe Thr Leu Ser Ile Asn Ser Val Glu Pro
            420                 425                 430

Glu Asp Val Gly Val Tyr Tyr Cys Gln Asn Gly His Ser Phe Pro Leu
        435                 440                 445

Thr Phe Gly Ala Gly Thr Lys Leu Glu Leu Lys
    450                 455

<210> SEQ ID NO 194
<211> LENGTH: 801
<212> TYPE: PRT
<213> ORGANISM: Artificial
<220> FEATURE:
<223> OTHER INFORMATION: Human-mouse chimeric

<400> SEQUENCE: 194

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
```

```
            20              25              30
Trp Ile Asn Trp Val Arg Gln Ala Pro Gly Gln Gly Leu Glu Trp Met
            35              40              45
Gly Arg Ile Phe Pro Gly Asp Gly Asp Thr Asp Tyr Asn Gly Lys Phe
            50              55              60
Lys Gly Arg Val Thr Ile Thr Ala Asp Lys Ser Thr Ser Thr Ala Tyr
65              70              75              80
Met Glu Leu Ser Ser Leu Arg Ser Glu Asp Thr Ala Val Tyr Tyr Cys
                85              90              95
Ala Arg Asn Val Phe Asp Gly Tyr Trp Leu Val Tyr Trp Gly Gln Gly
            100             105             110
Thr Leu Val Thr Val Ser Ser Ala Ser Thr Lys Gly Pro Ser Val Phe
            115             120             125
Pro Leu Ala Pro Ser Ser Lys Ser Thr Ser Gly Gly Thr Ala Ala Leu
            130             135             140
Gly Cys Leu Val Lys Asp Tyr Phe Pro Glu Pro Val Thr Val Ser Trp
145             150             155             160
Asn Ser Gly Ala Leu Thr Ser Gly Val His Thr Phe Pro Ala Val Leu
                165             170             175
Gln Ser Ser Gly Leu Tyr Ser Leu Ser Ser Val Val Thr Val Pro Ser
            180             185             190
Ser Ser Leu Gly Thr Gln Thr Tyr Ile Cys Asn Val Asn His Lys Pro
            195             200             205
Ser Asn Thr Lys Val Asp Lys Arg Val Glu Pro Lys Ser Cys Asp Lys
            210             215             220
Thr His Thr Ser Pro Pro Ser Pro Ala Pro Glu Leu Leu Gly Gly Pro
225             230             235             240
Ser Val Phe Leu Phe Pro Pro Lys Pro Lys Asp Thr Leu Met Ile Ser
                245             250             255
Arg Thr Pro Glu Val Thr Cys Val Val Val Asp Val Ser His Glu Asp
            260             265             270
Pro Glu Val Lys Phe Asn Trp Tyr Val Asp Gly Val Glu Val His Asn
            275             280             285
Ala Lys Thr Lys Pro Arg Glu Glu Gln Tyr Ser Ser Thr Tyr Arg Val
            290             295             300
Val Ser Val Leu Thr Val Leu His Gln Asp Trp Leu Asn Gly Lys Glu
305             310             315             320
Tyr Lys Cys Lys Val Ser Asn Lys Ala Leu Pro Ala Pro Ile Glu Lys
                325             330             335
Thr Ile Ser Lys Ala Lys Gly Gln Pro Arg Glu Pro Gln Val Tyr Thr
            340             345             350
Leu Pro Pro Ser Arg Glu Glu Met Thr Lys Asn Gln Val Ser Leu Thr
            355             360             365
Cys Leu Val Lys Gly Phe Tyr Pro Ser Asp Ile Ala Val Glu Trp Glu
            370             375             380
Ser Asn Gly Gln Pro Glu Asn Asn Tyr Lys Thr Thr Pro Pro Val Leu
385             390             395             400
Asp Ser Asp Gly Ser Phe Phe Leu Tyr Ser Lys Leu Thr Val Asp Lys
                405             410             415
Ser Arg Trp Gln Gln Gly Asn Val Phe Ser Cys Ser Val Met His Glu
            420             425             430
Ala Leu His Asn His Tyr Thr Gln Lys Ser Leu Ser Leu Ser Pro Gly
            435             440             445
```

Gly Gly Gly Gly Ser Gly Gly Gly Ser Gly Gly Gly Ser Gly
        450                 455                 460
Gln Pro Arg Glu Pro Gln Val Tyr Thr Leu Pro Pro Ser Arg Glu Glu
465                 470                 475                 480
Met Thr Lys Asn Gln Val Ser Leu Thr Cys Leu Val Lys Gly Phe Tyr
                485                 490                 495
Pro Ser Asp Ile Ala Val Glu Trp Glu Ser Asn Gly Gln Pro Glu Asn
            500                 505                 510
Asn Tyr Lys Thr Thr Pro Pro Val Leu Asp Ser Asp Gly Ser Phe Phe
        515                 520                 525
Leu Tyr Ser Lys Leu Thr Val Asp Lys Ser Arg Trp Gln Gln Gly Asn
    530                 535                 540
Val Phe Ser Cys Ser Val Met His Glu Ala Leu His Asn His Tyr Thr
545                 550                 555                 560
Gln Lys Ser Leu Ser Leu Ser Pro Gly Ser Thr Gly Ser Gln Val Gln
                565                 570                 575
Leu Gln Gln Pro Gly Ala Glu Leu Val Lys Pro Gly Ala Ser Val Lys
            580                 585                 590
Met Ser Cys Lys Ala Ser Gly Tyr Thr Phe Thr Ser Tyr Asn Met His
        595                 600                 605
Trp Val Lys Gln Thr Pro Gly Arg Gly Leu Glu Trp Ile Gly Ala Ile
    610                 615                 620
Tyr Pro Gly Asn Gly Asp Thr Ser Tyr Asn Gln Lys Phe Lys Gly Lys
625                 630                 635                 640
Ala Thr Leu Thr Ala Asp Lys Ser Ser Thr Ala Tyr Met Gln Leu
                645                 650                 655
Ser Ser Leu Thr Ser Glu Asp Ser Ala Val Tyr Tyr Cys Ala Arg Ser
            660                 665                 670
Thr Tyr Tyr Gly Gly Asp Trp Tyr Phe Asn Val Trp Gly Ala Gly Thr
        675                 680                 685
Thr Val Thr Val Ser Ala Arg Thr Val Ala Ala Pro Ser Val Phe Ile
    690                 695                 700
Phe Pro Pro Ser Asp Glu Gln Leu Lys Ser Gly Thr Ala Ser Val Val
705                 710                 715                 720
Cys Leu Leu Asn Asn Phe Tyr Pro Arg Glu Ala Lys Val Gln Trp Lys
                725                 730                 735
Val Asp Asn Ala Leu Gln Ser Gly Asn Ser Gln Glu Ser Val Thr Glu
            740                 745                 750
Gln Asp Ser Lys Asp Ser Thr Tyr Ser Leu Ser Ser Thr Leu Thr Leu
        755                 760                 765
Ser Lys Ala Asp Tyr Glu Lys His Lys Val Tyr Ala Cys Glu Val Thr
    770                 775                 780
His Gln Gly Leu Ser Ser Pro Val Thr Lys Ser Phe Asn Arg Gly Glu
785                 790                 795                 800
Cys

<210> SEQ ID NO 195
<211> LENGTH: 219
<212> TYPE: PRT
<213> ORGANISM: Artificial
<220> FEATURE:
<223> OTHER INFORMATION: Human-mouse chimeric

<400> SEQUENCE: 195

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 196
<211> LENGTH: 459
<212> TYPE: PRT
<213> ORGANISM: Artificial
<220> FEATURE:
<223> OTHER INFORMATION: Human - mouse chimeric

<400> SEQUENCE: 196

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ala Ser Thr Lys Gly Pro
            100                 105                 110

Ser Val Phe Pro Leu Ala Pro Ser Ser Lys Ser Thr Ser Gly Gly Thr
        115                 120                 125

Ala Ala Leu Gly Cys Leu Val Lys Asp Tyr Phe Pro Glu Pro Val Thr
    130                 135                 140
```

```
Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Val Val Thr
        165                 170                 175

Val Pro Ser Ser Ser Leu Gly Thr Gln Thr Tyr Ile Cys Asn Val Asn
                180                 185                 190

His Lys Pro Ser Asn Thr Lys Val Asp Lys Arg Val Glu Pro Lys Ser
        195                 200                 205

Cys Asp Lys Thr His Gly Gly Ser Ser Glu Val Gln Leu Gln Gln
    210                 215                 220

Ser Gly Pro Glu Leu Val Lys Pro Gly Ala Ser Val Lys Ile Ser Cys
225                 230                 235                 240

Lys Thr Ser Gly Tyr Thr Phe Thr Glu Tyr Thr Met His Trp Val Lys
                245                 250                 255

Gln Ser His Gly Lys Ser Leu Glu Trp Ile Gly Gly Ile Ser Pro Asn
        260                 265                 270

Ile Gly Gly Thr Ser Tyr Asn Gln Lys Phe Lys Gly Lys Ala Thr Leu
    275                 280                 285

Thr Val Asp Lys Ser Ser Thr Ala Tyr Met Glu Leu Arg Ser Leu
290                 295                 300

Thr Ser Glu Asp Ser Ala Val Tyr Tyr Cys Ala Arg Arg Gly Gly Ser
305                 310                 315                 320

Phe Asp Tyr Trp Gly Gln Gly Thr Thr Leu Thr Val Ser Ser Val Glu
                325                 330                 335

Gly Gly Ser Gly Gly Ser Gly Gly Ser Gly Gly Ser Gly Gly Val Asp
        340                 345                 350

Asp Ile Val Met Thr Gln Ser Pro Ala Thr Leu Ser Val Thr Pro Gly
        355                 360                 365

Asp Arg Val Ser Leu Ser Cys Arg Ala Ser Gln Ser Ile Ser Asp Tyr
    370                 375                 380

Leu His Trp Tyr Gln Gln Lys Ser His Glu Ser Pro Arg Leu Leu Ile
385                 390                 395                 400

Lys Tyr Ala Ser Gln Ser Ile Ser Gly Ile Pro Ser Arg Phe Ser Gly
                405                 410                 415

Ser Gly Ser Gly Ser Asp Phe Thr Leu Ser Ile Asn Ser Val Glu Pro
        420                 425                 430

Glu Asp Val Gly Val Tyr Tyr Cys Gln Asn Gly His Ser Phe Pro Leu
    435                 440                 445

Thr Phe Gly Ala Gly Thr Lys Leu Glu Leu Lys
    450                 455
```

<210> SEQ ID NO 197
<211> LENGTH: 928
<212> TYPE: PRT
<213> ORGANISM: Artificial
<220> FEATURE:
<223> OTHER INFORMATION: Human-mouse chimeric

<400> SEQUENCE: 197

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45
```

-continued

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

Gly Gly Gly Gly Ser Gly Gly Gly Gly Ser Gly Gly Gly Gly Ser Gln
            115                 120                 125

Val Gln Leu Val Gln Ser Gly Ala Glu Val Lys Lys Pro Gly Ser Ser
    130                 135                 140

Val Lys Val Ser Cys Lys Ala Ser Gly Tyr Ala Phe Ser Tyr Ser Trp
145                 150                 155                 160

Ile Asn Trp Val Arg Gln Ala Pro Gly Gln Gly Leu Glu Trp Met Gly
                165                 170                 175

Arg Ile Phe Pro Gly Asp Gly Asp Thr Asp Tyr Asn Gly Lys Phe Lys
                180                 185                 190

Gly Arg Val Thr Ile Thr Ala Asp Lys Ser Thr Ser Thr Ala Tyr Met
            195                 200                 205

Glu Leu Ser Ser Leu Arg Ser Glu Asp Thr Ala Val Tyr Tyr Cys Ala
    210                 215                 220

Arg Asn Val Phe Asp Gly Tyr Trp Leu Val Tyr Trp Gly Gln Gly Thr
225                 230                 235                 240

Leu Val Thr Val Ser Ser Ala Ser Thr Lys Gly Pro Ser Val Phe Pro
                245                 250                 255

Leu Ala Pro Ser Ser Lys Ser Thr Ser Gly Gly Thr Ala Ala Leu Gly
                260                 265                 270

Cys Leu Val Lys Asp Tyr Phe Pro Glu Pro Val Thr Val Ser Trp Asn
            275                 280                 285

Ser Gly Ala Leu Thr Ser Gly Val His Thr Phe Pro Ala Val Leu Gln
    290                 295                 300

Ser Ser Gly Leu Tyr Ser Leu Ser Ser Val Val Thr Val Pro Ser Ser
305                 310                 315                 320

Ser Leu Gly Thr Gln Thr Tyr Ile Cys Asn Val Asn His Lys Pro Ser
                325                 330                 335

Asn Thr Lys Val Asp Lys Arg Val Glu Pro Lys Ser Cys Asp Lys Thr
                340                 345                 350

His Thr Ser Pro Pro Ser Pro Ala Pro Glu Leu Leu Gly Gly Pro Ser
            355                 360                 365

Val Phe Leu Phe Pro Pro Lys Pro Lys Asp Thr Leu Met Ile Ser Arg
    370                 375                 380

Thr Pro Glu Val Thr Cys Val Val Val Asp Val Ser His Glu Asp Pro
385                 390                 395                 400

Glu Val Lys Phe Asn Trp Tyr Val Asp Gly Val Glu Val His Asn Ala
                405                 410                 415

Lys Thr Lys Pro Arg Glu Glu Gln Tyr Ser Ser Thr Tyr Arg Val Val
                420                 425                 430

Ser Val Leu Thr Val Leu His Gln Asp Trp Leu Asn Gly Lys Glu Tyr
            435                 440                 445

Lys Cys Lys Val Ser Asn Lys Ala Leu Pro Ala Pro Ile Glu Lys Thr
    450                 455                 460

Ile Ser Lys Ala Lys Gly Gln Pro Arg Glu Pro Gln Val Tyr Thr Leu

-continued

```
465                 470                 475                 480
Pro Pro Ser Arg Glu Glu Met Thr Lys Asn Gln Val Ser Leu Thr Cys
                485                 490                 495
Leu Val Lys Gly Phe Tyr Pro Ser Asp Ile Ala Val Glu Trp Glu Ser
                500                 505                 510
Asn Gly Gln Pro Glu Asn Asn Tyr Lys Thr Thr Pro Pro Val Leu Asp
                515                 520                 525
Ser Asp Gly Ser Phe Phe Leu Tyr Ser Lys Leu Thr Val Asp Lys Ser
                530                 535                 540
Arg Trp Gln Gln Gly Asn Val Phe Ser Cys Ser Val Met His Glu Ala
545                 550                 555                 560
Leu His Asn His Tyr Thr Gln Lys Ser Leu Ser Leu Ser Pro Gly Gly
                565                 570                 575
Gly Gly Gly Ser Gly Gly Gly Gly Ser Gly Gly Gly Gly Ser Gly Gln
                580                 585                 590
Pro Arg Glu Pro Gln Val Tyr Thr Leu Pro Pro Ser Arg Glu Glu Met
                595                 600                 605
Thr Lys Asn Gln Val Ser Leu Thr Cys Leu Val Lys Gly Phe Tyr Pro
                610                 615                 620
Ser Asp Ile Ala Val Glu Trp Glu Ser Asn Gly Gln Pro Glu Asn Asn
625                 630                 635                 640
Tyr Lys Thr Thr Pro Pro Val Leu Asp Ser Asp Gly Ser Phe Phe Leu
                645                 650                 655
Tyr Ser Lys Leu Thr Val Asp Lys Ser Arg Trp Gln Gln Gly Asn Val
                660                 665                 670
Phe Ser Cys Ser Val Met His Glu Ala Leu His Asn His Tyr Thr Gln
                675                 680                 685
Lys Ser Leu Ser Leu Ser Pro Gly Ser Thr Gly Ser Gln Val Gln Leu
                690                 695                 700
Gln Gln Pro Gly Ala Glu Leu Val Lys Pro Gly Ala Ser Val Lys Met
705                 710                 715                 720
Ser Cys Lys Ala Ser Gly Tyr Thr Phe Thr Ser Tyr Asn Met His Trp
                725                 730                 735
Val Lys Gln Thr Pro Gly Arg Gly Leu Glu Trp Ile Gly Ala Ile Tyr
                740                 745                 750
Pro Gly Asn Gly Asp Thr Ser Tyr Asn Gln Lys Phe Lys Gly Lys Ala
                755                 760                 765
Thr Leu Thr Ala Asp Lys Ser Ser Ser Thr Ala Tyr Met Gln Leu Ser
770                 775                 780
Ser Leu Thr Ser Glu Asp Ser Ala Val Tyr Tyr Cys Ala Arg Ser Thr
785                 790                 795                 800
Tyr Tyr Gly Gly Asp Trp Tyr Phe Asn Val Trp Gly Ala Gly Thr Thr
                805                 810                 815
Val Thr Val Ser Ala Arg Thr Val Ala Ala Pro Ser Val Phe Ile Phe
                820                 825                 830
Pro Pro Ser Asp Glu Gln Leu Lys Ser Gly Thr Ala Ser Val Val Cys
                835                 840                 845
Leu Leu Asn Asn Phe Tyr Pro Arg Glu Ala Lys Val Gln Trp Lys Val
                850                 855                 860
Asp Asn Ala Leu Gln Ser Gly Asn Ser Gln Glu Ser Val Thr Glu Gln
865                 870                 875                 880
Asp Ser Lys Asp Ser Thr Tyr Ser Leu Ser Ser Thr Leu Thr Leu Ser
                885                 890                 895
```

Lys Ala Asp Tyr Glu Lys His Lys Val Tyr Ala Cys Glu Val Thr His
                900             905                 910

Gln Gly Leu Ser Ser Pro Val Thr Lys Ser Phe Asn Arg Gly Glu Cys
        915                 920                 925

<210> SEQ ID NO 198
<211> LENGTH: 459
<212> TYPE: PRT
<213> ORGANISM: Artificial
<220> FEATURE:
<223> OTHER INFORMATION: Human - mouse chimeric

<400> SEQUENCE: 198

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ala Ser Thr Lys Gly Pro
            100                 105                 110

Ser Val Phe Pro Leu Ala Pro Ser Ser Lys Ser Thr Ser Gly Gly Thr
        115                 120                 125

Ala Ala Leu Gly Cys Leu Val Lys Asp Tyr Phe Pro Glu Pro Val Thr
    130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175

Val Pro Ser Ser Ser Leu Gly Thr Gln Thr Tyr Ile Cys Asn Val Asn
            180                 185                 190

His Lys Pro Ser Asn Thr Lys Val Asp Lys Arg Val Glu Pro Lys Ser
        195                 200                 205

Cys Asp Lys Thr His Gly Gly Ser Ser Glu Val Gln Leu Gln Gln
    210                 215                 220

Ser Gly Pro Glu Leu Val Lys Pro Gly Ala Ser Val Lys Ile Ser Cys
225                 230                 235                 240

Lys Thr Ser Gly Tyr Thr Phe Thr Glu Tyr Thr Met His Trp Val Lys
                245                 250                 255

Gln Ser His Gly Lys Ser Leu Glu Trp Ile Gly Gly Ile Ser Pro Asn
            260                 265                 270

Ile Gly Gly Thr Ser Tyr Asn Gln Lys Phe Lys Gly Lys Ala Thr Leu
        275                 280                 285

Thr Val Asp Lys Ser Ser Ser Thr Ala Tyr Met Glu Leu Arg Ser Leu
    290                 295                 300

Thr Ser Glu Asp Ser Ala Val Tyr Tyr Cys Ala Arg Arg Gly Gly Ser
305                 310                 315                 320

Phe Asp Tyr Trp Gly Gln Gly Thr Leu Thr Val Ser Ser Val Glu
                325                 330                 335

Gly Gly Ser Gly Gly Ser Gly Gly Ser Gly Gly Val Asp
              340             345             350

Asp Ile Val Met Thr Gln Ser Pro Ala Thr Leu Ser Val Thr Pro Gly
              355                 360                 365

Asp Arg Val Ser Leu Ser Cys Arg Ala Ser Gln Ser Ile Ser Asp Tyr
370                 375                 380

Leu His Trp Tyr Gln Gln Lys Ser His Glu Ser Pro Arg Leu Leu Ile
385                 390                 395                 400

Lys Tyr Ala Ser Gln Ser Ile Ser Gly Ile Pro Ser Arg Phe Ser Gly
              405                 410                 415

Ser Gly Ser Gly Ser Asp Phe Thr Leu Ser Ile Asn Ser Val Glu Pro
              420                 425                 430

Glu Asp Val Gly Val Tyr Tyr Cys Gln Asn Gly His Ser Phe Pro Leu
              435                 440                 445

Thr Phe Gly Ala Gly Thr Lys Leu Glu Leu Lys
              450                 455

<210> SEQ ID NO 199
<211> LENGTH: 120
<212> TYPE: PRT
<213> ORGANISM: Artificial
<220> FEATURE:
<223> OTHER INFORMATION: Chimeric

<400> SEQUENCE: 199

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
              20                  25                  30

Val Ile Asn Trp Val Arg Gln Ala Pro Gly Gln Gly Leu Glu Trp Met
              35                  40                  45

Gly Glu Ile Tyr Pro Gly Ser Gly Thr Asn Tyr Asn Glu Lys Phe
          50                  55                  60

Lys Ala Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
              85                  90                  95

Ala Arg Arg Gly Arg Tyr Gly Leu Tyr Ala Met Asp Tyr Trp Gly Gln
              100                 105                 110

Gly Thr Thr Val Thr Val Ser Ser
          115                 120

<210> SEQ ID NO 200
<211> LENGTH: 120
<212> TYPE: PRT
<213> ORGANISM: Artificial
<220> FEATURE:
<223> OTHER INFORMATION: Chimeric

<400> SEQUENCE: 200

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
              20                  25                  30

Val Ile Asn Trp Gly Arg Gln Ala Pro Gly Gln Gly Leu Glu Trp Ile
              35                  40                  45

Gly Glu Ile Tyr Pro Gly Ser Gly Thr Asn Tyr Tyr Asn Glu Lys Phe

```
                50                  55                  60
Lys Ala Lys Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Arg Gly Arg Tyr Gly Leu Tyr Ala Met Asp Tyr Trp Gly Gln
                100                 105                 110

Gly Thr Thr Val Thr Val Ser Ser
            115                 120

<210> SEQ ID NO 201
<211> LENGTH: 107
<212> TYPE: PRT
<213> ORGANISM: Artificial
<220> FEATURE:
<223> OTHER INFORMATION: Chimeric

<400> SEQUENCE: 201

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asn Thr Arg Pro Trp
                 85                  90                  95

Thr Phe Gly Gly Gly Thr Lys Val Glu Ile Lys
                100                 105

<210> SEQ ID NO 202
<211> LENGTH: 122
<212> TYPE: PRT
<213> ORGANISM: Artificial
<220> FEATURE:
<223> OTHER INFORMATION: Chimeric

<400> SEQUENCE: 202

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ser Ile Ser Ser Asp
             20                  25                  30

Tyr Ala Trp Asn Trp Ile Arg Gln Pro Pro Gly Lys Gly Leu Glu Trp
         35                  40                  45

Ile Gly Tyr Ile Thr Tyr Ser Gly Ser Thr Ser Tyr Asn Pro Ser Leu
 50                  55                  60

Glu Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Tyr Tyr Gly Ser Ser Trp Gly Val Phe Ala Tyr Trp
                100                 105                 110

Gly Gln Gly Thr Leu Val Thr Val Ser Ser
            115                 120
```

```
<210> SEQ ID NO 203
<211> LENGTH: 122
<212> TYPE: PRT
<213> ORGANISM: Artificial
<220> FEATURE:
<223> OTHER INFORMATION: Chimeric

<400> SEQUENCE: 203

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Ser Thr Ser Tyr Asn Pro Ser Leu
    50                  55                  60

Glu Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Tyr Gly Ser Ser Trp Gly Val Phe Ala Tyr Trp
            100                 105                 110

Gly Gln Gly Thr Leu Val Thr Val Ser Ser
        115                 120

<210> SEQ ID NO 204
<211> LENGTH: 122
<212> TYPE: PRT
<213> ORGANISM: Artificial
<220> FEATURE:
<223> OTHER INFORMATION: Chimeric

<400> SEQUENCE: 204

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Ser Thr Ser Tyr Asn Pro Ser Leu
    50                  55                  60

Glu Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Tyr Gly Ser Ser Trp Gly Val Phe Ala Tyr Trp
            100                 105                 110

Gly Gln Gly Thr Leu Val Thr Val Ser Ser
        115                 120

<210> SEQ ID NO 205
<211> LENGTH: 107
<212> TYPE: PRT
<213> ORGANISM: Artificial
<220> FEATURE:
<223> OTHER INFORMATION: Chimeric

<400> SEQUENCE: 205

Asp Ile Gln Met Thr Gln Ser Pro Ser Ser Leu Ser Ala Ser Val Gly
```

```
            1               5                  10                 15
Asp Arg Val Thr Ile Thr Cys Arg Val Ser Glu Asn Ile Tyr Ser Tyr
                20                  25                 30

Leu Ala Trp Tyr Gln Gln Lys Pro Gly Lys Ala Pro Lys Leu Leu Val
                35                  40                 45

Tyr Asn Ala Lys Thr Leu Ala Glu Gly Val Pro Ser Arg Phe Ser Gly
            50                  55                 60

Ser Gly Ser Gly Thr Asp Phe Thr Leu Thr Ile Ser Ser Leu Gln Pro
65                  70                  75                 80

Glu Asp Phe Ala Thr Tyr Tyr Cys Gln His His Tyr Gly Thr Pro Trp
                85                  90                 95

Thr Phe Gly Gly Gly Thr Lys Val Glu Ile Lys
                100                 105
```

```
<210> SEQ ID NO 206
<211> LENGTH: 116
<212> TYPE: PRT
<213> ORGANISM: Artificial
<220> FEATURE:
<223> OTHER INFORMATION: Chimeric

<400> SEQUENCE: 206

Gln Val Gln Leu Val Gln Ser Gly Ala Glu Val Lys Lys Pro Gly Ser
1               5                  10                 15

Ser Val Lys Val Ser Cys Lys Ala Ser Gly Tyr Thr Phe Ser Glu Tyr
                20                  25                 30

Thr Met His Trp Val Arg Gln Ala Pro Gly Gln Gly Leu Glu Trp Met
                35                  40                 45

Gly Gly Ile Ser Pro Asn Ile Gly Gly Thr Ser Tyr Asn Gln Lys Phe
            50                  55                 60

Lys Gly Arg Val Thr Ile Thr Ala Asp Lys Ser Thr Ser Thr Ala Tyr
65                  70                  75                 80

Met Glu Leu Ser Ser Leu Arg Ser Glu Asp Thr Ala Val Tyr Tyr Cys
                85                  90                 95

Ala Arg Arg Gly Gly Ser Phe Asp Tyr Trp Gly Gln Gly Thr Thr Val
                100                 105                110

Thr Val Ser Ser
        115
```

```
<210> SEQ ID NO 207
<211> LENGTH: 116
<212> TYPE: PRT
<213> ORGANISM: Artificial
<220> FEATURE:
<223> OTHER INFORMATION: Chimeric

<400> SEQUENCE: 207

Gln Val Gln Leu Val Gln Ser Gly Ala Glu Val Lys Lys Pro Gly Ser
1               5                  10                 15

Ser Val Lys Val Ser Cys Lys Ala Ser Gly Tyr Thr Phe Ser Glu Tyr
                20                  25                 30

Thr Met His Trp Val Arg Gln Ala Pro Gly Gln Gly Leu Glu Trp Ile
                35                  40                 45

Gly Gly Ile Ser Pro Asn Ile Gly Gly Thr Ser Tyr Asn Gln Lys Phe
            50                  55                 60

Lys Gly Arg Ala Thr Ile Thr Ala Asp Lys Ser Thr Ser Thr Ala Tyr
65                  70                  75                 80
```

```
Met Glu Leu Ser Ser Leu Arg Ser Glu Asp Thr Ala Val Tyr Tyr Cys
                85                  90                  95

Ala Arg Arg Gly Gly Ser Phe Asp Tyr Trp Gly Gln Gly Thr Thr Val
            100                 105                 110

Thr Val Ser Ser
        115

<210> SEQ ID NO 208
<211> LENGTH: 116
<212> TYPE: PRT
<213> ORGANISM: Artificial
<220> FEATURE:
<223> OTHER INFORMATION: Chimeric

<400> SEQUENCE: 208

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Glu Tyr
                20                  25                  30

Thr Met His Trp Val Arg Gln Ala Pro Gly Gln Gly Leu Glu Trp Ile
            35                  40                  45

Gly Gly Ile Ser Pro Asn Ile Gly Gly Thr Ser Tyr Asn Gln Lys Phe
    50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Phe Asp Tyr Trp Gly Gln Gly Thr Thr Val
            100                 105                 110

Thr Val Ser Ser
        115

<210> SEQ ID NO 209
<211> LENGTH: 107
<212> TYPE: PRT
<213> ORGANISM: Artificial
<220> FEATURE:
<223> OTHER INFORMATION: Chimeric

<400> SEQUENCE: 209

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asp Tyr
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 210
<211> LENGTH: 117
<212> TYPE: PRT
<213> ORGANISM: Artificial
```

```
<220> FEATURE:
<223> OTHER INFORMATION: Chimeric

<400> SEQUENCE: 210

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Thr Met His Trp Val Arg Gln Ala Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Gly Ser Ser Arg Gly Phe Asp Tyr Trp Gly Gln Gly Thr Leu
            100                 105                 110

Val Thr Val Ser Ser
        115

<210> SEQ ID NO 211
<211> LENGTH: 117
<212> TYPE: PRT
<213> ORGANISM: Artificial
<220> FEATURE:
<223> OTHER INFORMATION: Chimeric

<400> SEQUENCE: 211

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Thr Met His Trp Val Arg Gln Ala Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Arg Thr Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Gly Ser Ser Arg Gly Phe Asp Tyr Trp Gly Gln Gly Thr Leu
            100                 105                 110

Val Thr Val Ser Ser
        115

<210> SEQ ID NO 212
<211> LENGTH: 117
<212> TYPE: PRT
<213> ORGANISM: Artificial
<220> FEATURE:
<223> OTHER INFORMATION: Chimeric

<400> SEQUENCE: 212

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30
```

```
Thr Met His Trp Val Arg Gln Ala Pro Gly Gln Gly Leu Glu Trp Ile
         35                  40                  45

Gly Tyr Ile Asn Pro Ser Ser Gly Tyr Thr Glu Tyr Asn Gln Lys Phe
 50                  55                  60

Lys Asp Arg Thr Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Val Arg Gly Ser Ser Arg Gly Phe Asp Tyr Trp Gly Gln Gly Thr Leu
                100                 105                 110

Val Thr Val Ser Ser
            115
```

<210> SEQ ID NO 213
<211> LENGTH: 107
<212> TYPE: PRT
<213> ORGANISM: Artificial
<220> FEATURE:
<223> OTHER INFORMATION: Chimeric

<400> SEQUENCE: 213

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Ser Asn
                 20                  25                  30

Leu Ala Trp Phe Gln Gln Lys Pro Gly Lys Ala Pro Lys Leu Leu Val
             35                  40                  45

Tyr Ala Ala Thr Asn Leu Ala Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Gly Thr Pro Arg
                 85                  90                  95

Thr Phe Gly Gly Gly Thr Lys Val Glu Ile Lys
            100                 105
```

<210> SEQ ID NO 214
<211> LENGTH: 120
<212> TYPE: PRT
<213> ORGANISM: Artificial
<220> FEATURE:
<223> OTHER INFORMATION: Chimeric

<400> SEQUENCE: 214

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Asp
                 20                  25                  30

Tyr Ala Trp Asn Trp Ile Arg Gln Pro Pro Gly Lys Gly Leu Glu Trp
             35                  40                  45

Ile Gly Tyr Ile Thr Tyr Ser Gly Ser Thr Asn Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Cys Trp Asp Tyr Ala Leu Tyr Ala Met Asp Cys Trp Gly Gln
                100                 105                 110
```

```
Gly Thr Thr Val Thr Val Ser Ser
        115                 120

<210> SEQ ID NO 215
<211> LENGTH: 120
<212> TYPE: PRT
<213> ORGANISM: Artificial
<220> FEATURE:
<223> OTHER INFORMATION: Chimeric

<400> SEQUENCE: 215

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln Pro Pro Gly Lys Gly Leu Glu Trp
        35                  40                  45

Ile Gly Tyr Ile Thr Tyr Ser Gly Ser Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Cys Trp Asp Tyr Ala Leu Tyr Ala Met Asp Cys Trp Gly Gln
            100                 105                 110

Gly Thr Thr Val Thr Val Ser Ser
        115                 120

<210> SEQ ID NO 216
<211> LENGTH: 120
<212> TYPE: PRT
<213> ORGANISM: Artificial
<220> FEATURE:
<223> OTHER INFORMATION: Chimeric

<400> SEQUENCE: 216

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Ser Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Cys Trp Asp Tyr Ala Leu Tyr Ala Met Asp Cys Trp Gly Gln
            100                 105                 110

Gly Thr Thr Val Thr Val Ser Ser
        115                 120

<210> SEQ ID NO 217
<211> LENGTH: 107
<212> TYPE: PRT
<213> ORGANISM: Artificial
<220> FEATURE:
<223> OTHER INFORMATION: Chimeric
```

```
<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Cys Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Thr Pro Leu
                85                  90                  95

Thr Phe Gly Gln Gly Thr Lys Leu Glu Ile Lys
            100                 105

<210> SEQ ID NO 218
<211> LENGTH: 107
<212> TYPE: PRT
<213> ORGANISM: Artificial
<220> FEATURE:
<223> OTHER INFORMATION: Chimeric

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Cys Gln Gln Lys Pro Gly Lys Ala Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Thr Pro Leu
                85                  90                  95

Thr Phe Gly Gln Gly Thr Lys Leu Glu Ile Lys
            100                 105
```